US011952411B2

(12) United States Patent
Zwolak et al.

(10) Patent No.: US 11,952,411 B2
(45) Date of Patent: Apr. 9, 2024

(54) MATERIALS AND METHODS OF USING ENGINEERED LIGANDS

(71) Applicant: JANSSEN BIOTECH, INC., Horsham, PA (US)

(72) Inventors: Adam Zwolak, Bala Cynwyd, PA (US); Szeman Chan, Havertown, PA (US); Rajkumar Ganesan, Blue Bell, PA (US)

(73) Assignee: Janssen Biotech, Inc., Horsham, PA (US)

( * ) Notice: Subject to any disclaimer, the term of this patent is extended or adjusted under 35 U.S.C. 154(b) by 72 days.

(21) Appl. No.: 17/405,872

(22) Filed: Aug. 18, 2021

(65) Prior Publication Data

US 2022/0056104 A1 Feb. 24, 2022

Related U.S. Application Data

(60) Provisional application No. 63/149,174, filed on Feb. 12, 2021, provisional application No. 63/149,175, filed on Feb. 12, 2021, provisional application No. 63/149,177, filed on Feb. 12, 2021, provisional application No. 63/149,171, filed on Feb. 12, 2021, provisional application No. 63/149,173, filed on Feb. 12, 2021, provisional application No. 63/067,833, filed on Aug. 19, 2020, provisional application No. 63/067,820, filed on Aug. 19, 2020, provisional application No. 63/067,803, filed on Aug. 19, 2020, provisional application No. 63/067,813, filed on Aug. 19, 2020, provisional application No. 63/067,808, filed on Aug. 19, 2020.

(51) Int. Cl.
*C07K 14/705* (2006.01)
*A61K 38/00* (2006.01)
*A61P 37/04* (2006.01)
*C07K 14/765* (2006.01)

(52) U.S. Cl.
CPC ........ *C07K 14/70575* (2013.01); *A61P 37/04* (2018.01); *C07K 14/765* (2013.01); *A61K 38/00* (2013.01); *C07K 2319/30* (2013.01); *C07K 2319/31* (2013.01); *C07K 2319/74* (2013.01)

(58) Field of Classification Search
None
See application file for complete search history.

(56) References Cited

U.S. PATENT DOCUMENTS

| | | |
|---|---|---|
| 2014/0193410 A1 | 7/2014 | Podack et al. |
| 2015/0218250 A1 | 8/2015 | Auer et al. |
| 2018/0244753 A1* | 8/2018 | Gieffers ........... C07K 14/70575 |

FOREIGN PATENT DOCUMENTS

WO WO 2022040302 A1 2/2022

OTHER PUBLICATIONS

Morrison et al. (2001, Current Opinion in Chemical Biology 5(3):302-307).*
Banfield et al., 2020, "First-in-human, randomized dose-escalation study of the safety, tolerability, pharmacokinetics, pharmacodynamics and immunogenicity of PF-06480605 in healthy subjects," Br. J. Clin. Pharmacol., 86(4):812-824.
Blanchet et al., 2013, "Small-angle X-ray scattering on biological macromolecules and nanocomposites in solution," Annu. Rev. Phys. Chem., 64:37-54 (Epub 2012).
Franke et al., 2009, "DAMMIF, a program for rapid ab-initio shape determination in small-angle scattering," J. Appl. Crystallogr., 42:342-346.
Gentz et al., 1989, "Bioassay for trans-activation using purified human immunodeficiency virus tat-encoded protein: trans-activation requires mRNA synthesis," Proc. Natl. Acad. Sci. USA, 86(3):821-824.
Hsieh et al., 2017, "Decoy receptor 3: an endogenous immunomodulator in cancer growth and inflammatory reactions," J. Biomed. Sci., 24(1):39 (9 pages).
International Searching Authority, International Search Report and Written Opinion for International Patent Application No. PCT/US2021/046488 (Pub No. WO 2022040302) dated Jan. 31, 2022 (11 pages).
Lin et al., 2011, "Decoy receptor 3: a pleiotropic immunomodulator and biomarker for inflammatory diseases, autoimmune diseases and cancer," Biochem. Pharmacol., 81(7):838-847.
Liu et al., 2014, "Mechanistic basis for functional promiscuity in the TNF and TNF receptor superfamilies: structure of the LIGHT:DcR3 assembly," Structure, 22(9):1252-1262.
Otwinowski et al., 1997, "Processing of X-ray diffraction data collected in oscillation mode," Methods Enzymol., 276:307-326.
Pettersen et al., 2004, "UCSF Chimera—a visualization system for exploratory research and analysis," J. Comput. Chem., 25(13):1605-1612.
Wei et al., 2019, "DcR3 promotes proliferation and invasion of pancreatic cancer via a DcR3/STAT1/IRF1 feedback loop," Am. J. Cancer Res., 9(12):2618-2633.
Wilson et al., 1984, "The structure of an antigenic determinant in a protein," Cell, 37(3):767-778.
Zhan et al., 2009, "Biochemical and structural characterization of the human TL1A ectodomain," Biochemistry, 48(32):7636-7645.
Zhan et al., 2011, "Decoy strategies: the structure of TL1A:DcR3 complex," Structure, 19(2):162-171.
Zhang et al., 2017, "DcR3 promotes hepatoma cell migration by downregulating E-cadherin expression," Oncol. Rep., 38(1):377-383.

* cited by examiner

*Primary Examiner* — Elizabeth C. Kemmerer
(74) *Attorney, Agent, or Firm* — Riverside Law LLP

(57) ABSTRACT

Described herein are compositions and kits that comprise an engineered TL1A ligand that displays high stability, minimal binding to decoy receptor DcR3 while retaining functional activity via binding to its cell surface receptor, DR3, and the ability to activate T cells in vitro and in vivo. Methods of making an engineered TL1A ligand and methods of treating a disease or disorder in a subject by administering an engineered TL1A ligand are also provided.

18 Claims, 32 Drawing Sheets

Figure 1A:
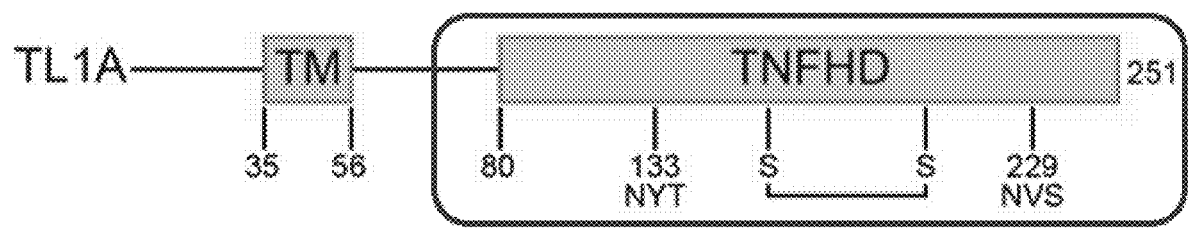

Specification includes a Sequence Listing.

MATERIALS AND METHODS OF USING ENGINEERED LIGANDS

CROSS-REFERENCE TO RELATED APPLICATIONS

This application claims the benefit of U.S. Ser. No. 63/067,808 filed Aug. 19, 2020; U.S. Ser. No. 63/067,803 filed Aug. 19, 2020; U.S. Ser. No. 63/067,820, filed Aug. 19, 2020; U.S. Ser. No. 63/067,833 filed Aug. 19, 2020; U.S. Ser. No. 63/067,813 filed Aug. 19, 2020; U.S. Ser. No. 63/149,171 filed Feb. 12, 2021; U.S. Ser. No. 63/149,173 filed Feb. 12, 2021; U.S. Ser. No. 63/149,174 filed Feb. 12, 2021; U.S. Ser. No. 63/149,175 filed Feb. 12, 2021; and U.S. Ser. No. 63/149,177 filed Feb. 12, 2021, the disclosure of each of which is incorporated by reference herein in its entirety.

1. FIELD

Described herein are compositions and kits that comprise an engineered TL1A ligand that displays high stability, minimal binding to decoy receptor DcR3 while retaining functional activity via binding to its cell surface receptor, DR3, and the ability to activate T cells in vitro and in vivo. Methods of making an engineered TL1A ligand and methods of treating a disease or disorder in a subject by administering an engineered TL1A ligand are also provided.

2. REFERENCE TO SEQUENCE LISTING SUBMITTED ELECTRONICALLY

This application contains a sequence listing, which is submitted electronically via EFS-Web as an ASCII formatted sequence listing with a file name of "14620-570-999_SUB_SEQ_LISTING.txt" and a creation date of Mar. 9, 2023 and having a size of 324,576 bytes. The sequence listing submitted via EFS-Web is part of the specification and is herein incorporated by reference in its entirety.

3. BACKGROUND

The tumor necrosis factor family member TNF-like factor 1A (TL1A) co-stimulatory receptor (also known as TNF superfamily member 15 (TNFSF15)) is expressed on a variety of cell types as a type II single-pass transmembrane protein. It can be cleaved from the cell surface, and soluble or membrane-bound TL1A binds to the co-stimulatory death receptor 3 (DR3). TL1A can also be bound up by the soluble decoy receptor DcR3 (TNFRSF6B), which mimics the structure of cell surface receptors but lacks a transmembrane or cytoplasmic region. DcR3 is structurally homologous to DR3 but shares only approximately 20% sequence identity with DR3. DcR3 is up-regulated in a variety of tumors and is associated with metastasis (Hsieh and Lin, 2017; Lin and Hsieh, 2011; Wei et al., 2019; Zhang et al., 2017). DcR3 decoy receptors can serve as a sink to prevent TNF ligands from activating T cells, and soluble decoy receptors can be up-regulated by tumors. Specifically, the decoy receptor DcR3 can bind to TL1A with higher affinity than its cell surface receptor, DR3, and can prevent TL1A-based T cell costimulation (Hsieh and Lin, 2017; Lin and Hsieh, 2011).

TL1A blocking antibodies have been used in the clinic to treat ulcerative colitis (Banfield et al., 2020). Interaction between TL1A and DR3 contributes to T cell activation, leading to increased inflammatory cytokine production and T cell proliferation. Significant challenges to therapeutic targeting of the TL1A:DR3 axis remain. The 3:3 stoichiometry of binding and the finely tuned affinity of interaction suggest a ligand-based approach can be more amenable to T cell activation compared to antibody-based approaches. However, the high levels of DcR3 require either higher dosing regimens or engineering to eliminate DcR3 binding. Thus, there is an unmet need for the production of engineered TL1A ligands that would form a stable trimer capable of binding DR3, but not DcR3, and which would be suitable for therapeutic development for T cell activation.

4. SUMMARY

In one aspect, provided herein is an engineered TL1A ligand, wherein the engineered TL1A ligand comprises a trimeric complex comprising: three TL1A monomers, wherein the three TL1A monomers form a non-covalent TL1A trimer; or three TL1A monomers, wherein the three TL1A monomers are covalently linked to form a single-chain TL1A (scTL1A) trimer.

In some embodiments, the engineered TL1A ligand further comprises a protein stabilizing region. In some embodiments, the protein stabilizing region comprises an Fc region, or a human serum albumin (HSA) region.

In some embodiments, provided herein is an engineered TL1A ligand comprising: the non-covalent TL1A trimer and one or more Fc regions; the non-covalent TL1A trimer and one or more HSA regions; the scTL1A trimer and one or more Fc regions; or the scTL1A trimer and one or more HSA regions. In some embodiments, the engineered TL1A ligand comprises: two non-covalent TL1A trimers and three Fc regions; two scTL1A trimers and one Fc region; one scTL1A trimer and one Fc region; one non-covalent TL1A trimer and three HSA regions; or one scTL1A trimer and one HSA region.

In some embodiments, the engineered TL1A ligand comprises three TL1A monomers, wherein the three TL1A monomers are covalently bound by a linker. In some embodiments, the linker is a peptide linker. In some embodiments, the linker has an amino acid sequence of Gly-Ser or multiple repeats thereof.

In some embodiments, the Fc region is a human IgG1, IgG2 or IgG4 Fc region. In some embodiments, the non-covalent TL1A trimer or the scTL1A trimer is fused to the C-terminus of the Fc region.

In some embodiments, the engineered TL1A ligand comprises the amino acid residues 72-251 of SEQ ID NO:94.

In some embodiments, provided herein is an engineered TL1A ligand, wherein the engineered TL1A ligand comprises at least one amino acid alteration of residues 72-251 of the amino acid sequence of SEQ ID NO:94. In some embodiments, the engineered TL1A ligand has one or more alterations at one or more residue positions of SEQ ID NO:94 selected from the group consisting of R103, K111, N112, F114, E120, L123, G124, R156, M158, Q167, R170, K173, S176, T185, D186, S187, Y188, P189, E190, T192, S206, N207, F209, Y238, T239, K240, and E241.

In some embodiments, the one or more alterations at one or more residue positions of SEQ ID NO:94 is an alteration selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173R, K173K, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q.

In some embodiments, the engineered TL1A ligand comprises at least two, three, four, five, six, seven, or more alterations of an amino acid sequence of residues 72-251 of SEQ ID NO:94. In some embodiments, the engineered TL1A ligand comprises one or more amino acid alterations of SEQ ID NO:94 selected from the group consisting of: K111A, L123K, M158Y, Q167A, S187L, E190F, and N207F.

In some embodiments, the engineered TL1A ligand comprises the amino acid sequence of any one of SEQ ID NO:1-93.

In some embodiments, the engineered TL1A ligand comprises: an amino acid sequence that is at least 80%, at least 85%, at least 90%, at least 95%, at least 98%, or 100% identical over its entire length to the amino acid sequence of SEQ ID NO:79; or an amino acid sequence that is at least 80%, at least 85%, at least 90%, at least 95%, at least 98%, or 100% identical over its entire length to the amino acid sequence of SEQ ID NO:72; or an amino acid sequence that is at least 80%, at least 85%, at least 90%, at least 95%, at least 98%, or 100% identical over its entire length to the amino acid sequence of SEQ ID NO:8; or an amino acid sequence that is at least 80%, at least 85%, at least 90%, at least 95%, at least 98%, or 100% identical over its entire length to the amino acid sequence of SEQ ID NO:65; or an amino acid sequence that is at least 80%, at least 85%, at least 90%, at least 95%, at least 98%, or 100% identical over its entire length to the amino acid sequence of SEQ ID NO:52; or an amino acid sequence that is at least 80%, at least 85%, at least 90%, at least 95%, at least 98%, or 100% identical over its entire length to the amino acid sequence of SEQ ID NO:14; or an amino acid sequence that is at least 80%, at least 85%, at least 90%, at least 95%, at least 98%, or 100% identical over its entire length to the amino acid sequence of SEQ ID NO:36; or an amino acid sequence that is at least 80%, at least 85%, at least 90%, at least 95%, at least 98%, or 100% identical over its entire length to the amino acid sequence of SEQ ID NO:90; or an amino acid sequence that is at least 80%, at least 85%, at least 90%, at least 95%, at least 98%, or 100% identical over its entire length to the amino acid sequence of SEQ ID NO:88; or an amino acid sequence that is at least 80%, at least 85%, at least 90%, at least 95%, at least 98%, or 100% identical over its entire length to the amino acid sequence of SEQ ID NO:91, or an amino acid sequence that is at least 80%, at least 85%, at least 90%, at least 95%, at least 98%, or 100% identical over its entire length to the amino acid sequence of SEQ ID NO:89.

In some embodiments, the engineered TL1A ligand comprises a bispecific antibody. In some embodiments, the engineered TL1A ligand is fused to a heterologous polypeptide. In some embodiments, the engineered TL1A ligand is conjugated to an agent. In some embodiments, the agent is a toxin.

In one aspect, provided herein is an engineered TL1A ligand comprising: a first means capable of binding DR3 with an affinity comparable to or higher than the affinity of wildtype TL1A and a second means capable of binding DcR3 with an affinity lower than the affinity of wildtype TL1A.

In some embodiments, the engineered TL1A ligand has a longer serum half-life than wildtype TL1A. In some embodiments, the engineered TL1A ligand has a high monodispersity and/or stability compared to wildtype TL1A. In some embodiments, the engineered TL1A ligand can co-stimulate T cells in vitro. In some embodiments, the engineered TL1A ligand can co-stimulate T cells in a subject.

In some embodiments, the engineered TL1A ligand can increase production of one or more cytokines in a subject in need thereof. In some embodiments, the one or more cytokines comprise IFNγ and TNFα.

In some embodiments, the subject has an autoimmune disorder or cancer. In some embodiments, the autoimmune disorder or cancer is selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and sarcomas, including rhabdomyosarcomas.

Further provided herein is a nucleic acid encoding the engineered TL1A ligand. In some embodiments, provided herein is a pharmaceutical composition, comprising the engineered TL1A ligand or the nucleic acid, and a pharmaceutically acceptable excipient.

In one aspect, provided herein is a method treating a disease or disorder in a subject, comprising administering to the subject an effective amount of an engineered TL1A ligand, wherein the engineered TL1A ligand is a trimeric complex comprising: three TL1A monomers, wherein the three TL1A monomers form a non-covalent TL1A trimer; or three TL1A monomers, wherein the three TL1A monomers are covalently linked to form a single-chain TL1A (scTL1A) trimer.

In some embodiments, the engineered TL1A ligand further comprises a protein stabilizing region. In some embodiments, the protein stabilizing region comprises an Fc region, or a HSA region.

In some embodiments, provided herein is a method wherein a multimeric engineered TL1A ligand comprises the engineered TL1A ligand, comprising: the non-covalent TL1A trimer and one or more Fc regions; the non-covalent TL1A trimer and one or more HSA regions; the scTL1A trimer and one or more Fc regions; or the scTL1A trimer and one or more HSA regions.

In some embodiments, the multimeric engineered TL1A ligand comprises: two non-covalent TL1A trimers and three Fc regions; two scTL1A trimers and one Fc region; one scTL1A trimer and one Fc region; one non-covalent TL1A trimer and three HSA regions; or one scTL1A trimer and one HSA region.

In some embodiments, the engineered TL1A ligand of the method comprises the scTL1A trimer and, wherein the three TL1A monomers are covalently bound by a linker. In some embodiments, the linker is a peptide linker. In some embodiments, the linker has an amino acid sequence of Gly-Ser or multiple repeats thereof. In some embodiments, the Fc region is a human IgG1, IgG2 or IgG4 Fc region. In some embodiments, the non-covalent TL1A trimer or the scTL1A trimer is fused to the C-terminus of the Fc region.

In some embodiments, the TL1A monomer comprises the amino acid residues 72-251 of SEQ ID NO:94. In some embodiments, the engineered TL1A ligand comprises at least one amino acid alteration of residues 72-251 of the amino acid sequence of SEQ ID NO:94.

In some embodiments, the engineered TL1A ligand of the method has one or more alterations at one or more residue positions of SEQ ID NO:94 selected from the group consisting of R103, K111, N112, F114, E120, L123, G124, R156, M158, Q167, R170, K173, S176, T185, D186, S187, Y188, P189, E190, T192, S206, N207, F209, Y238, T239, K240, and E241.

In some embodiments, the one or more alterations at one or more residue positions is an alteration selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173S, K173R, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q.

In some embodiments, the amino acid alteration comprises at least two, three, four, five, six, seven, or more alterations of an amino acid sequence of residues 72-251 of SEQ ID NO:94. In some embodiments, the engineered TL1A ligand comprises one or more amino acid alterations of SEQ ID NO:94 selected from the group consisting of: K111A, L123K, M158Y, Q167A, S187L, E190F, and N207F. In some embodiments of the method, the engineered TL1A ligand comprises the amino acid sequence of any one of SEQ ID NO:1-93. In some embodiments, the engineered TL1A ligand comprises: an amino acid sequence that is at least 80%, at least 85%, at least 90%, at least 95%, at least 98%, or 100% identical over its entire length to the amino acid sequence of SEQ ID NO:79; or an amino acid sequence that is at least 80%, at least 85%, at least 90%, at least 95%, at least 98%, or 100% identical over its entire length to the amino acid sequence of SEQ ID NO:72; or an amino acid sequence that is at least 80%, at least 85%, at least 90%, at least 95%, at least 98%, or 100% identical over its entire length to the amino acid sequence of SEQ ID NO:8; or an amino acid sequence that is at least 80%, at least 85%, at least 90%, at least 95%, at least 98%, or 100% identical over its entire length to the amino acid sequence of SEQ ID NO:65; or an amino acid sequence that is at least 80%, at least 85%, at least 90%, at least 95%, at least 98%, or 100% identical over its entire length to the amino acid sequence of SEQ ID NO:52; or an amino acid sequence that is at least 80%, at least 85%, at least 90%, at least 95%, at least 98%, or 100% identical over its entire length to the amino acid sequence of SEQ ID NO:14; or an amino acid sequence that is at least 80%, at least 85%, at least 90%, at least 95%, at least 98%, or 100% identical over its entire length to the amino acid sequence of SEQ ID NO:36; or an amino acid sequence that is at least 80%, at least 85%, at least 90%, at least 95%, at least 98%, or 100% identical over its entire length to the amino acid sequence of SEQ ID NO:90; or an amino acid sequence that is at least 80%, at least 85%, at least 90%, at least 95%, at least 98%, or 100% identical over its entire length to the amino acid sequence of SEQ ID NO:88; or an amino acid sequence that is at least 80%, at least 85%, at least 90%, at least 95%, at least 98%, or 100% identical over its entire length to the amino acid sequence of SEQ ID NO:91, or an amino acid sequence that is at least 80%, at least 85%, at least 90%, at least 95%, at least 98%, or 100% identical over its entire length to the amino acid sequence of SEQ ID NO:89. In some embodiments, an engineered TL1A ligand provided herein is for use in therapy. In some embodiments, an engineered TL1A ligand provided herein is for use in the treatment of an autoimmune disorder or cancer. In some embodiments, an engineered TL1A ligand provided herein is for use in the treatment of an autoimmune disorder or cancer, wherein the autoimmune disorder or cancer is selected from the group consisting of ulcerative colitis, lupus, IBD, COPD, arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and a sarcoma, wherein optionally the sarcoma is a rhabdomyosarcoma.

In some embodiments, provided herein is a method wherein the engineered TL1A ligand comprises a bispecific antibody. In some embodiments, the engineered TL1A ligand is fused to a heterologous polypeptide. In some embodiments, the engineered TL1A ligand is conjugated to an agent. In some embodiments, the agent is a toxin.

In one aspect, provided herein is a method of treating a disease or disorder in a subject, comprising administering to the subject an effective amount of the engineered TL1A ligand comprising: a first means capable of binding DR3 with an affinity comparable to or higher than the affinity of wildtype TL1A and a second means capable of binding DcR3 with an affinity lower than the affinity of wildtype TL1A In some embodiments, provided herein is a method wherein the engineered TL1A ligand has a longer serum half-life than wildtype TL1A. In some embodiments, the engineered TL1A ligand has a high monodispersity and/or stability compared to wildtype TL1A. In some embodiments, the engineered TL1A ligand can co-stimulate T cells in vitro. In some embodiments, the engineered TL1A ligand can co-stimulate T cells in the subject. In some embodiments, the engineered TL1A ligand can increase production of one or more cytokines in a subject in need thereof. In some embodiments, the one or more cytokines comprise IFNγ and TNFα.

In some embodiments, provided herein is a method wherein the disease or disorder is an autoimmune disorder or cancer. In some embodiments, the disease or disorder is selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and sarcomas, including rhabdomyosarcomas.

In one aspect, provided herein is a method of making an engineered TL1A ligand comprising (i) a step for performing the function of introducing at least one amino acid alteration of the amino acid sequence of SEQ ID NO:94 selected from the group consisting of: K111A, L123K, M158Y, Q167A, S187L, E190F, and N207F; and (ii) a step for performing the function of producing a population of engineered TL1A ligand. In some embodiments, the method further comprises the step of fusing the engineered TL1A ligand to a heterologous polypeptide.

In some embodiments, the heterologous polypeptide comprises a protein stabilizing region. In some embodiments, the protein stabilizing region comprises an Fc region, or a HSA region.

In some embodiments, the method further comprises a step of generating a multimeric engineered TL1A ligand. In some embodiments, the multimeric engineered TL1A ligand comprises: the non-covalent TL1A trimer and one or more Fc regions; the non-covalent TL1A trimer and one or more HSA regions; the scTL1A trimer and one or more Fc regions; or the scTL1A trimer and one or more HSA regions.

In some embodiments, the method further comprises a step of generating a multimeric engineered TL1A ligand, wherein the multimeric engineered TL1A ligand comprises: two non-covalent TL1A trimers and three Fc regions; two scTL1A trimers and one Fc region; one scTL1A trimer and one Fc region; one non-covalent TL1A trimer and three HSA regions; or one scTL1A trimer and one HSA region.

In some embodiments, provided herein is a method wherein the engineered TL1A ligand comprises the amino acid sequence of any one of SEQ ID NO:1-93.

In some embodiments, the engineered TL1A ligand comprises: an amino acid sequence that is at least 80%, at least 85%, at least 90%, at least 95%, at least 98%, or 100% identical over its entire length to the amino acid sequence of SEQ ID NO:79; or an amino acid sequence that is at least 80%, at least 85%, at least 90%, at least 95%, at least 98%, or 100% identical over its entire length to the amino acid sequence of SEQ ID NO:72; or an amino acid sequence that is at least 80%, at least 85%, at least 90%, at least 95%, at least 98%, or 100% identical over its entire length to the amino acid sequence of SEQ ID NO:8; or an amino acid sequence that is at least 80%, at least 85%, at least 90%, at least 95%, at least 98%, or 100% identical over its entire length to the amino acid sequence of SEQ ID NO:65; or an amino acid sequence that is at least 80%, at least 85%, at least 90%, at least 95%, at least 98%, or 100% identical over its entire length to the amino acid sequence of SEQ ID NO:52; or an amino acid sequence that is at least 80%, at least 85%, at least 90%, at least 95%, at least 98%, or 100% identical over its entire length to the amino acid sequence of SEQ ID NO:14; or an amino acid sequence that is at least 80%, at least 85%, at least 90%, at least 95%, at least 98%, or 100% identical over its entire length to the amino acid sequence of SEQ ID NO:36; or an amino acid sequence that is at least 80%, at least 85%, at least 90%, at least 95%, at least 98%, or 100% identical over its entire length to the amino acid sequence of SEQ ID NO:90; or an amino acid sequence that is at least 80%, at least 85%, at least 90%, at least 95%, at least 98%, or 100% identical over its entire length to the amino acid sequence of SEQ ID NO:88; or an amino acid sequence that is at least 80%, at least 85%, at least 90%, at least 95%, at least 98%, or 100% identical over its entire length to the amino acid sequence of SEQ ID NO:91, or an amino acid sequence that is at least 80%, at least 85%, at least 90%, at least 95%, at least 98%, or 100% identical over its entire length to the amino acid sequence of SEQ ID NO:89.

4.1 Terminology and Abbreviations

The term "soluble protein" as used herein refers to a protein or a fragment thereof that can be released from a cell membrane or secreted from a cell in soluble form.

The term "fusion protein" or "fusion polypeptide" as used herein refers to two or more separate amino acid sequences linked via a peptide bond or via a linker (e.g., a single chain TL1A fused onto the C-terminus of the Fc).

The term "linker" or "linker region" as used herein refers to a spacer inserted between a first amino acid sequence and a second amino acid sequence (e.g., TL1A monomers linked by a Gly-Ser linker to form a single chain scTL1A). In some embodiments, the linker is a peptide linker. Linkers should not adversely affect the expression, secretion, or bioactivity of the polypeptides. Preferably, linkers are not antigenic and do not elicit an immune response. In some embodiments, the linker is an endogenous amino acid sequences, an exogenous amino acid sequence (e.g., GS-rich sequence), or a non-peptide chemical linker.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain can vary, the human IgG heavy chain Fc region is generally defined to stretch from an amino acid residue at position Cys226 or from Pro230 (according to the EU numbering system), to the carboxyl-terminus thereof. The C-terminal lysine (residue 447 according to the EU numbering system) of the Fc region can be removed, for example, during production or purification of the antibody, or by recombinantly engineering the nucleic acid encoding a heavy chain of the antibody. An exemplary Fc region sequence is provided below:

(SEQ ID NO: 188)
GSCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQ

GNVFSCSVMHEALHNHYTQKSLSLSP.

The terms "selectively binds" or "specifically binds" mean that a polypeptide or molecule interacts more frequently, more rapidly, with greater duration, with greater affinity, or with some combination of the above to the epitope, protein, or target molecule than with alternative substances, including related and unrelated proteins. In some embodiments "specifically binds" means, for instance, that a polypeptide or molecule binds a protein or target with a KD of about 0.1 mM or less, but more usually less than about 1 µM. In some embodiments, "specifically binds" means that a polypeptide or molecule binds a target with a KD of at least about 0.1 µM or less, at least about 0.01 µM or less, or at least about 1 nM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in some embodiments, a polypeptide or molecule that specifically binds a first target (e.g., DR3) may or may not specifically bind a second target (e.g., DcR3). As such, "specific binding" does not necessarily require (although it can include) exclusive binding, i.e., binding to a single target. Thus, a polypeptide or molecule can, in some embodiments, specifically bind more than one target. In some embodiments, multiple targets can be bound by the same antigen-binding site on the polypeptide or molecule. For example, an antibody can, in certain instances, comprise two identical antigen-binding sites, each of which specifically binds the same epitope on two or more proteins. In certain alternative embodiments, an antibody can be bispecific and comprise at least two antigen-binding sites with differing specificities. Generally, but not necessarily, reference to "binding" means "specific binding".

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, where customary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, at least 96%, at least 97%, at least 98%, at least 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a side chain with similar chemical characteristics. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the disclosure do not abrogate the binding of the polypeptide, soluble protein, or antibody containing the amino acid sequence, to the target binding site. Methods of identifying amino acid conservative substitutions which do not eliminate binding are well-known in the art.

The terms "polypeptide" refers to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention can be based upon antibodies or other members of the immunoglobulin superfamily, in some embodiments, the polypeptides can occur as single chains. The term "polypeptide" also includes related polymers of amino acids that are naturally occurring structural variants, and synthetic non-naturally occurring analogs thereof linked via peptide bonds. Synthetic polypeptides can be synthesized, for example, using an automated polypeptide synthesizer.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, etc.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable carrier" or "pharmaceutically acceptable excipient, carrier or adjuvant" or refer to an excipient, carrier or adjuvant that can be administered to a subject, together with at least one agent of the present disclosure, and which does not destroy the pharmacological activity thereof and is nontoxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of a polypeptide or molecule described herein (e.g., a fusion protein, a soluble ligand, an antibody, a polypeptide, a polynucleotide) effective to "treat" a disease or disorder in a subject such as, a mammal. In the case of cancer or a tumor, the therapeutically effective amount of a polypeptide or molecule (e.g., polypeptide, soluble TL1A protein, or TL1A fusion) has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; increase number of tumor infiltrating lymphocytes (TILs, including CD8+/cytotoxic T-cells) in a solid tumor/tumor; form tertiary lymphoid structures in a solid tumor or a combination of such effects.

The term "neoplastic disease" refers to a condition characterized by uncontrolled, abnormal growth of cells. Neoplastic diseases include cancer. Examples of cancer include, but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. All of the possible cancers listed herein are included in, or can be excluded from, the present invention as individual species.

As used herein "engineered" or "variant" when used in reference to any polypeptide or nucleic acid described herein refers to a sequence having at least one variation or alteration at an amino acid position or nucleic acid position as compared to a parent sequence. The parent sequence can be, for example, an unmodified, wild-type sequence, a homolog thereof or a modified variant of, for example, a wild-type sequence or homolog thereof.

As used herein, the term "molecular modeling algorithm" refers to computational approaches for structure prediction of macromolecule. For instance, these can comprise comparative protein modeling methods including homology modeling methods or protein threading modeling methods, and can further comprise ab initio or de novo protein modeling methods, or a combination of any such approaches.

The term "TL1A ligand" as used herein includes variants, isoforms, and species homologs of TL1A ligand. TL1A ligand can refer to any functional fragment of TL1A, e.g., a fragment that can bind to a receptor for TL1A, e.g., DR3. The complete amino acid sequence of an exemplary human TL1A has Swiss-Prot accession number 095150 (hTL1A 1-251 (SEQ ID NO:94). TL1A is also known as TNFSF15; TNF-like protein 1A; VEGI; TNFyP. Human TL1A is designated GeneID: 9966 by Entrez Gene, and 15 HGNC: 11931 by HGNC. TL1A can be encoded by the gene designated TNFSF15/TL1A.

The term "protein stabilizing region" refers to an exogenous region that can be attached or fused to a protein or polypeptide (e.g., covalently attached), and can confer increased half-life or stability to the protein or polypeptide. Fusion technology is widely used in protein-drug development to increase activity, stability, and bioavailability of protein therapeutics, and many protein stabilizing moieties are known in the art. The protein stabilizing region can be any moiety known in the art, e.g., a peptide/polypeptide, nucleic acid, carbohydrate, fatty acid, organic molecule or combination thereof. As non-limiting examples, a protein stabilizing region described herein can be a HSA or a Fc region of immunoglobulin G. HSA, for example, is a highly abundant and well-studied serum protein with a half-life of 19-22 days (Peters, T. The Albumin Molecule in All About Albumin 9-75 (Elsevier, 1995).

5. BRIEF DESCRIPTION OF THE DRAWINGS

FIGS. 1A-1E depict the design of constructs. (A) Schematic diagram of TL1A, including the transmembrane region (TM) from residues 35 to 56 and the tumor necrosis factor homology domain (TNFHD) from residues 80 to 250. Residues N133 and N229 are glycosylation sites and residues C162 and C202 form a disulfide bond. (B) Ribbon diagram depiction of a TL1A monomer. (C) TL1A ligands were expressed having a C-terminal His-tag as a non-covalent trimer (TL1A) or as a single-chain trimer (scTL1A) (left and right panels, respectively). (D) TL1A was expressed as a fusion to the C-terminus of a human IgG1 Fc (Fc-TL1A), an Fc-scTL1A, or by co-expression of Fc-TL1A with His-TL1A (Fc-His-TL1A) (left, middle, and right panels, respectively). (E) TL1A was expressed to a HSA monomer (HSA-TL1A) or HSA-scTL1A (left and right panels, respectively).

FIGS. 2A-2F depict the analysis of the oligomeric state and function of TL1A constructs. (A) Preparative gel-filtration analysis of indicated TL1A constructs. Recombinant TNFα (His-scTNFα) was used as a control to show the population of trimers and oligomers. (B) Analytical SEC analysis of indicated TL1A constructs after preparative gel-filtration purification to isolate desired oligomeric species. The purified species were used in functional assays. (C)-(D) ELISA analysis of the ability of TL1A constructs to bind immobilized DR3 (C) or DcR3 (D). Molar concentrations of TL1A for each construct were normalized to the concentration of TL1A trimers in each molecule. (E)-(F) Pan T cells from healthy donors were incubated with plate-bound anti-CD3 antibody (0.01 µg/mL). Indicated TL1A ligands were added at 0, 0.03, 0.1, 0.3, 1, 3, 10, 30 or 100 nM (trimer molarity) to α-CD3-activated T cells (bars from left to right). Levels of IFNγ (E) and TNFα (F) produced by the activated T cells are shown.

Figure 3:
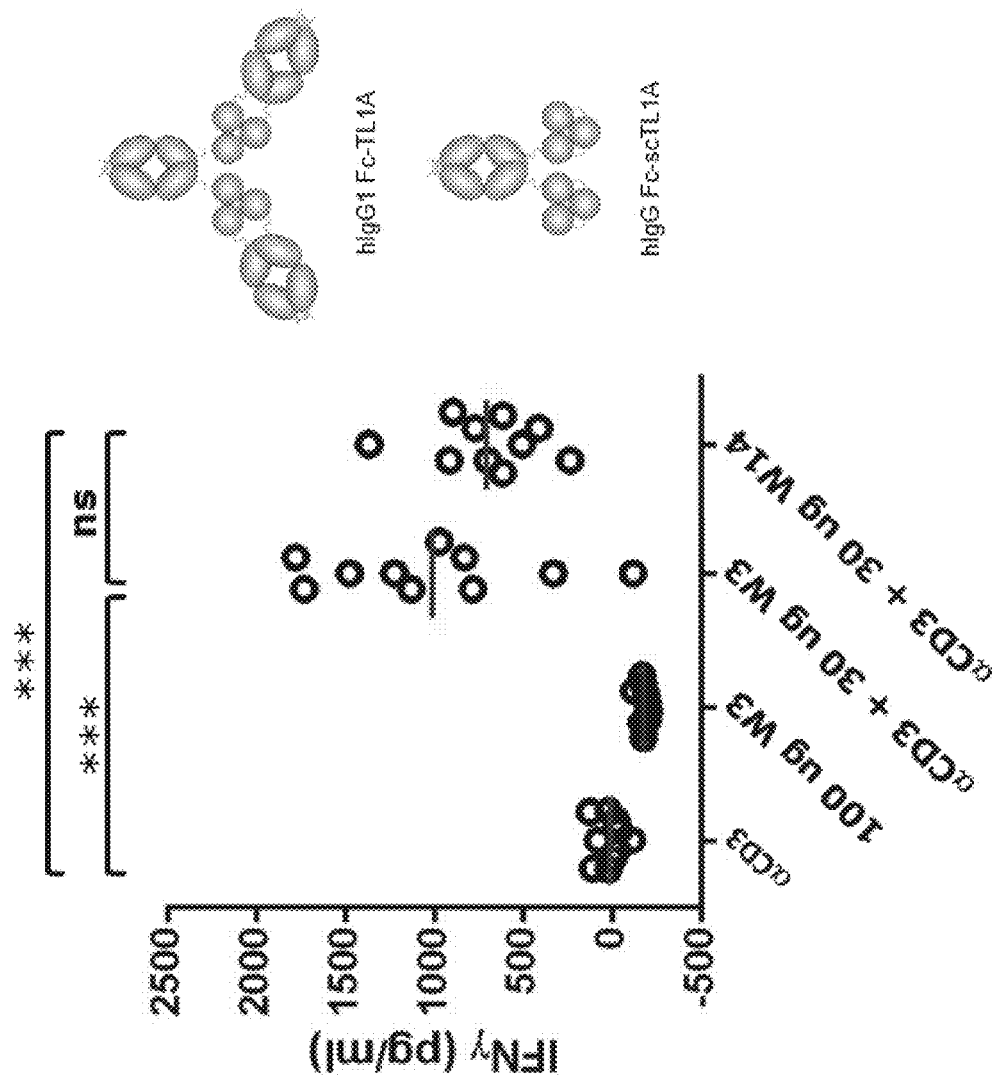

FIG. 3 depicts that Fc-TL1A ligands activate T cells in vivo. Mice were treated with anti-CD3 antibody and Fc-TL1A or Fc-scTL1A and serum concentrations of IFNγ were measured. IFNγ levels are shown in pg/mL and constructs are indicated on the graph.

FIGS. 4A-4G depict optimization of TL1A monodispersity. (A) Structural depiction of the crystal structure of the TL1A trimer, adapted from Protein Data Bank (PDB) ID 2RE9 showing the three subunits of TL1A. One subunit is shown in ribbons while the other two subunits are shown as gray surfaces. The position of the C162-C202 disulfide bond, which is critical for maintenance of DR3 binding, is indicated by an arrow. (B) Analytical SEC analysis of Fc-scTL1A (TL1W14; SEQ ID NO:87) after protein A capture (gray line) showing target dimer species (medium gray fill), undesired tetrameric species (light gray fill), and undesired heterogeneous oligomeric species (dark gray fill). Elution profile of Fc-scTL1A under reducing conditions is shown as the black trace. (C) ELISA analysis of the abilities of C162/C202 mutants to bind DR3. TL1A variants were designed as His-TL1A (non-covalent trimers) and identities are indicated in the graph. (D) TL1A-C162S, C202S can bind DcR3 but not DR3. Selected TL1A variants in His-TL1A format were analyzed for their abilities to bind DR3 (left) and DcR3 (right) by surface plasmon resonance (SPR). Fc-DR3/DcR3 was immobilized using goat anti-human Fc and indicated TL1A variants were flowed over the immobilized receptor. (E) Analytical SEC analysis of Fc-scTL1A (TL1W14; SEQ ID NO:87) after protein A purification, in non-reducing buffer (black trace), after redox in 1×PBS (medium gray trace with peak on left) and after redox in low salt buffer (light gray trace). (F) ELISA comparison of the binding of Fc-scTL1A (TL1W14; SEQ ID NO:87) purified by gel filtration or after redox to recover dimeric target species. Bars indicate an increase in TL1A ligand from 0-300 nM, left to right. (G) Solution x-ray scattering analysis of the Fc-scTL1A (TL1W14; SEQ ID NO:87) molecule showing the scTL1A moieties oriented away from the Fc.

FIGS. 5A-5F depict the design of constructs to specifically reduce DcR3 binding. (A) Cartoon representation of the complex of DcR3 bound to TL1A, based on PDB ID 3K51. DcR3 molecules are shown as ribbons, and TL1A subunits are shown as surfaces. The binding surface on TL1A for DcR3, at the interface between adjacent monomers is boxed. The boxed area is shown in FIG. 5B. (B) Illustration of the residues on TL1A that interact with DcR3 (left) based on PDB ID 3K51, or with DR3 (right), based on a structural model of the TL1A:DR3 complex. Residues mutated in this study are circled in dark gray. (C-F) ELISA analysis of the abilities of indicated single point mutants of TL1A (C-D) or combination mutants (E-F) to bind DR3 (C, E) or DcR3 (D, F). Mutations are indicated in the figures.

FIGS. 6A-6B depict Fc-TL1A-AKALFF was immune to DcR3-based inhibition. (A) Schematic of TL1A variant Fc-scTL1A-AKALFF co-stimulation of T cells and resistance to DcR3-mediated competition. (B) T cells were treated with 0.1 μg of immobilized anti-CD3 antibody alone or in the presence of exogenous DcR3 at 10 μg/mL. Either Fc-scTL1A (SEQ ID NO:87) (dark gray, middle panel) or Fc-scTL1A AKALFF (SEQ ID NO:91) (light gray, left panel) was used to co-stimulate T cells. Anti-CD28 Ab was used as a co-stimulatory positive control. Anti-CD3-activated T cells without co-stimulatory signal was used as negative control. IFNγ levels were measured by MSD assay (Meso Scale Discovery electrochemiluminescence assay).

FIGS. 7A-7D depict solution x-ray scattering analysis. (A) Buffer subtracted scattering curves generated by AAP displayed in Primus and scaled to one another based on points 10-100. Point 1-170 shown. Inset shows a magnification of the same at the low q range. Curves indicate little aggregation of sample at 11.85 mg/mL. (B) Distance distribution (P(r)) and Kratky plots of scattering data. (C) Guinier analysis of scattering data. (D) Manual docking of TL1A and Fc components of TL1W14 (SEQ ID NO:87) into bead model for 11.85 mg/mL concentration. Fc dimer generated from PDB ID 1L6X. TL1A trimers from PDB ID 2RE9.

FIGS. 8A-8C depict an ELISA-based analysis of TL1A variants for DR3 binding. (A) ELISA analysis of the binding of indicated single-point variants of TL1A to DR3. (B) ELISA analysis of the binding of indicated single-point variants of TL1A to DcR3. (C) ELISA analysis of the DR3 binding of indicated TL1A mutants designed to assess effect of glycosylation on binding.

6. DETAILED DESCRIPTION

The tumor necrosis factor family member TNF-like factor 1A (TL1A), also known as TNF-like protein 1A (TNFSF15), is a homo-trimeric TNF superfamily ligand. TL1A is expressed on a variety of cell types as a type II single-pass transmembrane protein. It can be cleaved from the cell surface to enter circulation as a soluble ligand and it binds to the T cell co-stimulatory death receptor 3 (DR3). TL1A can also be bound up by the soluble decoy receptor DcR3 (TNFRSF6B), which is structurally homologous to DR3 but shares only approximately 20% sequence identity with DR3.

The present disclosure is based, at least in part, on the recognition of therapeutic strategy that promotes specific TL1A ligand binding to DR3 and not DcR3. Its potential as a co-stimulatory receptor to overcome T cell exhaustion in solid tumors makes DR3 an attractive immune checkpoint target.

6.1 TL1A Ligands

In some embodiments, engineered TL1A ligands for use with the methods described herein are capable of binding the TNFRSF member death receptor 3 (DR3). In some embodiments, engineered TL1A ligands disclosed herein are capable of binding DR3 with a 3:3 stoichiometry of interaction with DR3 receptors. In some embodiments, the engineered TL1A ligands bind disclosed herein bind specifically to DR3. In some embodiments, the engineered TL1A ligands disclosed herein bind to DR3 with affinity similar to that of wild-type TL1A. In some embodiments, the engineered TL1A ligands bind to DR3 with higher affinity than that of wild-type TL1A, e.g., by at least about 10% higher affinity, at least about 20% higher affinity, at least about 30% higher affinity, at least about 40% higher affinity, at least about 50% higher affinity, at least about 60% higher affinity, at least about 70% higher affinity, at least about 80% higher affinity, at least about 90% higher affinity, at least 100% higher affinity, at least 200% higher affinity, at least 400% higher affinity or more.

In some embodiments, the engineered TL1A ligands bind to DR3 with at least about 10% higher affinity than that of wild-type TL1A. In some embodiments, the engineered TL1A ligands bind to DR3 with at least about 20% higher affinity than that of wild-type TL1A. In some embodiments, the engineered TL1A ligands bind to DR3 with at least about 30% higher affinity than that of wild-type TL1A. In some embodiments, the engineered TL1A ligands bind to DR3 with at least about 40% higher affinity than that of wild-type TL1A. In some embodiments, the engineered TL1A ligands bind to DR3 with at least about 50% higher affinity than that of wild-type TL1A. In some embodiments, the engineered TL1A ligands bind to DR3 with at least about 60% higher affinity than that of wild-type TL1A. In some embodiments, the engineered TL1A ligands bind to DR3 with at least about 70% higher affinity than that of wild-type TL1A. In some embodiments, the engineered TL1A ligands bind to DR3 with at least about 80% higher affinity than that of wild-type TL1A. In some embodiments, the engineered TL1A ligands bind to DR3 with at least about 90% higher affinity than that of wild-type TL1A. In some embodiments, the engineered TL1A ligands bind to DR3 with at least 100% higher affinity than that of wild-type TL1A. In some embodiments, the engineered TL1A ligands bind to DR3 with at least 200% higher affinity than that of wild-type TL1A. In some embodiments, the engineered TL1A ligands bind to DR3 with at least 400% higher affinity than that of wild-type TL1A. In some embodiments, the engineered TL1A ligands bind to DR3 with from about 10% to about 100% higher affinity than that of wild-type TL1A. In some embodiments, the engineered TL1A ligands bind to DR3 with from about 10% to about 50% higher affinity than that of wild-type TL1A. In some embodiments, the engineered TL1A ligands bind to DR3 with from about 10% to about 20% higher affinity than that of wild-type TL1A. In some embodiments, the engineered TL1A ligands bind to DR3 with from about 20% to about 400% higher affinity than that of wild-type TL1A. In some embodiments, the engineered TL1A ligands bind to DR3 with from about 50% to about 400% higher affinity than that of wild-type TL1A. In some embodiments, the engineered TL1A ligands bind to DR3 with from about 100% to about 400% higher affinity than that of wild-type TL1A. In some embodiments, the engineered TL1A ligands bind to DR3 with from about 20% to about 50% higher affinity than that of wild-type TL1A. In some embodiments, the engineered TL1A ligands bind to DR3 with from about 50% to about 100% higher affinity than that of wild-type TL1A. Other intermediate ranges of these percentages are also contemplated.

In some embodiments, the engineered TL1A ligands disclosed herein bind to DcR3 with an affinity less than that of wild-type TL1A. In some embodiments, the engineered TL1A bind to DcR3 with a lower affinity than that of wild-type TL1A, e.g., by at least about 10% lower affinity, at least about 20% lower affinity, at least about 30% lower affinity, at least about 40% lower affinity, at least about 50% lower affinity, at least about 60% lower affinity, at least about 70% lower affinity, at least about 80% lower affinity, at least about 90% lower affinity, at least 100% lower affinity, at least 200% lower affinity or more.

In some embodiments, the engineered TL1A ligands bind to DcR3 with at least about 10% lower affinity than that of wild-type TL1A. In some embodiments, the engineered TL1A ligands bind to DcR3 with at least about 20% lower affinity than that of wild-type TL1A. In some embodiments, the engineered TL1A ligands bind to DcR3 with at least about 30% lower affinity than that of wild-type TL1A. In some embodiments, the engineered TL1A ligands bind to DcR3 with at least about 40% lower affinity than that of wild-type TL1A. In some embodiments, the engineered TL1A ligands bind to DcR3 with at least about 50% lower affinity than that of wild-type TL1A. In some embodiments, the engineered TL1A ligands bind to DcR3 with at least about 60% lower affinity than that of wild-type TL1A. In some embodiments, the engineered TL1A ligands bind to DcR3 with at least about 70% lower affinity than that of wild-type TL1A. In some embodiments, the engineered TL1A ligands bind to DcR3 with at least about 80% lower affinity than that of wild-type TL1A. In some embodiments, the engineered TL1A ligands bind to DcR3 with at least about 90% lower affinity than that of wild-type TL1A. In some embodiments, the engineered TL1A ligands bind to DcR3 with at least 100% lower affinity than that of wild-type TL1A. In some embodiments, the engineered TL1A ligands bind to DcR3 with at least 200% lower affinity than that of wild-type TL1A. In some embodiments, the engineered TL1A ligands bind to DcR3 with at least 400% lower affinity than that of wild-type TL1A. In some embodiments, the engineered TL1A ligands bind to DcR3 with from about 10% to about 100% lower affinity than that of wild-type TL1A. In some embodiments, the engineered TL1A ligands bind to DcR3 with from about 10% to about 50% lower affinity than that of wild-type TL1A. In some embodiments, the engineered TL1A ligands bind to DcR3 with from about 10% to about 20% lower affinity than that of wild-type TL1A. In some embodiments, the engineered TL1A ligands bind to DcR3 with from about 20% to about 400% lower affinity than that of wild-type TL1A. In some embodiments, the engineered TL1A ligands bind to DcR3 with from about 50% to about 400% lower affinity than that of wild-type TL1A. In some embodiments, the engineered TL1A ligands bind to DcR3 with from about 100% to about 400% lower affinity than that of wild-type TL1A. In some embodiments, the engineered TL1A ligands bind to DcR3 with from about 20% to about 50% lower affinity than that of wild-type TL1A. In some embodiments, the engineered TL1A ligands bind to DcR3 with from about 50% to about 100% lower affinity than that of wild-type TL1A. Other intermediate ranges of these percentages are also contemplated.

In some embodiments, the engineered TL1A ligands disclosed herein do not bind to DcR3. In some embodiments, the engineered TL1A ligands display no measurable binding to DcR3.

In some embodiments, the engineered TL1A ligands disclosed herein comprise a trimeric ligand. In some embodiments, the engineered TL1A ligands disclosed herein comprise a trimeric ligand that specifically binds to DR3 via a trimeric interface. In some embodiments, the engineered TL1A ligands trimerize through native, non-covalent interactions. In some embodiments, the engineered TL1A ligands trimerize as a single-chain (sc), e.g., using a linker. The linker can be any linker known in the art. In some embodiments, the linker is a peptide linker. In some embodiments, the linker does not adversely affect the expression, secretion, or bioactivity of the engineered TL1A ligand. In some embodiments, the linker does not adversely affect the expression of the engineered TL1A ligand. In some embodiments, the linker does not adversely affect the secretion of the engineered TL1A ligand. In some embodiments, the linker does not adversely affect the bioactivity of the engineered TL1A ligand. In some embodiments, the linker is not antigenic and does not elicit an immune response. In some embodiments, the linker is not antigenic. In some embodiments, the linker does not elicit an immune response. In some embodiments, the linker is an endogenous amino acid sequence, an exogenous amino acid sequence (e.g., GS-rich sequence), or a non-peptide chemical linker. In some embodiments, the linker is an endogenous amino acid sequence. In some embodiments, the linker is an exogenous amino acid sequence. In some embodiments, the linker is a GS-rich sequence. In some embodiments, the linker is non-peptide chemical linker.

In some embodiments, the engineered TL1A ligands disclosed herein comprise the C-terminal extracellular domain of TL1A, comprising the TNF homology domain which forms into a jellyroll fold. In some embodiments, the engineered TL1A ligands disclosed herein comprise an amino acid sequence of residues 72-251 of the wild-type human TL1A amino acid sequence. In some embodiments, the engineered TL1A ligands disclosed herein comprise an amino acid sequence of residues 72-251 of SEQ ID NO:94. In some embodiments, the engineered TL1A ligands disclosed herein comprise a functional fragment of TL1A capable of specifically binding to DR3. In some embodiments, the engineered TL1A ligands disclosed herein comprise a functional fragment of SEQ ID NO:94 capable of specifically binding to DR3. In some embodiments, the engineered TL1A ligands disclosed herein comprise a functional fragment of TL1A capable of forming a soluble ligand for DR3. In some embodiments, the engineered TL1A ligands disclosed herein comprise one or more amino acid alterations relative to the wild-type amino acid sequence of TL1A (e.g., at least two, three, four, five, six, seven, or more alterations of an amino acid sequence of residues 72-251 of SEQ ID NO:94).

6.2 Biological Activities of TL1A Ligands

In some embodiments, engineered TL1A ligands described herein bind to DR3 on CD4+ T cells. In some embodiments, engineered TL1A ligands described herein bind to DR3 on CD8+ T cells. In some embodiments, the T cells are effector T cells. In some embodiments, binding of engineered TL1A ligands described herein to DR3 (e.g., DR3 on CD4+ or CD8+ effector T cells) In some embodiments, binding of engineered TL1A ligands described herein to DR3 (e.g., DR3 on CD4+ or CD8+ effector T cells) can induce a DR3-dependent signaling pathway. In some embodiments, binding of engineered TL1A ligands described herein to DR3 can promote DR3-mediated activation of a pro-inflammatory, survival-promoting signaling cascade. In some embodiments, binding of engineered TL1A ligands described herein to DR3 triggers the membrane-distal CRD domains (termed the pre-ligand assembly domain (PLAD)) of the receptor to re-organize. In some embodiments, binding of engineered TL1A ligands described herein to DR3 disrupts PLAD interactions. In some embodiments, the central CRDs interact with the engineered TL1A ligands described herein. In some embodiments, binding of engineered TL1A ligands described herein to DR3 triggers recruitment of one or more adapter proteins (e.g., recruitment of TNFR-associated death domain (TRADD) via its DD to the cytoplasmic DD of DR3). In some embodiments, binding of engineered TL1A ligands described herein to DR3 is capable of triggering a conformational re-arrangement of the DR3. In some embodiments, binding of engineered TL1A ligands described herein to DR3 is capable of enhancing DR3 internalization. In some embodiments, the conformational change is transmitted through the transmembrane helix of each receptor subunit to allow cis-interactions of the cytoplasmic TRADD domains. In some embodiments, the conformational change resulting from binding of engineered TL1A ligands described herein to DR3 is capable of leading to NF-kB signaling and T cell activation. In some embodiments, binding of engineered TL1A ligands described herein to DR3 on T cells (e.g., CD4+ or CD8+ effector T cells) induces downstream signaling pathways (e.g., NF-κB signaling). In some embodiments, binding of engineered TL1A ligands described herein to DR3 on CD4+ or CD8+ effector T cells leads to T cell proliferation. In some embodiments, binding of engineered TL1A ligands described herein to DR3 on T cells leads to an increase in the production and/or secretion of one or more cytokines (e.g., IL-2, IFNγ and TNFα).

In some embodiments, binding of engineered TL1A ligands described herein to DR3 acts as costimulator on T cells. In some embodiments, binding of engineered TL1A ligands described herein to DR3 leads to DR3 activation. In some embodiments, binding of engineered TL1A ligands described herein to DR3 leads to activation of the DR3-TL1A axis. In some embodiments, binding of engineered TL1A ligands described herein to DR3 is capable of increasing costimulation of immune effector cells. In some embodiments, binding of engineered TL1A ligands described herein to DR3 leads to enhanced anti-tumor immunity.

It will be understood that the effect of DR3 activation by an engineered TL1A ligand disclosed herein will vary between T-cell subsets. In some embodiments, binding leads to an increase in interleukin-2 (IL-2) signaling. In some embodiments, the increase in IL-2 signaling is an increased IL-2 production in activated T cells. In some embodiments, the increase in IL-2 signaling is increased IL-2 receptor expression in activated T cells. In some embodiments, binding of engineered TL1A ligands described herein to DR3 is capable of upregulating IFNγ. In some embodiments, binding is not limited to Th1 immune response, but can promote IL-4 as well as other Th2-type cytokines. In some embodiments, an engineered TL1A ligand disclosed herein can modulate an immune response. As a non-limiting example, modulating an immune response can include an immune increasing T-cell activation (e.g., CD8+ T-cell activation), increasing T-cell proliferation, and/or increasing cytokine production. In some embodiments, the modulation of the immune response comprises increasing T-cell activation. In one embodiment, the T-cell activation is CD8+ T-cell activation. In some embodiments, the modulation of the immune response comprises increasing T-cell proliferation. In some embodiments, the modulation of the immune response comprises increasing cytokine production.

In some embodiments, an engineered TL1A ligand disclosed herein forms a stable target oligomer. In one embodiment, the stable target oligomer is a monomer. In one embodiment, the stable target oligomer is a dimer. In one embodiment, the stable target oligomer is a trimer. In one embodiment, the stable target oligomer is a hexamer. In some embodiments, an engineered TL1A ligand disclosed herein forms a stable target oligomer, wherein the target oligomer is a monomer (e.g., a HSA-scTL1A such as SEQ ID NO:84 or a HIS-scTL1A, such as SEQ ID NO:86). In one embodiment, the stable target monomer is a HSA-scTL1A. In one embodiment, the stable target monomer is a HSA-scTL1A comprising SEQ ID NO:84. In one embodiment, the stable target monomer is a HIS-scTL1A. In one embodiment, the stable target monomer is a HIS-scTL1A comprising SEQ ID NO:86. In some embodiments, an engineered TL1A ligand disclosed herein forms a stable target oligomer, wherein the target oligomer is a dimer (e.g., Fc-His-TL1A such as SEQ ID NO:92 or an Fc-scTL1A such as SEQ ID NO:87). In one embodiment, the stable target dimer comprises Fc-His-TL1A. In one embodiment, the stable target dimer comprises a Fc-His-TL1A comprising SEQ ID NO:92. In one embodiment, the stable target dimer comprises a Fc-scTL1A. In one embodiment, the stable target dimer comprises a Fc-scTL1A comprising SEQ ID NO:87. In some embodiments, an engineered TL1A ligand disclosed herein forms a stable target oligomer, wherein the target oligomer is a trimer (e.g., His-TL1A such as SEQ ID NO:20 or a HSA-TL1A such as SEQ ID NO:85). In one embodiment, the stable target trimer comprises a His-TL1A. In one embodiment, the stable target trimer comprises a His-TL1A comprising SEQ ID NO:20. In one embodiment, the stable target trimer comprises a HSA-TL1A. In one embodiment, the stable target trimer comprises a HSA-TL1A comprising SEQ ID NO:85. In some embodiments, an engineered TL1A ligand disclosed herein forms a stable target oligomer, wherein the target oligomer is a hexamer (e.g., Fc-TL1A such as SEQ ID NO:93). In one embodiment, the stable target hexamer comprises a Fc-TL1A. In one embodiment, the stable target hexamer comprises a Fc-TL1A comprising SEQ ID NO:93.

In some embodiments, an engineered TL1A ligand disclosed herein displays high monodispersity and stability. In some embodiments, an engineered TL1A ligand disclosed herein displays high monodispersity and stability than that of wild-type TL1A ligand. In some embodiments, an engineered TL1A ligand disclosed herein displays high monodispersity. In some embodiments, an engineered TL1A ligand disclosed herein displays high stability. In some embodiments, the population of target species of an engineered TL1A ligand disclosed herein, purified for example, following preparative gel-filtration analysis, is more than about 40%, more than about 50%, more than about 60%, more than about 70%, more than about 80%, more than about 90% or more.

In some embodiments, the population of target species of an engineered TL1A ligand disclosed herein is more than about 40%. In some embodiments, the population of target species of an engineered TL1A ligand disclosed herein is more than about 50%. In some embodiments, the population of target species of an engineered TL1A ligand disclosed herein is more than about 60%. In some embodiments, the population of target species of an engineered TL1A ligand disclosed herein is more than about 70%. In some embodiments, the population of target species of an engineered TL1A ligand disclosed herein is more than about 80%. In some embodiments, the population of target species of an engineered TL1A ligand disclosed herein is more than about 90%. In certain embodiments, the percentages are following purification. In some embodiments, the percentages are following preparative gel-filtration analysis In some embodiments, the population of off-target species (i.e., % high molecular weight species and/or low molecular weight species) of an engineered TL1A ligand disclosed herein purified, for example, following preparative gel-filtration analysis, is less than about 50%, less than about 40%, less than about 30%, less than about 20%, less than about 10% or less.

In some embodiments, the population of off-target species of an engineered TL1A ligand disclosed herein is less than about 50%. In some embodiments, the population of off-target species of an engineered TL1A ligand disclosed herein is less than about 40%. In some embodiments, the population of off-target species of an engineered TL1A ligand disclosed herein is less than about 30%. In some embodiments, the population of off-target species of an engineered TL1A ligand disclosed herein is less than about 20%. In some embodiments, the population of off-target species of an engineered TL1A ligand disclosed herein is less than about 10%. In certain embodiments, the percentages are following purification. In some embodiments, the percentages are following preparative gel-filtration analysis In some embodiments, the monodispersity of an engineered TL1A ligand disclosed herein can be improved (e.g., by reduction of HMW and/or LMW species) using any method disclosed herein or known in the art. As a non-limiting example, monodispersity can be improved by altering the polypeptide sequence to alter disulfide bonding. In some embodiments, the monodispersity of an engineered TL1A ligand disclosed herein can be improved (e.g., by reduction of HMW and/or LMW species) by employing any method known in the art during purification of the engineered TL1A ligand (e.g., by changing buffer conditions). In some embodiments, the monodispersity of an engineered TL1A ligand disclosed herein can be improved (e.g., formation of the HMW species could be prevented) by employing a redox approach during purification. As a non-limiting example, in certain embodiments, an engineered TL1A ligand disclosed herein can be purified using a method including redox in a buffer consisting of only 20 mM sodium phosphate, pH 6.8 (with no added NaCl).

The biological activities of engineered TL1A ligands disclosed herein can be demonstrated using various assays described herein and known in the art. Non-limiting examples of assays to test binding engineered TL1A ligand to DR3 or DcR3 are known in the art and described herein (e.g., immunohistochemistry, immunoassays, immunoprecipitation, ELISA, flow cytometry, CyTOF, etc.). In vivo and in vitro assays for determining whether engineered TL1A ligand modulates a DR3-mediated response are known in the art or are being developed.

In some embodiments, an engineered TL1A ligand disclosed herein binds a human DR3 with a half maximal effective concentration ($EC_{50}$) of about 1 µM or less, about 100 nM or less, about 40 nM or less, about 20 nM or less, about 10 nM or less, about 1 nM or less, or about 0.1 nM or less. In some embodiments, an engineered TL1A ligand disclosed herein binds a human DR3 with a $EC_{50}$ of about 1 µM or less. In some embodiments, an engineered TL1A ligand disclosed herein binds a human DR3 with a $EC_{50}$ of about 100 nM or less. In some embodiments, an engineered TL1A ligand disclosed herein binds a human DR3 with a $EC_{50}$ of about 40 nM or less. In some embodiments, an engineered TL1A ligand disclosed herein binds a human DR3 with a $EC_{50}$ of about 20 nM or less. In some embodiments, an engineered TL1A ligand disclosed herein binds a human DR3 with a $EC_{50}$ of about 10 nM or less. In some embodiments, an engineered TL1A ligand disclosed herein binds a human DR3 with a $EC_{50}$ of about 1 nM or less. In some embodiments, an engineered TL1A ligand disclosed herein binds a human DR3 with a $EC_{50}$ of about 0.1 nM or less.

Without being limited by theory, engineered TL1A ligands disclosed herein can also be potent co-stimulators of T cells and increase cell proliferation in a dose-dependent manner. In some embodiments, engineered TL1A ligand can also have a greater co-stimulatory effect on the CD8+ T cell subset than on the CD4+ T cell subset. In addition, the compounds can have anti-inflammatory properties against myeloid cell responses, yet efficiently co-stimulate T cells to produce greater amounts of IL-2, IFN-γ, and to enhance T cell proliferation and CD8+ T cell cytotoxic activity. Any methods of assaying T cell co-stimulation, T cell activation, or T cell proliferation known in the art can be used to assess the effect of engineered TL1A ligands on T cells.

In some embodiments, engineered TL1A ligands disclosed herein can increase the production and/or secretion of one or more cytokines. In some embodiments, engineered TL1A ligands disclosed herein increase the production of one or more cytokines. In some embodiments, engineered TL1A ligands disclosed herein increase the secretion of one or more cytokines. As a non-limiting example, engineered TL1A ligands disclosed herein can increase the production and/or secretion of IL2, TNFα, and/or IFNγ. In some embodiments, engineered TL1A ligands disclosed herein can increase the production and/or secretion of one or more cytokines in CD3-activated T cells (e.g., IL-2, IFN-γ, TNFα). In one embodiment, the cytokine is IL-2. In one embodiment, the cytokine is IFN-γ In one embodiment, the cytokine is TNFα. In one embodiment, the cytokine is a CD3-activated cytokine.

In some embodiments, the engineered TL1A ligands disclosed herein enhance antigen-specific T cell activation (e.g., CD4+ or CD8+ T cell activation) in a dose-dependent manner. In one embodiment, the T cell is a CD4+ T cell. In one embodiment, the T cell is a CD8+ T cell. In some embodiments, the engineered TL1A ligands disclosed herein enhances antigen-specific T cell activation as measured using the cytomegalovirus antigen recall assay (e.g., in the presence of CD3).

In some embodiments, the engineered TL1A ligands disclosed herein retain specific binding to DR3, while exhibiting reduced binding to DcR3. In one embodiment, the DcR3 is a circulating DcR3. In some embodiments, the engineered TL1A ligands disclosed herein comprise amino acid residues that make different contacts with DcR3 compared to DR3. In some embodiments, the engineered TL1A ligands disclosed herein comprise amino acid residues (e.g., residues altered relative to the wild-type TL1A amino acid sequence) that disrupt the interactions of the engineered TL1A ligands with DcR3.

As a non-limiting example, in some embodiments, the engineered TL1A ligands disclosed herein comprise one or more amino acid alterations at residues R103, K111, N112, F114, E120, L123, G124, R156, M158, Q167, R170, K173, S176, T185, D186, S187, Y188, P189, E190, T192, S206, N207, F209, Y238, T239, K240, and E241 of human TL1A (e.g., SEQ ID NO:94) that disrupt interactions with DcR3. In one embodiment, an engineered TL1A ligand disclosed herein comprises an amino acid alteration at residue R103. In one embodiment, an engineered TL1A ligand disclosed herein comprises an amino acid alteration at residue K111. In one embodiment, an engineered TL1A ligand disclosed herein comprises an amino acid alteration at residue N112. In one embodiment, an engineered TL1A ligand disclosed herein comprises an amino acid alteration at residue F114. In one embodiment, an engineered TL1A ligand disclosed herein comprises an amino acid alteration at residue E120. In one embodiment, an engineered TL1A ligand disclosed herein comprises an amino acid alteration at residue L123. In one embodiment, an engineered TL1A ligand disclosed herein comprises an amino acid alteration at residue G124. In one embodiment, an engineered TL1A ligand disclosed herein comprises an amino acid alteration at residue R156. In one embodiment, an engineered TL1A ligand disclosed herein comprises an amino acid alteration at residue M158. In one embodiment, an engineered TL1A ligand disclosed herein comprises an amino acid alteration at residue Q167. In one embodiment, an engineered TL1A ligand disclosed herein comprises an amino acid alteration at residue R170. In one embodiment, an engineered TL1A ligand disclosed herein comprises an amino acid alteration at residue K173. In one embodiment, an engineered TL1A ligand disclosed herein comprises an amino acid alteration at residue S176. In one embodiment, an engineered TL1A ligand disclosed herein comprises an amino acid alteration at residue T185. In one embodiment, an engineered TL1A ligand disclosed herein comprises an amino acid alteration at residue D186. In one embodiment, an engineered TL1A ligand disclosed herein comprises an amino acid alteration at residue S187. In one embodiment, an engineered TL1A ligand disclosed herein comprises an amino acid alteration at residue Y188. In one embodiment, an engineered TL1A ligand disclosed herein comprises an amino acid alteration at residue P189. In one embodiment, an engineered TL1A ligand disclosed herein comprises an amino acid alteration at residue E190. In one embodiment, an engineered TL1A ligand disclosed herein comprises an amino acid alteration at residue T192. In one embodiment, an engineered TL1A ligand disclosed herein comprises an amino acid alteration at residue S206. In one embodiment, an engineered TL1A ligand disclosed herein comprises an amino acid alteration at residue N207. In one embodiment, an engineered TL1A ligand disclosed herein comprises an amino acid alteration at residue F209. In one embodiment, an engineered TL1A ligand disclosed herein comprises an amino acid alteration at residue Y238. In one embodiment, an engineered TL1A ligand disclosed herein comprises an amino acid alteration at residue T239. In one embodiment, an engineered TL1A ligand disclosed herein comprises an amino acid alteration at residue K240. In one embodiment, an engineered TL1A ligand disclosed herein comprises an amino acid alteration at residue E241. In certain embodiments, the amino acid alteration is of human TL1A. In certain embodiments, the human TL1A is wild-type TL1A. In certain embodiments, the human TL1A comprises the amino acid sequence of SEQ ID NO:94. In certain embodiments, the amino acid alteration disrupts an interaction with DcR3.

In some embodiments, the engineered TL1A ligands disclosed herein comprise one or more amino acid alterations at residues K111, L123, M158, Q167, S187, E190, and N207 that disrupt interactions with DcR3. In one embodiment, an engineered TL1A ligand disclosed herein comprises an amino acid alteration at residue K111. In one embodiment, an engineered TL1A ligand disclosed herein comprises an amino acid alteration at residue L123. In one embodiment, an engineered TL1A ligand disclosed herein comprises an amino acid alteration at residue M158. In one embodiment, an engineered TL1A ligand disclosed herein comprises an amino acid alteration at residue Q167. In one embodiment, an engineered TL1A ligand disclosed herein comprises an amino acid alteration at residue S187. In one embodiment, an engineered TL1A ligand disclosed herein comprises an amino acid alteration at residue E190. In one embodiment, an engineered TL1A ligand disclosed herein comprises an amino acid alteration at residue N207. In certain embodiments, the amino acid alteration is of human TL1A. In certain embodiments, the human TL1A comprises the amino acid sequence of SEQ ID NO:94. In certain embodiments, the amino acid alteration disrupts an interaction with DcR3.

In some embodiments, the engineered TL1A ligands disclosed herein comprise one or more amino acid alterations of K111A, L123K, M158Y, Q167A, S187L, E190F, and N207F that disrupt interactions with DcR3. In one embodiment, an engineered TL1A ligand disclosed herein comprises an amino acid alteration at residue K111A. In one embodiment, an engineered TL1A ligand disclosed herein comprises an amino acid alteration at residue L123K. In one embodiment, an engineered TL1A ligand disclosed herein comprises an amino acid alteration at residue M158Y. In one embodiment, an engineered TL1A ligand disclosed herein comprises an amino acid alteration at residue Q167A. In one embodiment, an engineered TL1A ligand disclosed herein comprises an amino acid alteration at residue S187L. In one embodiment, an engineered TL1A ligand disclosed herein comprises an amino acid alteration at residue E190F. In one embodiment, an engineered TL1A ligand disclosed herein comprises an amino acid alteration at residue N207F. In one embodiment, an engineered TL1A ligand disclosed herein comprises an amino acid alteration at residue N207. In certain embodiments, the amino acid alteration is of human TL1A. In certain embodiments, the human TL1A is wild-type TL1A. In certain embodiments, the human TL1A comprises the amino acid sequence of SEQ ID NO:94. In certain embodiments, the amino acid alteration disrupts an interaction with DcR3.

In some embodiments, the engineered TL1A ligands disclosed herein comprise at least two, three, four, five, six, seven, or more alterations of an amino acid sequence of residues 72-251 of SEQ ID NO:94. In some embodiments, an engineered TL1A ligand comprises two alterations of an amino acid sequence of residues 72-251 of SEQ ID NO:94. In some embodiments, an engineered TL1A ligand comprises three alterations of an amino acid sequence of residues 72-251 of SEQ ID NO:94. In some embodiments, an engineered TL1A ligand comprises four alterations of an amino acid sequence of residues 72-251 of SEQ ID NO:94. In some embodiments, an engineered TL1A ligand comprises five alterations of an amino acid sequence of residues 72-251 of SEQ ID NO:94. In some embodiments, an engineered TL1A ligand comprises six alterations of an amino acid sequence of residues 72-251 of SEQ ID NO:94. In some embodiments, an engineered TL1A ligand comprises seven alterations of an amino acid sequence of residues 72-251 of SEQ ID NO:94. In some embodiments, an engineered TL1A ligand comprises more than two alterations of an amino acid sequence of residues 72-251 of SEQ ID NO:94. In some embodiments, an engineered TL1A ligand comprises more than three alterations of an amino acid sequence of residues 72-251 of SEQ ID NO:94. In some embodiments, an engineered TL1A ligand comprises more than four alterations of an amino acid sequence of residues 72-251 of SEQ ID NO:94. In some embodiments, an engineered TL1A ligand comprises more than five alterations of an amino acid sequence of residues 72-251 of SEQ ID NO:94. In some embodiments, an engineered TL1A ligand comprises more than six alterations of an amino acid sequence of residues 72-251 of SEQ ID NO:94. In some embodiments, an engineered TL1A ligand comprises more than seven alterations of an amino acid sequence of residues 72-251 of SEQ ID NO:94.

In some embodiments, the engineered TL1A ligands disclosed herein comprise at least two, three, four, five, six, seven, or more alterations of an amino acid sequence of residues K111, L123, M158, Q167, S187, E190, and N207 of wild-type human TL1A (e.g., SEQ ID NO:94). In one embodiment, an engineered TL1A ligand disclosed herein comprises an amino acid alteration at residue K111. In one embodiment, an engineered TL1A ligand disclosed herein comprises an amino acid alteration at residue L123. In one embodiment, an engineered TL1A ligand disclosed herein comprises an amino acid alteration at residue M158. In one embodiment, an engineered TL1A ligand disclosed herein comprises an amino acid alteration at residue Q167. In one embodiment, an engineered TL1A ligand disclosed herein comprises an amino acid alteration at residue S187. In one embodiment, an engineered TL1A ligand disclosed herein comprises an amino acid alteration at residue E190. In one embodiment, an engineered TL1A ligand disclosed herein comprises an amino acid alteration at residue N207. In certain embodiments, the amino acid alteration is of human TL1A. In some embodiments, an engineered TL1A ligand comprises two of the above-referenced amino acid alterations. In some embodiments, an engineered TL1A ligand comprises three of the above-referenced amino acid alterations. In some embodiments, an engineered TL1A ligand comprises four of the above-referenced amino acid alterations. In some embodiments, an engineered TL1A ligand comprises five of the above-referenced amino acid alterations. In some embodiments, an engineered TL1A ligand comprises six of the above-referenced amino acid alterations. In some embodiments, an engineered TL1A ligand comprises seven of the above-referenced amino acid alterations. In some embodiments, an engineered TL1A ligand comprises two or more of the above-referenced amino acid alterations. In some embodiments, an engineered TL1A ligand comprises three or more of the above-referenced amino acid alterations. In some embodiments, an engineered TL1A ligand comprises four or more of the above-referenced amino acid alterations. In some embodiments, an engineered TL1A ligand comprises five or more of the above-referenced amino acid alterations. In some embodiments, an engineered TL1A ligand comprises six or more of the above-referenced amino acid alterations. In some embodiments, an engineered TL1A ligand comprises seven or more of the above-referenced amino acid alterations. In certain embodiments, the human TL1A comprises the amino acid sequence of SEQ ID NO:94. In certain embodiments, the amino acid alteration disrupts an interaction with DcR3.

6.3 Polypeptides with TL1A Ligand Capability

TNF ligands are comprised of jellyroll-type domains that trimerize to form the functional signaling unit. TNF ligands generally bind with 3:3 stoichiometry to their TNF-family receptors, which are comprised of three or four cysteine-rich domains (CRDs). Some TNF ligands, such as TRAIL and TL1A can be bound up by soluble decoy receptors, CRD domain-containing proteins which mimic the structure of cell surface receptors but which lack a transmembrane or cytoplasmic region. These decoy receptors can serve as a sink to prevent TNF ligands from activating T cells, and indeed soluble decoy receptors can be up-regulated by tumors. DcR3 can bind to Fas ligand (FasL), LIGHT (homologous to lymphotoxin, exhibits inducible expression, and competes with HSV glycoprotein D for herpesvirus entry mediator (HVEM), a receptor expressed on T lymphocytes), or TL1A and is upregulated in several tumor settings. Without being bound by theory, in some embodiments, DcR3 is upregulated in a number of solid tumor types (e.g., colon, pancreatic, or stomach cancer), suggesting that DcR3 in these tumors may be a mechanism of T cell inhibition and that T cells within these tumors could be stimulated by a TL1A ligand which can overcome the DcR3-mediated sink.

In some embodiments, an engineered TL1A ligand disclosed herein comprises the TL1A C-terminal extracellular domain, which comprises the TNF homology domain. In some embodiments, an engineered TL1A ligand of this disclosure comprises a trimeric complex, wherein the trimer complex comprises three TL1A monomers. In some embodiments, the three TL1A monomers form a non-covalent TL1A trimer. In some embodiments, the three TL1A monomers are covalently linked to form a single-chain TL1A (scTL1A) trimer.

In some embodiments, an engineered TL1A ligand is a single chain ligand (e.g., comprises three copies of the TL1A C-terminal extracellular domain linked via a linker). In some embodiments, an engineered TL1A ligand disclosed herein is a single chain ligand (e.g., comprises an amino acid sequence comprising three copies of the amino acid residues 72-251 of SEQ ID NO:94).

In some embodiments, the engineered TL1A ligands disclosed herein comprise one or more amino acid alterations at residues R103, K111, N112, F114, E120, L123, G124, R156, M158, Q167, R170, K173, S176, T185, D186, S187, Y188, P189, E190, T192, S206, N207, F209, Y238, T239, K240, and E241 of human TL1A (e.g., SEQ ID NO:94). In one embodiment, an engineered TL1A ligand provided herein comprises an amino acid alteration at residue R103. In one embodiment, an engineered TL1A ligand provided herein comprises an amino acid alteration at residue K111. In one embodiment, an engineered TL1A ligand provided herein comprises an amino acid alteration at residue N112. In one embodiment, an engineered TL1A ligand provided herein comprises an amino acid alteration at residue F114. In one embodiment, an engineered TL1A ligand provided herein comprises an amino acid alteration at residue E120. In one embodiment, an engineered TL1A ligand provided herein comprises an amino acid alteration at residue L123. In one embodiment, an engineered TL1A ligand provided herein comprises an amino acid alteration at residue G124. In one embodiment, an engineered TL1A ligand provided herein comprises an amino acid alteration at residue R156. In one embodiment, an engineered TL1A ligand provided herein comprises an amino acid alteration at residue M158. In one embodiment, an engineered TL1A ligand provided herein comprises an amino acid alteration at residue Q167. In one embodiment, an engineered TL1A ligand provided herein comprises an amino acid alteration at residue R170. In one embodiment, an engineered TL1A ligand provided herein comprises an amino acid alteration at residue K173. In one embodiment, an engineered TL1A ligand provided herein comprises an amino acid alteration at residue S176. In one embodiment, an engineered TL1A ligand provided herein comprises an amino acid alteration at residue T185. In one embodiment, an engineered TL1A ligand provided herein comprises an amino acid alteration at residue D186. In one embodiment, an engineered TL1A ligand provided herein comprises an amino acid alteration at residue S187. In one embodiment, an engineered TL1A ligand provided herein comprises an amino acid alteration at residue Y188. In one embodiment, an engineered TL1A ligand provided herein comprises an amino acid alteration at residue P189. In one embodiment, an engineered TL1A ligand provided herein comprises an amino acid alteration at residue E190. In one embodiment, an engineered TL1A ligand provided herein comprises an amino acid alteration at residue T192. In one embodiment, an engineered TL1A ligand provided herein comprises an amino acid alteration at residue S206. In one embodiment, an engineered TL1A ligand provided herein comprises an amino acid alteration at residue N207. In one embodiment, an engineered TL1A ligand provided herein comprises an amino acid alteration at residue F209. In one embodiment, an engineered TL1A ligand provided herein comprises an amino acid alteration at residue Y238. In one embodiment, an engineered TL1A ligand provided herein comprises an amino acid alteration at residue T239. In one embodiment, an engineered TL1A ligand provided herein comprises an amino acid alteration at residue K240. In one embodiment, an engineered TL1A ligand provided herein comprises an amino acid alteration at residue E241. In certain embodiments, the amino acid alteration is of human TL1A. In certain embodiments, the human TL1A is wild-type TL1A. In certain embodiments, the human TL1A comprises the amino acid sequence of SEQ ID NO:94.

In some embodiments, the engineered TL1A ligands disclosed herein comprise one or more amino acid alterations at residues K111, L123, M158, Q167, S187, E190, and N207. In one embodiment, an engineered TL1A ligand provided herein comprises an amino acid alteration at residue K111. In one embodiment, an engineered TL1A ligand provided herein comprises an amino acid alteration at residue L123. In one embodiment, an engineered TL1A ligand provided herein comprises an amino acid alteration at residue M158. In one embodiment, an engineered TL1A ligand provided herein comprises an amino acid alteration at residue Q167. In one embodiment, an engineered TL1A ligand provided herein comprises an amino acid alteration at residue S187. In one embodiment, an engineered TL1A ligand provided herein comprises an amino acid alteration at residue E190. In one embodiment, an engineered TL1A ligand provided herein comprises an amino acid alteration at residue N207. In certain embodiments, the amino acid alteration is of human TL1A. In certain embodiments, the human TL1A is wild-type TL1A. In certain embodiments, the human TL1A comprises the amino acid sequence of SEQ ID NO:94.

In some embodiments, the engineered TL1A ligands disclosed herein comprise one or more amino acid alterations of K111A, L123K, M158Y, Q167A, S187L, E190F, and N207F. In one embodiment, an engineered TL1A ligand provided herein comprises an amino acid alteration at residue K111A. In one embodiment, an engineered TL1A ligand provided herein comprises an amino acid alteration at residue L123K. In one embodiment, an engineered TL1A ligand provided herein comprises an amino acid alteration at residue M158Y. In one embodiment, an engineered TL1A ligand provided herein comprises an amino acid alteration at residue Q167A. In one embodiment, an engineered TL1A ligand provided herein comprises an amino acid alteration at residue S187L. In one embodiment, an engineered TL1A ligand provided herein comprises an amino acid alteration at residue E190F. In one embodiment, an engineered TL1A ligand provided herein comprises an amino acid alteration at residue N207F. In certain embodiments, the amino acid alteration is of human TL1A. In certain embodiments, the human TL1A is wild-type TL1A. In certain embodiments, the human TL1A comprises the amino acid sequence of SEQ ID NO:94.

In some embodiments, the engineered TL1A ligands disclosed herein comprise at least two, three, four, five, six, seven, or more alterations of an amino acid sequence of residues 72-251 of SEQ ID NO:94. In some embodiments, the engineered TL1A ligands disclosed herein comprise two, three, four, five, six, seven, or more alterations of an amino acid sequence of residues 72-251 of SEQ ID NO:94. In some embodiments, the engineered TL1A ligands disclosed herein comprise two alterations of an amino acid sequence of residues 72-251 of SEQ ID NO:94. In some embodiments, the engineered TL1A ligands disclosed herein comprise three alterations of an amino acid sequence of residues 72-251 of SEQ ID NO:94. In some embodiments, the engineered TL1A ligands disclosed herein comprise four alterations of an amino acid sequence of residues 72-251 of SEQ ID NO:94. In some embodiments, the engineered TL1A ligands disclosed herein comprise five alterations of an amino acid sequence of residues 72-251 of SEQ ID NO:94. In some embodiments, the engineered TL1A ligands disclosed herein comprise six alterations of an amino acid sequence of residues 72-251 of SEQ ID NO:94. In some embodiments, the engineered TL1A ligands disclosed herein comprise seven alterations of an amino acid sequence of residues 72-251 of SEQ ID NO:94. In some embodiments, the engineered TL1A ligands disclosed herein comprise at least two alterations of an amino acid sequence of residues 72-251 of SEQ ID NO:94. In some embodiments, the engineered TL1A ligands disclosed herein comprise at least three alterations of an amino acid sequence of residues 72-251 of SEQ ID NO:94. In some embodiments, the engineered TL1A ligands disclosed herein comprise at least four alterations of an amino acid sequence of residues 72-251 of SEQ ID NO:94. In some embodiments, the engineered TL1A ligands disclosed herein comprise at least five alterations of an amino acid sequence of residues 72-251 of SEQ ID NO:94. In some embodiments, the engineered TL1A ligands disclosed herein comprise at least six alterations of an amino acid sequence of residues 72-251 of SEQ ID NO:94. In some embodiments, the engineered TL1A ligands disclosed herein comprise at least seven alterations of an amino acid sequence of residues 72-251 of SEQ ID NO:94.

In some embodiments, the engineered TL1A ligands disclosed herein comprise at least two, three, four, five, six, seven, or more alterations of an amino acid sequence of residues K111, L123, M158, Q167, S187, E190, and N207 of wild-type human TL1A (e.g., SEQ ID NO:94). In one embodiment, an engineered TL1A ligand provided herein comprises an amino acid alteration at residue K111. In one embodiment, an engineered TL1A ligand provided herein comprises an amino acid alteration at residue L123. In one embodiment, an engineered TL1A ligand provided herein comprises an amino acid alteration at residue M158. In one embodiment, an engineered TL1A ligand provided herein comprises an amino acid alteration at residue Q167. In one embodiment, an engineered TL1A ligand provided herein comprises an amino acid alteration at residue S187. In one embodiment, an engineered TL1A ligand provided herein comprises an amino acid alteration at residue E190. In one embodiment, an engineered TL1A ligand provided herein comprises an amino acid alteration at residue N207. In certain embodiments, the amino acid alteration is of human TL1A. In certain embodiments, the human TL1A is wild-type TL1A. In certain embodiments, the human TL1A comprises the amino acid sequence of SEQ ID NO:94.

In some embodiments, the engineered TL1A ligand comprises one or more alterations at one or more residue positions of the TL1A amino acid sequence, wherein the one or more alterations are selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173S, K173R, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q. In one embodiment, an engineered TL1A ligand provided herein comprises an amino acid alteration at residue R103A. In one embodiment, an engineered TL1A ligand provided herein comprises an amino acid alteration at residue R103H. In one embodiment, an engineered TL1A ligand provided herein comprises an amino acid alteration at residue R103Q. In one embodiment, an engineered TL1A ligand provided herein comprises an amino acid alteration at residue R103E. In one embodiment, an engineered TL1A ligand provided herein comprises an amino acid alteration at residue R103E. In one embodiment, an engineered TL1A ligand provided herein comprises an amino acid alteration at residue K111A. In one embodiment, an engineered TL1A ligand provided herein comprises an amino acid alteration at residue K111S. In one embodiment, an engineered TL1A ligand provided herein comprises an amino acid alteration at residue K111E. In one embodiment, an engineered TL1A ligand provided herein comprises an amino acid alteration at residue NI12E. In one embodiment, an engineered TL1A ligand provided herein comprises an amino acid alteration at residue F114A. In one embodiment, an engineered TL1A ligand provided herein comprises an amino acid alteration at residue E120A. In one embodiment, an engineered TL1A ligand provided herein comprises an amino acid alteration at residue E120K. In one embodiment, an engineered TL1A ligand provided herein comprises an amino acid alteration at residue E120H. In one embodiment, an engineered TL1A ligand provided herein comprises an amino acid alteration at residue L123G. In one embodiment, an engineered TL1A ligand provided herein comprises an amino acid alteration at residue L123S. In one embodiment, an engineered TL1A ligand provided herein comprises an amino acid alteration at residue L123E. In one embodiment, an engineered TL1A ligand provided herein comprises an amino acid alteration at residue L123K. In one embodiment, an engineered TL1A ligand provided herein comprises an amino acid alteration at residue G124S. In one embodiment, an engineered TL1A ligand provided herein comprises an amino acid alteration at residue G124K. In one embodiment, an engineered TL1A ligand provided herein comprises an amino acid alteration at residue G124D. In one embodiment, an engineered TL1A ligand provided herein comprises an amino acid alteration at residue R156A. In one embodiment, an engineered TL1A ligand provided herein comprises an amino acid alteration at residue R156Y. In one embodiment, an engineered TL1A ligand provided herein comprises an amino acid alteration at residue R156K. In one embodiment, an engineered TL1A ligand provided herein comprises an amino acid alteration at residue R156E. In one embodiment, an engineered TL1A ligand provided herein comprises an amino acid alteration at residue M158Y. In one embodiment, an engineered TL1A ligand provided herein comprises an amino acid alteration at residue M158K. In one embodiment, an engineered TL1A ligand provided herein comprises an amino acid alteration at residue M158E. In one embodiment, an engineered TL1A ligand provided herein comprises an amino acid alteration at residue Q167A. In one embodiment, an engineered TL1A ligand provided herein comprises an amino acid alteration at residue R170E. In one embodiment, an engineered TL1A ligand provided herein comprises an amino acid alteration at residue K173S. In one embodiment, an engineered TL1A ligand provided herein comprises an amino acid alteration at residue K173R. In one embodiment, an engineered TL1A ligand provided herein comprises an amino acid alteration at residue S176A. In one embodiment, an engineered TL1A ligand provided herein comprises an amino acid alteration at residue S176L. In one embodiment, an engineered TL1A ligand provided herein comprises an amino acid alteration at residue S176. In one embodiment, an engineered TL1A ligand provided herein comprises an amino acid alteration at residue S176K. In one embodiment, an engineered TL1A ligand provided herein comprises an amino acid alteration at residue T185A. In one embodiment, an engineered TL1A ligand provided herein comprises an amino acid alteration at residue T185L. In one embodiment, an engineered TL1A ligand provided herein comprises an amino acid alteration at residue T185N. In one embodiment, an engineered TL1A ligand provided herein comprises an amino acid alteration at residue T185D. In one embodiment, an engineered TL1A ligand provided herein comprises an amino acid alteration at residue D186Y. In one embodiment, an engineered TL1A ligand provided herein comprises an amino acid alteration at residue S187A. In one embodiment, an engineered TL1A ligand provided herein comprises an amino acid alteration at residue S187L. In one embodiment, an engineered TL1A ligand provided herein comprises an amino acid alteration at residue S187K. In one embodiment, an engineered TL1A ligand provided herein comprises an amino acid alteration at residue S187D. In one embodiment, an engineered TL1A ligand provided herein comprises an amino acid alteration at residue Y188A. In one embodiment, an engineered TL1A ligand provided herein comprises an amino acid alteration at residue Y188S. In one embodiment, an engineered TL1A ligand provided herein comprises an amino acid alteration at residue P189A. In one embodiment, an engineered TL1A ligand provided herein comprises an amino acid alteration at residue P189K. In one embodiment, an engineered TL1A ligand provided herein comprises an amino acid alteration at residue P189F. In one embodiment, an engineered TL1A ligand provided herein comprises an amino acid alteration at residue P189S. In one embodiment, an engineered TL1A ligand provided herein comprises an amino acid alteration at residue E190G. In one embodiment, an engineered TL1A ligand provided herein comprises an amino acid alteration at residue E190F. In one embodiment, an engineered TL1A ligand provided herein comprises an amino acid alteration at residue T192A. In one embodiment, an engineered TL1A ligand provided herein comprises an amino acid alteration at residue T192F. In one embodiment, an engineered TL1A ligand provided herein comprises an amino acid alteration at residue T192K. In one embodiment, an engineered TL1A ligand provided herein comprises an amino acid alteration at residue T192E. In one embodiment, an engineered TL1A ligand provided herein comprises an amino acid alteration at residue S206A. In one embodiment, an engineered TL1A ligand provided herein comprises an amino acid alteration at residue S206F. In one embodiment, an engineered TL1A ligand provided herein comprises an amino acid alteration at residue S206K. In one embodiment, an engineered TL1A ligand provided herein comprises an amino acid alteration at residue S206E. In one embodiment, an engineered TL1A ligand provided herein comprises an amino acid alteration at residue N207A. In one embodiment, an engineered TL1A ligand provided herein comprises an amino acid alteration at residue N207F. In one embodiment, an engineered TL1A ligand provided herein comprises an amino acid alteration at residue N207S. In one embodiment, an engineered TL1A ligand provided herein comprises an amino acid alteration at residue N207K. In one embodiment, an engineered TL1A ligand provided herein comprises an amino acid alteration at residue N207E. In one embodiment, an engineered TL1A ligand provided herein comprises an amino acid alteration at residue F209A. In one embodiment, an engineered TL1A ligand provided herein comprises an amino acid alteration at residue F209W. In one embodiment, an engineered TL1A ligand provided herein comprises an amino acid alteration at residue Y238A. In one embodiment, an engineered TL1A ligand provided herein comprises an amino acid alteration at residue Y238S. In one embodiment, an engineered TL1A ligand provided herein comprises an amino acid alteration at residue Y238K. In one embodiment, an engineered TL1A ligand provided herein comprises an amino acid alteration at residue Y238R. In one embodiment, an engineered TL1A ligand provided herein comprises an amino acid alteration at residue Y238E. In one embodiment, an engineered TL1A ligand provided herein comprises an amino acid alteration at residue T239A. In one embodiment, an engineered TL1A ligand provided herein comprises an amino acid alteration at residue T239E. In one embodiment, an engineered TL1A ligand provided herein comprises an amino acid alteration at residue T239F. In one embodiment, an engineered TL1A ligand provided herein comprises an amino acid alteration at residue T239K. In one embodiment, an engineered TL1A ligand provided herein comprises an amino acid alteration at residue T239W. In one embodiment, an engineered TL1A ligand provided herein comprises an amino acid alteration at residue K240A. In one embodiment, an engineered TL1A ligand provided herein comprises an amino acid alteration at residue K240F. In one embodiment, an engineered TL1A ligand provided herein comprises an amino acid alteration at residue K240S. In one embodiment, an engineered TL1A ligand provided herein comprises an amino acid alteration at residue K240D. In one embodiment, an engineered TL1A ligand provided herein comprises an amino acid alteration at residue E241A. In one embodiment, an engineered TL1A ligand provided herein comprises an amino acid alteration at residue E241L. In one embodiment, an engineered TL1A ligand provided herein comprises an amino acid alteration at residue E241Q. Combinations of two or more of the above-referenced amino acid alterations are also contemplated. In certain embodiments, the amino acid alteration is of human TL1A. In certain embodiments, the human TL1A is wild-type TL1A. In certain embodiments, the human TL1A comprises the amino acid sequence of SEQ ID NO:94.

In some embodiments, the engineered TL1A ligand comprises an amino acid sequence of residues 72-251 of SEQ ID NO:94, comprising amino acid alterations K111A, L123K, M158Y, Q167A, S187L, E190F, and N207F.

In some embodiments, an engineered TL1A ligand provided herein comprises any two of the above-referenced amino acid alterations. In some embodiments, an engineered TL1A ligand provided herein comprises any thee of the above-referenced amino acid alterations. In some embodiments, an engineered TL1A ligand provided herein comprises any four of the above-referenced amino acid alterations. In some embodiments, an engineered TL1A ligand provided herein comprises any five of the above-referenced amino acid alterations. In some embodiments, an engineered TL1A ligand provided herein comprises any six of the above-referenced amino acid alterations. In some embodiments, an engineered TL1A ligand provided herein comprises any seven of the above-referenced amino acid alterations. In some embodiments, an engineered TL1A ligand provided herein comprises at least two of the above-referenced amino acid alterations. In some embodiments, an engineered TL1A ligand provided herein comprises at least three of the above-referenced amino acid alterations. In some embodiments, an engineered TL1A ligand provided herein comprises at least four of the above-referenced amino acid alterations. In some embodiments, an engineered TL1A ligand provided herein comprises at least five of the above-referenced amino acid alterations. In some embodiments, an engineered TL1A ligand provided herein comprises at least six of the above-referenced amino acid alterations. In some embodiments, an engineered TL1A ligand provided herein comprises at least seven of the above-referenced amino acid alterations. In some embodiments, an engineered TL1A ligand provided herein comprises from one to ten of the above-referenced amino acid alterations. In some embodiments, an engineered TL1A ligand provided herein comprises from one to seven of the above-referenced amino acid alterations. In some embodiments, an engineered TL1A ligand provided herein comprises from one to five of the above-referenced amino acid alterations. In some embodiments, an engineered TL1A ligand provided herein comprises from two to ten of the above-referenced amino acid alterations. In some embodiments, an engineered TL1A ligand provided herein comprises from two to five of the above-referenced amino acid alterations. In some embodiments, an engineered TL1A ligand provided herein comprises from five to seven of the above-referenced amino acid alterations.

In some embodiments, the engineered TL1A ligand comprises the amino acid sequence of any one of SEQ ID NO:1-93, or a fragment thereof capable of forming a soluble TL1A ligand. In some embodiments, the engineered TL1A ligand comprises the amino acid sequence of any one of SEQ ID NO:1-93, or a fragment thereof capable of binding to DR3.

In one embodiment, an engineered TL1A ligand comprises the amino acid sequence of SEQ ID NO:1. In one embodiment, an engineered TL1A ligand comprises the amino acid sequence of SEQ ID NO:2. In one embodiment, an engineered TL1A ligand comprises the amino acid sequence of SEQ ID NO:3. In one embodiment, an engineered TL1A ligand comprises the amino acid sequence of SEQ ID NO:4. In one embodiment, an engineered TL1A ligand comprises the amino acid sequence of SEQ ID NO:5. In one embodiment, an engineered TL1A ligand comprises the amino acid sequence of SEQ ID NO:6. In one embodiment, an engineered TL1A ligand comprises the amino acid sequence of SEQ ID NO:7. In one embodiment, an engineered TL1A ligand comprises the amino acid sequence of SEQ ID NO:8. In one embodiment, an engineered TL1A ligand comprises the amino acid sequence of SEQ ID NO:9. In one embodiment, an engineered TL1A ligand comprises the amino acid sequence of SEQ ID NO:10. In one embodiment, an engineered TL1A ligand comprises the amino acid sequence of SEQ ID NO:11. In one embodiment, an engineered TL1A ligand comprises the amino acid sequence of SEQ ID NO:12. In one embodiment, an engineered TL1A ligand comprises the amino acid sequence of SEQ ID NO:13. In one embodiment, an engineered TL1A ligand comprises the amino acid sequence of SEQ ID NO:14. In one embodiment, an engineered TL1A ligand comprises the amino acid sequence of SEQ ID NO:15. In one embodiment, an engineered TL1A ligand comprises the amino acid sequence of SEQ ID NO:16. In one embodiment, an engineered TL1A ligand comprises the amino acid sequence of SEQ ID NO:17. In one embodiment, an engineered TL1A ligand comprises the amino acid sequence of SEQ ID NO:18. In one embodiment, an engineered TL1A ligand comprises the amino acid sequence of SEQ ID NO:19. In one embodiment, an engineered TL1A ligand comprises the amino acid sequence of SEQ ID NO:20. In one embodiment, an engineered TL1A ligand comprises the amino acid sequence of SEQ ID NO:21. In one embodiment, an engineered TL1A ligand comprises the amino acid sequence of SEQ ID NO:22. In one embodiment, an engineered TL1A ligand comprises the amino acid sequence of SEQ ID NO:23. In one embodiment, an engineered TL1A ligand comprises the amino acid sequence of SEQ ID NO:24. In one embodiment, an engineered TL1A ligand comprises the amino acid sequence of SEQ ID NO:25. In one embodiment, an engineered TL1A ligand comprises the amino acid sequence of SEQ ID NO:26. In one embodiment, an engineered TL1A ligand comprises the amino acid sequence of SEQ ID NO:27. In one embodiment, an engineered TL1A ligand comprises the amino acid sequence of SEQ ID NO:28. In one embodiment, an engineered TL1A ligand comprises the amino acid sequence of SEQ ID NO:29. In one embodiment, an engineered TL1A ligand comprises the amino acid sequence of SEQ ID NO:30. In one embodiment, an engineered TL1A ligand comprises the amino acid sequence of SEQ ID NO:31. In one embodiment, an engineered TL1A ligand comprises the amino acid sequence of SEQ ID NO:32. In one embodiment, an engineered TL1A ligand comprises the amino acid sequence of SEQ ID NO:33. In one embodiment, an engineered TL1A ligand comprises the amino acid sequence of SEQ ID NO:34. In one embodiment, an engineered TL1A ligand comprises the amino acid sequence of SEQ ID NO:35. In one embodiment, an engineered TL1A ligand comprises the amino acid sequence of SEQ ID NO:36. In one embodiment, an engineered TL1A ligand comprises the amino acid sequence of SEQ ID NO:37. In one embodiment, an engineered TL1A ligand comprises the amino acid sequence of SEQ ID NO:38. In one embodiment, an engineered TL1A ligand comprises the amino acid sequence of SEQ ID NO:39. In one embodiment, an engineered TL1A ligand comprises the amino acid sequence of SEQ ID NO:40. In one embodiment, an engineered TL1A ligand comprises the amino acid sequence of SEQ ID NO:41. In one embodiment, an engineered TL1A ligand comprises the amino acid sequence of SEQ ID NO:42. In one embodiment, an engineered TL1A ligand comprises the amino acid sequence of SEQ ID NO:43. In one embodiment, an engineered TL1A ligand comprises the amino acid sequence of SEQ ID NO:44. In one embodiment, an engineered TL1A ligand comprises the amino acid sequence of SEQ ID NO:45. In one embodiment, an engineered TL1A ligand comprises the amino acid sequence of SEQ ID NO:46. In one embodiment, an engineered TL1A ligand comprises the amino acid sequence of SEQ ID NO:47. In one embodiment, an engineered TL1A ligand comprises the amino acid sequence of SEQ ID NO:48. In one embodiment, an engineered TL1A ligand comprises the amino acid sequence of SEQ ID NO:49. In one embodiment, an engineered TL1A ligand comprises the amino acid sequence of SEQ ID NO:50. In one embodiment, an engineered TL1A ligand comprises the amino acid sequence of SEQ ID NO:51. In one embodiment, an engineered TL1A ligand comprises the amino acid sequence of SEQ ID NO:52. In one embodiment, an engineered TL1A ligand comprises the amino acid sequence of SEQ ID NO:53. In one embodiment, an engineered TL1A ligand comprises the amino acid sequence of SEQ ID NO:54. In one embodiment, an engineered TL1A ligand comprises the amino acid sequence of SEQ ID NO:55. In one embodiment, an engineered TL1A ligand comprises the amino acid sequence of SEQ ID NO:56. In one embodiment, an engineered TL1A ligand comprises the amino acid sequence of SEQ ID NO:57. In one embodiment, an engineered TL1A ligand comprises the amino acid sequence of SEQ ID NO:58. In one embodiment, an engineered TL1A ligand comprises the amino acid sequence of SEQ ID NO:59. In one embodiment, an engineered TL1A ligand comprises the amino acid sequence of SEQ ID NO:60. In one embodiment, an engineered TL1A ligand comprises the amino acid sequence of SEQ ID NO:61. In one embodiment, an engineered TL1A ligand comprises the amino acid sequence of SEQ ID NO:62. In one embodiment, an engineered TL1A ligand comprises the amino acid sequence of SEQ ID NO:63. In one embodiment, an engineered TL1A ligand comprises the amino acid sequence of SEQ ID NO:64. In one embodiment, an engineered TL1A ligand comprises the amino acid sequence of SEQ ID NO:65. In one embodiment, an engineered TL1A ligand comprises the amino acid sequence of SEQ ID NO:66. In one embodiment, an engineered TL1A ligand comprises the amino acid sequence of SEQ ID NO:67. In one embodiment, an engineered TL1A ligand comprises the amino acid sequence of SEQ ID NO:68. In one embodiment, an engineered TL1A ligand comprises the amino acid sequence of SEQ ID NO:69. In one embodiment, an engineered TL1A ligand comprises the amino acid sequence of SEQ ID NO:70. In one embodiment, an engineered TL1A ligand comprises the amino acid sequence of SEQ ID NO:71. In one embodiment, an engineered TL1A ligand comprises the amino acid sequence of SEQ ID NO:72. In one embodiment, an engineered TL1A ligand comprises the amino acid sequence of SEQ ID NO:73. In one embodiment, an engineered TL1A ligand comprises the amino acid sequence of SEQ ID NO:74. In one embodiment, an engineered TL1A ligand comprises the amino acid sequence of SEQ ID NO:75. In one embodiment, an engineered TL1A ligand comprises the amino acid sequence of SEQ ID NO:76. In one embodiment, an engineered TL1A ligand comprises the amino acid sequence of SEQ ID NO:77. In one embodiment, an engineered TL1A ligand comprises the amino acid sequence of SEQ ID NO:78. In one embodiment, an engineered TL1A ligand comprises the amino acid sequence of SEQ ID NO:79. In one embodiment, an engineered TL1A ligand comprises the amino acid sequence of SEQ ID NO:80. In one embodiment, an engineered TL1A ligand comprises the amino acid sequence of SEQ ID NO:81. In one embodiment, an engineered TL1A ligand comprises the amino acid sequence of SEQ ID NO:82. In one embodiment, an engineered TL1A ligand comprises the amino acid sequence of SEQ ID NO:83. In one embodiment, an engineered TL1A ligand comprises the amino acid sequence of SEQ ID NO:84. In one embodiment, an engineered TL1A ligand comprises the amino acid sequence of SEQ ID NO:85. In one embodiment, an engineered TL1A ligand comprises the amino acid sequence of SEQ ID NO:86. In one embodiment, an engineered TL1A ligand comprises the amino acid sequence of SEQ ID NO:87. In one embodiment, an engineered TL1A ligand comprises the amino acid sequence of SEQ ID NO:88. In one embodiment, an engineered TL1A ligand comprises the amino acid sequence of SEQ ID NO:89. In one embodiment, an engineered TL1A ligand comprises the amino acid sequence of SEQ ID NO:90. In one embodiment, an engineered TL1A ligand comprises the amino acid sequence of SEQ ID NO:91. In one embodiment, an engineered TL1A ligand comprises the amino acid sequence of SEQ ID NO:92. In one embodiment, an engineered TL1A ligand comprises the amino acid sequence of SEQ ID NO:93. In some embodiments, the engineered TL1A ligand disclosed herein comprises an amino acid sequence that is at least 80% identical over its entire length to an amino acid sequence identified above. In some embodiments, the engineered TL1A ligand disclosed herein comprises an amino acid sequence that is at least 85% identical over its entire length to an amino acid sequence identified above. In some embodiments, the engineered TL1A ligand disclosed herein comprises an amino acid sequence that is at least 90% identical over its entire length to an amino acid sequence identified above. In some embodiments, the engineered TL1A ligand disclosed herein comprises an amino acid sequence that is at least 95% identical over its entire length to an amino acid sequence identified above. In some embodiments, the engineered TL1A ligand disclosed herein comprises an amino acid sequence that is at least 98% identical over its entire length to an amino acid sequence identified above.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:79. In some embodiments, the engineered TL1A ligand disclosed herein comprises an amino acid sequence that is at least 80% identical over its entire length to the amino acid sequence of SEQ ID NO:79. In some embodiments, the engineered TL1A ligand disclosed herein comprises an amino acid sequence that is at least 85% identical over its entire length to the amino acid sequence of SEQ ID NO:79. In some embodiments, the engineered TL1A ligand disclosed herein comprises an amino acid sequence that is at least 90% identical over its entire length to the amino acid sequence of SEQ ID NO:79. In some embodiments, the engineered TL1A ligand disclosed herein comprises an amino acid sequence that is at least 95% identical over its entire length to the amino acid sequence of SEQ ID NO:79. In some embodiments, the engineered TL1A ligand disclosed herein comprises an amino acid sequence that is at least 98% identical over its entire length to the amino acid sequence of SEQ ID NO:79. In some embodiments, the engineered TL1A ligand disclosed herein comprises an amino acid sequence that is at least 100% identical over its entire length to the amino acid sequence of SEQ ID NO:79.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:72. In some embodiments, the engineered TL1A ligand disclosed herein comprises an amino acid sequence that is at least 80% identical over its entire length to the amino acid sequence of SEQ ID NO:72. In some embodiments, the engineered TL1A ligand disclosed herein comprises an amino acid sequence that is at least 85% identical over its entire length to the amino acid sequence of SEQ ID NO:72. In some embodiments, the engineered TL1A ligand disclosed herein comprises an amino acid sequence that is at least 90% identical over its entire length to the amino acid sequence of SEQ ID NO:72. In some embodiments, the engineered TL1A ligand disclosed herein comprises an amino acid sequence that is at least 95% identical over its entire length to the amino acid sequence of SEQ ID NO:72. In some embodiments, the engineered TL1A ligand disclosed herein comprises an amino acid sequence that is at least 98% identical over its entire length to the amino acid sequence of SEQ ID NO:72. In some embodiments, the engineered TL1A ligand disclosed herein comprises an amino acid sequence that is at least 100% identical over its entire length to the amino acid sequence of SEQ ID NO:72.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:8. In some embodiments, the engineered TL1A ligand disclosed herein comprises an amino acid sequence that is at least 80% identical over its entire length to the amino acid sequence of SEQ ID NO:8. In some embodiments, the engineered TL1A ligand disclosed herein comprises an amino acid sequence that is at least 85% identical over its entire length to the amino acid sequence of SEQ ID NO:8. In some embodiments, the engineered TL1A ligand disclosed herein comprises an amino acid sequence that is at least 90% identical over its entire length to the amino acid sequence of SEQ ID NO:8. In some embodiments, the engineered TL1A ligand disclosed herein comprises an amino acid sequence that is at least 95% identical over its entire length to the amino acid sequence of SEQ ID NO:8. In some embodiments, the engineered TL1A ligand disclosed herein comprises an amino acid sequence that is at least 98% identical over its entire length to the amino acid sequence of SEQ ID NO:8. In some embodiments, the engineered TL1A ligand disclosed herein comprises an amino acid sequence that is at least 100% identical over its entire length to the amino acid sequence of SEQ ID NO:8.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:65. In some embodiments, the engineered TL1A ligand disclosed herein comprises an amino acid sequence that is at least 80% identical over its entire length to the amino acid sequence of SEQ ID NO:65. In some embodiments, the engineered TL1A ligand disclosed herein comprises an amino acid sequence that is at least 85% identical over its entire length to the amino acid sequence of SEQ ID NO:65. In some embodiments, the engineered TL1A ligand disclosed herein comprises an amino acid sequence that is at least 90% identical over its entire length to the amino acid sequence of SEQ ID NO:65. In some embodiments, the engineered TL1A ligand disclosed herein comprises an amino acid sequence that is at least 95% identical over its entire length to the amino acid sequence of SEQ ID NO:65. In some embodiments, the engineered TL1A ligand disclosed herein comprises an amino acid sequence that is at least 98% identical over its entire length to the amino acid sequence of SEQ ID NO:65. In some embodiments, the engineered TL1A ligand disclosed herein comprises an amino acid sequence that is at least 100% identical over its entire length to the amino acid sequence of SEQ ID NO:65.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:52. In some embodiments, the engineered TL1A ligand disclosed herein comprises an amino acid sequence that is at least 80% identical over its entire length to the amino acid sequence of SEQ ID NO:52. In some embodiments, the engineered TL1A ligand disclosed herein comprises an amino acid sequence that is at least 85% identical over its entire length to the amino acid sequence of SEQ ID NO:52. In some embodiments, the engineered TL1A ligand disclosed herein comprises an amino acid sequence that is at least 90% identical over its entire length to the amino acid sequence of SEQ ID NO:52. In some embodiments, the engineered TL1A ligand disclosed herein comprises an amino acid sequence that is at least 95% identical over its entire length to the amino acid sequence of SEQ ID NO:52. In some embodiments, the engineered TL1A ligand disclosed herein comprises an amino acid sequence that is at least 98% identical over its entire length to the amino acid sequence of SEQ ID NO:52. In some embodiments, the engineered TL1A ligand disclosed herein comprises an amino acid sequence that is at least 100% identical over its entire length to the amino acid sequence of SEQ ID NO:52.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:14. In some embodiments, the engineered TL1A ligand disclosed herein comprises an amino acid sequence that is at least 80% identical over its entire length to the amino acid sequence of SEQ ID NO:14. In some embodiments, the engineered TL1A ligand disclosed herein comprises an amino acid sequence that is at least 85% identical over its entire length to the amino acid sequence of SEQ ID NO:14. In some embodiments, the engineered TL1A ligand disclosed herein comprises an amino acid sequence that is at least 90% identical over its entire length to the amino acid sequence of SEQ ID NO:14. In some embodiments, the engineered TL1A ligand disclosed herein comprises an amino acid sequence that is at least 95% identical over its entire length to the amino acid sequence of SEQ ID NO:14. In some embodiments, the engineered TL1A ligand disclosed herein comprises an amino acid sequence that is at least 98% identical over its entire length to the amino acid sequence of SEQ ID NO:14. In some embodiments, the engineered TL1A ligand disclosed herein comprises an amino acid sequence that is at least 100% identical over its entire length to the amino acid sequence of SEQ ID NO:14.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:36. In some embodiments, the engineered TL1A ligand disclosed herein comprises an amino acid sequence that is at least 80% identical over its entire length to the amino acid sequence of SEQ ID NO:36. In some embodiments, the engineered TL1A ligand disclosed herein comprises an amino acid sequence that is at least 85% identical over its entire length to the amino acid sequence of SEQ ID NO:36. In some embodiments, the engineered TL1A ligand disclosed herein comprises an amino acid sequence that is at least 90% identical over its entire length to the amino acid sequence of SEQ ID NO:36. In some embodiments, the engineered TL1A ligand disclosed herein comprises an amino acid sequence that is at least 95% identical over its entire length to the amino acid sequence of SEQ ID NO:36. In some embodiments, the engineered TL1A ligand disclosed herein comprises an amino acid sequence that is at least 98% identical over its entire length to the amino acid sequence of SEQ ID NO:36. In some embodiments, the engineered TL1A ligand disclosed herein comprises an amino acid sequence that is at least 100% identical over its entire length to the amino acid sequence of SEQ ID NO:36.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:90. In some embodiments, the engineered TL1A ligand disclosed herein comprises an amino acid sequence that is at least 80% identical over its entire length to the amino acid sequence of SEQ ID NO:90. In some embodiments, the engineered TL1A ligand disclosed herein comprises an amino acid sequence that is at least 85% identical over its entire length to the amino acid sequence of SEQ ID NO:90. In some embodiments, the engineered TL1A ligand disclosed herein comprises an amino acid sequence that is at least 90% identical over its entire length to the amino acid sequence of SEQ ID NO:90. In some embodiments, the engineered TL1A ligand disclosed herein comprises an amino acid sequence that is at least 95% identical over its entire length to the amino acid sequence of SEQ ID NO:90. In some embodiments, the engineered TL1A ligand disclosed herein comprises an amino acid sequence that is at least 98% identical over its entire length to the amino acid sequence of SEQ ID NO:90. In some embodiments, the engineered TL1A ligand disclosed herein comprises an amino acid sequence that is at least 100% identical over its entire length to the amino acid sequence of SEQ ID NO:90.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:88. In some embodiments, the engineered TL1A ligand disclosed herein comprises an amino acid sequence that is at least 80% identical over its entire length to the amino acid sequence of SEQ ID NO:88. In some embodiments, the engineered TL1A ligand disclosed herein comprises an amino acid sequence that is at least 85% identical over its entire length to the amino acid sequence of SEQ ID NO:88. In some embodiments, the engineered TL1A ligand disclosed herein comprises an amino acid sequence that is at least 90% identical over its entire length to the amino acid sequence of SEQ ID NO:88. In some embodiments, the engineered TL1A ligand disclosed herein comprises an amino acid sequence that is at least 95% identical over its entire length to the amino acid sequence of SEQ ID NO:88. In some embodiments, the engineered TL1A ligand disclosed herein comprises an amino acid sequence that is at least 98% identical over its entire length to the amino acid sequence of SEQ ID NO:88. In some embodiments, the engineered TL1A ligand disclosed herein comprises an amino acid sequence that is at least 100% identical over its entire length to the amino acid sequence of SEQ ID NO:88.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:91. In some embodiments, the engineered TL1A ligand disclosed herein comprises an amino acid sequence that is at least 80% identical over its entire length to the amino acid sequence of SEQ ID NO:91. In some embodiments, the engineered TL1A ligand disclosed herein comprises an amino acid sequence that is at least 85% identical over its entire length to the amino acid sequence of SEQ ID NO:91. In some embodiments, the engineered TL1A ligand disclosed herein comprises an amino acid sequence that is at least 90% identical over its entire length to the amino acid sequence of SEQ ID NO:91. In some embodiments, the engineered TL1A ligand disclosed herein comprises an amino acid sequence that is at least 95% identical over its entire length to the amino acid sequence of SEQ ID NO:91. In some embodiments, the engineered TL1A ligand disclosed herein comprises an amino acid sequence that is at least 98% identical over its entire length to the amino acid sequence of SEQ ID NO:91. In some embodiments, the engineered TL1A ligand disclosed herein comprises an amino acid sequence that is at least 100% identical over its entire length to the amino acid sequence of SEQ ID NO:91.

In some embodiments, the engineered TL1A ligand disclosed herein comprises an amino acid sequence that is at least 80%, at least 85%, at least 90%, at least 95%, at least 98%, or 100% identical over its entire length to the amino acid sequence of SEQ ID NO:89. In some embodiments, the engineered TL1A ligand disclosed herein comprises an amino acid sequence that is at least 80% identical over its entire length to the amino acid sequence of SEQ ID NO:89. In some embodiments, the engineered TL1A ligand disclosed herein comprises an amino acid sequence that is at least 85% identical over its entire length to the amino acid sequence of SEQ ID NO:89. In some embodiments, the engineered TL1A ligand disclosed herein comprises an amino acid sequence that is at least 90% identical over its entire length to the amino acid sequence of SEQ ID NO:89. In some embodiments, the engineered TL1A ligand disclosed herein comprises an amino acid sequence that is at least 95% identical over its entire length to the amino acid sequence of SEQ ID NO:89. In some embodiments, the engineered TL1A ligand disclosed herein comprises an amino acid sequence that is at least 98% identical over its entire length to the amino acid sequence of SEQ ID NO:89. In some embodiments, the engineered TL1A ligand disclosed herein comprises an amino acid sequence that is at least 100% identical over its entire length to the amino acid sequence of SEQ ID NO:89.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:79, SEQ ID NO:72, SEQ ID NO:8, SEQ ID NO:65, SEQ ID NO:52, SEQ ID NO:14, SEQ ID NO:36, SEQ ID NO:90, SEQ ID NO:88, SEQ ID NO:91, or SEQ ID NO:89, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:79, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:79, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:72, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:72, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:8, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:8, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:65, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:65, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:52, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:52, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:14, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:14, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:36, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:36, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:90, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:90, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:88, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:88, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:91, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:91, wherein the minimal fragment is capable of forming a trimeric complex that specifically binds to DR3.

In some embodiments, the engineered TL1A ligand disclosed herein comprises an amino acid sequence that is at least 80%, at least 85%, at least 90%, at least 95%, at least 98%, or 100% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 80% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 85% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 90% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 95% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 98% identical over its entire length to an amino acid that comprises a minimal fragment of the amino acid sequence of SEQ ID NO:89, wherein the minimal fragment is capable of forming a trimeric complex that specifically binds to DR3. In some embodiments, the engineered TL1A ligand disclosed herein comprises an amino acid sequence that is at least 100% identical over its entire length to an amino acid that comprises a minimal fragment of the amino acid sequence of SEQ ID NO:89, wherein the minimal fragment is capable of forming a trimeric complex that specifically binds to DR3.

6.4 Fc and HSA Fusion Proteins

Also described herein are engineered TL1A ligands that are recombinantly linked or conjugated (covalent or non-covalent conjugations, directly or indirectly) to a heterologous protein or polypeptide (or fragment thereof, for example, to a polypeptide (e.g., of about 10 or more, about 20 or more, about 30 or more, about 40 or more, about 50 or more, about 60 or more, about 70 or more, about 80 or more, about 90 or more, or about 100 or more amino acids) to generate fusion proteins, as well as uses thereof. In particular, described herein are fusion proteins comprising an engineered TL1A ligand and a heterologous protein, polypeptide, or peptide. In some embodiments, the heterologous polypeptide or protein comprises a protein stabilizing region. Any protein stabilizing region described herein or known in the art can be used.

Without being bound by theory, fusion of proteins to certain polypeptides, for example, an Fc or HSA region, both of which display long serum half-lives due to their abilities to undergo FcRn-mediated recycling, have been successful methods to extend the half-life of protein therapeutics. Any protein fusion technologies known in the art or described herein can be used in the compositions or methods disclosed herein. As a non-limiting example, Fc fusion proteins, fusion to human serum albumin, fusion to carboxy-terminal peptide, and other polypeptide fusion approaches can be used. In addition, other approaches to half-life extension known in the art can be employed, for example, pegylation or glycosylation.

In some embodiments, an engineered TL1A ligand disclosed herein can be fused to the N-terminus or the C-terminus of an Fc region. In some embodiments, an engineered TL1A ligand disclosed herein can be fused to the N-terminus or the C-terminus of a HSA region.

In some embodiments, fusion of an engineered TL1A ligand disclosed herein to one or more heterologous protein or polypeptides, wherein the one or more heterologous protein or polypeptides is a protein stabilizing region, can increase the serum half-life of the engineered TL1A ligand. In some embodiments, fusion of an engineered TL1A ligand disclosed herein to one or more protein stabilizing regions can increase the serum half-life of an engineered TL1A ligand disclosed herein by about 2-fold or more, about 3-fold or more, about 4-fold or more, about 5-fold or more, about 10-fold or more, about 20-fold or more, about 40-fold or more, about 60-fold or more, about 80-fold or more, about 100-fold or more, about 200-fold or more, or about 500-fold or more.

In some embodiments, the heterologous protein, polypeptide, or peptide that an engineered TL1A ligand is fused to is useful for targeting an engineered TL1A ligand to a particular cell (e.g., a tumor cell).

Moreover, an engineered TL1A ligand described herein can be linked (directly or indirectly) to marker or "tag" sequences, such as a peptide, to facilitate purification. In some embodiments, the marker or tag amino acid sequence is a hexa-histidine peptide, such as the tag provided in a vector (see, e.g., QIAGEN, Inc.), many of which are commercially available. For example, as described in Gentz et al., 1989, Proc. Natl. Acad. Sci. USA 86:821-24, hexa-histidine provides for convenient purification of a fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for linking or conjugating (directly or indirectly) moieties (including polypeptides) to antibodies are well known in the art, any one of which can be used to make fusion protein described herein.

In some embodiments, an engineered TL1A ligand described herein is a fusion protein. The term "fusion protein" as used herein refers to a polypeptide that comprises an amino acid sequence of an engineered TL1A ligand and an amino acid sequence of a heterologous polypeptide or protein (e.g., a polypeptide or protein not normally a part of the TL1A). In certain embodiments, the fusion protein retains the biological activity of an engineered TL1A ligand disclosed herein.

It will be appreciated by one of skill in the art that the present disclosure also includes functional fragments of the engineered TL1A ligands described herein, wherein the functional fragments do not comprise any heterologous polypeptide or proteins (e.g., linkers, tags, Fc region, or HAS region), and wherein the functional fragments are capable of forming TL1A trimers and specifically binding to DR3.

Fusion proteins can be generated, for example, through the techniques of gene-shuffling, motif-shuffling, exon-shuffling, and/or codon-shuffling (collectively referred to as "DNA shuffling"). DNA shuffling can be employed to alter the activities of an engineered TL1A ligand, as described herein, including, for example, TL1A ligands with higher affinities for receptors and/or lower dissociation rates. In some embodiments, engineered TL1A ligands can be altered by being subjected to random mutagenesis by error-prone PCR, random nucleotide insertion, or other methods prior to recombination. A polynucleotide encoding an engineered TL1A ligand described herein can be recombined with one or more components, motifs, sections, parts, domains, fragments, etc. of one or more heterologous molecules.

An engineered TL1A ligand, described herein can also be attached to solid supports, which are useful for immunoassays or purification of the target antigen. Such solid supports include, but are not limited to, glass, cellulose, polyacrylamide, nylon, polystyrene, polyvinyl chloride, or polypropylene.

An engineered TL1A ligand described herein can also be linked or conjugated (directly or indirectly) to a second antibody to form an antibody heteroconjugate.

In some embodiments, an engineered TL1A ligand described herein is a multimeric engineered TL1A ligand, wherein the engineered TL1A ligand comprises: a non-covalent TL1A trimer and one or more Fc regions, a non-covalent TL1A trimer and one or more HSA regions, a scTL1A trimer and one or more Fc regions, or a scTL1A trimer and one or more HSA regions.

In some embodiments, an engineered TL1A ligand described herein is a multimeric engineered TL1A ligand comprising: two non-covalent TL1A trimers and three Fc regions, two scTL1A trimers and one Fc region, one scTL1A trimer and one Fc region, one non-covalent TL1A trimer and three HSA regions, or one scTL1A trimer and one HSA region.

In some embodiments, the Fc region is a human IgG1, IgG2 or IgG4 Fc region.

In some embodiments, an engineered TL1A ligand disclosed herein can comprise an Fc region of an immunoglobulin. Those skilled in the art will appreciate that some of the molecules, polypeptides or agents described herein will comprise fusion proteins or other polypeptides in which at least a portion of the Fc region has been deleted or otherwise altered so as to provide desired biochemical characteristics, such as increased cancer cell localization, increased tumor penetration, reduced serum half-life, or increased serum half-life, when compared with a fusion protein of approximately the same immunogenicity comprising a native or unaltered Fc region. Modifications to the Fc region can include additions, deletions, or substitutions of one or more amino acids in one or more domains. The modified fusion proteins or other polypeptides disclosed herein can comprise alterations or modifications to one or more of the two heavy chain constant domains (CH2 or CH3) or to the hinge region. In other embodiments, the entire CH2 domain can be removed (ΔCH2 constructs). In some embodiments, the omitted constant region domain is replaced by a short amino acid spacer (e.g., 10 aa residues) that provides some of the molecular flexibility typically imparted by the absent constant region domain.

In some embodiments, the modified fusion proteins or other polypeptides can have only a partial deletion of a constant domain or substitution of a few or even a single amino acid. For example, the mutation of a single amino acid in selected areas of the CH2 domain can be enough to substantially reduce Fc binding and thereby increase cancer cell localization and/or tumor penetration. Similarly, in some embodiments, it can be desirable to simply delete that part of one or more constant region domains that control a specific effector. Such partial deletions of the constant regions can improve selected characteristics of the polypeptide or molecule (e.g., serum half-life) while leaving other desirable functions associated with the subject constant region domain intact.

6.5 Encoding Polynucleotides

Further provided herein are polynucleotide(s) encoding an engineered TL1A ligand disclosed herein. In some embodiments, the polynucleotide disclosed herein can be modified in a number of different manners using recombinant DNA technology to generate alternative or variant proteins. Site-directed or high-density mutagenesis of a protein can be used to optimize specificity, affinity, stability, etc. of a recombinant protein.

In certain aspects, provided herein are polynucleotides comprising a nucleotide sequence encoding an engineered TL1A ligand or a fragment thereof that specifically binds to a DR3, and vectors, e.g., vectors comprising such polynucleotides for recombinant expression in host cells (e.g., *E. coli* and mammalian cells). Provided herein are polynucleotides comprising nucleotide sequences encoding any of the engineered TL1A ligands provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an engineered TL1A ligand described herein is isolated or purified.

In particular aspects, provided herein are polynucleotides comprising nucleotide sequences encoding engineered TL1A ligands or DR3-binding fragments thereof, which specifically bind to a DR3 protein (e.g., human DR3) and comprises an amino acid sequence as described herein.

In certain aspects, provided herein are polynucleotides comprising a nucleotide sequence encoding the engineered TL1A ligands described herein. In certain embodiments, a polynucleotide described herein comprises a nucleotide sequence encoding amino acid residues 72-251 of SEQ ID NO:94. In certain embodiments, a polynucleotide described herein comprises a nucleotide sequence encoding at least one amino acid alteration of residues 72-251 of the amino acid sequence of SEQ ID NO:94.

In some embodiments, polynucleotides disclosed herein encode an engineered TL1A ligand that has one or more alterations at one or more residue positions of SEQ ID NO:94 selected from the group consisting of R103, K111, N112, F114, E120, L123, G124, R156, M158, Q167, R170, K173, S176, T185, D186, S187, Y188, P189, E190, T192, S206, N207, F209, Y238, T239, K240, and E241.

In some embodiments, polynucleotides disclosed herein encode an engineered TL1A ligand wherein the one or more alterations at one or more residue positions of SEQ ID NO:94 is an alteration selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173S, K173R, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q.

In some embodiments, polynucleotides disclosed herein encode an engineered TL1A ligand that comprises at least two, three, four, five, six, seven, or more alterations of an amino acid sequence of residues 72-251 of SEQ ID NO:94. In some embodiments, polynucleotides disclosed herein encode an engineered TL1A ligand that comprises one or more amino acid alterations of SEQ ID NO:94 selected from the group consisting of: K111A, L123K, M158Y, Q167A, S187L, E190F, and N207F. In some embodiments, polynucleotides disclosed herein encode an engineered TL1A ligand that comprises the amino acid sequence of any one of SEQ ID NO:1-93 or any fragment thereof.

In some embodiments, polynucleotides disclosed herein encode an engineered TL1A ligand that comprises: an amino acid sequence that is at least 80%, at least 85%, at least 90%, at least 95%, at least 98%, or 100% identical over its entire length to the amino acid sequence of SEQ ID NO:79; an amino acid sequence that is at least 80%, at least 85%, at least 90%, at least 95%, at least 98%, or 100% identical over its entire length to the amino acid sequence of SEQ ID NO:72; an amino acid sequence that is at least 80%, at least 85%, at least 90%, at least 95%, at least 98%, or 100% identical over its entire length to the amino acid sequence of SEQ ID NO:8; an amino acid sequence that is at least 80%, at least 85%, at least 90%, at least 95%, at least 98%, or 100% identical over its entire length to the amino acid sequence of SEQ ID NO:65; an amino acid sequence that is at least 80%, at least 85%, at least 90%, at least 95%, at least 98%, or 100% identical over its entire length to the amino acid sequence of SEQ ID NO:52; an amino acid sequence that is at least 80%, at least 85%, at least 90%, at least 95%, at least 98%, or 100% identical over its entire length to the amino acid sequence of SEQ ID NO:14; an amino acid sequence that is at least 80%, at least 85%, at least 90%, at least 95%, at least 98%, or 100% identical over its entire length to the amino acid sequence of SEQ ID NO:36; an amino acid sequence that is at least 80%, at least 85%, at least 90%, at least 95%, at least 98%, or 100% identical over its entire length to the amino acid sequence of SEQ ID NO:90; an amino acid sequence that is at least 80%, at least 85%, at least 90%, at least 95%, at least 98%, or 100% identical over its entire length to the amino acid sequence of SEQ ID NO:88; an amino acid sequence that is at least 80%, at least 85%, at least 90%, at least 95%, at least 98%, or 100% identical over its entire length to the amino acid sequence of SEQ ID NO:91; an amino acid sequence that is at least 80%, at least 85%, at least 90%, at least 95%, at least 98%, or 100% identical over its entire length to the amino acid sequence of SEQ ID NO:89.

Also disclosed herein are polynucleotides that encode an engineered TL1A ligand that is fused to a heterologous polypeptide. In some embodiments, polynucleotides disclosed herein encode a bispecific antibody comprising an engineered TL1A ligand disclosed herein.

In some embodiments, a polynucleotide provided herein comprises a nucleotide sequence encoding an engineered TL1A ligand described herein (or a fragment thereof), which specifically binds a DR3 polypeptide, e.g., a human DR3 polypeptide, wherein the engineered TL1A ligand antibody comprises an Fc region. In some embodiments, the Fc region is a human IgG1, IgG2 or IgG4 Fc region.

In some embodiments, provided herein are polynucleotides that encode an engineered TL1A ligand, wherein the polynucleotide comprises the nucleotide sequence of SEQ ID NO:95-SEQ ID NO:187. In some embodiments, provided herein are polynucleotides that encode an engineered TL1A ligand, wherein the polynucleotide comprises a nucleic acid sequence that is at least 80%, at least 85%, at least 90%, at least 95%, at least 98%, or 100% identical over its entire length to the nucleic acid sequence of SEQ ID NO:173; a nucleic acid sequence that is at least 80%, at least 85%, at least 90%, at least 95%, at least 98%, or 100% identical over its entire length to the nucleic acid sequence of SEQ ID NO:166; a nucleic acid sequence that is at least 80%, at least 85%, at least 90%, at least 95%, at least 98%, or 100% identical over its entire length to the nucleic acid sequence of SEQ ID NO:102; a nucleic acid sequence that is at least 80%, at least 85%, at least 90%, at least 95%, at least 98%, or 100% identical over its entire length to the nucleic acid sequence of SEQ ID NO:159; or a nucleic acid sequence that is at least 80%, at least 85%, at least 90%, at least 95%, at least 98%, or 100% identical over its entire length to the nucleic acid sequence of SEQ ID NO:146; a nucleic acid sequence that is at least 80%, at least 85%, at least 90%, at least 95%, at least 98%, or 100% identical over its entire length to the nucleic acid sequence of SEQ ID NO:108; a nucleic acid sequence that is at least 80%, at least 85%, at least 90%, at least 95%, at least 98%, or 100% identical over its entire length to the nucleic acid sequence of SEQ ID NO:130; a nucleic acid sequence that is at least 80%, at least 85%, at least 90%, at least 95%, at least 98%, or 100% identical over its entire length to the nucleic acid sequence of SEQ ID NO:184; a nucleic acid sequence that is at least 80%, at least 85%, at least 90%, at least 95%, at least 98%, or 100% identical over its entire length to the nucleic acid sequence of SEQ ID NO:182; a nucleic acid sequence that is at least 80%, at least 85%, at least 90%, at least 95%, at least 98%, or 100% identical over its entire length to the nucleic acid sequence of SEQ ID NO:185; or a nucleic acid sequence that is at least 80%, at least 85%, at least 90%, at least 95%, at least 98%, or 100% identical over its entire length to the nucleic acid sequence of SEQ ID NO:183.

In some embodiments, provided herein are polynucleotides that encode an engineered TL1A ligand, wherein the polynucleotide comprises a fragment of the nucleotide sequence of SEQ ID NO:95-SEQ ID NO:187, wherein the fragment encodes an engineered TL1A ligand capable of binding to DR3.

Those skilled in the art will appreciate that some of the polynucleotides described herein will comprise sequences that encode tags, fusion proteins or other polypeptides (e.g., a tag, such as poly-histidine, a sequence that is recognized by TEV protease (e.g., Glu-Asn-Leu-Tyr-Phe-Gln-(Gly/Ser) (SEQ ID NO:189)), and that these sequences can either be cleaved or not cleaved. In some embodiments, fusion proteins or other polypeptides (e.g., a tag, such as poly-histidine) can be replaced by another tag known in the art.

6.6 Methods of Making Polypeptides

In some embodiments, the engineered TL1A ligand is a polypeptide. The polypeptide comprises a recombinant polypeptide, a natural polypeptide, or a synthetic polypeptide that binds DR3.

Provided herein are methods of making an engineered TL1A ligand disclosed herein, wherein the method comprising a step for performing the function of introducing at least one amino acid alteration of the amino acid sequence of SEQ ID NO:94. In some embodiments, the at least one amino acid alteration is selected from the group consisting of: K111A, L123K, M158Y, Q167A, S187L, E190F, and N207F. In some embodiments, the amino acid alteration is K111A. In some embodiments, the amino acid alteration is L123K. In some embodiments, the amino acid alteration is M158Y. In some embodiments, the amino acid alteration is Q167A. In some embodiments, the amino acid alteration is S187L. In some embodiments, the amino acid alteration is E190F. In some embodiments, the amino acid alteration is N207F. Further provided herein are methods of making an engineered TL1A ligand disclosed herein comprising a step for performing the function of producing a population of engineered TL1A ligand.

It will be recognized in the art that some amino acid sequences described herein can be varied without significant effect of the structure or function of the protein. Thus, in some embodiments, provided herein are variations of the polypeptides which show substantial binding activity to DR3. In some embodiments, amino acid sequence variations of the polypeptides include deletions, insertions, inversions, repeats, and/or other types of substitutions.

The polypeptides, analogs, and variants thereof, can be further modified to contain additional chemical moieties not normally part of the polypeptide. The derivatized moieties can improve the solubility, the biological half-life, and/or absorption of the polypeptide. The moieties can also reduce or eliminate undesirable side effects of the polypeptides and variants. An overview for chemical moieties can be found in Remington: The Science and Practice of Pharmacy, 22nd Edition, 2012, Pharmaceutical Press, London.

In some embodiments, the engineered TL1A ligand disclosed herein can be modified to increase the serum half-life. In some embodiments, the engineered TL1A ligand disclosed herein can be modified to increase structural stability of the ligand.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest can be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

The methods provided herein can further comprise the step of fusing the engineered TL1A ligand to a heterologous polypeptide.

In some embodiments, the engineered TL1A ligand can be further modified to contain additional heterologous polypeptides or moieties not normally part of the polypeptide. The derivatized heterologous polypeptides or moieties can improve the ligand's solubility, the biological half-life (e.g., serum half-life), stability, expression level, monodispersity, binding activity, absorption and/or ability to activate T cells. The heterologous polypeptides or moieties can also reduce or eliminate undesirable side effects of the polypeptides and variants. In some embodiments, the heterologous moieties are chemical moieties. An overview for chemical moieties can be found in Remington: The Science and Practice of Pharmacy, 22nd Edition, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, methods of using molecular modeling algorithms that are known in the art or disclosed herein can be used to model the protein structure of an engineered TL1A ligand disclosed herein. In some embodiments, methods of using molecular modeling algorithms that are known in the art or disclosed herein can be used to model the protein structure of an engineered TL1A ligand disclosed herein bound to a receptor (e.g., DR3 and/or DcR3). In some embodiments, methods of using molecular modeling algorithms that are known in the art or disclosed herein can be used to further introduce further modifications to an engineered TL1A ligand disclosed herein to alter one or more of its characteristics (e.g., stability, monodispersity, binding to DR3, binding to DcR3, serum half-life). In some embodiments, methods of using molecular modeling algorithms that are known in the art or disclosed herein can be used in conjunction with additional sequence and/or structural information to model the protein structure of an engineered TL1A ligand disclosed herein, either unbound or bound to a receptor (e.g., DR3 and/or DcR3).

6.7 Targeting to Cells

In some embodiments, provided herein is a method of activating or enhancing DR3 signaling in a cell comprising contacting the cell with an effective amount of an engineered TL1A ligand described herein (e.g., a single-chain or non-covalent TL1A trimer that binds DR3). In some embodiments, a method of activating or enhancing DR3 signaling in a cell comprises contacting the cell with an effective amount of an engineered TL1A ligand described herein. In some embodiments, the engineered TL1A ligand described herein comprises a targeting moiety that binds to an antigen on the surface of the cell (e.g., a tumor-associated antigen). In some embodiments, the method is an in vivo method wherein the step of contacting the cell with the engineered TL1A ligand described herein comprises administering a therapeutically effective amount of the engineered TL1A ligand to the subject. In some embodiments, the method is an in vitro or ex vivo method. In some embodiments, the cell is a tumor cell.

Any methods known in the art for determining whether a tumor or cancer has an elevated level of expression of a nucleic acid or protein (e.g., a tumor-associated antigen) can be employed, and can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a blood sample. In some embodiments, the sample is a plasma sample. In some embodiments, the sample is processed to a cell lysate. In some embodiments, the sample is processed to DNA or RNA.

In a further aspect, provided herein are methods of determining the level of expression of a target, i.e., a tumor-associated antigen (TAA). In some embodiments, the level of expression of a TAA is determined. Methods for determining the level of nucleic acid expression in a cell, tumor, or cancer are known by those of skill in the art. These methods include, but are not limited to, PCR-based assays, microarray analyses, and nucleotide sequencing (e.g., Next-Gen sequencing). Methods for determining the level of protein expression in a cell, tumor, or cancer include, but are not limited to, Western blot analyses, protein arrays, ELISA, immunohistochemistry (IHC), and FACS.

6.8 Methods of Treatment

Provided herein are uses of the engineered TL1A ligands disclosed herein to mediate increased production of cytokines, such as IFN-7. Thus, provided herein are uses of such the engineered TL1A ligands in the treatment of diseases and conditions that can be treated with cytokines, such as cancer. In some embodiments, provided herein are uses of the engineered TL1A ligands in mediating increased T-cell (e.g., CD4+ or CD8+ T cell) activity or proliferation. Thus, provided in some embodiments are the use of the engineered TL1A ligands disclosed herein in the treatment of diseases and conditions that are treatable by increasing T cell activity or proliferation, such as cancer. In some embodiments, provided herein are uses of the engineered TL1A ligands as described herein to mediate both increased T cell activity and increased T cell proliferation.

One of skill in the art will appreciate that any TL1A ligand disclosed herein can be used according to the methods disclosed herein to activate T cells. As a non-limiting example, in some embodiments, an Fc-scTL1A-AKALFF TL1A variant (SEQ ID NO:91) can activate T cells in vitro and/or in vivo. In some embodiments, a TL1A ligand disclosed herein (e.g., an Fc-scTL1A-AKALFF variant) can co-stimulate anti-CD3-activated T cells at levels similar to wildtype TL1A. In some embodiments, wherein a TL1A ligand disclosed herein (e.g., an Fc-scTL1A-AKALFF variant) can co-stimulate anti-CD3-activated T cells in the presence of DcR3.

Up-modulation of the immune system is particularly desirable in the treatment of cancers. Additionally, DcR3 decoy receptors can serve as a sink to prevent TNF ligands such as TL1A ligands from activating T cells, and soluble decoy receptors can be up-regulated by tumors. For example, DcR3 can bind to TL1A with higher affinity than its cell surface receptor, DR3 and prevent TL1A-based T cell costimulation. In certain embodiments, engineered TL1A ligands described herein can co-stimulate T cells, thereby overcoming T cell exhaustion in solid tumors. Thus, provided herein are methods of cancer treatment. A cancer refers to a neoplasm or tumor resulting from abnormal uncontrolled growth of cells. A cancer can be a primary cancer or a metastatic cancer.

In addition, in some embodiments, provided herein is a method of inhibiting the growth of a tumor in a subject, comprising administering to the subject a therapeutically effective amount of an engineered TL1A ligand described herein. In some embodiments, the tumor comprises cancer stem cells. In addition, in some embodiments, provided herein is a method of reducing the tumorigenicity of a tumor in a subject, comprising administering to the subject a therapeutically effective amount of an engineered TL1A ligand described herein.

In some embodiments of the methods described herein, the tumor is a solid tumor. As a non-limiting example, in some embodiments, the tumor is a tumor selected from the group consisting of: colorectal tumor, kidney tumor, prostate tumor, neuroendocrine tumor, pancreatic tumor, lung tumor, ovarian tumor, liver tumor, breast tumor, gastrointestinal tumor, melanoma, cervical tumor, bladder tumor, glioblastoma, and head and neck tumor. In some embodiments, the tumor is a colorectal tumor. In some embodiments, the tumor is an ovarian tumor. In some embodiments, the tumor is a lung tumor. In some embodiments, the tumor is a pancreatic tumor. In some embodiments, the tumor is a melanoma tumor. In some embodiments, the tumor is a bladder tumor.

In some aspects, provided herein are methods for treating cancer in a subject comprising administering to the subject a therapeutically effective amount of an engineered TL1A ligand described herein wherein the solid tumor does not have microsatellite instability or does not have loss of mismatch repair protein expression.

In some aspects, a method disclosed herein is effective in recruiting tumor-infiltrating lymphocytes to the neoplasm, cancer, or solid tumor; and/or promoting and/or enhancing the formation of lymphoid structure within a tumor or tumor microenvironment; and/or increasing cytotoxic T cell activity within the tumor or tumor microenvironment; and/or reducing the size of the neoplasm, cancer, or solid tumor; and/or inhibiting growth of a tumor or neoplasm; and/or increasing the responsiveness of a tumor to treatment with a second therapeutic agent. Without being bound by theory, tumors exploit co-signaling cascades to evade immune surveillance, either by promoting co-inhibitory signals, such as CTLA-4 or by disrupting co-stimulatory signaling. In a certain aspect, provided herein are methods whereby administration of an engineered TL1A ligand disclosed herein is capable of co-stimulating T cells in a tumor, allowing activation against tumor cells. In some embodiments, an engineered TL1A ligand disclosed herein reduces tumor immune suppression.

In some aspects, provided herein are methods for treating a disease or disorder in a subject, wherein the disease or disorder is an autoimmune disease or an inflammatory disorder. As a non-limiting example, the disease or disorder can be selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, or atherosclerosis.

Provided herein is an engineered TL1A ligand as described herein for use in therapy. Also provided herein is an engineered TL1A ligand as described herein for use in the treatment of an autoimmune disorder or cancer. The autoimmune disorder or cancer may be selected from the group consisting of ulcerative colitis, lupus, IBD, COPD, arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and a sarcoma, wherein optionally the sarcoma is a rhabdomyosarcoma.

6.9 Administration

Further provided herein are compositions (e.g., pharmaceutical compositions) comprising an engineered TL1A ligand described herein. In some embodiments, also provided herein are pharmaceutical compositions comprising an engineered TL1A ligand described herein and a pharmaceutically acceptable carrier or vehicle. In some embodiments, the pharmaceutical compositions find use in immunotherapy. In some embodiments, the pharmaceutical compositions find use in immuno-oncology. In some embodiments, the compositions can find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient). In some embodiments, the engineered TL1A ligand is formulated in a pharmaceutical composition that is suitable for administration to a subject (e.g., a human subject).

A particular administration regimen of engineered TL1A ligand for a particular subject will depend, in part, upon the engineered TL1A ligand used, the amount of engineered TL1A ligand administered, the route of administration, and the cause and extent of any side effects. The amount of an engineered TL1A ligand administered to a subject (e.g., a mammal, such as a human) should be sufficient to effect the desired response over a reasonable time frame. According, in some embodiments, the amount of engineered TL1A ligand or pharmaceutical composition described herein administered to a subject is an effective amount. In some embodiments, the amount of engineered TL1A ligand or pharmaceutical composition described herein administered to a subject is a therapeutically effective amount. In some aspects, the method comprises administering, e.g., from about 0.1 µg/kg to up to about 100 mg/kg or more. In some embodiments, the dosage ranges from about 1 µg/kg up to about 100 mg/kg; or about 5 µg/kg up to about 100 mg/kg; or about 10 µg/kg up to about 100 mg/kg; or about 1 mg/kg up to about 50 mg/kg; or about 2 mg/kg up to about 30 mg/kg; or about 3 mg/kg up to about 25 mg/kg; or about 3 mg/kg up to about 25 mg/kg; or about 5 mg/kg up to about 10 mg/kg; or about 10 mg/kg up to about 20 mg/kg; or about 10 mg/kg up to about 30 mg/kg. Some conditions or disease states can require multiple administrations (e.g., every day, three times a week, once a week, once every two weeks, or once every month for a treatment period of three days, seven days, two weeks, three weeks, one month, three months, six months, nine months, 12 months, 15 months, 18 months, 21 months, two years, or more).

Suitable routes of administering pharmaceutical compositions are well known in the art. As a non-limiting example, administration can be through injection by intravenous, subcutaneous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. Although more than one route can be used to administer an engineered TL1A ligand, a particular route can provide a more immediate and more effective reaction than another route.

In some embodiments, the present disclosure provides a composition, such as pharmaceutical composition, comprising an engineered TL1A ligand disclosed herein and a carrier (e.g., a pharmaceutically acceptable carrier). The particular carrier employed can depend on chemico-physical considerations, such as solubility and lack of reactivity with the engineered TL1A ligand or co-therapy, and by the route of administration. In some embodiments, provided herein are engineered TL1A ligands and any pharmaceutically acceptable carriers known in the art.

6.10 Combination Therapies

In some embodiments, in addition to administering an engineered TL1A ligand described herein to a subject, the method or treatment further comprises administering at least one additional therapeutic agent. An additional therapeutic agent can be administered prior to, concurrently with, and/or subsequently to, administration of an engineered TL1A ligand. Also provided herein are pharmaceutical compositions comprising an engineered TL1A ligand and the additional therapeutic agent(s). In some embodiments, the at least one additional therapeutic agent comprises 1, 2, 3, or more additional therapeutic agents.

In some embodiments, combination therapy with two or more therapeutic agents can employ agents that work by different mechanisms of action. In some embodiments, combination therapy using agents with different mechanisms of action can result in additive or synergetic effects. In certain embodiments, combination therapy can allow for a lower dose of each agent than is used in monotherapy, thereby reducing toxic side effects and/or increasing the therapeutic index of the engineered TL1A ligand and/or the one or more additional therapeutic agent. In some embodiments, combination therapy can decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of an engineered TL1A ligand described herein and at least one additional therapeutic agent results in additive or synergistic results. In some embodiments, the combination therapy results in an increase in the therapeutic index of the engineered TL1A ligand and/or an increase in the therapeutic index of the additional therapeutic agent(s).

Any known useful classes of additional therapeutic agents can be used. As a non-limiting example, in some embodiments of the methods described herein, an engineered TL1A ligand can be administered in combination with an immune checkpoint inhibitors (e.g., immune-checkpoint blockade therapies targeting PD-1, PD-L1, and CTLA-4), TLR agonists (e.g., TLR7 agonists, TLR8 agonists, TLR9 agonists, etc.), DNA minor groove binders, DNA replication inhibitors, anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent can be an alkylating agent, an antimetabolite, an antimitotic, a topoisomerase inhibitor, or an angiogenesis inhibitor. In some embodiments, therapeutic agents that can be administered in combination with the polypeptides or agents described herein include chemotherapeutic agents.

In some embodiments, the method or treatment involves the administration of an engineered TL1A ligand of the present disclosure in combination with a chemotherapeutic agent or in combination with a cocktail of chemotherapeutic agents. Treatment an engineered TL1A ligand can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA.

In some embodiments of the methods described herein, the treatment involves the administration of an engineered TL1A ligand of the present disclosure in combination with radiation therapy. In some embodiments, treatment with an engineered TL1A ligand can occur prior to, concurrently with, or subsequent to administration of radiation therapy. Dosing schedules for such radiation therapy can be determined by the skilled medical practitioner.

In some embodiments, the combined use of an engineered TL1A ligand with an additional therapeutic agent (e.g. a polypeptide) can be a TL1A bispecific compound (e.g., a bispecific antibody). In some embodiments, the bispecific compound comprises an engineered TL1A ligand and a tumor-targeting moiety. In some embodiments, a bispecific compound that comprises an engineered TL1A ligand disclosed herein is capable of target a cancer cell or tumor. In some embodiments, a bispecific compound that comprises an engineered TL1A ligand disclosed herein can exhibit reduced toxicity associated with cytokine release via systemic or off-tumor T cell activation. In some embodiments, a bispecific compound that comprises an engineered TL1A ligand disclosed herein can result in reduced reactivation-induced T cell death (e.g., reduced apoptosis of tumor-infiltrating T cells (TILS) in response to over-activation by bispecific T cell engagers (bsTCE)).

In some embodiments, a bispecific compound disclosed herein can bind both co-stimulatory receptors and to a tumor antigen. In some embodiments, a bispecific compound disclosed herein can function as a module which can be joined with a tumor-targeting moiety to specifically activate T cells in the tumor micro-environment. In some embodiments, a bispecific compound disclosed herein can effectively mediate anti-tumor activity in a subject. One of skill in the art will appreciate that any TL1A ligand disclosed herein can be designed to function as a module which can be joined with a tumor-targeting moiety to specifically activate T cells. In some embodiments, a TL1A ligand with favorable monodispersity, stability, and/or activity can be used in a bispecific compound. As a non-limiting example, in some embodiments, an Fc-scTL1A-AKALFF TL1A variant (SEQ ID NO:91) can be used in a bispecific compound (e.g., joined with a tumor-targeting moiety).

6.11 Methods of Use

In some embodiments, a method of increasing an immune response in a subject comprises administering to a subject a therapeutically effective amount of an engineered TL1A ligands described herein, wherein the engineered TL1A ligands binds human DR3 with an affinity comparable to or higher than the affinity of wild-type TL1A and binds DcR3 with an affinity lower than the affinity of wild-type TL1A. In some embodiments of the methods described herein, a method of activating or enhancing a persistent or long-term immune response to a tumor comprises administering to a subject a therapeutically effective amount of an engineered TL1A ligands that binds human DR3 with an affinity comparable to or higher than the affinity of wild-type TL1A and binds DcR3 with an affinity lower than the affinity of wild-type TL1A. In some embodiments of the methods described herein, a method of inducing a persistent or long-term immunity which inhibits tumor relapse or tumor regrowth comprises administering to a subject a therapeutically effective amount of an engineered TL1A ligands that binds human DR3 with an affinity comparable to or higher than the affinity of wild-type TL1A and binds DcR3 with an affinity lower than the affinity of wild-type TL1A.

In some embodiments of the methods described herein, a method of increasing T-cell activity in a subject comprises administering to a subject a therapeutically effective amount of an engineered TL1A ligands that binds human DR3 with an affinity comparable to or higher than the affinity of wild-type TL1A and binds DcR3 with an affinity lower than the affinity of wild-type TL1A. In some embodiments, further provided herein are methods for inhibiting the growth of a tumor using an engineered TL1A ligand described herein. In some embodiments, the method of inhibiting the growth of a tumor comprises contacting cells (e.g., CD4+ or CD8+ T cells) with an engineered TL1A ligand described herein in vivo.

Provided herein are methods treating a disease or disorder in a subject, comprising administering to the subject an effective amount of the engineered TL1A ligand disclosed herein, wherein the engineered TL1A ligand comprises a first means capable of binding DR3 with an affinity comparable to or higher than the affinity of wild-type TL1A and a second means capable of binding DcR3 with an affinity lower than the affinity of wild-type TL1A. Further provided herein are methods treating a disease or disorder in a subject, comprising administering to the subject an effective amount of the engineered TL1A ligand disclosed herein, wherein the engineered TL1A ligand comprises a first means capable of binding DR3 with an affinity comparable to or higher than the affinity of wild-type TL1A and a second means capable of binding DcR3 with an affinity lower than the affinity of wild-type TL1A, and wherein the engineered TL1A ligand has a longer serum half-life than wild-type TL1A.

In some embodiments, an engineered TL1A ligand used according to the methods disclosed herein has a high monodispersity and/or stability compared to wild-type TL1A. In some embodiments, the methods disclosed herein provide an engineered TL1A ligand that is capable of co-stimulating T cells in vitro and/or in vivo (e.g., in a subject).

Provided herein are methods treating a disease or disorder in a subject, comprising administering to the subject an effective amount of the engineered TL1A ligand disclosed herein, wherein the disease or disorder is an autoimmune disorder or cancer.

The present disclosure provides kits that comprise the engineered TL1A ligands (e.g., polypeptides, molecules, nucleic acids) described herein and that can be used to perform the methods described herein. In some embodiments, a kit comprises at least one purified agent in one or more containers. In some embodiments, the kits contain all of the components necessary and/or sufficient to perform a method disclosed herein. One skilled in the art will readily recognize that the disclosed engineered TL1A ligands of the present disclosure can be readily incorporated into one of the established kit formats which are well known in the art.

Further provided are kits that comprise an engineered TL1A ligand as well as at least one additional therapeutic agent. In some embodiments, the additional therapeutic agent is disclosed herein or known in the art (e.g., a chemotherapeutic agent).

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

7. EMBODIMENTS

This invention provides the following non-limiting embodiments.

In one set of embodiments, provided are:

A1. An engineered TL1A ligand, wherein the engineered TL1A ligand comprises a trimeric complex comprising:
  a. three TL1A monomers, wherein the three TL1A monomers form a non-covalent TL1A trimer; or
  b. three TL1A monomers, wherein the three TL1A monomers are covalently linked to form a single-chain TL1A (scTL1A) trimer.

A2. The engineered TL1A ligand of embodiment A1, further comprising a protein stabilizing region.

A3. The engineered TL1A ligand of embodiment A2, wherein the protein stabilizing region comprises an Fc region, or a human serum albumin (HSA) region.

A4. The engineered TL1A ligand of embodiment A3, comprising:
  a. the non-covalent TL1A trimer and one or more Fc regions;
  b. the non-covalent TL1A trimer and one or more HSA regions;
  c. the scTL1A trimer and one or more Fc regions; or
  d. the scTL1A trimer and one or more HSA regions.

A5. The engineered TL1A ligand of embodiment A4 comprising:
  a. two non-covalent TL1A trimers and three Fc regions;
  b. two scTL1A trimers and one Fc region;
  c. one scTL1A trimer and one Fc region;
  d. one non-covalent TL1A trimer and three HSA regions; or
  e. one scTL1A trimer and one HSA region.

A6. The engineered TL1A ligand of any one of embodiments A1-A5, wherein the three TL1A monomers are covalently bound by a linker.

A7. The engineered TL1A ligand of embodiment A6, wherein the linker is a peptide linker.

A8. The engineered TL1A ligand of embodiment A7, wherein the linker has an amino acid sequence of Gly-Ser or multiple repeats thereof.

A9. The engineered TL1A ligand of any one of embodiments A1-A8, wherein the Fc region is a human IgG1, IgG2 or IgG4 Fc region.

A10. The engineered TL1A ligand of embodiment A9, wherein non-covalent TL1A trimer or the scTL1A trimer is fused to the C-terminus of the Fc region.

A11. The engineered TL1A ligand of any one of embodiments A1-A10 wherein the engineered TL1A ligand comprises the amino acid residues 72-251 of SEQ ID NO:94.

A12. An engineered TL1A ligand of embodiment A11, wherein the engineered TL1A ligand comprises at least one amino acid alteration of residues 72-251 of the amino acid sequence of SEQ ID NO:94.

A13. The engineered TL1A ligand of embodiment A12, wherein the engineered TL1A ligand has one or more alterations at one or more residue positions of SEQ ID NO:94 selected from the group consisting of R103, K111, N112, F114, E120, L123, G124, R156, M158, Q167, R170, K173, 5176, T185, D186, S187, Y188, P189, E190, T192, S206, N207, F209, Y238, T239, K240, and E241.

A14. The engineered TL1A ligand of embodiment A13, wherein the one or more alterations at one or more residue positions of SEQ ID NO:94 is an alteration selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173S, K173R, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q.

A15. The engineered TL1A ligand of any one of embodiments A12-A14, wherein the engineered TL1A ligand comprises at least two, three, four, five, six, seven, or more alterations of an amino acid sequence of residues 72-251 of SEQ ID NO:94.

A16. The engineered TL1A ligand of any one of embodiments A12-A15, wherein the engineered TL1A ligand comprises one or more amino acid alterations of SEQ ID NO:94 selected from the group consisting of: K111A, L123K, M158Y, Q167A, S187L, E190F, and N207F.

A17. The engineered TL1A ligand of any one of embodiments A12-A16, wherein the engineered TL1A ligand comprises the amino acid sequence of any one of SEQ ID NO:1-93.

A18. The engineered TL1A ligand of any one of embodiments A12-A17, wherein, the engineered TL1A ligand comprises:
  a. an amino acid sequence that is at least 80%, at least 85%, at least 90%, at least 95%, at least 98%, or 100% identical over its entire length to the amino acid sequence of SEQ ID NO:79; or
  b. an amino acid sequence that is at least 80%, at least 85%, at least 90%, at least 95%, at least 98%, or 100% identical over its entire length to the amino acid sequence of SEQ ID NO:72; or c. an amino acid sequence that is at least 80%, at least 85%, at least 90%, at least 95%, at least 98%, or 100% identical over its entire length to the amino acid sequence of SEQ ID NO:8; or d. an amino acid sequence that is at least 80%, at least 85%, at least 90%, at least 95%, at least 98%, or 100% identical over its entire length to the amino acid sequence of SEQ ID NO:65; or e. an amino acid sequence that is at least 80%, at least 85%, at least 90%, at least 95%, at least 98%, or 100% identical over its entire length to the amino acid sequence of SEQ ID NO:52; or f. an amino acid sequence that is at least 80%, at least 85%, at least 90%, at least 95%, at least 98%, or 100% identical over its entire length to the amino acid sequence of SEQ ID NO:14; or g. an amino acid sequence that is at least 80%, at least 85%, at least 90%, at least 95%, at least 98%, or 100% identical over its entire length to the amino acid sequence of SEQ ID NO:36; or h. an amino acid sequence that is at least 80%, at least 85%, at least 90%, at least 95%, at least 98%, or 100% identical over its entire length to the amino acid sequence of SEQ ID NO:90; or i. an amino acid sequence that is at least 80%, at least 85%, at least 90%, at least 95%, at least 98%, or 100% identical over its entire length to the amino acid sequence of SEQ ID NO:88; or j. an amino acid sequence that is at least 80%, at least 85%, at least 90%, at least 95%, at least 98%, or 100% identical over its entire length to the amino acid sequence of SEQ ID NO:91, or k. an amino acid sequence that is at least 80%, at least 85%, at least 90%, at least 95%, at least 98%, or 100% identical over its entire length to the amino acid sequence of SEQ ID NO:89.

A19. The engineered TL1A ligand of any one of embodiments A1-A18, which comprises a bispecific antibody.

A20. The engineered TL1A ligand of any one of embodiments A1-A19, which is fused to a heterologous polypeptide.

A21. The engineered TL1A ligand of any one of embodiments A1-A20, which is conjugated to an agent.

A22. The engineered TL1A ligand of embodiment A21, wherein the agent is a toxin.

In a second set of embodiments, provided are:

B1. An engineered TL1A ligand comprising: a first means capable of binding DR3 with an affinity comparable to or higher than the affinity of wildtype TL1A and a second means capable of binding DcR3 with an affinity lower than the affinity of wildtype TL1A.

B2. The engineered TL1A ligand of embodiment B1, wherein the engineered TL1A ligand has a longer serum half-life than wildtype TL1A.

B3. The engineered TL1A ligand of any one of embodiments B1-B2, wherein the engineered TL1A ligand has a high monodispersity and/or stability compared to wildtype TL1A.

B4. The engineered TL1A ligand of any one of embodiments B1-B3, wherein the engineered TL1A ligand can co-stimulate T cells in vitro.

B5. The engineered TL1A ligand of any one of embodiments B1-B4, wherein the engineered TL1A ligand can co-stimulate T cells in a subject.

B6. The engineered TL1A ligand of any one of embodiments B1-B5, wherein the engineered TL1A ligand can increase production of one or more cytokines in a subject in need thereof.

B7. The engineered TL1A ligand of embodiment B6, wherein the one or more cytokines comprise IFNγ and TNFα.

B8. The engineered TL1A ligand of any one of embodiments B5-B6, wherein the subject has an autoimmune disorder or cancer.

B9. The engineered TL1A ligand of embodiment B8, wherein the autoimmune disorder or cancer is selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and sarcomas, including rhabdomyosarcomas.

B10. A nucleic acid encoding the engineered TL1A ligand of any one of embodiments B1-B9.

B11. A pharmaceutical composition, comprising the engineered TL1A ligand of any one of embodiments B1-B9 or the nucleic acid of embodiment B10, and a pharmaceutically acceptable excipient.

In a third set of embodiments, provided are:

C1. A method treating a disease or disorder in a subject, comprising administering to the subject an effective amount of an engineered TL1A ligand, wherein the engineered TL1A ligand is a trimeric complex comprising:

a. three TL1A monomers, wherein the three TL1A monomers form a non-covalent TL1A trimer; or b. three TL1A monomers, wherein the three TL1A monomers are covalently linked to form a single-chain TL1A (scTL1A) trimer.

C2. The method of embodiment C1, wherein the engineered TL1A ligand further comprises a protein stabilizing region.

C3. The method of embodiment C2, wherein the protein stabilizing region comprises an Fc region, or a HSA region.

C4. The method of embodiment C3, comprising a multimeric engineered TL1A ligand comprising the engineered TL1A ligand of embodiment C3, comprising:

a. the non-covalent TL1A trimer and one or more Fc regions;

b. the non-covalent TL1A trimer and one or more HSA regions;

c. the scTL1A trimer and one or more Fc regions; or d. the scTL1A trimer and one or more HSA regions.

C5. The method of embodiment C4, wherein the multimeric engineered TL1A ligand comprises:

a. two non-covalent TL1A trimers and three Fc regions;

b. two scTL1A trimers and one Fc region;

c. one scTL1A trimer and one Fc region;

d. one non-covalent TL1A trimer and three HSA regions; or e. one scTL1A trimer and one HSA region.

C6. The method of any one of embodiments C1-C5, wherein the engineered TL1A ligand comprises the scTL1A trimer and, wherein the three TL1A monomers are covalently bound by a linker.

C7. The method of embodiment C6, wherein the linker is a peptide linker.

C8. The method of embodiment C7, wherein the linker has an amino acid sequence of Gly-Ser or multiple repeats thereof.

C9. The method of any one of embodiments C1-C8, wherein the Fc region is a human IgG1, IgG2 or IgG4 Fc region.

C10. The method of embodiment C9, wherein the non-covalent TL1A trimer or the scTL1A trimer is fused to the C-terminus of the Fc region.

C11. The method of any one of embodiments C1-C10, wherein the TL1A monomer comprises the amino acid residues 72-251 of SEQ ID NO:94.

C12. The method of embodiment C11, wherein the engineered TL1A ligand comprises at least one amino acid alteration of residues 72-251 of the amino acid sequence of SEQ ID NO:94.

C13. The method of embodiment C12, wherein the engineered TL1A ligand has one or more alterations at one or more residue positions of SEQ ID NO:94 selected from the group consisting of R103, K111, N112, F114, E120, L123, G124, R156, M158, Q167, R170, K173, S176, T185, D186, S187, Y188, P189, E190, T192, S206, N207, F209, Y238, T239, K240, and E241.

C14. The method of embodiment C13, wherein the one or more alterations at one or more residue positions is an alteration selected from R103A, R103H, R103Q, R103E, R103E, K111A, K111S, K111E, N112E, F114A, E120A, E120K, E120H, L123G, L123S, L123E, L123K, G124S, G124K, G124D, R156A, R156Y, R156K, R156E, M158Y, M158K, M158E, Q167A, R170E, K173S, K173R, S176A, S176L, S176, S176K, T185A, T185L, T185N, T185D, D186Y, S187A, S187L, S187K, S187D, Y188A, Y188S, P189A, P189K, P189F, P189S, E190G, E190F, T192A, T192F, T192K, T192E, S206A, S206F, S206K, S206E, N207A, N207F, N207S, N207K, N207E, F209A, F209W, Y238A, Y238S, Y238K, Y238R, Y238E, T239A, T239E, T239F, T239K, T239W, K240A, K240F, K240S, K240D, E241A, E241L, and E241Q.

C15. The method of any one of embodiments C12-C14, wherein the amino acid alteration comprises at least two, three, four, five, six, seven, or more alterations of an amino acid sequence of residues 72-251 of SEQ ID NO:94.

C16. The method of any one of embodiments C12-C15, wherein the engineered TL1A ligand comprises one or more amino acid alterations of SEQ ID NO:94 selected from the group consisting of: K111A, L123K, M158Y, Q167A, S187L, E190F, and N207F.

C17. The method of any one of embodiments C12-C16, wherein the engineered TL1A ligand comprises the amino acid sequence of any one of SEQ ID NO:1-93.

C18. The method of any one of embodiments C12-C17, wherein, the engineered TL1A ligand comprises:
   a. an amino acid sequence that is at least 80%, at least 85%, at least 90%, at least 95%, at least 98%, or 100% identical over its entire length to the amino acid sequence of SEQ ID NO:79; or
   b. an amino acid sequence that is at least 80%, at least 85%, at least 90%, at least 95%, at least 98%, or 100% identical over its entire length to the amino acid sequence of SEQ ID NO:72; or
   c. an amino acid sequence that is at least 80%, at least 85%, at least 90%, at least 95%, at least 98%, or 100% identical over its entire length to the amino acid sequence of SEQ ID NO:8; or
   d. an amino acid sequence that is at least 80%, at least 85%, at least 90%, at least 95%, at least 98%, or 100% identical over its entire length to the amino acid sequence of SEQ ID NO:65; or
   e. an amino acid sequence that is at least 80%, at least 85%, at least 90%, at least 95%, at least 98%, or 100% identical over its entire length to the amino acid sequence of SEQ ID NO:52; or
   f. an amino acid sequence that is at least 80%, at least 85%, at least 90%, at least 95%, at least 98%, or 100% identical over its entire length to the amino acid sequence of SEQ ID NO:14; or
   g. an amino acid sequence that is at least 80%, at least 85%, at least 90%, at least 95%, at least 98%, or 100% identical over its entire length to the amino acid sequence of SEQ ID NO:36; or
   h. an amino acid sequence that is at least 80%, at least 85%, at least 90%, at least 95%, at least 98%, or 100% identical over its entire length to the amino acid sequence of SEQ ID NO:90; or
   i. an amino acid sequence that is at least 80%, at least 85%, at least 90%, at least 95%, at least 98%, or 100% identical over its entire length to the amino acid sequence of SEQ ID NO:88; or
   j. an amino acid sequence that is at least 80%, at least 85%, at least 90%, at least 95%, at least 98%, or 100% identical over its entire length to the amino acid sequence of SEQ ID NO:91, or
   k. an amino acid sequence that is at least 80%, at least 85%, at least 90%, at least 95%, at least 98%, or 100% identical over its entire length to the amino acid sequence of SEQ ID NO:89.

C19. The method of any one of embodiments C1-C18, wherein the engineered TL1A ligand comprises a bispecific antibody.

C20. The method of any one of embodiments C1-C19, wherein the engineered TL1A ligand is fused to a heterologous polypeptide.

C21. The method of any one of embodiments C1-C20, wherein the engineered TL1A ligand is conjugated to an agent.

C22. The method of embodiment C21, wherein the agent is a toxin.

In a fourth set of embodiments, provided are:

D1. A method treating a disease or disorder in a subject, comprising administering to the subject an effective amount of the engineered TL1A ligand comprising: a first means capable of binding DR3 with an affinity comparable to or higher than the affinity of wildtype TL1A and a second means capable of binding DcR3 with an affinity lower than the affinity of wildtype TL1A D2. The method of embodiment D1, wherein the engineered TL1A ligand has a longer serum half-life than wildtype TL1A.

D3. The method of any one of embodiments D1 or D2, wherein the engineered TL1A ligand has a high monodispersity and/or stability compared to wildtype TL1A.

D4. The method of any one of embodiments D1 or D2, wherein the engineered TL1A ligand can co-stimulate T cells in vitro.

D5. The method of any one of embodiments D1 or D2, wherein the engineered TL1A ligand can co-stimulate T cells in the subject.

D6. The method of any one of embodiments D1-D5, wherein the engineered TL1A ligand can increase production of one or more cytokines in a subject in need thereof.

D7. The method of embodiment D6, wherein the one or more cytokines comprise IFNγ and TNFα.

D8. The method of any one of embodiments D1-D4, wherein the disease or disorder is an autoimmune disorder or cancer.

D9. The method of embodiment D8, wherein the disease or disorder is selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and sarcomas, including rhabdomyosarcomas.

In a fifth set of embodiments, provided are:

E1. A method of making an engineered TL1A ligand comprising (i) a step for performing the function of introducing at least one amino acid alteration of the amino acid sequence of SEQ ID NO:94 selected from the group consisting of: K111A, L123K, M158Y, Q167A, S187L, E190F, and N207F; and (ii) a step for performing the function of producing a population of engineered TL1A ligand.

E2. The method of embodiment E1, further comprising the step of fusing the engineered TL1A ligand to a heterologous polypeptide.

E3. The method of embodiment E2, wherein the heterologous polypeptide comprises a protein stabilizing region.

E4. The method of embodiment E3, wherein the protein stabilizing region comprises an Fc region, or a HSA region.

E5. The method of embodiment E4, further comprising a step of generating a multimeric engineered TL1A ligand.

E6. The method of embodiment E5, wherein the multimeric engineered TL1A ligand comprises:
  a. the non-covalent TL1A trimer and one or more Fc regions;
  b. the non-covalent TL1A trimer and one or more HSA regions;
  c. the scTL1A trimer and one or more Fc regions; or
  d. the scTL1A trimer and one or more HSA regions.

E7. The method of embodiment E6, wherein the multimeric engineered TL1A ligand comprises:
  a. two non-covalent TL1A trimers and three Fc regions;
  b. two scTL1A trimers and one Fc region;
  c. one scTL1A trimer and one Fc region;
  d. one non-covalent TL1A trimer and three HSA regions; or
  e. one scTL1A trimer and one HSA region.

E8. The method of any one of embodiments E1-E7, wherein the engineered TL1A ligand comprises the amino acid sequence of any one of SEQ ID NO:1-93.

E9. The method of any one of embodiments E1-E8, wherein, the engineered TL1A ligand comprises:
  a. an amino acid sequence that is at least 80%, at least 85%, at least 90%, at least 95%, at least 98%, or 100% identical over its entire length to the amino acid sequence of SEQ ID NO:79; or
  b. an amino acid sequence that is at least 80%, at least 85%, at least 90%, at least 95%, at least 98%, or 100% identical over its entire length to the amino acid sequence of SEQ ID NO:72; or
  c. an amino acid sequence that is at least 80%, at least 85%, at least 90%, at least 95%, at least 98%, or 100% identical over its entire length to the amino acid sequence of SEQ ID NO:8; or
  d. an amino acid sequence that is at least 80%, at least 85%, at least 90%, at least 95%, at least 98%, or 100% identical over its entire length to the amino acid sequence of SEQ ID NO:65; or
  e. an amino acid sequence that is at least 80%, at least 85%, at least 90%, at least 95%, at least 98%, or 100% identical over its entire length to the amino acid sequence of SEQ ID NO:52; or
  f. an amino acid sequence that is at least 80%, at least 85%, at least 90%, at least 95%, at least 98%, or 100% identical over its entire length to the amino acid sequence of SEQ ID NO:14; or
  g. an amino acid sequence that is at least 80%, at least 85%, at least 90%, at least 95%, at least 98%, or 100% identical over its entire length to the amino acid sequence of SEQ ID NO:36; or
  h. an amino acid sequence that is at least 80%, at least 85%, at least 90%, at least 95%, at least 98%, or 100% identical over its entire length to the amino acid sequence of SEQ ID NO:90; or
  i. an amino acid sequence that is at least 80%, at least 85%, at least 90%, at least 95%, at least 98%, or 100% identical over its entire length to the amino acid sequence of SEQ ID NO:88; or
  j. an amino acid sequence that is at least 80%, at least 85%, at least 90%, at least 95%, at least 98%, or 100% identical over its entire length to the amino acid sequence of SEQ ID NO:91, or
  k. an amino acid sequence that is at least 80%, at least 85%, at least 90%, at least 95%, at least 98%, or 100% identical over its entire length to the amino acid sequence of SEQ ID NO:89.

E10. An engineered TL1A ligand of any one of embodiments A1 to A22, B1 to B11, C1 to C22, D1 to D9, and E1 to E9 for use in therapy.

E11. An engineered TL1A ligand of any one of embodiments A1 to A22, B1 to B11, C1 to C22, D1 to D9, and E1 to E9 for use in the treatment of an autoimmune disorder or cancer.

E12. An engineered TL1A ligand for use according to embodiment E11, wherein the autoimmune disorder or cancer is selected from the group consisting of ulcerative colitis, lupus, IBD, COPD, arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and a sarcoma, wherein optionally the sarcoma is a rhabdomyosarcoma.

8. EXAMPLES

Figure 1B:
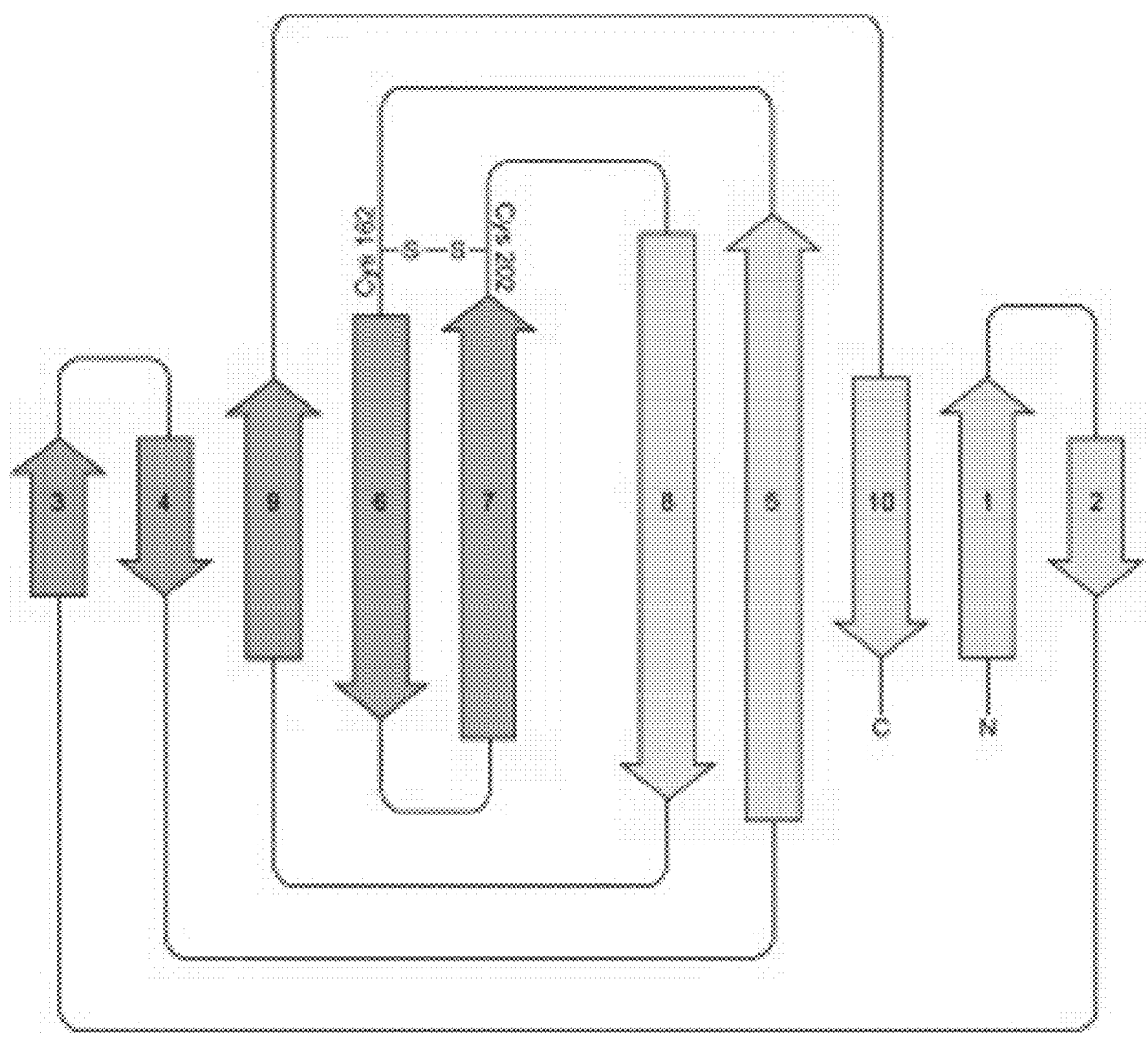
Figure 1C:
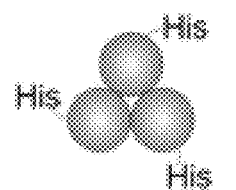
Figure 1C:
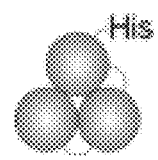
Figure 1D:
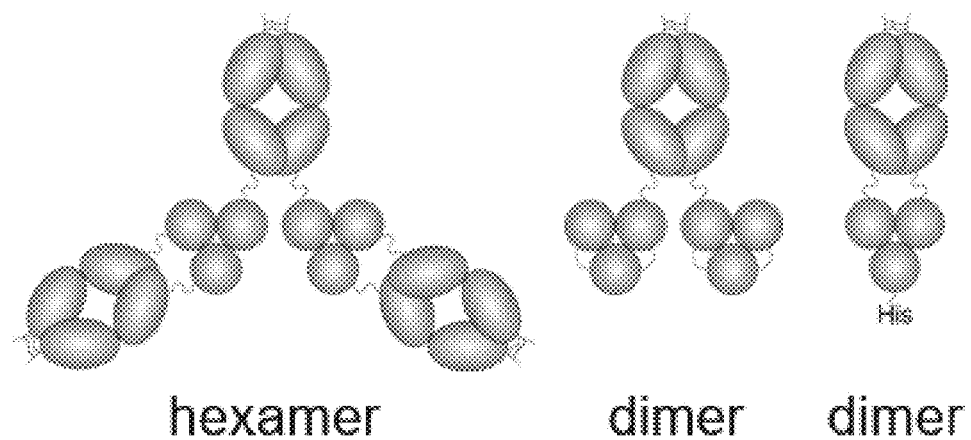
Figure 1E:
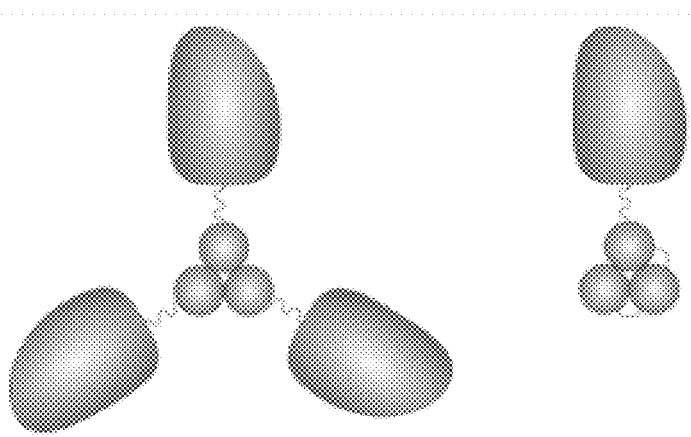

8.1 Example 1. Generation of Recombinant TL1A Ligands: His-scTL1A, Fc-scTL1A, and HSA-scTL1A TNFSF ligands generally require a 3:3 stoichiometry of interaction with their cognate receptors to induce downstream signaling. To develop TL1A ligands as a therapeutic, engineered TL1A ligands were generated, focusing on the C-terminal extracellular domain (i.e., residues 72-251) comprising the TNF homology domain which forms into a jellyroll fold (FIG. 1A, 1B). The jellyroll fold is comprised of two sets of five β-sheets which connected by unstructured loops (FIG. 1B). TL1A ligands were designed to trimerize either through native, non-covalent interactions or as a single-chain (sc) using a linker peptide (e.g., a Gly-Ser linker) (FIG. 1C, 1D, 1E). Each format was evaluated for its expression level, monodispersity, binding activity, and ability to activate T cells. The Fc+His-TL1A molecule (SEQ ID NO:92) was generated by co-transfection of His-TL1A with Fc-TL1A at a molar DNA ratio of 1:2 and the desired product was purified by protein A and Ni-NTA tandem affinity chromatography.

Since soluble TL1A (FIG. 1C) is expected to have a short serum half-life, to increase the short serum half-life, ligands were also fused to either an IgG1 Fc or to HSA (FIGS. 1D and 1E, respectively).

Briefly, TL1A constructs and variants were optimized for human codon usage and cloned into a mammalian expression vector. Constructs were transfected into Expi293 cells (Thermo) and expressed according to the manufacturer's protocol. Proteins were purified by either Ni-NTA affinity chromatography (His-TL1A and HSA-TL1A) or by mAb-Select SuRe (GE Healthcare Life Sciences) (Fc-TL1A) according to the manufacturer's protocol.

After expression and initial affinity capture, proteins were purified by preparative gel filtration and the relative population of target species of each molecule was quantified. Preparative gel-filtration was performed using a Sepax SRT-C SEC-300 column (Sepax Technologies, Inc.). Gel-filtration was performed in buffer consisting of 20 mM sodium phosphate, pH 6.8.

The molecule design dictated the stoichiometry of Fc/HSA:TL1A trimers, such that for Fc fusion, the ratio of Fc:TL1A trimers was 3:2 (FIG. 1D, left), for Fc-scTL1A, the ratio was 1:2 (FIG. 1D, middle), and for a combination of Fc-TL1A+ TL1A monomer, the ratio was 1:1 (FIG. 1D, right). For HSA-TL1A, the ratio of HSA to TL1A was 3:1 (FIG. 1E, left), and for HSA-scTL1A, the ratio was 1:1 (FIG. 1E, right).

Figure 2A:
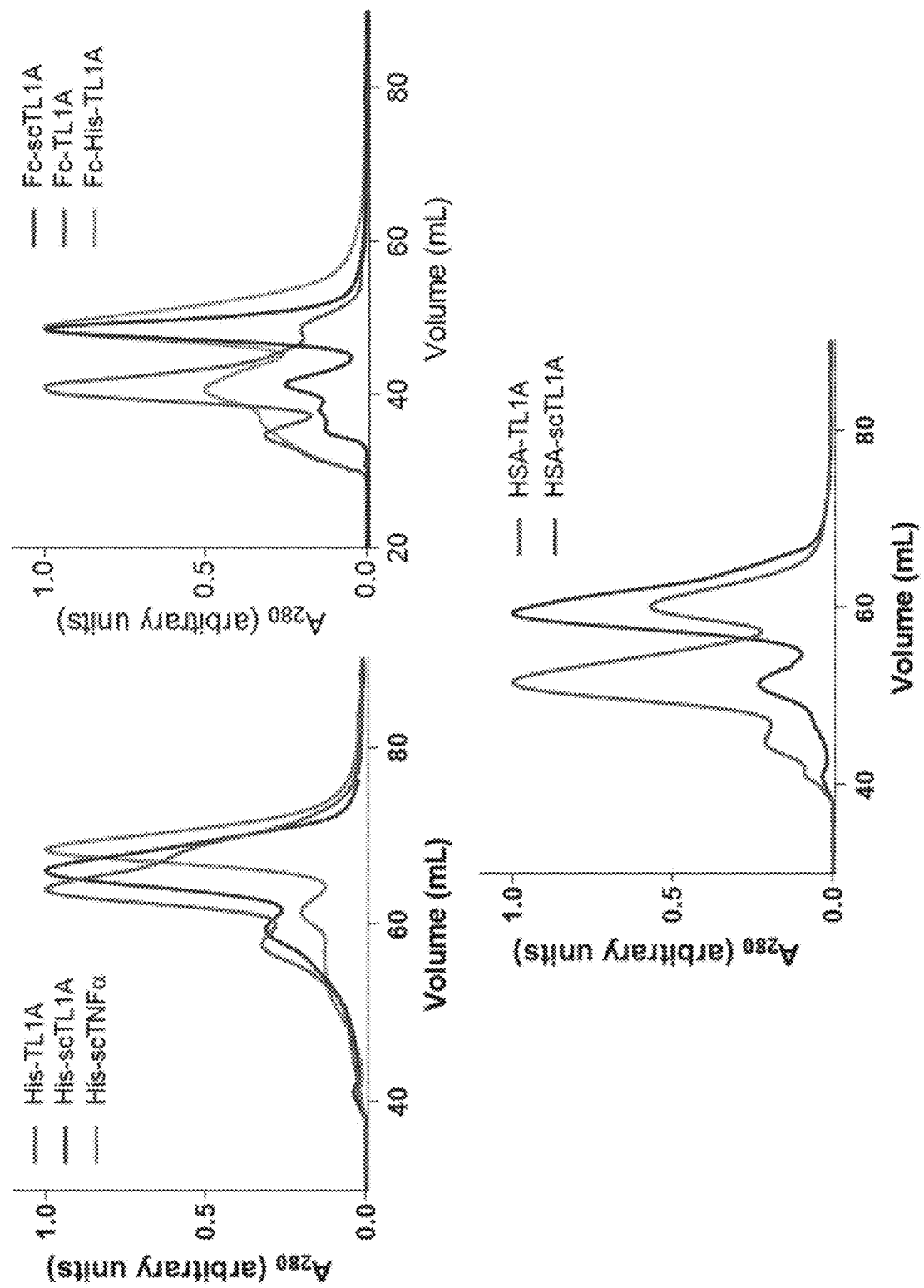

Exemplary results of preparative gel-filtration analysis of indicated TL1A constructs are shown in FIG. 2A. Recombinant TNFα (His-scTNFα) was used as a control to show the population of trimer vs oligomers. Results are summarized in Table 1, showing the percent high molecular weight species (% HMW species), the % target species (i.e., monomer, dimer, trimer, or hexamer), and the percent low molecular weight species (% LMW species).

Results indicate that all constructs in which the TL1A subunits were not fused with a linker peptide displayed high levels of off-target low molecular weight (LMW) species, although the subunit interface is comprised mainly of hydrophobic residues and comprises >4,000 A2 (based on PDB ID 2RE9). A comparison of the single chain scTL1A constructs, His-scTL1A, Fc-scTL1A, and HSA-scTL1A, showed that each had a target species of over 70, with Fc- and HSA-scTL1A displaying approximately 80% target oligomer (Table 1).

TABLE 1

Measurement of Monodispersity of TL1A molecules

| Molecule (SEQ ID NO) | Target oligomer | % HMW species | % Target species | % LMW species |
| --- | --- | --- | --- | --- |
| His-TL1A (TL1W2) (SEQ ID NO: 20) | Trimer | 22 | 54 | 24 |
| His-scTL1A (TL1W19) (SEQ ID NO: 86) | Monomer | 27 | 73 | NA |
| His-scTNFα | Monomer | 30 | 70 | NA |
| Fc-TL1A (TL1W3) (SEQ ID NO: 93) | Hexamer | 23 | 67 | 10 |
| Fc-His-TL1A (TL1W61) (SEQ ID NO: 92) | Dimer | 46 | 46 | 8 |
| Fc-scTL1A (TL1W14) (SEQ ID NO: 87) | Dimer | 22 | 78 | NA |
| HSA-TL1A (TL1W9) (SEQ ID NO: 85) | Trimer | 10 | 60 | 30 |
| HSA-scTL1A (TL1W15) (SEQ ID NO: 84) | Monomer | 18 | 82 | NA |

Figure 2B:
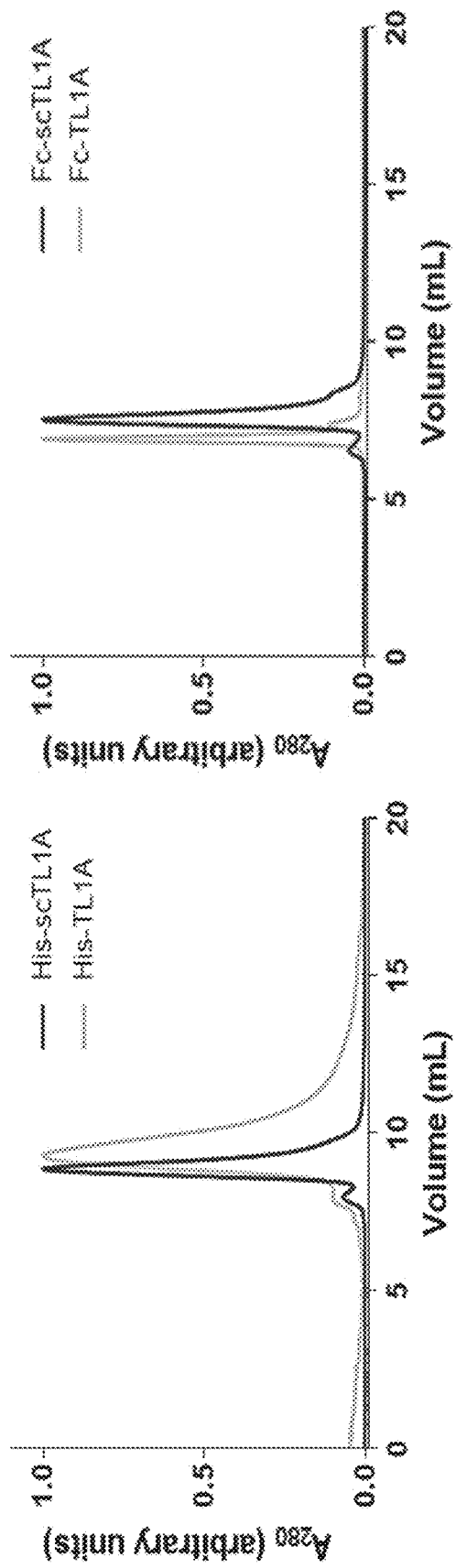
Figure 2B:
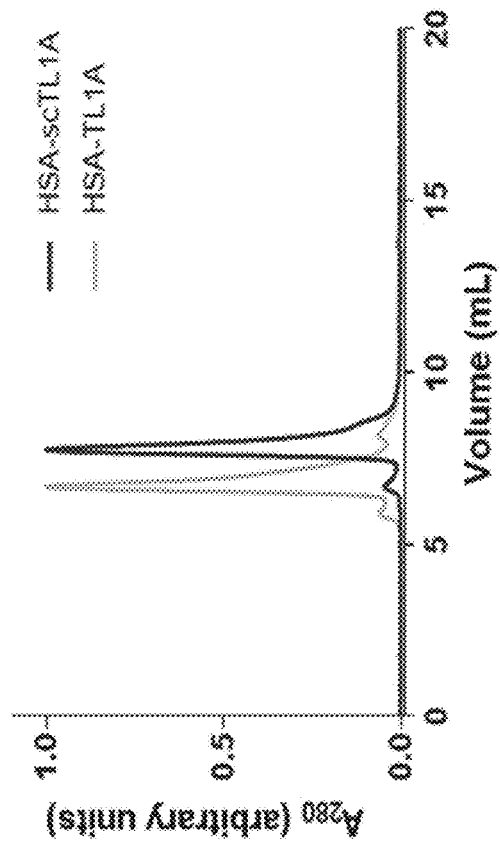

Molecules were purified by gel-filtration to >95% target oligomer for functional testing. Exemplary results of analytical SEC analysis of indicated TL1A constructs after preparative gel-filtration purification to isolate desired oligomeric species is shown in FIG. 2B. The purified species were used in functional assays.

8.2 Example 2. DR3 Receptor Binding of Recombinant TL1A Ligands

Each TL1A ligand was tested for the ability to bind to recombinant DR3 receptor, using an ELISA assay.

All ELISA-based measurements were collected in triplicate, and error values report the standard error between measurements. Recombinant DR3-Fc (R&D Systems, cat. #943-D33), dimeric MVW ~92 kDa, was non-specifically immobilized onto plates (Nunc maxisorp, cat. #436110) in 100 μL DR3-Fc, diluted to 10 μg/mL onto a 96-well White Maxisorp plate (Nunc, cat #436110) (O/N, 4° C.). Plates were block for 1 hour at room temperature with 250 μl/well of casein buffer and blocking buffer was removed. 50 μL of TL1A variants were diluted in StartingBlock PBS (Thermo Fisher Scientific), at 25 μg/mL, diluting 3× over each well, according to the plate map description for 20160623) per well on a 96-well White Maxisorp plate (Nunc, cat #: 436110) (overnight at 4° C.).

TL1A variant concentrations were normalized to moles of TL1A trimer per molecule, since the trimeric form is the functional unit for DR3 binding. This allowed comparison of the binding activity per TL1A trimer in each format, and therefore allowed assessment of whether molecules having two TL1A trimers (Fc-TL1A or Fc-scTL1A) would display an increase in binding avidity compared to molecules having a single TL1A tirimer (His-TL1A, His-scTL1A, Fc-TL1A+ His-TL1A, HSA-TL1A and HSA-scTL1A) (FIGS. 1C, 1D and 1E). For example, 1 molecule of His-TL1A contains 1 TL1A trimer, and thus 25 μg/mL of TL1W2 (SEQ ID NO:20) contains 376 nM TL1A trimers. Conversely, TL1W14 (SEQ ID NO:87) contains 2 TL1A trimers per molecule, and has a different molecular weight. Thus, 25 μg/mL TL1W14 is 290 nM. Therefore, 376 nM is equivalent to 32.4 μg/mL.

Plates were washed three times with TBST. 100 μl/well polyclonal rabbit anti-human TL1A-biotin antibody (diluted 1:1000 in Starting Block PBS) was added and plates were incubated for 1 hour at room temperature with shaking at 150 rpm. TL1A-biotin antibody was removed and 100

µl/well streptavidin-HRP conjugate (diluted 1:10,000 in Starting Block PBS) was added to plates. Plates were incubated for 1 hour at room temperature with shaking at 150 rpm. Plates were washed three times with TBST. 100 µl/well POD Chemiluminescence substrate (Roche, cat #: 11582950001) was added immediately prior to reading plate luminescence using a Molecular Devices M5 plate reader with a delay setting of 100 ms.

Figure 2C:
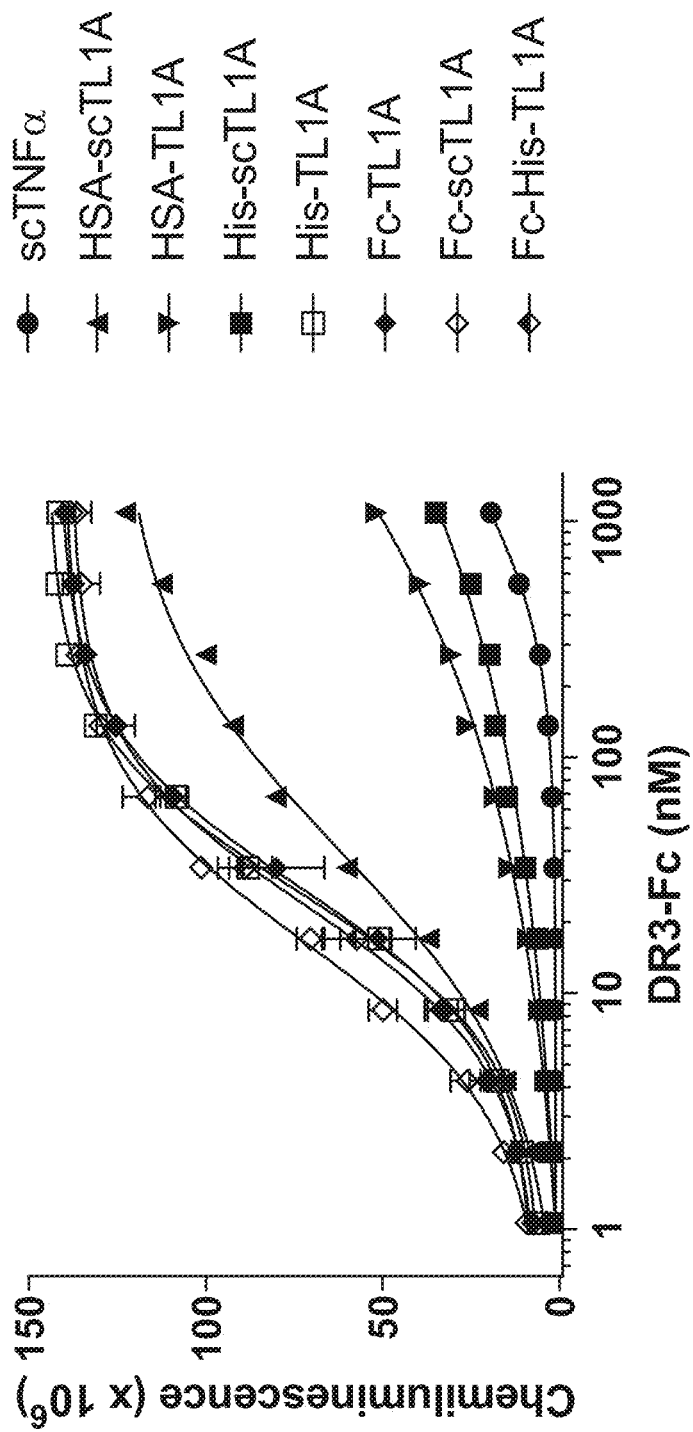

Exemplary results of ELISA analysis of the ability of indicated TL1A ligands to bind to DR3 are shown in FIG. 2C and $EC_{50}$ values are summarized in Table 2. "N.B." indicates no binding. Results show that most TL1A constructs displayed an $EC_{50}$ for binding to immobilized DR3 of approximately 24 nM. The HSA-scTL1A molecule bound weaker, with $EC_{50}$ of 168 nM, suggesting that the architecture of this molecule interfered with binding to TL1A.

Figure 2D:
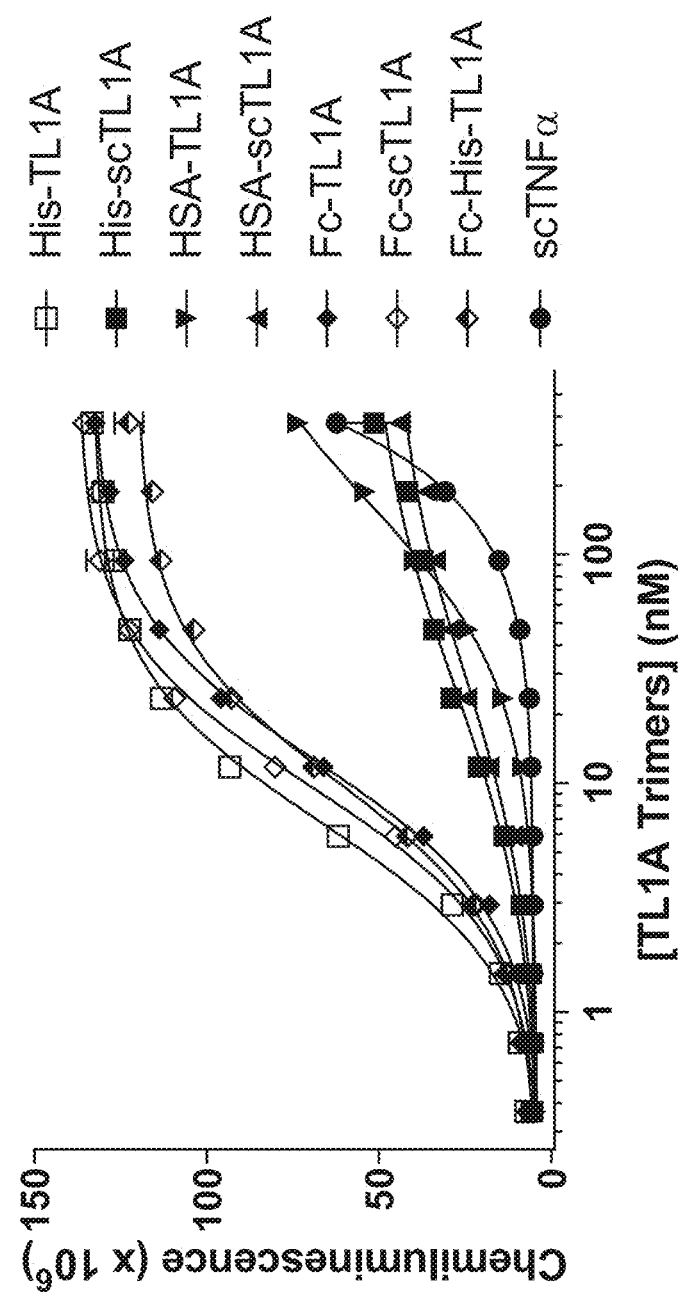

To confirm that TL1A molecules could bind DR3 in the reversed format, the TL1A molecules were immobilized and DR3 was titrated as described above. Exemplary results are shown in FIG. 2D and Table 2. In this format, the molecules displayed $EC_{50}$ values that were approximately 3-7-fold tighter for binding, but several constructs failed to bind significantly, including the HSA-scTL1A and His-scTL1A molecules. Thus, immobilized DR3 was employed for further ELISA analysis.

The two HSA-TL1A proteins (SEQ ID NO:84 and 85) displayed significantly weaker binding in both formats, suggesting that the HSA-fusion partner may have inhibited the ability of the TL1A moiety to bind its receptor (FIG. 2D). Additionally, the His-scTL1A molecule (SEQ ID NO:86) had an $EC_{50}$ approximately 3-fold weaker than other molecules. As a negative control, it was demonstrated that scTNFα did not show significant binding to DR3.

TABLE 2

ELISA results for TL1A constructs binding to DR3

| Molecule (SEQ ID NO) | Target oligomer | $EC_{50}$ (nM): DR3 immobilized | $EC_{50}$ (nM): TL1A immobilized |
|---|---|---|---|
| His-TL1A (TL1W2) (SEQ ID NO: 20) | trimer | 6.8 ± 1.0 | 2.5 ± 1.0 |
| His-scTL1A TL1W19 (SEQ ID NO: 86) | Monomer | 27.3 ± 1.3 | N.B. |
| His-scTNFα | Monomer | N.B. | N.B. |
| Fc-TL1A (TL1W3) (SEQ ID NO: 93) | Hexamer | 12.4 ± 1.0 | 2.6 ± 1.1 |
| Fc-His-TL1A (TL1W61) (SEQ ID NO: 92) | Dimer | 10.2 ± 1.0 | 2.2 ± 1.1 |
| Fc-scTL1A (TL1W14) (SEQ ID NO: 87) | Dimer | 9.7 ± 1.0 | 1.5 ± 1.1 |
| HSA-TL1A (TL1W9) (SEQ ID NO: 85) | Trimer | 167.6 ± 1.1 | >4,000 ± 283 |
| HSA-scTL1A (TL1W15) (SEQ ID NO: 84) | Monomer | 29.2 ± 1.2 | 3.8 ± 1.1 |

8.3 Example 3. T Cell Co-Stimulation and Cytokine Production and In Vivo T Cell Activation TL1A constructs were evaluated for the ability to co-stimulate T cells and lead to cytokine production using a T cell activation assay. 96-well U-bottom tissue culture plates (Midwest Scientific, cat. #TP92097) were coated with 10 ng/ml of anti-CD3 (BioLegend, cat. #317304, clone OKT3) in PBS overnight at 4° C. Plates were then washed three times with complete RPMI media (RPMI+10% FBS). Pan T cells were isolated from peripheral blood mononuclear cells using negative selection (Miltenyi Biotec, cat. #130-096-535). 30,000 pan T cells were plated in each well of anti-CD3 pre-coated 96-well U-bottom plates. Engineered TL1A ligands and/or 0.1 µg/mL anti-CD28 (BioLegend, cat. #302914) were added to appropriate wells. To assess DcR3-mediated inhibition on T cell activation, recombinant DcR3 protein (R&D cat #142-DC-100) was added to a final concentration of 30 nM to anti-CD3 stimulated T cells with or without TL1A ligands.

Cytokine production was measured using a MSD electro-chemiluminsence cytokine assay (Meso Scale Discovery). Briefly, U-PLEX TH1 TH2 cytokine plates (Meso Scale Discovery, cat #K15010B-2) were coated with 25 µl of cell culture supernatant overnight at 4° C. The plates were washed three times with PBS with 0.05% Tween 20 (PBST). Anti-human Fc detection reagent was applied at 2 µg/ml final concentration for one hour at room temperature with shaking. The plates were washed three times with PBST, 150 µl of 2× read buffer was added to the plates and data was collected on an MSD instrument. Standard curves were prepared according to manufacturer's protocol. Raw data was processed in MSD Discovery Workbench and imported into GraphPad Prism 8 software. Data was analyzed and plotted based on the results of three separate experiments and statistics were generated in the GraphPad Prism 8 program.

Figure 2E:
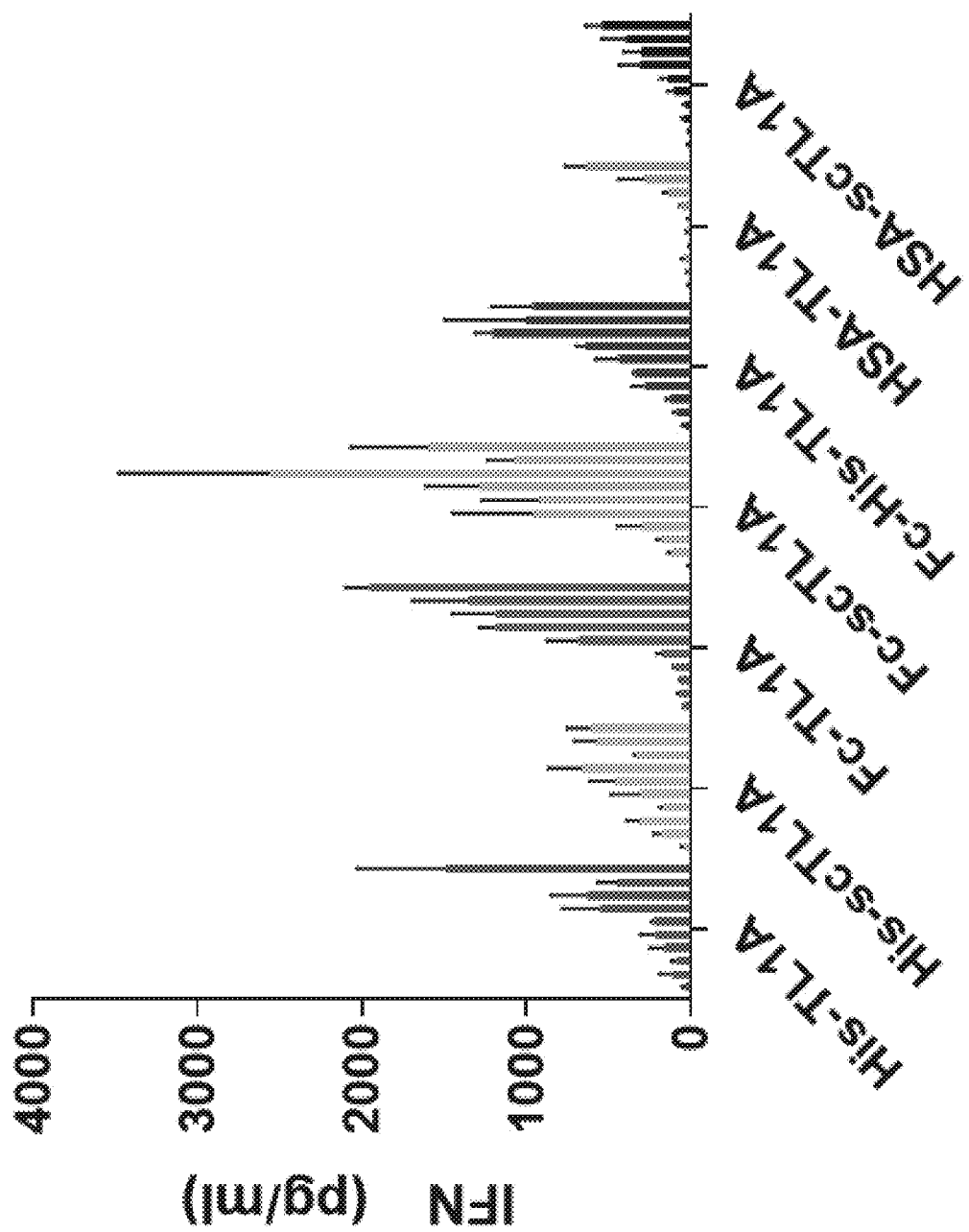
Figure 2F:
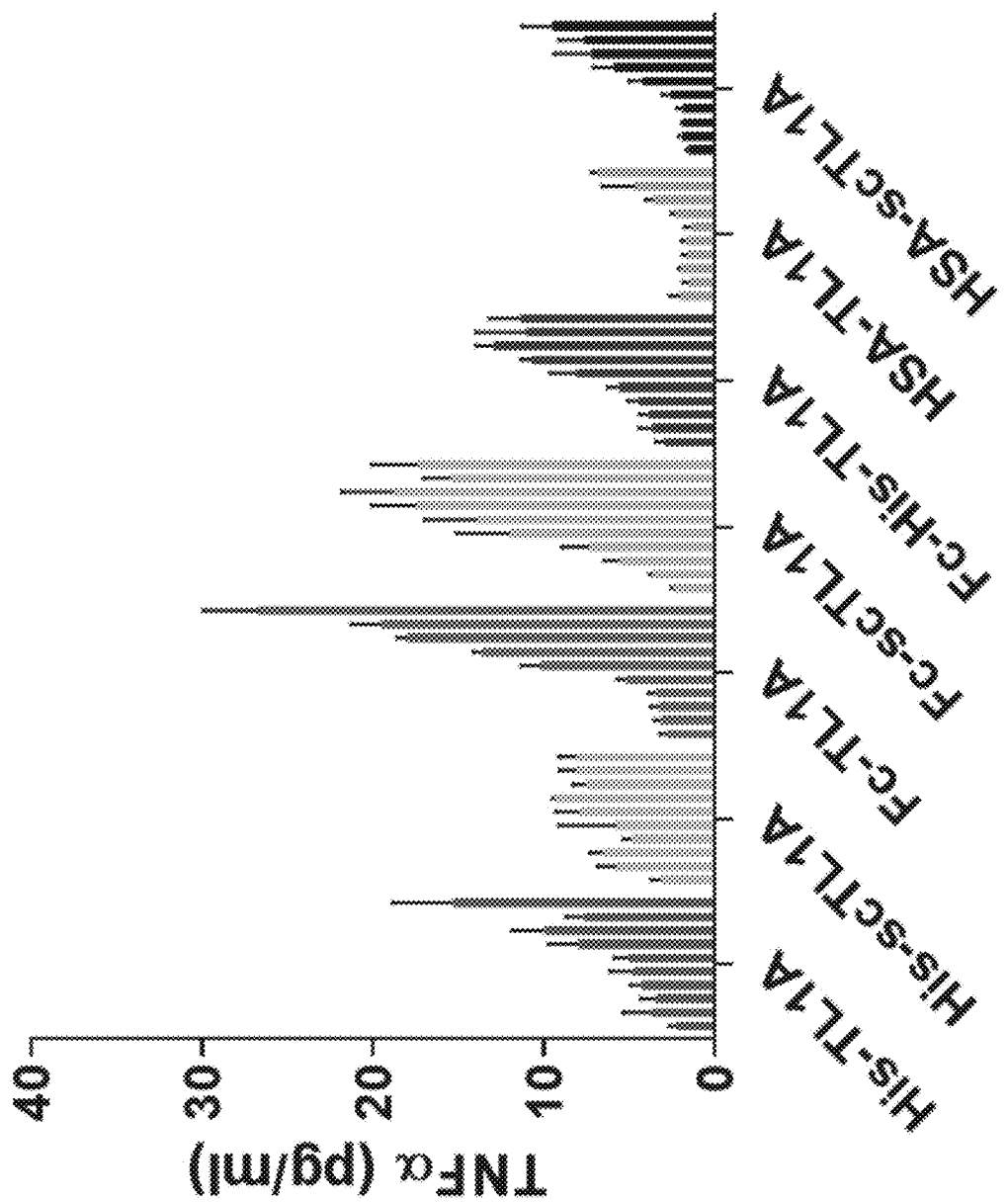

Exemplary results for the ability of indicated TL1A constructs to induce IFNγ and TNFα production of CD3-activated T cells are shown in FIGS. 2E and 2F, respectively. Bars from left to right indicate TL1A ligand concentrations at 0, 0.03, 0.1, 0.3, 1, 3, 10, 30, 100 and 300 nM. In the absence of anti-CD3 antibody (OKT3, Biolegend cat. #317301), the TL1A molecules could not stimulate T cells, as expected due to lack of T cell receptor stimulation (FIGS. 2E and 2F). In the presence of sub-optimal anti-CD3 antibody concentrations (0.01 or 0.1 g/ml), T cells could be stimulated by the TL1A molecules to produce IFNγ and TNFα in a dose-dependent manner.

Results show that the HSA-TL1A molecules, which displayed only weak binding to DR3 (FIGS. 2C and 2D), likewise showed the weakest co-stimulatory activities compared to the other TL1A constructs. While the His-TL1A molecules displayed some co-stimulatory activity, the three Fc-tagged TL1A molecules displayed the highest abilities to co-stimulate T cells to produce cytokines. While all three Fc-TL1A formats could co-stimulate T cells (FIGS. 2E and 2F), the Fc-scTL1A displayed the most consistent T cell co-stimulatory function and favorable monodispersity (Table 1).

TL1A constructs were evaluated for the ability to co-stimulate T cells to produce cytokine in an in vivo mouse model. Suboptimal dose of anti-mouse CD3 antibody (2 µg/mouse) (BioXCell, cat. #BE0001-1FAB) was injected intravenously into C57BL/6 mice. Fc-TL1A W3 or Fc-scTL1A W14 (30 µg per mouse) was injected intraperitoneally. Fc-TL1A W3 (100 µg per mouse) was also injected intraperitoneally into mice in the absence of anti-mouse CD3 stimulation (FIG. 3). Mice were bled 6 hours later. Sera were collected and frozen. Frozen sera were thawed and diluted 1:10 for mouse IFNγ ELISA (Invitrogen, cat. #88-8314-86). Briefly, Nunc MaxiSorp 96-well plates were pre-coated with capture antibody overnight at 4° C. Plates were washed and then blocked with ELISA diluent for 1 hour at room temperature. Plates were washed with Wash Buffer. Diluted samples were loaded into plates and incubated for 2 hours at room temperature. Plates were washed with Wash Buffer 3 to 5 times. Diluted detection antibody was added to each well, incubated for 1 hour at room temperature, and washed. Diluted Streptavidin-TRP detection reagent was added, incubated for 30 minutes at room temperature, and washed. TMB substrate solution (tetramethyl benzidine) was added and incubated at room temperature for 15 minutes. Stop solution was added to each well. Plates were read in a SpectraMax ELISA plate reader (Molecular Devices).

Results indicate that treatment with either anti-CD3 antibody or Fc-TL1A alone had no effect on T cell activation, whereas treatment with anti-CD3 antibody in combination with either Fc-TL1A or Fc-scTL1A resulted in similar levels of T cell activation, as determined by elevated levels of serum IFNγ (FIG. 3).

8.4 Example 4. Optimization of Monodispersity

Although the Fc-scTL1A molecule displayed the most favorable properties for therapeutic development, the recombinant protein was approximately 20% oligomer; therefore, the monodispersity of the molecule was optimized. Some TNFSF ligands contain two cysteine residues, and these cysteine residues form an intra-subunit disulfide bond between the membrane-distal CD and EF loops, but are solvent exposed and can be reactive in solution.

Figure 4A:
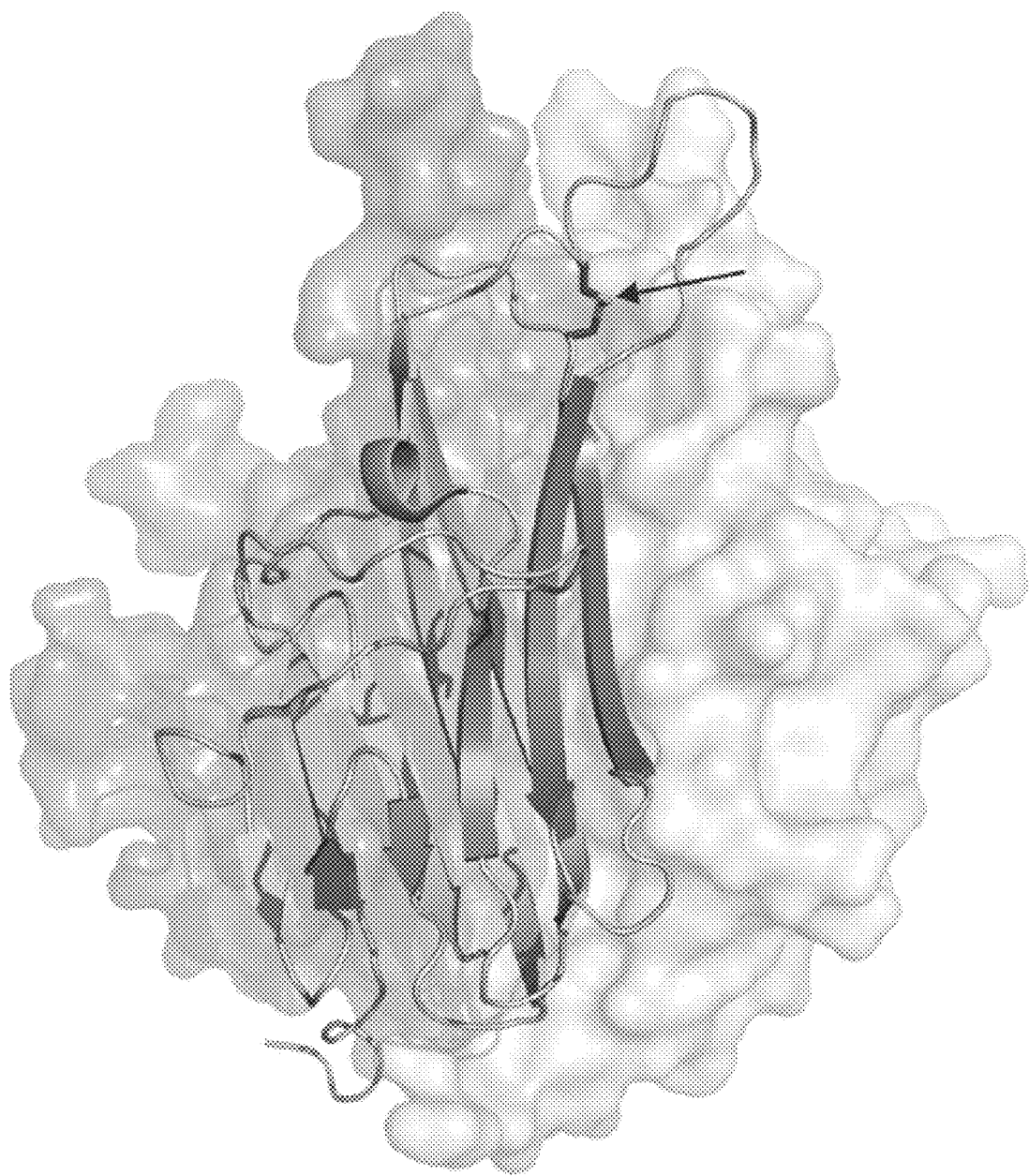

FIG. 4A depicts of the crystal structure of the TL1A trimer (adapted from PDB ID 2RE9) showing the three subunits of TL1A. One subunit is shown in bold the foreground while the other two subunits are shown as light gray surfaces in the background. The position of the C162-C202 disulfide bond, which is critical for maintenance of DR3 binding, is indicated with an arrow.

Figure 4B:
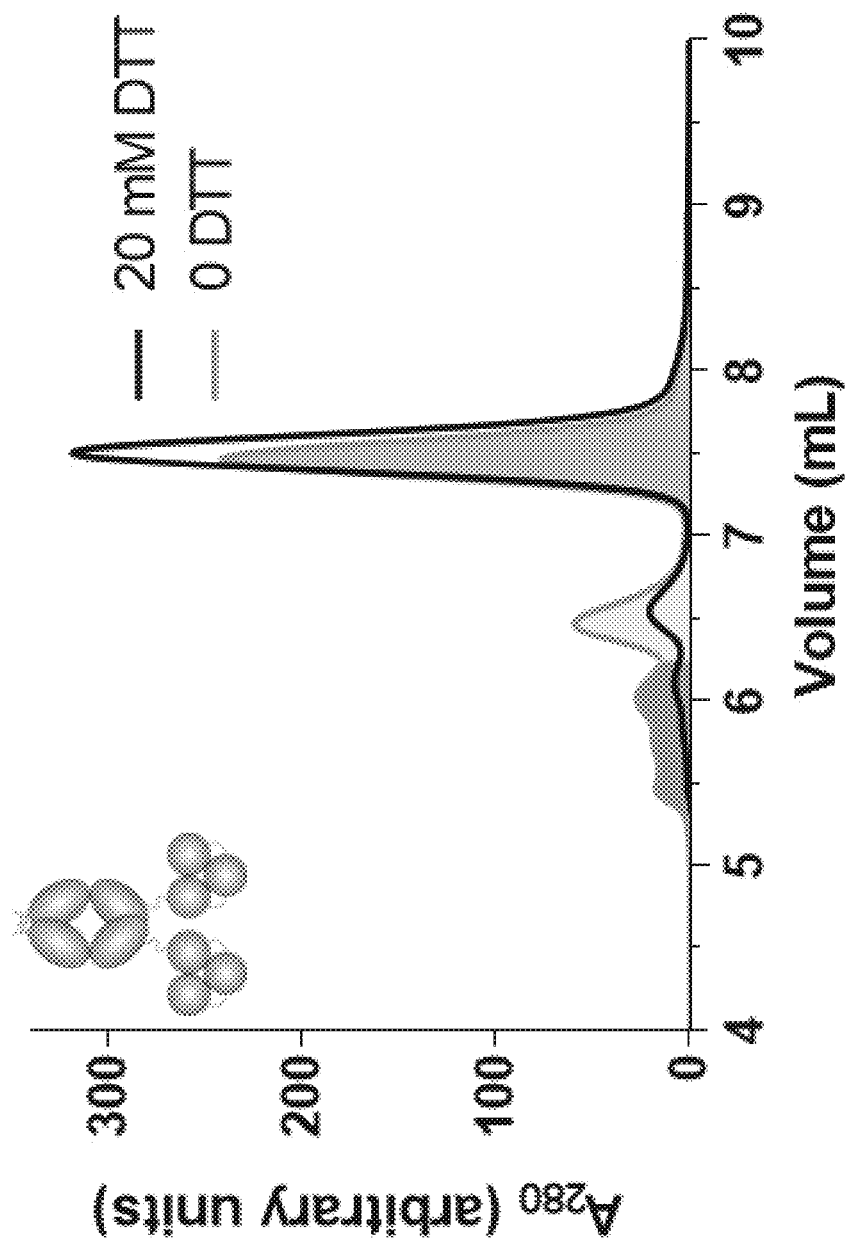

Analytical size-exclusion chromatography (SEC) was used to determine whether the high molecular weight species were mediated by improper inter-molecular disulfide bonding by these cysteine residues. Exemplary results for Fc-scTL1A (SEQ ID NO:87) are shown in FIG. 4B. After reduction with 20 mM DTT, the population of high molecular weight species in the Fc-scTL1A molecule was decreased from 22% to less than 10%, suggesting that improper inter-molecular disulfide bonding was largely responsible for the high molecular weight species.

Figure 4C:
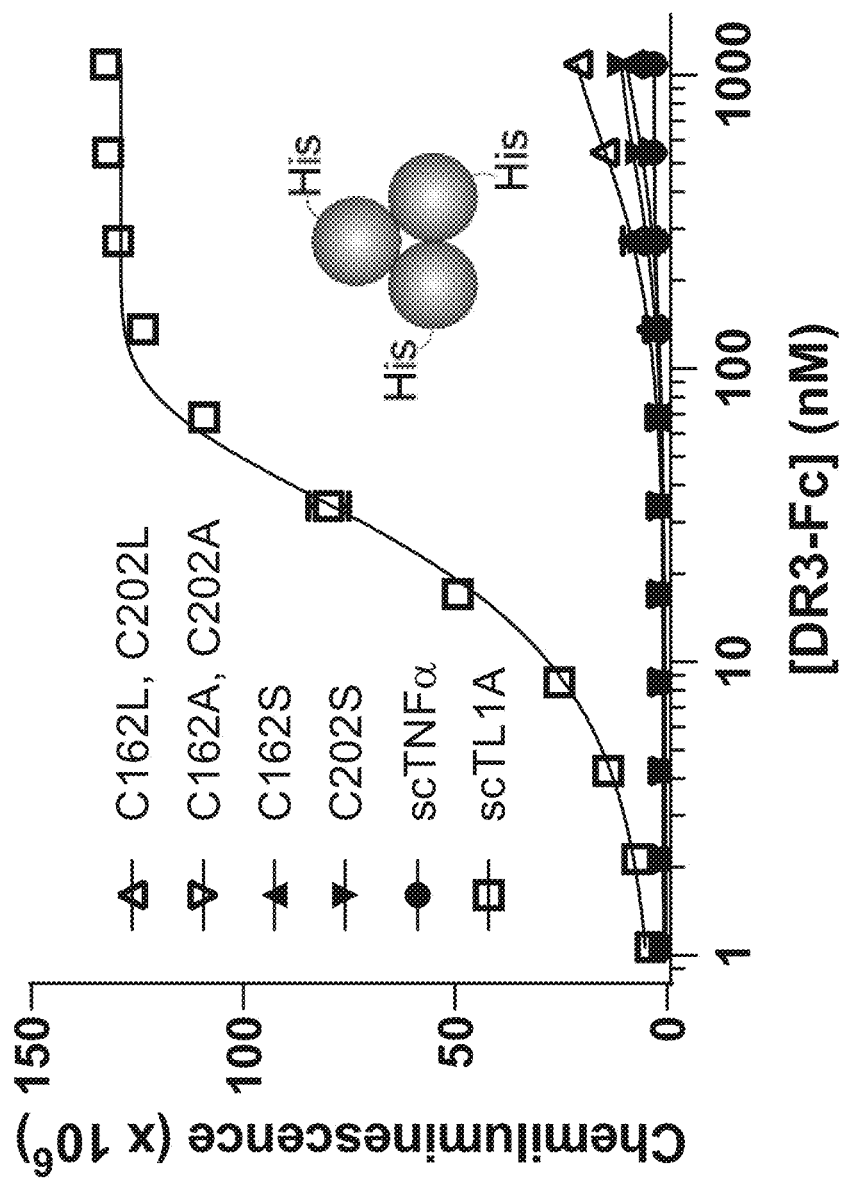

C162 and C202 residues were altered and ELISA analysis was used to determine the ability of C162/C202 mutants to bind DR3. Surprisingly, mutation of C162, C202 or both cysteines to either serine, leucine, or alanine resulted in a complete loss of binding to DR3 (FIG. 4C).

Cysteine mutants were tested for maintenance of DcR3 binding using surface plasmon resonance (SPR). Briefly, goat anti-human-Fc was immobilized at 30 µg/ml, acetate buffer, pH 5.0 on vertical channels L1-L6. DR3 and DcR3 were immobilized at 5 or 1 µg/mL. For either indirect capture format or immobilization formats, the desired absolute ligand levels were the range that can produce final analyte binding signals between 50-200 resonance units (RUs). BSA was used as a non-binding analyte control. Experiments were performed at 25° C., with PBST (1× DPBS, 0.005% Tween) as the running buffer. A koff screen for each of the 14 TL1A variants was performed first at 1 µM to evaluate the optimal capture level, analyte concentration, and dissociation time needed. Each of the variants was analyzed at 0.1 µM in 3 fold dilution series over DcR3 captured 4 different ligand densities. Raw data were processed and analyzed in ProteOn Manager software (BioRad, version 3.1.0.6). Kinetic analysis was done by grouping the kon, koff and RUmax, and holding the refractive index (RI) constant and equal to zero. The chi-square (Chi2) value was used to assess the quality of the fit. An arbitrary range was defined for a fit with "good", "acceptable", "suboptimal" and "poor" quality. Due to weak binding to DR3 and bi-phasic binding to DcR3, data were evaluated only qualitatively.

Figure 4D:
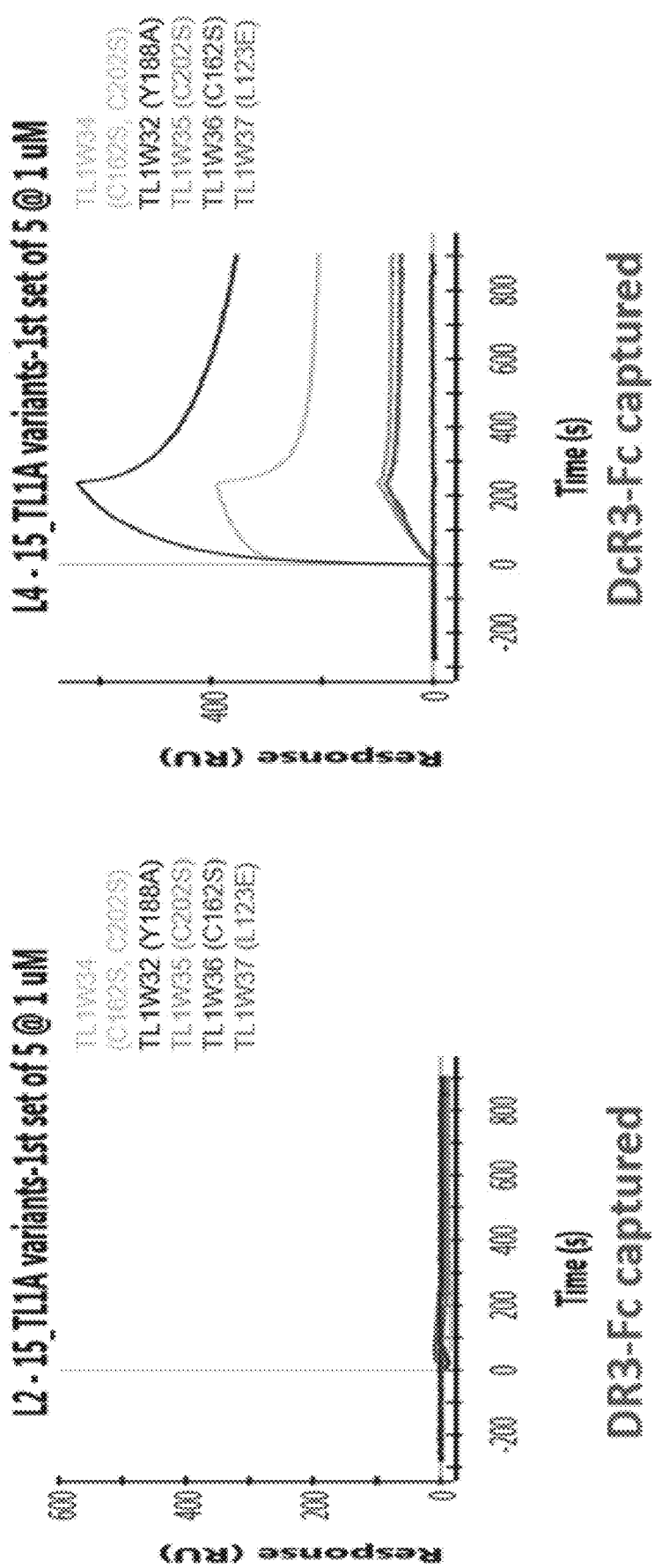

Results indicate that TL1W32 (Y188A) had the strongest binding to DcR3, while TL1W34 (C162S, C202S) also showed strong binding, and TL1W35 (C202S) and TL1W37 (L123E) had weaker binding (FIG. 4D, right panels). The SPR-based binding analysis confirmed that the C162S, C202S TL1A variant could bind only DcR3 but not DR3 (FIG. 4D, right and left panels, respectively). These data suggested that either the cysteine residues themselves were involved in binding DR3 but not DcR3 or that the disulfide bond was necessary for a structural conformation required for binding DR3 only.

Since these two cysteine residues were shown to be required for binding to DR3, it was next determined whether formation of the high-molecular weight (HMW) species could be prevented by employing a redox approach during purification of Fc-scTL1A. Exemplary results of analytical SEC analysis of Fc-scTL1A (TL1W14; SEQ ID NO:87) after protein A purification, in non-reducing buffer (black trace), after redox in 1×PBS (dark grey trace) and after redox in low salt buffer (light grey trace) are shown in FIG. 4E.

Figure 4E:
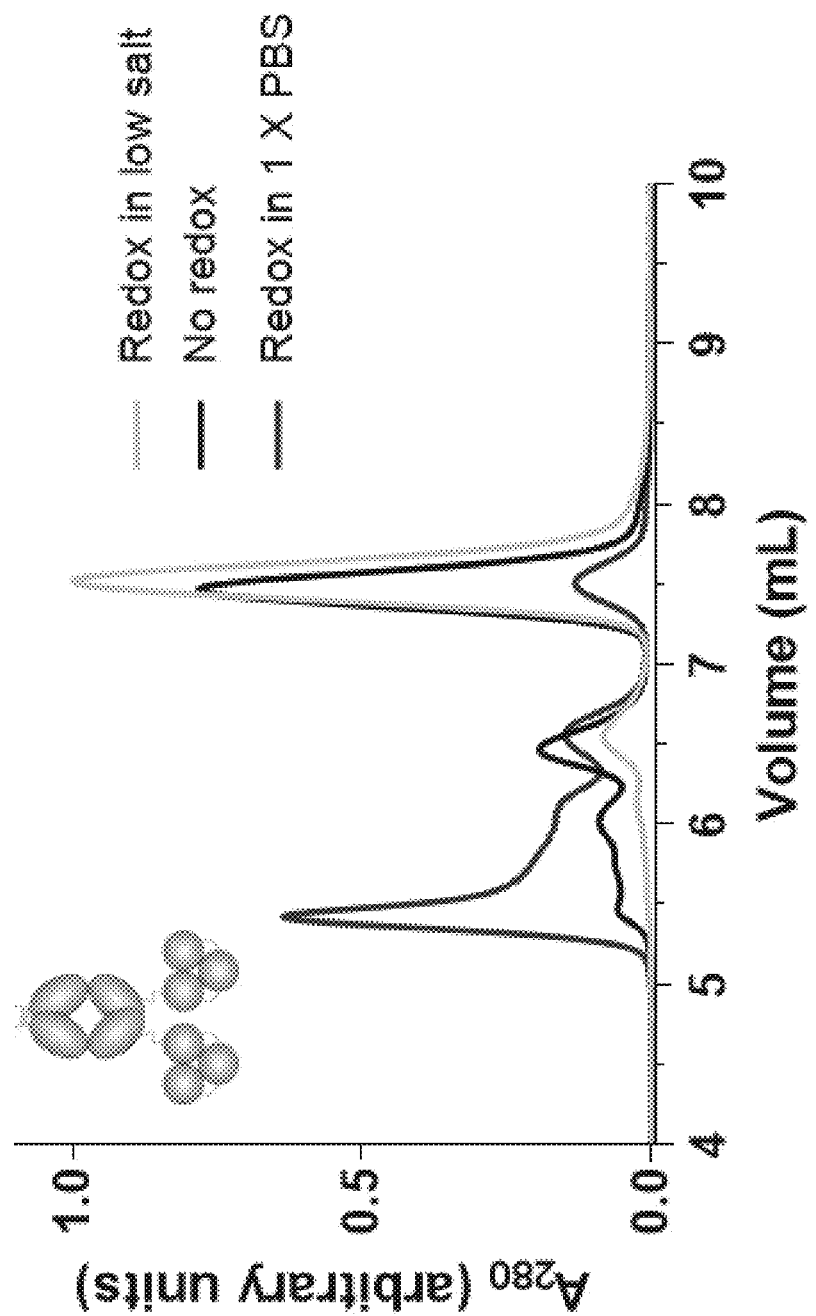
Figure 4F:
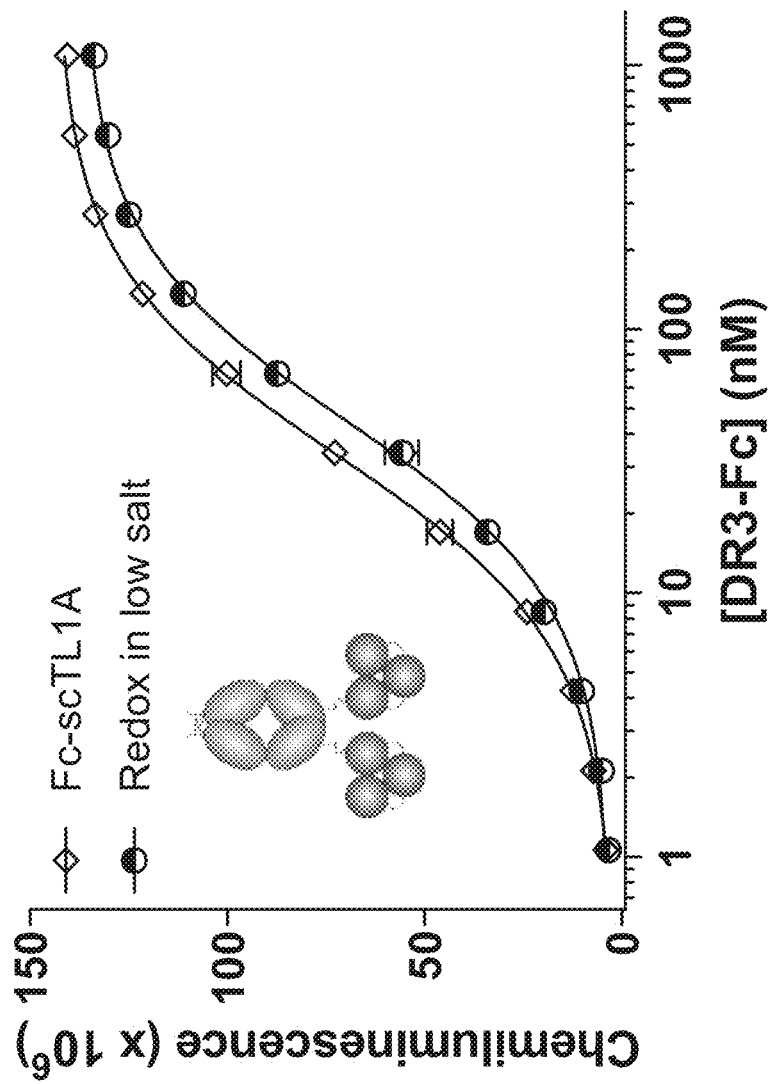
Figure 4G:
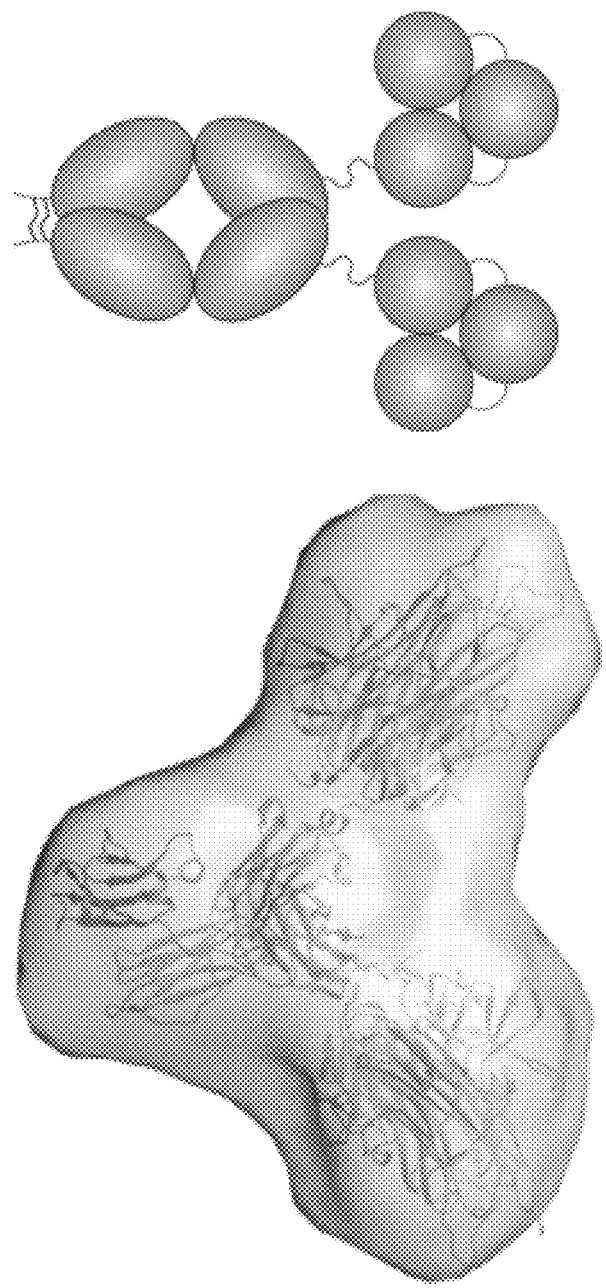

Incubation of Fc-scTL1A with 20 mM DTT followed by dialysis into 1×PBS resulted in approximately 70% HMW species, suggesting that the intermolecular interactions were not solely due to disulfide bonding (FIG. 4E, "Redox in 1×PBS"). Thus, if TL1A could form transient non-covalent interactions that favored formation of intermolecular disulfide bonds, then these interactions could be inhibited by changing buffer conditions. Redox in a buffer consisting of only 20 mM sodium phosphate, pH 6.8 (without additional NaCl) resulted in approximately 90% target dimeric species that retained identical binding properties as the SEC-purified material (FIGS. 4E and 4F, "Redox in low salt").

8.5 Example 5. Solution X-Ray Scattering

Although the trimeric interface was thought to represent a tight binding site for monomer subunits of the TL1A trimer, individual TL1A subunits in the scTL1A format could have paired in trans with subunits from another TL1A molecule or with subunits from the TL1A molecule on the adjacent Fc subunit. To address the latter, the low-resolution structural model of Fc-scTL1A was determined by solution x-ray scattering.

Briefly, scattering data collection was carried out on an x-ray source at 20° C. Fc-scTL1A samples were analyzed in 20 mM HEPES HCl pH 6.5, 100 mM NaCl. To limit radiation damage, the samples were continuously oscillated inside the cuvette during the exposures. Independent measurements were collected from each sample at different concentrations (3, 6, or 12 mg/mL), checking the linear dependence of the scattering intensity at zero angle as a function of concentration to ensure lack of aggregation. Data normalization, solvent subtraction and Guinier analysis were done using the BioXTAS RAW software. Data analysis was carried out using the ATSAS software suite, including the programs GNOM (Otwinowski and Minor, 1997), used to calculate the distance distribution function P(r), and DAMMIF (Franke and Svergun, 2009), used in automated bead modelling for shape determination. To generate the models of Fc-scTL1A, two-fold symmetry constraints were imposed, which produces more reliable envelopes by reducing noise (Blanchet and Svergun, 2013). For each sample, five independent shape models calculated with DAMMIF were averaged using DAMAVER to produce the final ab initio envelopes. Surface rending was done with Chimera (Pettersen et al., 2004).

Exemplary results of the low-resolution structural model of Fc-scTL1A, as determined by solution x-ray scattering are shown in FIG. 4G, FIG. 7A-7D, and Table 3. The reconstructed molecular envelope suggests that the two TL1A moieties are splayed away from one another in the structure and that pairing across subunits was unlikely. Additionally, the consistency in scattering curves across three concentrations (3, 6, and 12 mg/mL) suggested the molecule did not undergo concentration-dependent aggregation.

TABLE 3

Solution X-Ray scattering analysis

| Concentration | 0 (extrapolated) | 2.97 | 5.93 | 11.85 |
|---|---|---|---|---|
| I(0)/concentration | 1.55 | 1.5 | 1.53 | 1.55 |
| Guinier Points | 1 | 3 | 3 | 3 |
|  | 9 | 13 | 12 | 12 |
| Quality | 99% | 86% | 90% | 91% |
| RgGuinier | 48.6 | 48.7 | 49.4 | 48.9 |
| RgP(r) | 49.8 | 49.4 | 49.4 | 48.5 |
| Dmax | 166 | 163 | 166 | 160 |
| VPorod (Å3) | 341.8 | 331.4 | 332.2 | 320.9 |
| VDAM (Å3) | 387.6 | 375.9 | 383.8 | 372.8 |
| MWPorod (kDa) | 213.6 | 207.1 | 207.6 | 200.6 |
| MWPorod (kDa) | 193.8 | 188 | 191.9 | 186.4 |

8.6 Example 6. Design of Engineered TL1A Ligands and Testing for Selectivity TL1A-mediated co-stimulation of T cells can be dampened in vivo by circulating DcR3. TL1A ligands were engineered to generate a variant of TL1A which would retain binding to DR3 but which would not be bound up by DcR3.

Figure 5A:
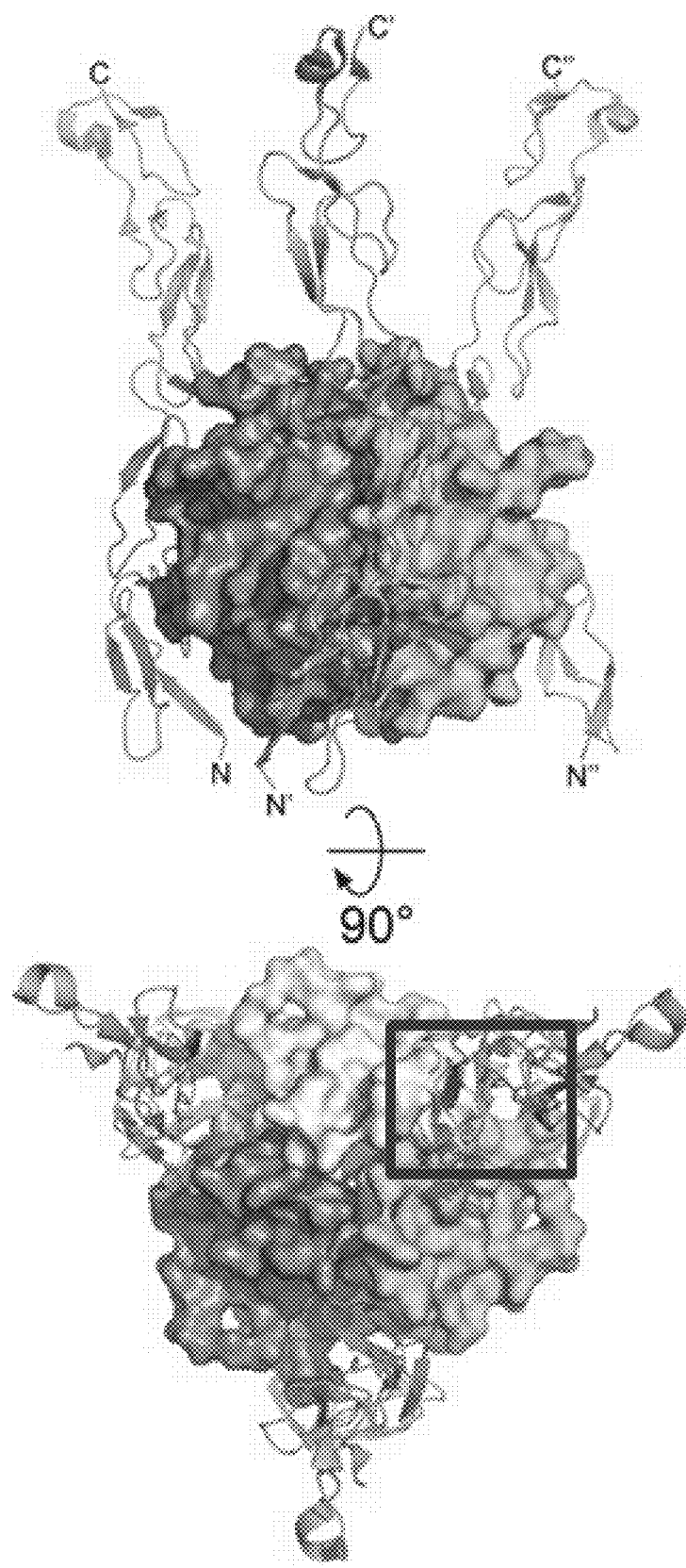

Mutations can be made in TL1A to modulate its interactions with DcR3. In particular, mutation of E120A, E122A, L123A, G124D, Y188F, K240A, E241A, D242A, and K243A have been shown to disrupt interaction with DcR3, although the effect of these mutations on DR3 binding was not tested (Zhan et al., 2009). Although the cysteine-rich domains of DR3 and DcR3 are structurally similar (FIGS. 5A and 5B), they share only 26% sequence identity, presenting an opportunity for differential binding by a TL1A variant.

Models of DR3 were generated using the protein modeling component of MOE (2016.08; Chemical Computing Group, Inc., Montreal, QC, Canada). The sequence of DR3 (Uniprot ID O95407) and the structure of TL1A bound to DcR3 (PDB ID 3K51) (Zhan et al., 2011) were used as inputs to model TL1A bound to DR3 to guide mutagenesis.

Figure 5B:
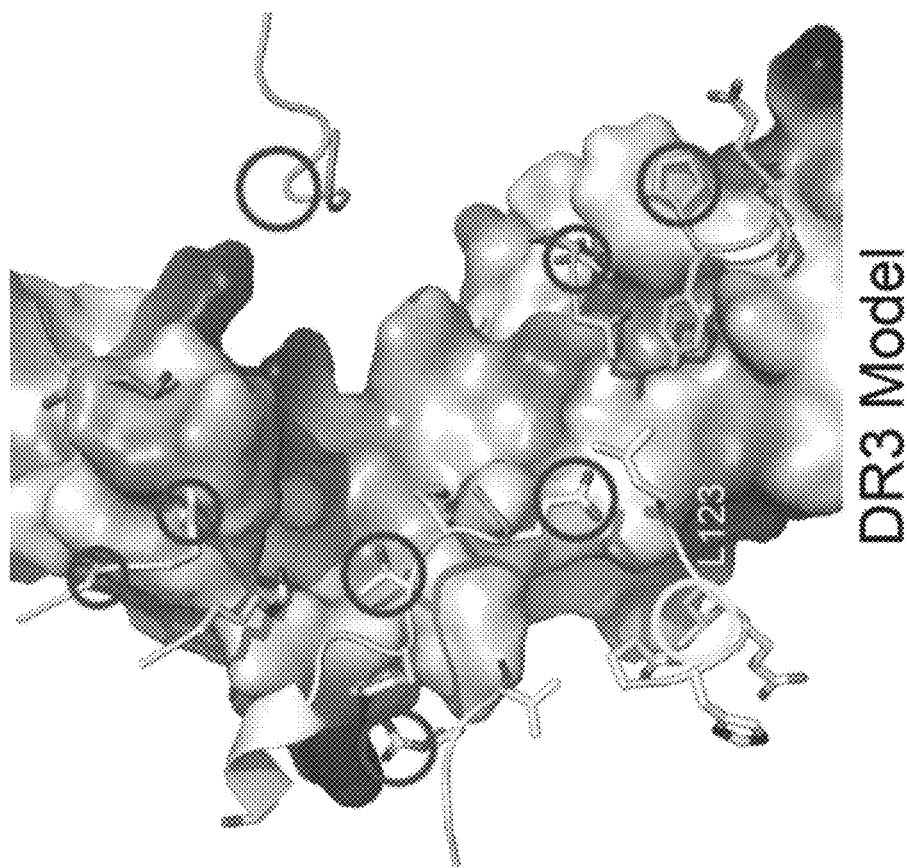
Figure 5B:
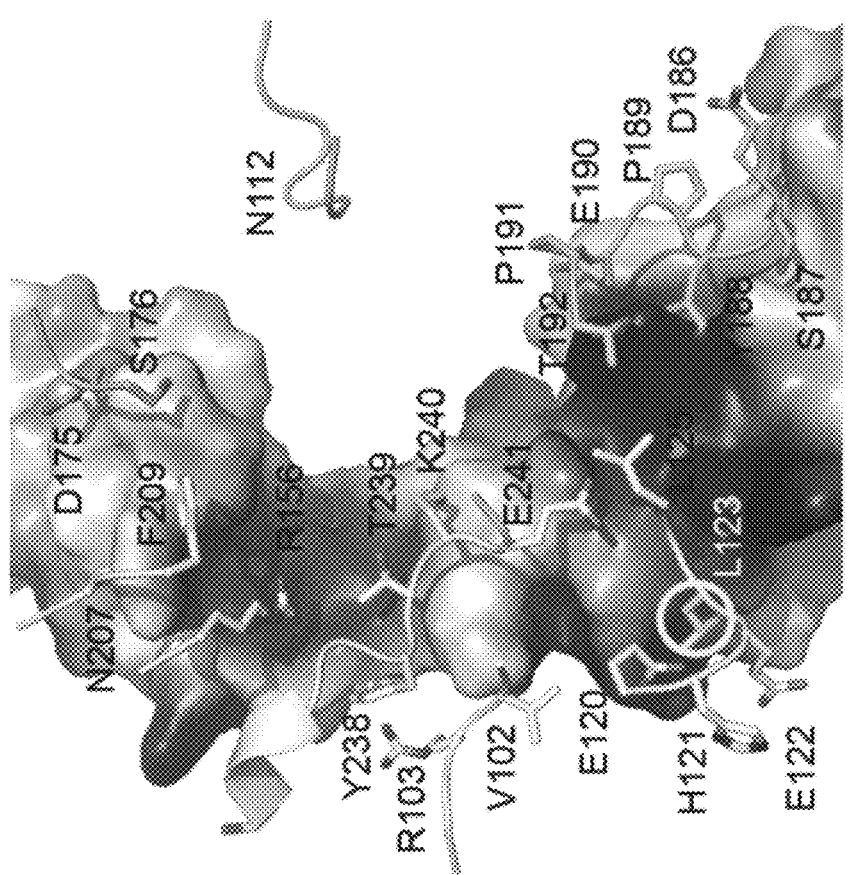

Several residues in TL1A appeared to make significantly different contacts with DcR3 compared to DR3, and these were chosen for mutagenesis (FIG. 5B, circled residues). The identities of the mutations were chosen to optimize the side-chain interactions between TL1A and DR3 and to simultaneously disrupt interactions with DcR3.

Variants of TL1A were generated and tested for binding to DR3 and DcR3 by ELISA as described. Exemplary results of DR3 and DcR3 are shown in FIGS. 5C and 5D, respectively, and results are summarized in Table 4.

Figure 5C:
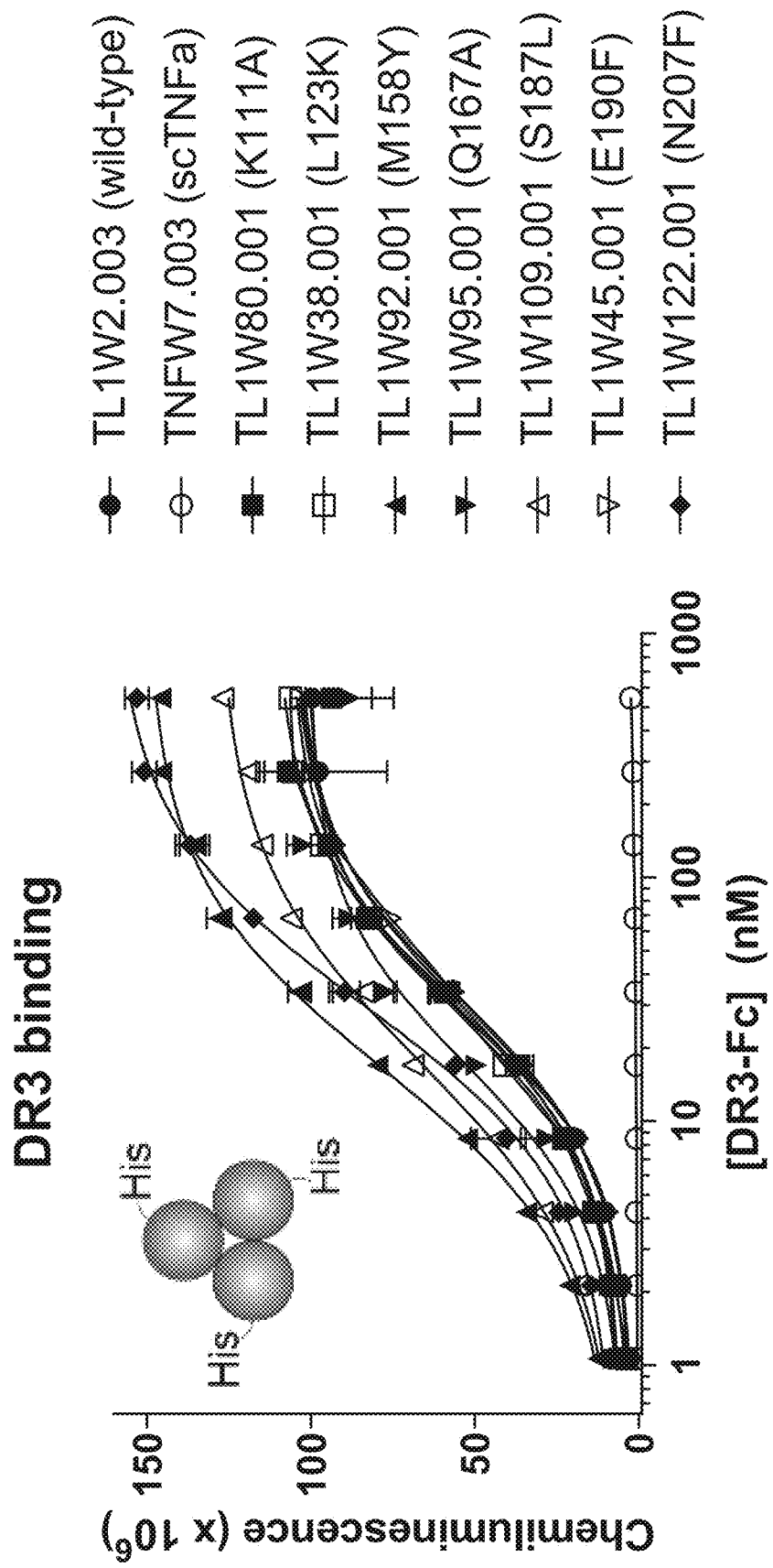
Figure 5D:
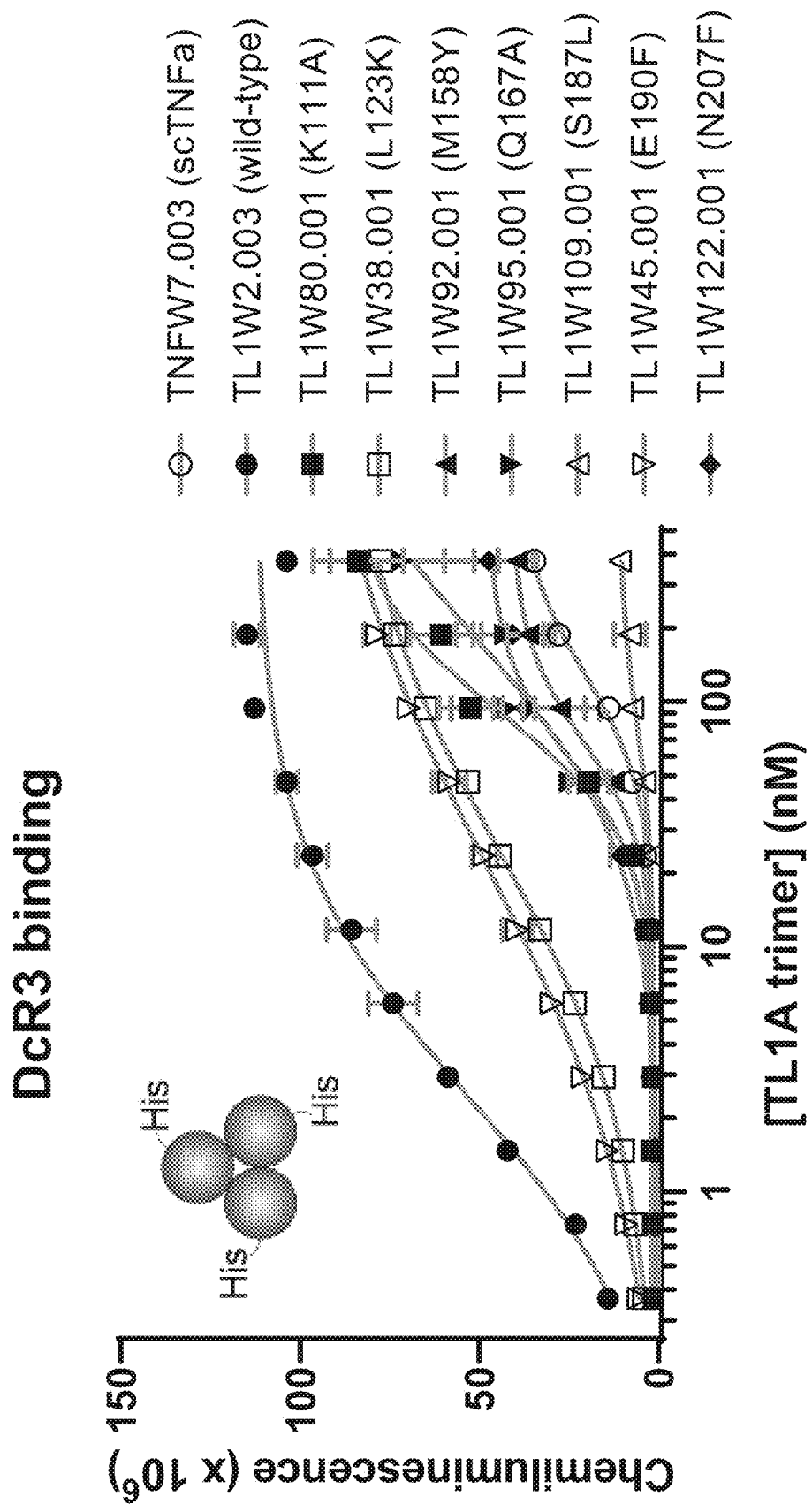
Figure 8A:
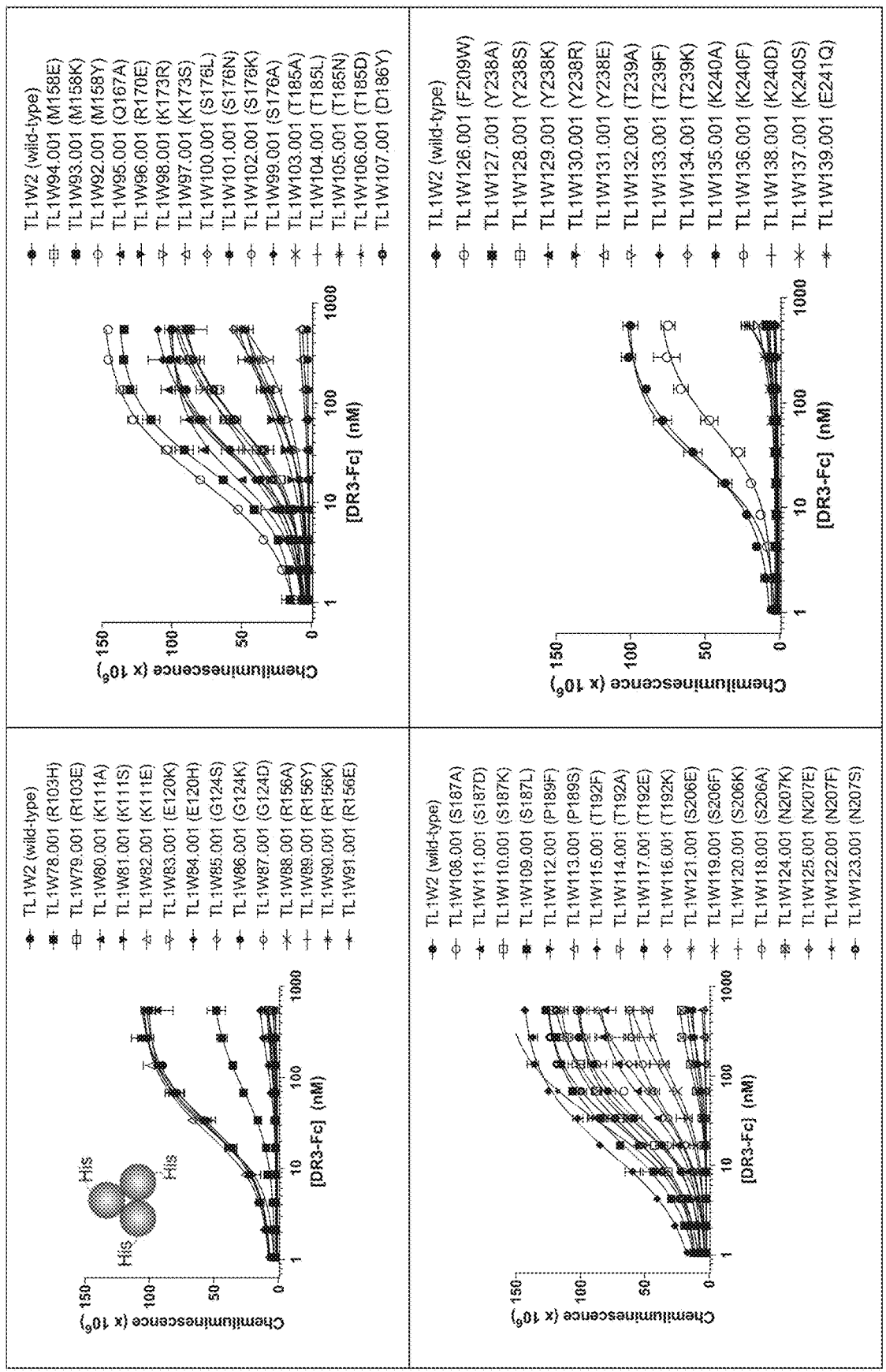
Figure 8B:
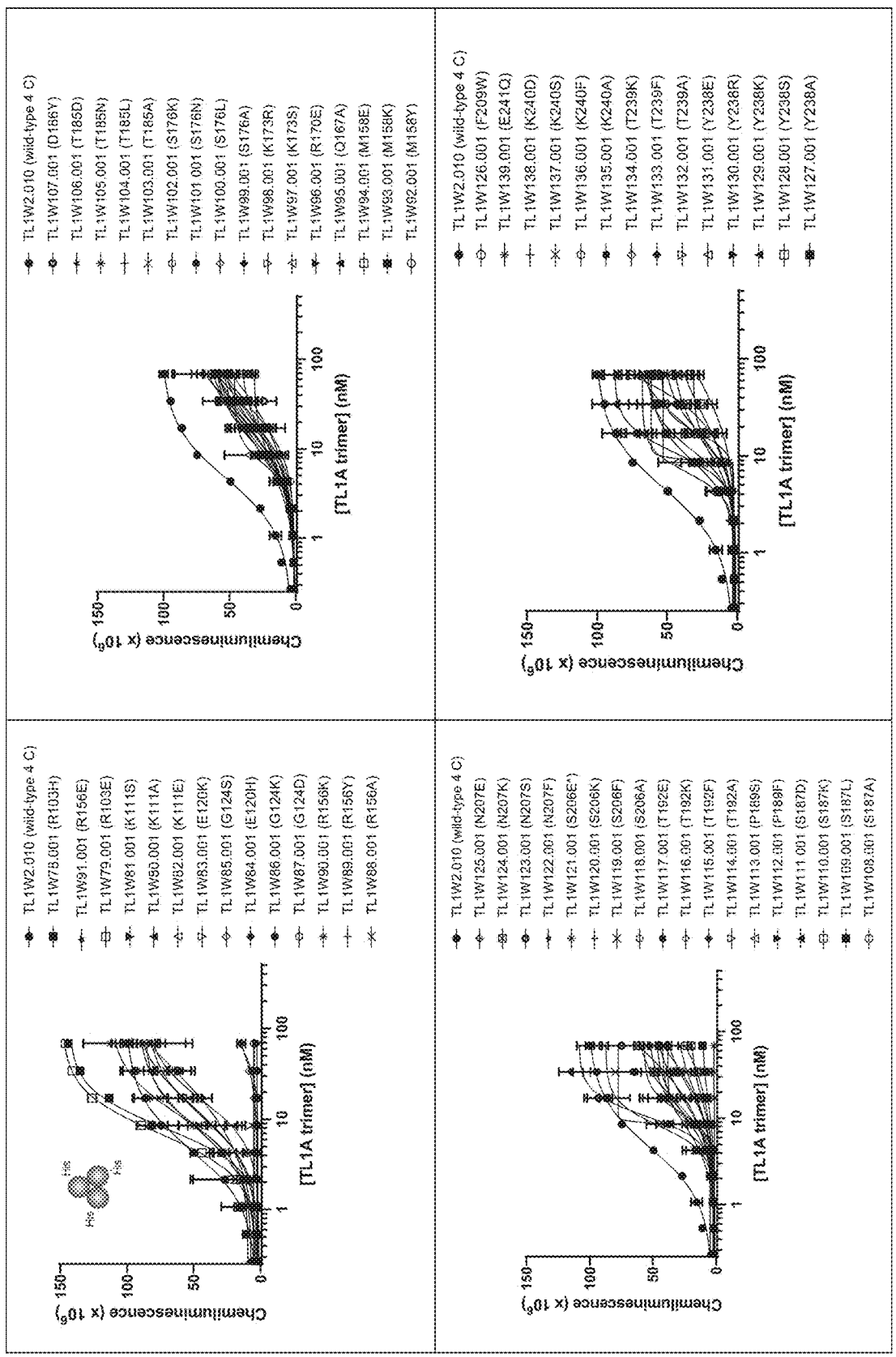
Figure 8C:
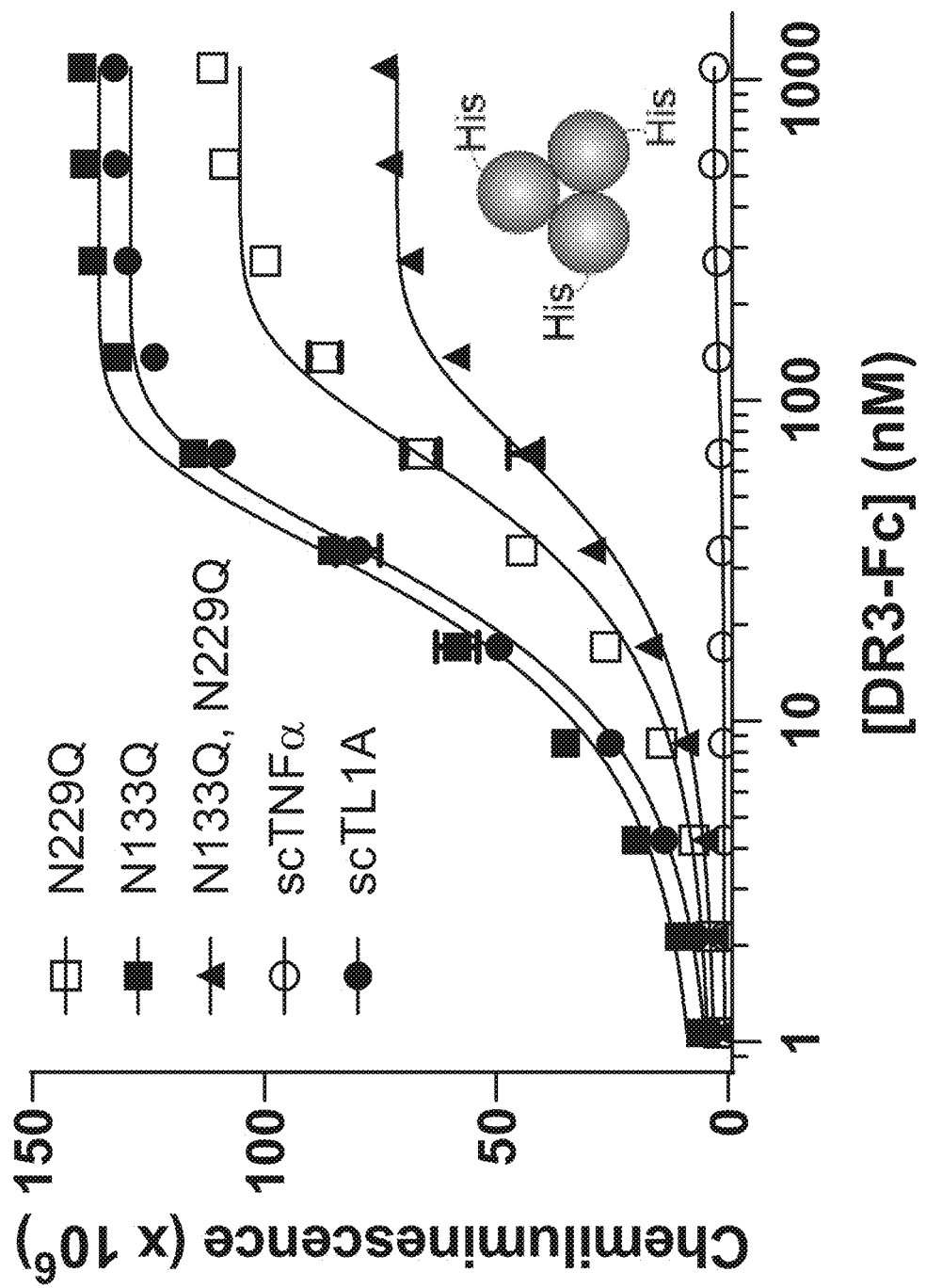

Of the 83 variants tested in His-TL1A format, several retained or enhanced binding to DR3 and disrupted binding to DcR3 (Table 4, FIGS. 5C and 5D, respectively, and FIG. 8A and ion, respectively). In particular, mutation of L123, Y188, or E241 was shown to significantly disrupt binding to DcR3 in both experiments. Non-antibody biologics often display heterogeneity of glycosylation which presents a challenge for characterization of clinical batches. Mutants were also designed to assess whether glycosylation was involved in TL1A binding to DR3. Mutation of N133Q but not N229Q in TL1A could maintain binding affinity to DR3 with no apparent changes in solubility or expression (FIG. 8C).

TABLE 4

ELISA results for TL1A variants binding to DR3 and DcR3

| Molecule (SEQ ID NO) | EC50 (nM): DR3 | Rel EC50 (nM) DR3 | EC50 (nM): DcR3 | Rel EC50 (nM) DcR3 |
|---|---|---|---|---|
| Fc-scTL1A (SEQ ID NO: 87) | 26.2 ± 1.9 | 1.0 | 6.5 ± 0.9 | 1.0 |
| TL1W2 (wt) (SEQ ID NO: 20) | 26.2 | 1.0 | 4.6 | 1.0 |
| TL1W33 (R103A) (SEQ ID NO: 83) | 25 | 1.0 | 3.3 | 0.7 |
| TL1W78 (R103H) (SEQ ID NO: 81) | 77.2 | 2.9 | 8.1 | 1.8 |
| TL1W31 (R103Q) (SEQ ID NO: 80) | 9.5 | 0.4 | 2.5 | 0.5 |
| TL1W79 (R103E) (SEQ ID NO: 82) | 203.7 | 7.8 | 7.1 | 1.5 |
| TL1W80 (K111A) (SEQ ID NO: 79) | 30 | 1.1 | 16.3 | 3.5 |
| TL1W81 (K111S) (SEQ ID NO: 1) | 34.4 | 1.3 | 50.9 | 11.1 |
| TL1W82 (K111E) (SEQ ID NO: 78) | 25.8 | 1.0 | 10.6 | 2.3 |
| TL1W30 (N112E) (SEQ ID NO: 77) | 16.4 | 0.6 | 4.7 | 1.0 |
| TL1W42 (F114A) (SEQ ID NO: 76) | 77.7 | 3.0 | 11.4 | 2.5 |
| TL1W41 (E120A) (SEQ ID NO: 75) | 100.5 | 3.8 | 32.6 | 7.1 |
| TL1W83 (E120K) (SEQ ID NO: 2) | NA |  | 2.2 | 0.5 |
| TL1W84 (E120H) (SEQ ID NO: 3) | 182.3 | 7.0 | 55.7 | 12.1 |
| TL1W39 (L123G) (SEQ ID NO: 73) | 184.3 | 7.0 | 38.2 | 8.3 |
| TL1W40 (L123S) (SEQ ID NO: 4) | 30.7 | 1.2 | 16.4 | 3.6 |
| TL1W37 (L123E) (SEQ ID NO: 74) | 422.9 | 16.1 | 24.3 | 5.3 |
| TL1W38 (L123K) (SEQ ID NO: 72) | 29.5 | 1.1 | 24.7 | 5.4 |
| TL1W85 (G124S) (SEQ ID NO: 5) | 295.8 | 11.3 | 57.1 | 12.4 |
| TL1W86 (G124K) (SEQ ID NO: 6) | NA |  | 2.9 | 0.6 |
| TL1W87 (G124D) (SEQ ID NO: 71) | 14.8 | 0.6 | NA | NA |
| TL1W88 (R156A) (SEQ ID NO: 70) | NA |  | 13.5 | 2.9 |
| TL1W89 (R156Y) (SEQ ID NO: 7) | NA |  | 8.0 | 1.7 |
| TL1W90 (R156K) (SEQ ID NO: 68) | 187.6 | 7.2 | 11.0 | 2.4 |
| TL1W91 (R156E) (SEQ ID NO: 69) | NA |  | 8.3 | 1.8 |
| TL1W92 (M158Y) (SEQ ID NO: 8) | 16.6 | 0.6 | 12.6 | 2.7 |
| TL1W93 (M158K) (SEQ ID NO: 66) | 22.5 | 0.9 | 55.9 | 12.1 |
| TL1W94 (M158E) (SEQ ID NO: 67) | 58.7 | 2.2 | 18.7 | 4.1 |
| TL1W95 (Q167A) (SEQ ID NO: 65) | 17.1 | 0.7 | 32.0 | 7.0 |
| TL1W96 (R170E) (SEQ ID NO: 64) | 87 | 3.3 | 16.4 | 3.6 |
| TL1W97 (K173S) (SEQ ID NO: 9) | 131.3 | 5.0 | 6.7 | 1.5 |

TABLE 4-continued

ELISA results for TL1A variants binding to DR3 and DcR3

| Molecule (SEQ ID NO) | EC50 (nM): DR3 | Rel EC50 (nM) DR3 | EC50 (nM): DcR3 | Rel EC50 (nM) DcR3 |
|---|---|---|---|---|
| TL1W98 (K173R) (SEQ ID NO: 10) | 2054 | 78.4 | 27.8 | 6.0 |
| TL1W99 (S176A) (SEQ ID NO: 63) | 34.8 | 1.3 | 11.5 | 2.5 |
| TL1W100 (S176L) (SEQ ID NO: 61) | 323.9 | 12.4 | 15.0 | 3.3 |
| TL1W101 (S176N) (SEQ ID NO: 60) | NA | | 20.4 | 4.4 |
| TL1W102 (S176K) (SEQ ID NO: 62) | 181.5 | 6.9 | 29.2 | 6.3 |
| TL1W103 (T185A) (SEQ ID NO: 59) | 57.9 | 2.2 | 11.5 | 2.5 |
| TL1W104 (T185L) (SEQ ID NO: 57) | 49.4 | 1.9 | 19.3 | 4.2 |
| TL1W105 (T185N) (SEQ ID NO: 56) | 179.5 | 6.9 | 11.3 | 2.4 |
| TL1W106 (T185D) (SEQ ID NO: 58) | 123.5 | 4.7 | 79.9 | 17.4 |
| TL1W107 (D186Y) (SEQ ID NO: 11) | 63.8 | 2.4 | 6.2 | 1.4 |
| TL1W108 (S187A) (SEQ ID NO: 55) | 39.1 | 1.5 | NA | NA |
| TL1W109 (S187L) (SEQ ID NO: 52) | 17.7 | 0.7 | 15.5 | 3.4 |
| TL1W110 (S187K) (SEQ ID NO: 53) | 33.7 | 1.3 | 15.8 | 3.4 |
| TL1W111 (S187D) (SEQ ID NO: 54) | 44.2 | 1.7 | 16.7 | 3.6 |
| TL1W32 (Y188A) (SEQ ID NO: 51) | 565.1 | 21.6 | 7.6 | 1.7 |
| TL1W43 (Y188S) (SEQ ID NO: 50) | 206.6 | 7.9 | 72.2 | 15.7 |
| TL1W29 (P189A) (SEQ ID NO: 49) | 710.1 | 27.1 | 7.6 | 1.7 |
| TL1W44 (P189K) (SEQ ID NO: 47) | 167.6 | 6.4 | 59.1 | 12.8 |
| TL1W112 (P189F) (SEQ ID NO: 48) | 202.4 | 7.7 | 66.1 | 14.4 |
| TL1W113 (P189S) (SEQ ID NO: 12) | 1002 | 38.2 | 19.8 | 4.3 |
| TL1W28 (E190G) (SEQ ID NO: 13) | 22.6 | 0.9 | 5.7 | 1.2 |
| TL1W45 (E190F) (SEQ ID NO: 14) | 31.4 | 1.2 | NB | |
| TL1W114 (T192A) (SEQ ID NO: 46) | 23.3 | 0.9 | 10.0 | 2.2 |
| TL1W115 (T192F) (SEQ ID NO: 44) | 14.2 | 0.5 | 10.6 | 2.3 |
| TL1W116 (T192K) (SEQ ID NO: 43) | 77 | 2.9 | 23.3 | 5.1 |
| TL1W117 (T192E) (SEQ ID NO: 45) | 112.9 | 4.3 | 12.0 | 2.6 |
| TL1W118 (S206A) (SEQ ID NO: 42) | 41.7 | 1.6 | 8.8 | 1.9 |
| TL1W119 (S206F) (SEQ ID NO: 40) | 87.5 | 3.3 | 8.1 | 1.8 |
| TL1W120 (S206K) (SEQ ID NO: 39) | 114.4 | 4.4 | 91.0 | 19.8 |
| TL1W121 (S206E) (SEQ ID NO: 41) | 105.3 | 4.0 | 17.2 | 3.7 |
| TL1W25 (N207A) (SEQ ID NO: 38) | 13.4 | 0.5 | 3.7 | 0.8 |
| TL1W122 (N207F) (SEQ ID NO: 36) | 30.2 | 1.2 | 10.6 | 2.3 |
| TL1W123 (N207S) (SEQ ID NO: 15) | 26.8 | 1.0 | 8.6 | 1.9 |
| TL1W124 (N207K) (SEQ ID NO: 35) | 110.1 | 4.2 | 15.4 | 3.4 |
| TL1W125 (N207E) (SEQ ID NO: 37) | 506.1 | 19.3 | 9.8 | 2.1 |
| TL1W24 (F209A) (SEQ ID NO: 34) | 280.6 | 10.7 | 30.7 | 6.7 |
| TL1W126 (F209W) (SEQ ID NO: 16) | 56.8 | 2.2 | 13.7 | 3.0 |
| TL1W127 (Y238A) (SEQ ID NO: 33) | 4624 | 176.5 | 8.9 | 1.9 |
| TL1W128 (Y238S) (SEQ ID NO: 29) | NA | | 10.5 | 2.3 |
| TL1W129 (Y238K) (SEQ ID NO: 31) | 445.6 | 17.0 | 9.0 | 2.0 |
| TL1W130 (Y238R) (SEQ ID NO: 30) | NA | | 16.9 | 3.7 |
| TL1W131 (Y238E) (SEQ ID NO: 32) | 300.3 | 11.5 | 6.6 | 1.4 |
| TL1W132 (T239A) (SEQ ID NO: 28) | 144.4 | 5.5 | 27.2 | 5.9 |
| TL1W27 (T239E) (SEQ ID NO: 27) | | 0.0 | 34.3 | 7.5 |
| TL1W133 (T239F) (SEQ ID NO: 26) | NA | | 10.8 | 2.3 |
| TL1W134 (T239K) (SEQ ID NO: 25) | NA | | 21.5 | 4.7 |
| TL1W46 (T239W) (SEQ ID NO: 17) | 283.7 | 10.8 | NA | NA |
| TL1W135 (K240A) (SEQ ID NO: 24) | NA | | 8.5 | 1.9 |
| TL1W136 (K240F) (SEQ ID NO: 22) | 265.5 | 10.1 | 178.1 | 38.7 |
| TL1W137 (K240S) (SEQ ID NO: 18) | 335.7 | 12.8 | 11.8 | 2.6 |
| TL1W138 (K240D) (SEQ ID NO: 23) | NA | | 59.5 | 12.9 |
| TL1W47 (E241A) (SEQ ID NO: 21) | 259.9 | 9.9 | 1311.0 | 285.0 |
| TL1W33 (E241L) (SEQ ID NO: 83) | NA | | 5.7 | 1.2 |
| TL1W139 (E241Q) (SEQ ID NO: 19) | NA | | 17.3 | 3.8 |

Figure 5E:
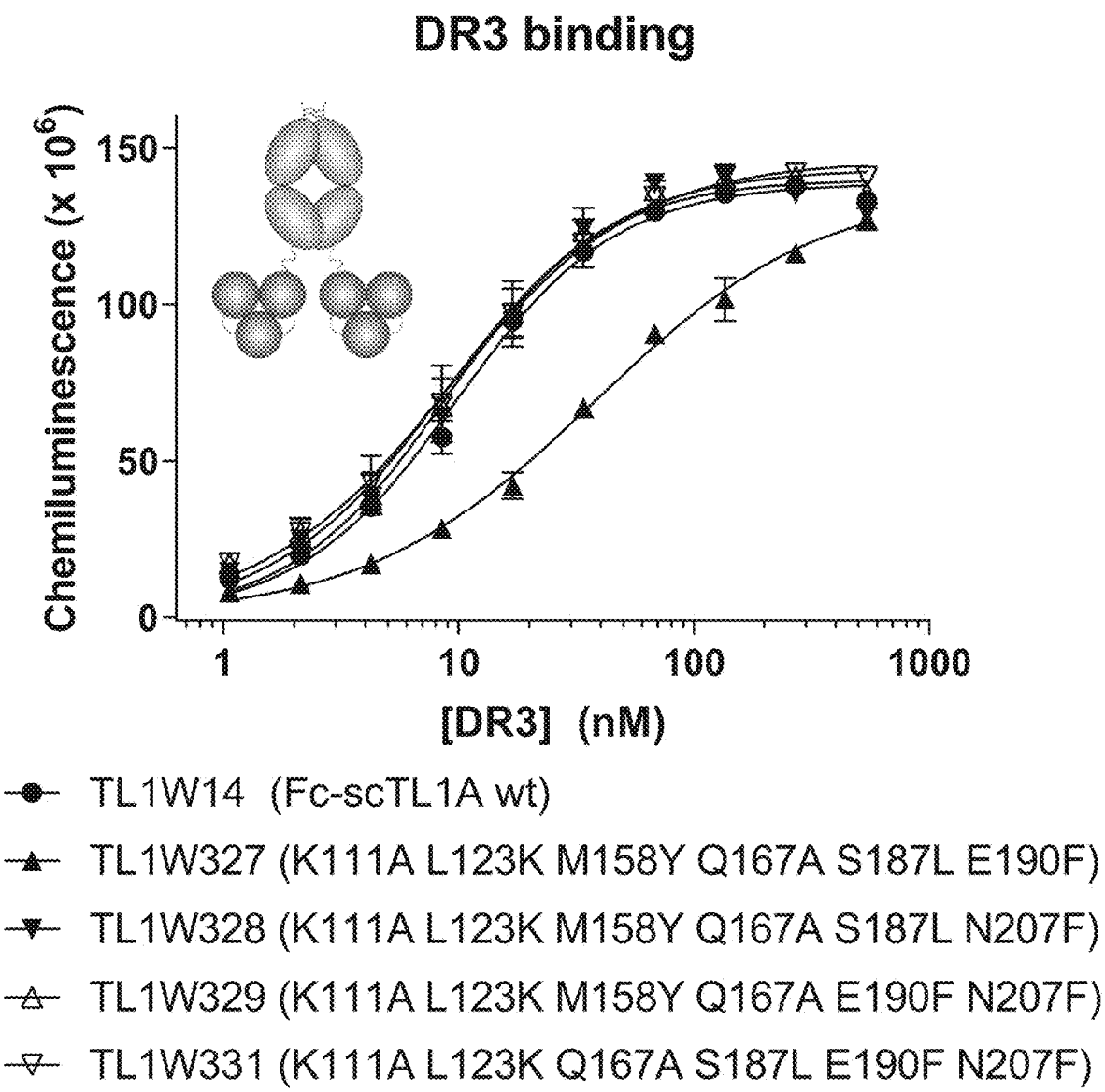
Figure 5F:
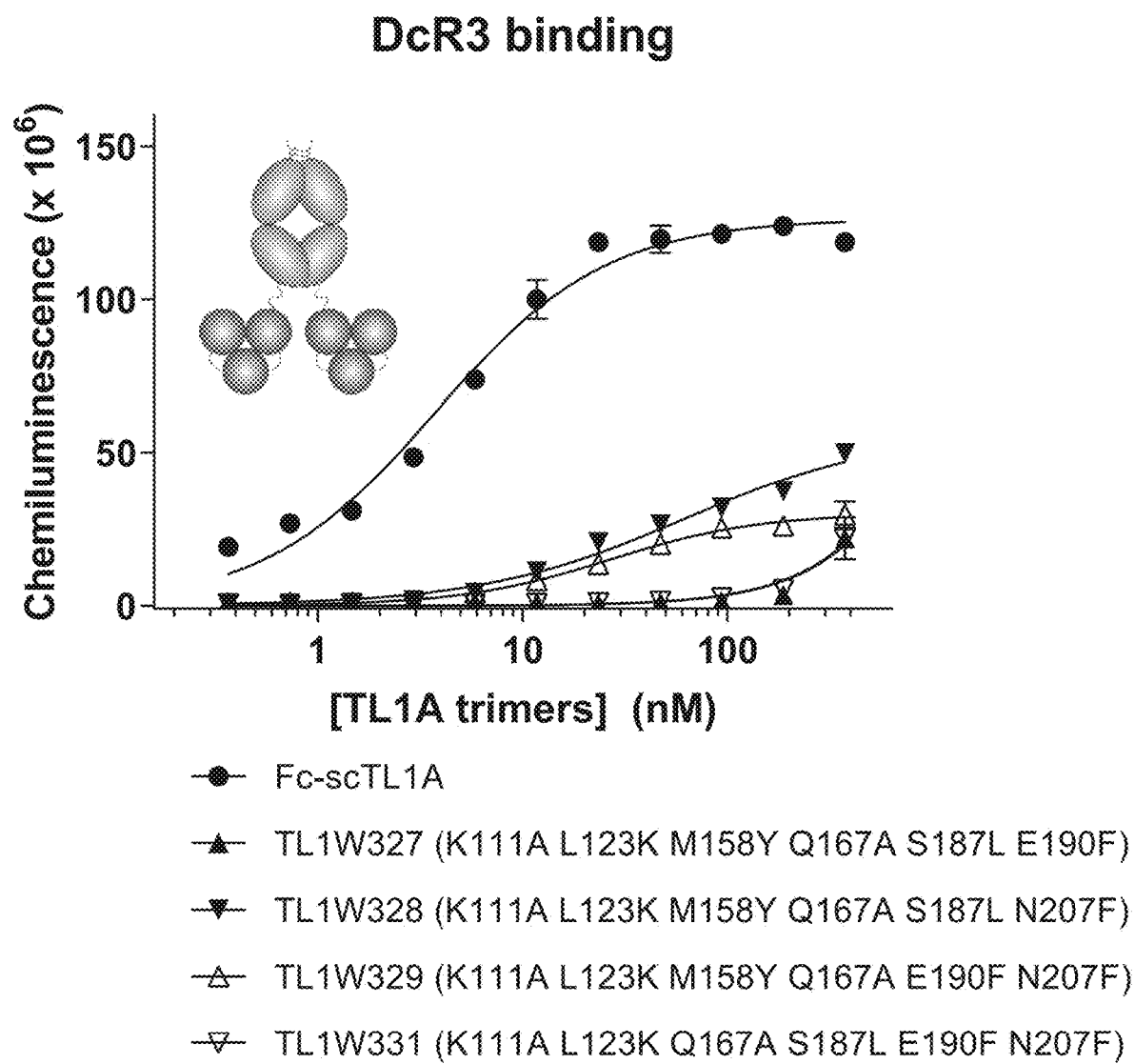

Seven TL1A single point mutations were selected to generate combination mutants in a Fc-scTL1A format and screened for binding to DR3 or DcR3 by ELISA (FIGS. 5C and 5D). These combination mutants were tested for binding to DR3 and DcR3 (FIGS. 5E and 5F, respectively). Exemplary results are summarized in Table 5. Favorable combination mutants were characterized as having binding to DR3 that was comparable or enhanced compared to wild-type TL1A (relative $EC_{50}$<1) and weaker binding to DcR3 (relative $EC_{50}$>1). Tested combination mutants showed no significant binding to DcR3 while maintaining similar binding to DR3 (compared to wild-type TL1A), except for the K111A, L123K, M158Y, Q167A, S187L, E190F variant (SEQ ID NO:88), which showed modestly decreased DR3 binding (FIG. 5E). The Fc-scTL1A-AKALFF variant, (SEQ ID NO:91), harboring the K111A, L123K, Q167A, S187L, E190F, N207F mutations had an $EC_{50}$ value of 9.0±2.7 nM for binding to DR3 and no detectable binding to DcR3 (Table 5).

These results suggested that the individual modifications to enhance the stability, monodispersity, and specificity of TL1A could be combined to generate a therapeutically viable molecule. Indeed, the Fc-scTL1A-AKALFF variant (SEQ ID NO:91) displayed identical binding to DR3 (compared to wild-type TL1A) but displayed no significant binding to DcR3.

TABLE 5

ELISA results for TL1A variants binding to DR3

| Molecule | EC$_{50}$ (nM): DR3 | Rel EC$_{50}$ DR3 | EC$_{50}$ (nM): DcR3 | Rel EC$_{50}$ DcR3 |
|---|---|---|---|---|
| TL1W2 (SEQ ID NO: 20) | 26.2 ± 1.9 | 1.0 | 4.6 ± 0.9 | 1.0 |
| Fc-scTL1A (TL1W14) (SEQ ID NO: 87) | 9.7 ± 1.0 | 1.0 | 6.5 ± 0.9 | |
| TNFα | No binding | NA | No binding | NA |
| TL1W80 (K111A) (SEQ ID NO: 79) | 30.0 ± 12.2 | 1.1 | 89.8 ± 1.1 | |
| TL1W38 (L123K) (SEQ ID NO: 72) | 29.4 ± 4.1 | 1.1 | 24.7 ± 1.4 | |
| TL1W92 (M158Y) (SEQ ID NO: 8) | 16.6 ± 2.9 | 0.6 | 69.2 ± 1.8 | |
| TL1W95 (Q167A) (SEQ ID NO: 65) | 17.1 ± 11.5 | 0.7 | 175.9 ± 2.3 | |
| TL1W109 (S187L) (SEQ ID NO: 52) | 17.7 ± 6.3 | 0.7 | 85.5 ± 1.9 | |
| TL1W45 (E190F) (SEQ ID NO: 14) | 31.4 ± 4.3 | 1.2 | 21.2 ± 1.3 | |
| TL1W122 (N207F) (SEQ ID NO: 36) | 30.2 ± 5.8 | 1.2 | 58.5 ± 1.8 | |
| TL1W328.001 (K111A L123K M158Y Q167A S187L N207F) (SEQ ID NO: 90) | 8.8 ± 2.8 | 0.8 | No binding | NA |
| TL1W329.001 (K111A L123K M158Y Q167A E190F N207F) (SEQ ID NO: 88) | 8.7 ± 2.6 | 0.9 | No binding | NA |
| TL1W331.001 (K111A L123K Q167A S187L E190F N207F) (SEQ ID NO: 91) | 9.0 ± 2.7 | 0.9 | No binding | NA |
| TL1W327.001 (K111A L123K M158Y Q167A S187L E190F) (SEQ ID NO: 89) | 37.5 ± 3.6 | 3.9 | No binding | NA |

8.7 Example 7. T Cell Co-Stimulation Mediated by TL1A Variants

Figure 6A:
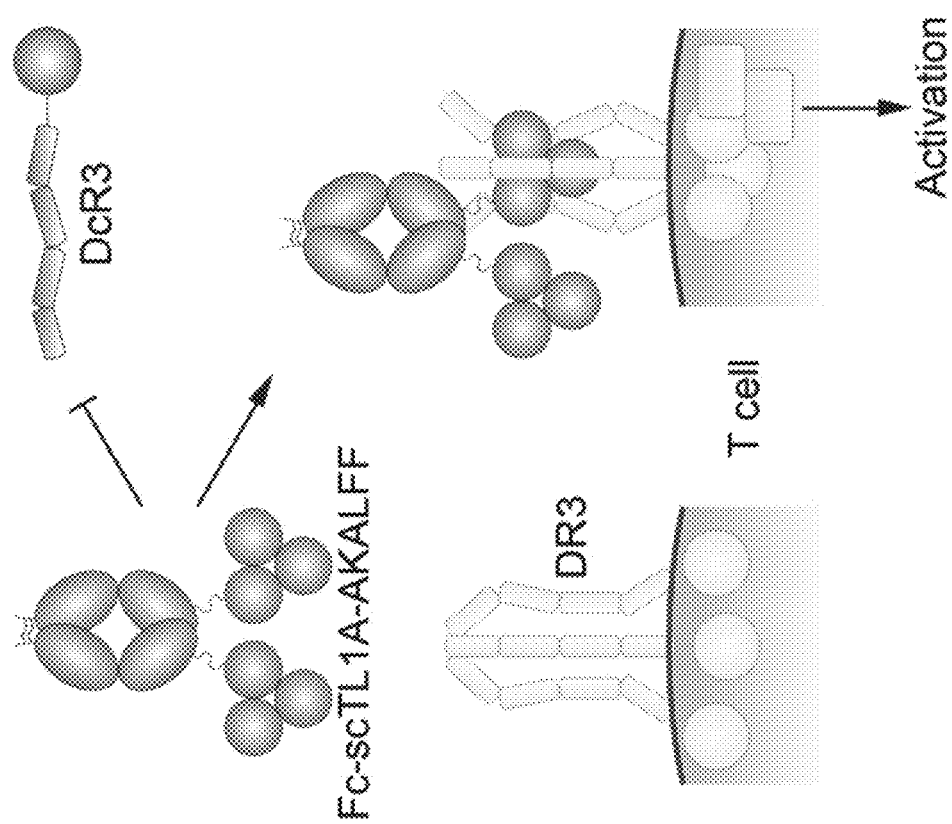
Figure 6B:
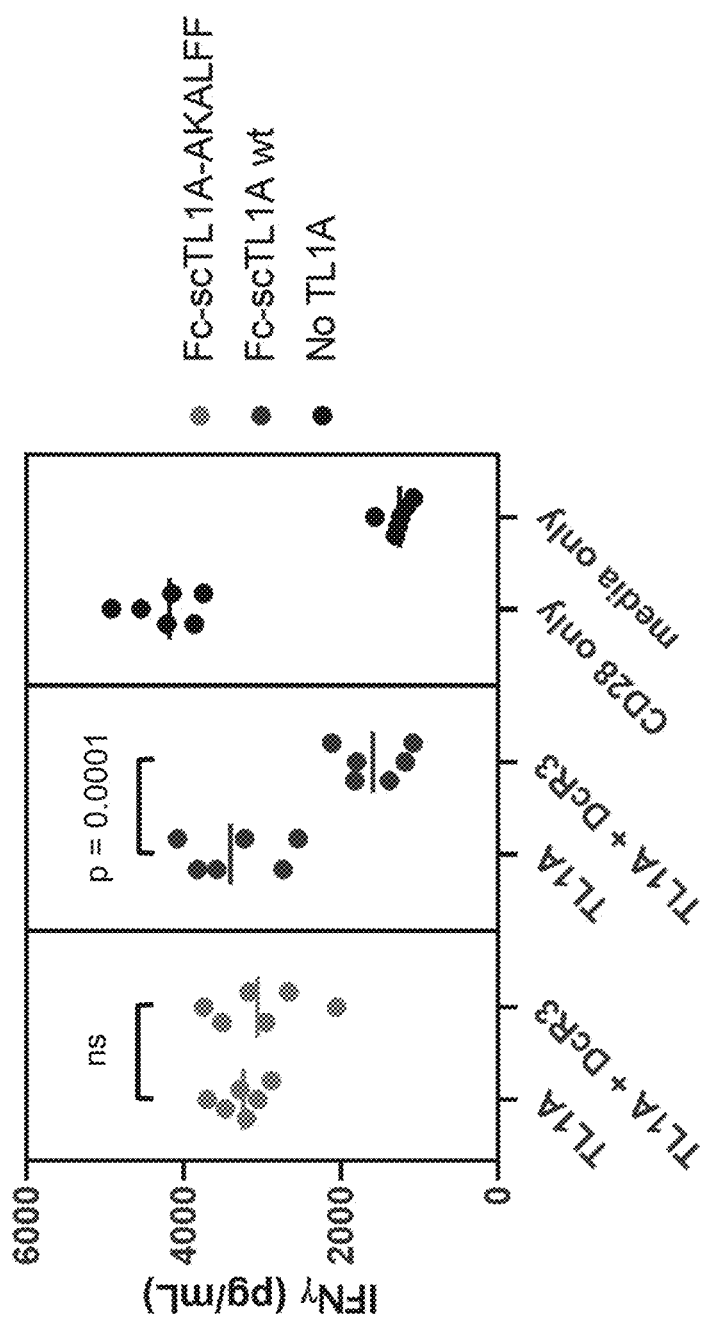
Figure 7A:
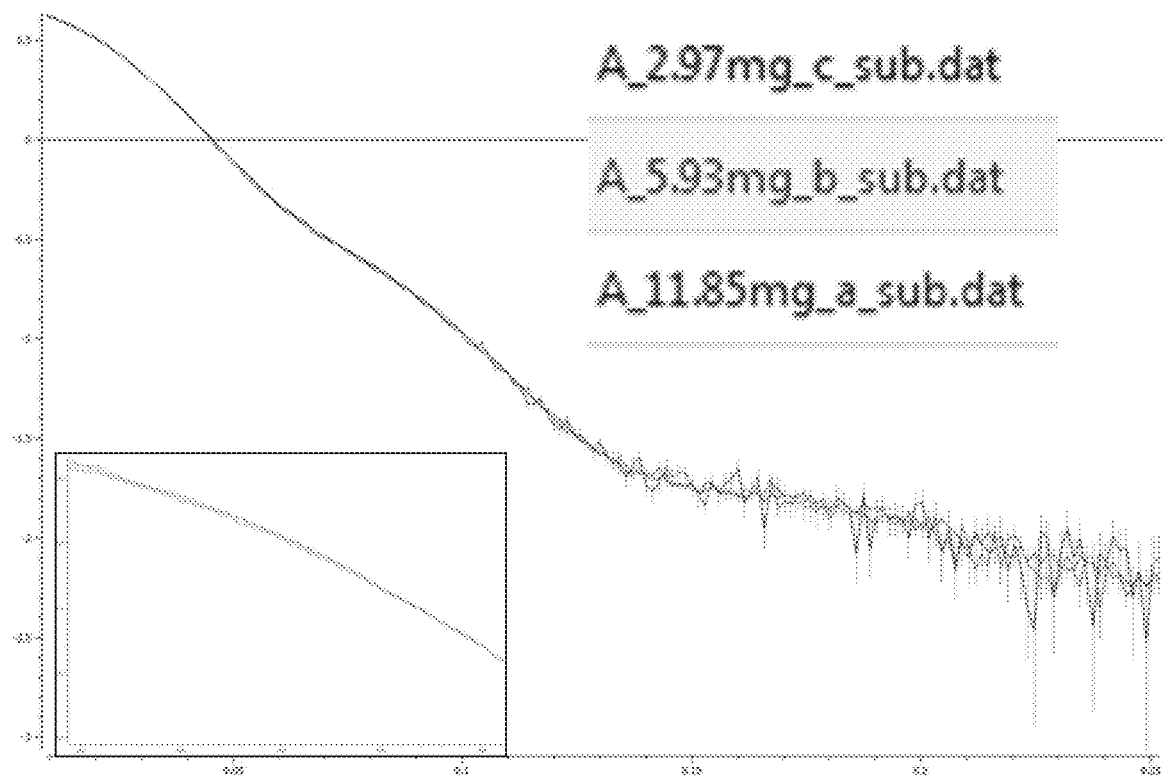
Figure 7B:
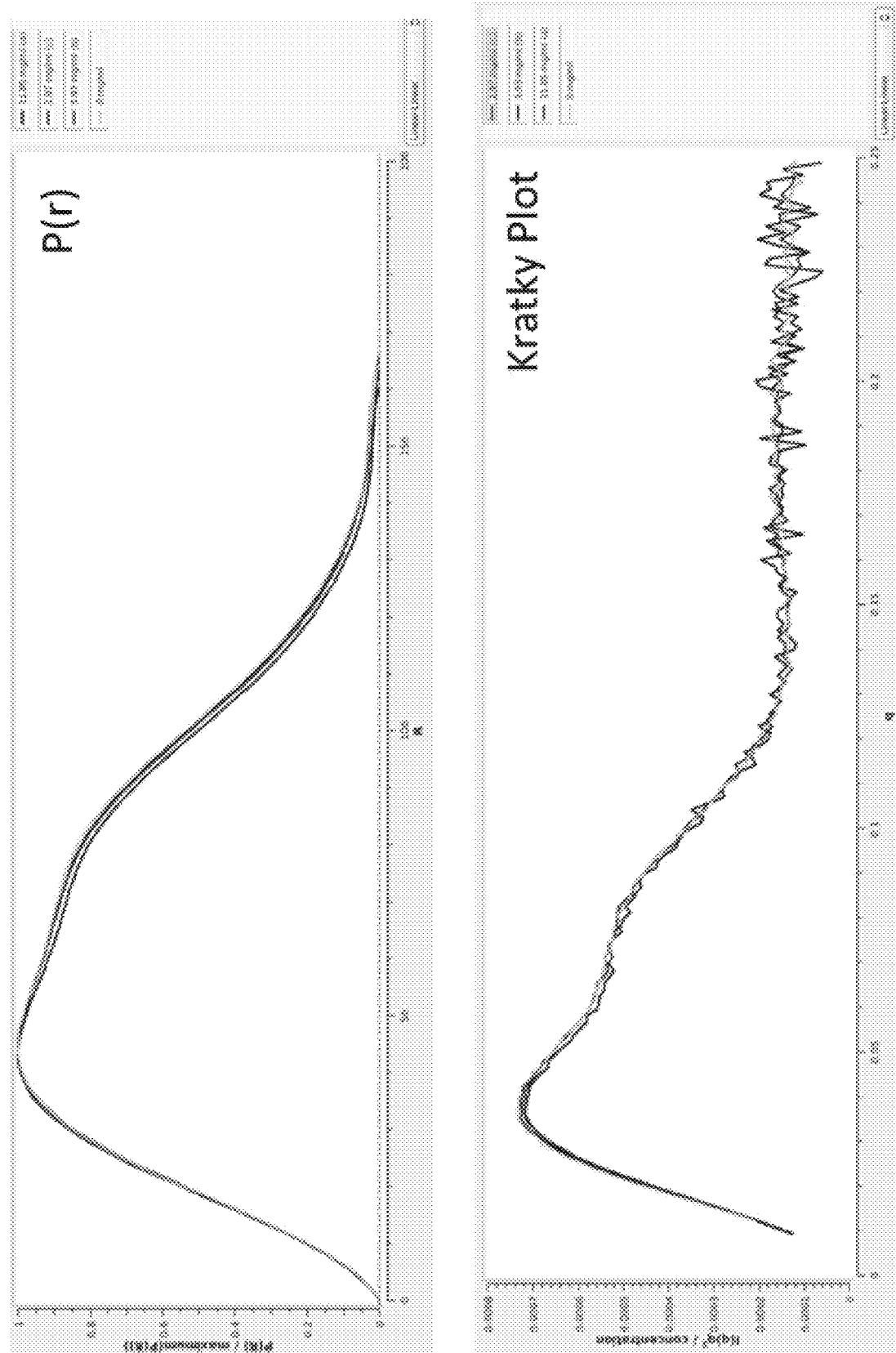
Figure 7C:
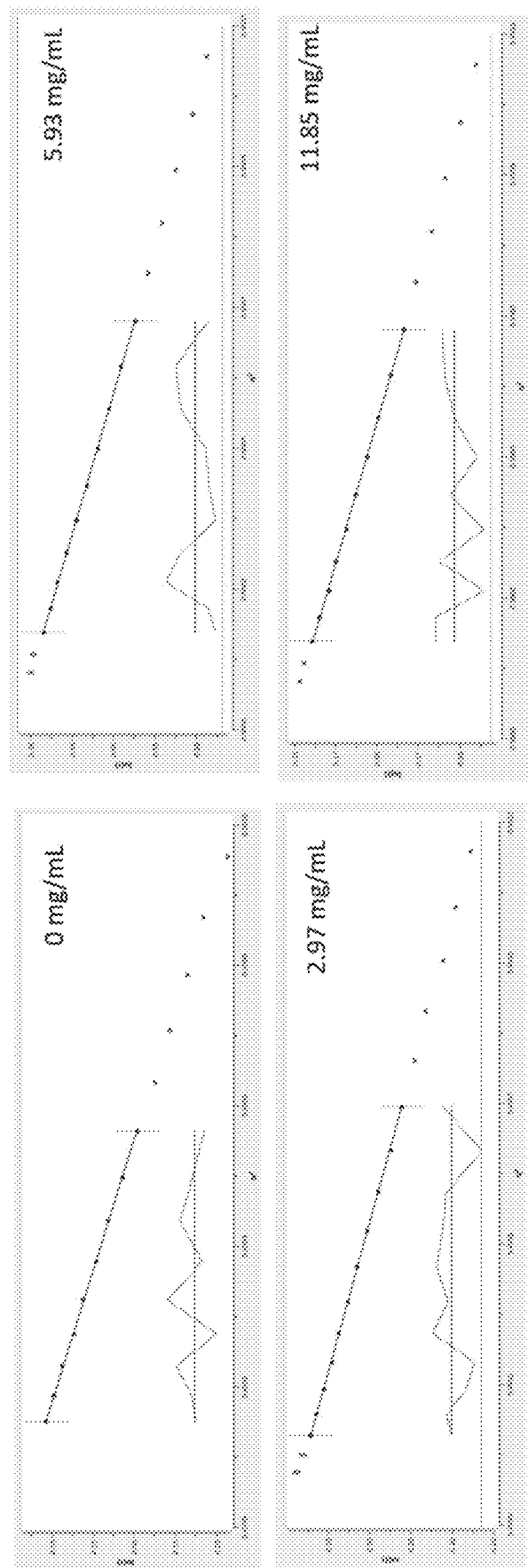
Figure 7D:
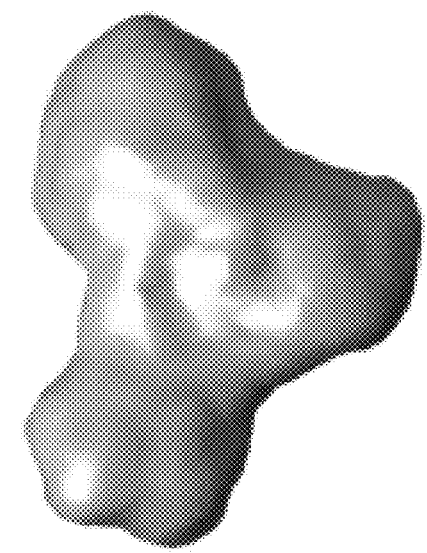
Figure 7D:
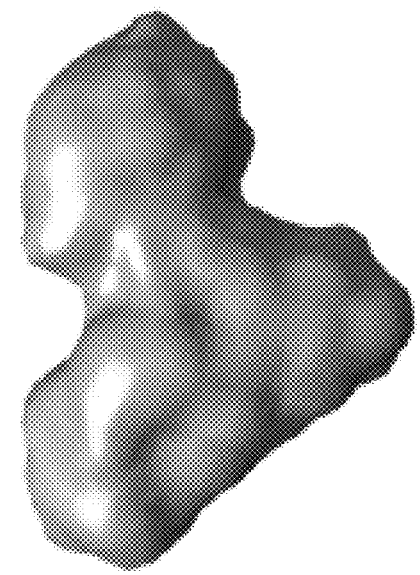
Figure 7D:
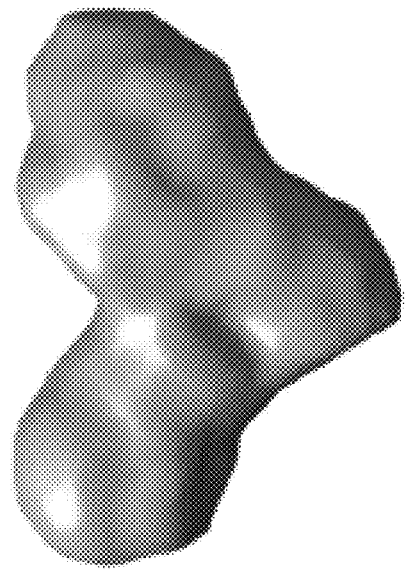

TL1A variant Fc-scTL1A-AKALFF, Fc-scTLiA K111A, L123K, Q167A, 5187L, E190F, N207F (SEQ TD NO:91), was evaluated for the ability to co-stimulate T cells and resist DcR3-mediated competition (FIG. 6A). Cytokine production was measured using a MSD electrochemiluminescence cytokine assay as describe in Example 3. Exemplary results of the in vitro analysis of the ability of this engineered TL1A variant Fc-scTL1A-AKALFF to co-stimulate CD-3 activated T cells in the presence or absence of exogenous soluble DcR3 is shown in FIG. 6B. Results show that the binding specificity was recapitulated in the T cell activation assay, where addition of exogenous DcR3 could inhibit T cell activation only by Fc-scTL1A (FIG. 3, SEQ ID NO:87) but not by Fc-scTL1A-AKALFF (SEQ ID NO:91) (FIG. 6B). This is consistent with binding data showing AKALFF mutations abolished binding to DcR3 without affecting binding to DR3 (Table 5).

These findings suggest that engineered TL1A ligands had co-stimulatory functions on both antigen-naïve and antigen-experienced T cells and even on exhausted T cells. Furthermore, engineered TL1A ligands were effective co-stimulators in combination with anti-PD1 checkpoint inhibitor, demonstrating their therapeutic potential.

9. SEQUENCES

Exemplary sequences are provided below.

```
TL1W81 (His-TEV-TL1A K111S) amino acid sequence
                                                           (SEQ ID NO: 1)
HHHHHHENLYFQGLKGQEFAPSHQQVYAPLRADGDKPRAHLTVVRQTPTQHFSNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W83 (His-TEV-TL1A E120K) amino acid sequence
                                                           (SEQ ID NO: 2)
HHHHHHENLYFQGLKGQEFAPSHQQVYAPLRADGDKPRAHLTVVRQTPTQHFKNQFPALHWKHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W84 (His-TEV-TL1A E120H) amino acid sequence
                                                           (SEQ ID NO: 3)
HHHHHHENLYFQGLKGQEFAPSHQQVYAPLRADGDKPRAHLTVVRQTPTQHFKNQFPALHWHHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W40 (His-TEV-TL1A L123S) amino acid sequence
                                                           (SEQ ID NO: 4)
HHHHHHENLYFQGLKGQEFAPSHQQVYAPLRADGDKPRAHLTVVRQTPTQHFKNQFPALHWEHESGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W85 (His-TEV-TL1A G124S) amino acid sequence
                                                           (SEQ ID NO: 5)
HHHHHHENLYFQGLKGQEFAPSHQQVYAPLRADGDKPRAHLTVVRQTPTQHFKNQFPALHWEHELSLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W86 (His-TEV-TL1A G124K) amino acid sequence
                                                           (SEQ ID NO: 6)
HHHHHHENLYFQGLKGQEFAPSHQQVYAPLRADGDKPRAHLTVVRQTPTQHFKNQFPALHWEHELKLAFT
```

-continued

KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL

TL1W89 (His-TEV-TL1A R156Y) amino acid sequence
(SEQ ID NO: 7)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFYGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W92 (His-TEV-TL1A M158Y) amino acid sequence
(SEQ ID NO: 8)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGYTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W97 (His-TEV-TL1A K173S) amino acid sequence
(SEQ ID NO: 9)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNSPDSITVVITKVTDSYPEPTQLLMGT
KSVCEVGSNWFQPIYLGAMFSLQEGDKLMVNVSDISLVDYTKEDKTFFGAFLL TL1W98 (His-TEV-TL1A K173R) amino acid sequence
(SEQ ID NO: 10)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNRPDSITVVITKVTDSYPEPTQLLMGT
KSVCEVGSNWFQPIYLGAMFSLQEGDKLMVNVSDISLVDYTKEDKTFFGAFLL TL1W107 (His-TEV-TL1A D186Y) amino acid sequence
(SEQ ID NO: 11)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTYSYPEPTQLLMGT
KSVCEVGSNWFQPIYLGAMFSLQEGDKLMVNVSDISLVDYTKEDKTFFGAFLL TL1W113 (His-TEV-TL1A P189S) amino acid sequence
(SEQ ID NO: 12)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYSEPTQLLMGT
KSVCEVGSNWFQPIYLGAMFSLQEGDKLMVNVSDISLVDYTKEDKTFFGAFLL TL1W28 (His-TEV-hTL1A 72-251 E190G) amino acid sequence
(SEQ ID NO: 13)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPGPTQLLMGT
KSVCEVGSNWFQPIYLGAMFSLQEGDKLMVNVSDISLVDYTKEDKTFFGAFLL TL1W45 (His-TEV-TL1A E190F) amino acid sequence
(SEQ ID NO: 14)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPFPTQLLMGT
KSVCEVGSNWFQPIYLGAMFSLQEGDKLMVNVSDISLVDYTKEDKTFFGAFLL TL1W123 (His-TEV-TL1A N207S) amino acid sequence
(SEQ ID NO: 15)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSSWFQPIYLGAMFSLQEGDKLMVNVSDISLVDYTKEDKTFFGAFLL TL1W126 (His-TEV-TL1A F209W) amino acid sequence
(SEQ ID NO: 16)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWWQPIYLGAMFSLQEGDKLMVNVSDISLVDYTKEDKTFFGAFLL TL1W46 (His-TEV-TL1A T239W) amino acid sequence
(SEQ ID NO: 17)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYWKEDKTFFGAFLL TL1W137 (His-TEV-TL1A K240S) amino acid sequence
(SEQ ID NO: 18)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTSEDKTFFGAFLL TL1W139 (His-TEV-TL1A E241Q) amino acid sequence
(SEQ ID NO: 19)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKQDKTFFGAFLL -continued TL1W2 (His-TEV-hTL1A 72-251) amino acid sequence
(SEQ ID NO: 20)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W47 (His-TEV-TL1A E241A) amino acid sequence
(SEQ ID NO: 21)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKADKTFFGAFLL TL1W136 (His-TEV-TL1A K240F) amino acid sequence
(SEQ ID NO: 22)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTFEDKTFFGAFLL TL1W138 (His-TEV-TL1A K240D) amino acid sequence
(SEQ ID NO: 23)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTDEDKTFFGAFLL TL1W135 (His-TEV-TL1A K240A) amino acid sequence
(SEQ ID NO: 24)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTAEDKTFFGAFLL TL1W134 (His-TEV-TL1A T239K) amino acid sequence
(SEQ ID NO: 25)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYKKEDKTFFGAFLL TL1W133 (His-TEV-TL1A T239F) amino acid sequence
(SEQ ID NO: 26)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYFKEDKTFFGAFLL TL1W27 (His-TEV-hTL1A 72-251 T239E) amino acid sequence
(SEQ ID NO: 27)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYEKEDKTFFGAFLL TL1W132 (His-TEV-TL1A T239A) amino acid sequence
(SEQ ID NO: 28)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYAKEDKTFFGAFLL TL1W128 (His-TEV-TL1A Y238S) amino acid sequence
(SEQ ID NO: 29)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDSTKEDKTFFGAFLL TL1W130 (His-TEV-TL1A Y238R) amino acid sequence
(SEQ ID NO: 30)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDRTKEDKTFFGAFLL TL1W129 (His-TEV-TL1A Y238K) amino acid sequence
(SEQ ID NO: 31)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDKTKEDKTFFGAFLL TL1W131 (His-TEV-TL1A Y238E) amino acid sequence
(SEQ ID NO: 32)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDETKEDKTFFGAFLL TL1W127 (His-TEV-TL1A Y238A) amino acid sequence
(SEQ ID NO: 33)
HHHHHHENLYFQGLKGQEFAPSHQQVYAPLRADGDKPRAHLTVVRQTPTQHFKNQFPALHWEHELGLAFT -continued KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDATKEDKTFFGAFLL TL1W24 (His-TEV-hTL1A 72-251 F209A) amino acid sequence
(SEQ ID NO: 34)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWAQPIYLGAMFSLQEGDKLMVNVSDISLVDYTKEDKTFFGAFLL TL1W124 (His-TEV-TL1A N207K) amino acid sequence
(SEQ ID NO: 35)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSKWFQPIYLGAMFSLQEGDKLMVNVSDISLVDYTKEDKTFFGAFLL TL1W122 (His-TEV-TL1A N207F) amino acid sequence
(SEQ ID NO: 36)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSFWFQPIYLGAMFSLQEGDKLMVNVSDISLVDYTKEDKTFFGAFLL TL1W125 (His-TEV-TL1A N207E) amino acid sequence+10
(SEQ ID NO: 37)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSEWFQPIYLGAMFSLQEGDKLMVNVSDISLVDYTKEDKTFFGAFLL TL1W25 (His-TEV-hTL1A 72-251 N207A) amino acid sequence
(SEQ ID NO: 38)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSAWFQPIYLGAMFSLQEGDKLMVNVSDISLVDYTKEDKTFFGAFLL TL1W120 (His-TEV-TL1A S206K) amino acid sequence
(SEQ ID NO: 39)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGKNWFQPIYLGAMFSLQEGDKLMVNVSDISLVDYTKEDKTFFGAFLL TL1W119 (His-TEV-TL1A S206F) amino acid sequence
(SEQ ID NO: 40)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGFNWFQPIYLGAMFSLQEGDKLMVNVSDISLVDYTKEDKTFFGAFLL TL1W121 (His-TEV-TL1A S206E) amino acid sequence
(SEQ ID NO: 41)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGENWFQPIYLGAMFSLQEGDKLMVNVSDISLVDYTKEDKTFFGAFLL TL1W118 (His-TEV-TL1A S206A) amino acid sequence
(SEQ ID NO: 42)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGANWFQPIYLGAMFSLQEGDKLMVNVSDISLVDYTKEDKTFFGAFLL TL1W116 (His-TEV-TL1A T192K) amino acid sequence
(SEQ ID NO: 43)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPKQLLMGT
KSVCEVGSNWFQPIYLGAMFSLQEGDKLMVNVSDISLVDYTKEDKTFFGAFLL TL1W115 (His-TEV-TL1A T192F) amino acid sequence+10
(SEQ ID NO: 44)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPFQLLMGT
KSVCEVGSNWFQPIYLGAMFSLQEGDKLMVNVSDISLVDYTKEDKTFFGAFLL TL1W117 (His-TEV-TL1A T192E) amino acid sequence
(SEQ ID NO: 45)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPEQLLMGT
KSVCEVGSNWFQPIYLGAMFSLQEGDKLMVNVSDISLVDYTKEDKTFFGAFLL TL1W114 (His-TEV-TL1A T192A) amino acid sequence
(SEQ ID NO: 46)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYPEPAQLLMGT
KSVCEVGSNWFQPIYLGAMFSLQEGDKLMVNVSDISLVDYTKEDKTFFGAFLL -continued TL1W44 (His-TEV-TL1A P189K) amino acid sequence
(SEQ ID NO: 47)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYKEPTQLLMGT
KSVCEVGSNWFQPIYLGAMFSLQEGDKLMVNVSDISLVDYTKEDKTFFGAFLL TL1W112 (His-TEV-TL1A P189F) amino acid sequence
(SEQ ID NO: 48)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYFEPTQLLMGT
KSVCEVGSNWFQPIYLGAMFSLQEGDKLMVNVSDISLVDYTKEDKTFFGAFLL TL1W29 (His-TEV-hTL1A 72-251 P189) amino acid sequence
(SEQ ID NO: 49)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSYAEPTQLLMGT
KSVCEVGSNWFQPIYLGAMFSLQEGDKLMVNVSDISLVDYTKEDKTFFGAFLL TL1W43 (His-TEV-TL1A Y188S) amino acid sequence
(SEQ ID NO: 50)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSSPEPTQLLMGT
KSVCEVGSNWFQPIYLGAMFSLQEGDKLMVNVSDISLVDYTKEDKTFFGAFLL TL1W32 (His-TEV-hTL1A 72-251 Y188A) amino acid sequence
(SEQ ID NO: 51)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDSAPEPTQLLMGT
KSVCEVGSNWFQPIYLGAMFSLQEGDKLMVNVSDISLVDYTKEDKTFFGAFLL TL1W109 (His-TEV-TL1A S187L) amino acid sequence
(SEQ ID NO: 52)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDLYPEPTQLLMGT
KSVCEVGSNWFQPIYLGAMFSLQEGDKLMVNVSDISLVDYTKEDKTFFGAFLL TL1W110 (His-TEV-TL1A S187K) amino acid sequence
(SEQ ID NO: 53)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDKYPEPTQLLMGT
KSVCEVGSNWFQPIYLGAMFSLQEGDKLMVNVSDISLVDYTKEDKTFFGAFLL TL1W111 (His-TEV-TL1A S187D) amino acid sequence
(SEQ ID NO: 54)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDDYPEPTQLLMGT
KSVCEVGSNWFQPIYLGAMFSLQEGDKLMVNVSDISLVDYTKEDKTFFGAFLL TL1W108 (His-TEV-TL1A S187A) amino acid sequence
(SEQ ID NO: 55)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVTDAYPEPTQLLMGT
KSVCEVGSNWFQPIYLGAMFSLQEGDKLMVNVSDISLVDYTKEDKTFFGAFLL TL1W105 (His-TEV-TL1A T185N) amino acid sequence
(SEQ ID NO: 56)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVNDSYPEPTQLLMGT
KSVCEVGSNWFQPIYLGAMFSLQEGDKLMVNVSDISLVDYTKEDKTFFGAFLL TL1W104 (His-TEV-TL1A T185L) amino acid sequence
(SEQ ID NO: 57)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVLDSYPEPTQLLMGT
KSVCEVGSNWFQPIYLGAMFSLQEGDKLMVNVSDISLVDYTKEDKTFFGAFLL TL1W106 (His-TEV-TL1A T185D) amino acid sequence
(SEQ ID NO: 58)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVDDSYPEPTQLLMGT
KSVCEVGSNWFQPIYLGAMFSLQEGDKLMVNVSDISLVDYTKEDKTFFGAFLL TL1W103 (His-TEV-TL1A T185A) amino acid sequence
(SEQ ID NO: 59)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDSITVVITKVADSYPEPTQLLMGT
KSVCEVGSNWFQPIYLGAMFSLQEGDKLMVNVSDISLVDYTKEDKTFFGAFLL TL1W101 (His-TEV-TL1A S176N) amino acid sequence
(SEQ ID NO: 60)
HHHHHHENLYFQGLKGQEFAPSHQQVYAPLRADGDKPRAHLTVVRQTPTQHFKNQFPALHWEHELGLAFT -continued KNRMNYTNKFLLIPESGDYFIYSQVTFRGMTSECSEIRQAGRPNKPDNITVVITKVTDSYPEPTQLLMGT
KSVCEVGSNWFQPIYLGAMFSLQEGDKLMVNVSDISLVDYTKEDKTFFGAFLL TL1W100 (His-TEV-TL1A S176L) amino acid sequence
                                                           (SEQ ID NO: 61)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDLITVVITKVTDSYPEPTQLLMGT
KSVCEVGSNWFQPIYLGAMFSLQEGDKLMVNVSDISLVDYTKEDKTFFGAFLL TL1W102 (His-TEV-TL1A S176K) amino acid sequence
                                                           (SEQ ID NO: 62)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDKITVVITKVTDSYPEPTQLLMGT
KSVCEVGSNWFQPIYLGAMFSLQEGDKLMVNVSDISLVDYTKEDKTFFGAFLL TL1W99 (His-TEV-TL1A S176A) amino acid sequence
                                                           (SEQ ID NO: 63)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGRPNKPDAITVVITKVTDSYPEPTQLLMGT
KSVCEVGSNWFQPIYLGAMFSLQEGDKLMVNVSDISLVDYTKEDKTFFGAFLL TL1W96 (His-TEV-TL1A R170E) amino acid sequence
                                                           (SEQ ID NO: 64)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRQAGEPNKPDSITVVITKVTDSYPEPTQLLMGT
KSVCEVGSNWFQPIYLGAMFSLQEGDKLMVNVSDISLVDYTKEDKTFFGAFLL TL1W95 (His-TEV-TL1A Q167A) amino acid sequence
                                                           (SEQ ID NO: 65)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGMTSECSEIRAAGRPNKPDSITVVITKVTDSYPEPTQLLMGT
KSVCEVGSNWFQPIYLGAMFSLQEGDKLMVNVSDISLVDYTKEDKTFFGAFLL TL1W93 (His-TEV-TL1A M158K) amino acid sequence
                                                           (SEQ ID NO: 66)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGKTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W94 (His-TEV-TL1A M158E) amino acid sequence
                                                           (SEQ ID NO: 67)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFRGETSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W90 (His-TEV-TL1A R156K) amino acid sequence
                                                           (SEQ ID NO: 68)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFKGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W91 (His-TEV-TL1A R156E) amino acid sequence
                                                           (SEQ ID NO: 69)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFEGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W88 (His-TEV-TL1A R156A) amino acid sequence
                                                           (SEQ ID NO: 70)
HHHHHHENLYFQGLKGQEFAPSHQQVYAPLRADGDKPRAHLTVVRQTPTQHFKNQFPALHWEHELGLAFT
KNRMNYTNKFLLIPESGDYFIYSQVTFAGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W87 (His-TEV-TL1A G124D) amino acid sequence
                                                           (SEQ ID NO: 71)
HHHHHHENLYFQGLKGQEFAPSHQQVYAPLRADGDKPRAHLTVVRQTPTQHFKNQFPALHWEHELDLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W38 (His-TEV-TL1A L123K) amino acid sequence
                                                           (SEQ ID NO: 72)
HHHHHHENLYFQGLKGQEFAPSHQQVYAPLRADGDKPRAHLTVVRQTPTQHFKNQFPALHWEHEKGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W39 (His-TEV-TL1A L123G) amino acid sequence
                                                           (SEQ ID NO: 73)
HHHHHHENLYFQGLKGQEFAPSHQQVYAPLRADGDKPRAHLTVVRQTPTQHFKNQFPALHWEHEGGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL -continued TL1W37 (His-TEV-TL1A L123E) amino acid sequence
(SEQ ID NO: 74)
HHHHHHENLYFQGLKGQEFAPSHQQVYAPLRADGDKPRAHLTVVRQTPTQHFKNQFPALHWEHEEGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W41 (His-TEV-TL1A E120A) amino acid sequence
(SEQ ID NO: 75)
HHHHHHENLYFQGLKGQEFAPSHQQVYAPLRADGDKPRAHLTVVRQTPTQHFKNQFPALHWAHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W42 (His-TEV-TL1A F114A) amino acid sequence
(SEQ ID NO: 76)
HHHHHHENLYFQGLKGQEFAPSHQQVYAPLRADGDKPRAHLTVVRQTPTQHFKNQAPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W30 (His-TEV-hTL1A 72-251 N112E) amino acid sequence
(SEQ ID NO: 77)
HHHHHHENLYFQGLKGQEFAPSHQQVYAPLRADGDKPRAHLTVVRQTPTQHFKEQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W82 (His-TEV-TL1A K111E) amino acid sequence
(SEQ ID NO: 78)
HHHHHHENLYFQGLKGQEFAPSHQQVYAPLRADGDKPRAHLTVVRQTPTQHFENQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W80 (His-TEV-TL1A K111A) amino acid sequence
(SEQ ID NO: 79)
HHHHHHENLYFQGLKGQEFAPSHQQVYAPLRADGDKPRAHLTVVRQTPTQHFANQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W31 (GD: Single chain MMB in CBIS; His-TEV-hTL1A 72-251 R103Q)
amino acid sequence
(SEQ ID NO: 80)
HHHHHHENLYFQGLKGQEFAPSHQQVYAPLRADGDKPRAHLTVVQQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W78 (His-TEV-TL1A R103H) amino acid sequence
(SEQ ID NO: 81)
HHHHHHENLYFQGLKGQEFAPSHQQVYAPLRADGDKPRAHLTVVHQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W79 (His-TEV-TL1A R103E) amino acid sequence
(SEQ ID NO: 82)
HHHHHHENLYFQGLKGQEFAPSHQQVYAPLRADGDKPRAHLTVVEQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W33 (His-TEV-hTL1A 72-251 R103A) amino acid sequence
(SEQ ID NO: 83)
HHHHHHENLYFQGLKGQEFAPSHQQVYAPLRADGDKPRAHLTVVAQTPTQHFKNQFPALHWEHELGLAFT
KNRMNYTNKFLLIPESGDYFIYSQVTFRGMTSECSEIRQAGRPNKPDSITVVITKVTDSYPEPTQLLMGT
KSVCEVGSNWFQPIYLGAMFSLQEGDKLMVNVSDISLVDYTKEDKTFFGAFLL TL1W15 (GD: Single chain protein in CBIS -> HSA C-terminal Fusion;
His-TEV-HSA(C34S)-G4S-TL1A-3(G3S)-TL1A-3(G3S)-TL1A) amino acid
sequence
(SEQ ID NO: 84)
HHHHHHENLYFQGDAHKSEVAHRFKDLGEENFKALVLIAFAQYLQQSPFEDHVKLVNEVTEFAKTCVADE
SAENCDKSLHTLFGDKLCTVATLRETYGEMADCCAKQEPERNECFLQHKDDNPNLPRLVRPEVDVMCTAF
HDNEETFLKKYLYEIARRHPYFYAPELLFFAKRYKAAFTECCQAADKAACLLPKLDELRDEGKASSAKQR
LKCASLQKFGERAFKAWAVARLSQRFPKAEFAEVSKLVTDLTKVHTECCHGDLLECADDRADLAKYICEN
QDSISSKLKECCEKPLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKQNCELFEQLGEYKFQNAL
LVRYTKKVPQVSTPTLVEVSRNLGKVGSKCCKHPEAKRMPCAEDYLSVVLNQLCVLHEKTPVSDRVTKCC
TESLVNRRPCFSALEVDETYVPKEFNAETFTFHADICTLSEKERQIKKQTALVELVKHKPKATKEQLKAV
MDDFAAFVEKCCKADDKETCFAEEGKKLVAASQAALGLGGGGSVYAPLRADGDKPRAHLTVVRQTPTQHF
KNQFPALHWEHELGLAFTKNRMNYTNKFLLIPESGDYFIYSQVTFRGMTSECSEIRQAGRPNKPDSITVV
ITKVTDSYPEPTQLLMGTKSVCEVGSNWFQPIYLGAMFSLQEGDKLMVNVSDISLVDYTKEDKTFFGAFL
LGGGSGGGSGGGSVYAPLRADGDKPRAHLTVVRQTPTQHFKNQFPALHWEHELGLAFTKNRMNYTNKFLL
IPESGDYFIYSQVTFRGMTSECSEIRQAGRPNKPDSITVVITKVTDSYPEPTQLLMGTKSVCEVGSNWFQ
PIYLGAMFSLQEGDKLMVNVSDISLVDYTKEDKTFFGAFLLGGGSGGGSGGGSVYAPLRADGDKPRAHLT
VVRQTPTQHFKNQFPALHWEHELGLAFTKNRMNYTNKFLLIPESGDYFIYSQVTFRGMTSECSEIRQAGR -continued PNKPDSITVVITKVTDSYPEPTQLLMGTKSVCEVGSNWFQPIYLGAMFSLQEGDKLMVNVSDISLVDYTK
EDKTFFGAFLL TL1W9 (GD: Single chain protein in CBIS -> HSA C-terminal Fusion;
His-TEV-G-HSA (C34S)-2(G4S)-TL1A) amino acid sequence (SEQ ID NO: 85)

HHHHHHENLYFQGDAHKSEVAHRFKDLGEENFKALVLIAFAQYLQQSPFEDHVKLVNEVTEFAKTCVADE
SAENCDKSLHTLFGDKLCTVATLRETYGEMADCCAKQEPERNECFLQHKDDNPNLPRLVRPEVDVMCTAF
HDNEETFLKKYLYEIARRHPYFYAPELLFFAKRYKAAFTECCQAADKAACLLPKLDELRDEGKASSAKQR
LKCASLQKFGERAFKAWAVARLSQRFPKAEFAEVSKLVTDLTKVHTECCHGDLLECADDRADLAKYICEN
QDSISSKLKECCEKPLLEKSHCIAEVENDEMPADLPSLAADFVESKDVCKNYAEAKDVFLGMFLYEYARR
HPDYSVVLLLRLAKTYETTLEKCCAAADPHECYAKVFDEFKPLVEEPQNLIKONCELFEQLGEYKFQNAL
LVRYTKKVPQVSTPTLVEVSRNLGKVGSKCCKHPEAKRMPCAEDYLSVVLNQLCVLHEKTPVSDRVTKCC
TESLVNRRPCFSALEVDETYVPKEFNAETFTFHADICTLSEKERQIKKQTALVELVKHKPKATKEQLKAV
MDDFAAFVEKCCKADDKETCFAEEGKKLVAASQAALGLGGGGSGGGGSLKGQEFAPSHQQVYAPLRADGD
KPRAHLTVVRQTPTQHFKNQFPALHWEHELGLAFTKNRMNYTNKFLLIPESGDYFIYSQVTFRGMTSECS
EIRQAGRPNKPDSITVVITKVTDSYPEPTQLLMGTKSVCEVGSNWFQPIYLGAMFSLQEGDKLMVNVSDI
SLVDYTKEDKTFFGAFLL

TL1W19 (His-TEV-TL1A-TL1A-TL1A) amino acid sequence (SEQ ID NO: 86)

HHHHHHENLYFQGAPLRADGDKPRAHLTVVRQTPTQHFKNQFPALHWEHELGLAFTKNRMNYTNKFLLIP
ESGDYFIYSQVTFRGMTSECSEIRQAGRPNKPDSITVVITKVTDSYPEPTQLLMGTKSVCEVGSNWFQPI
YLGAMFSLQEGDKLMVNVSDISLVDYTKEDKTFFGAFLLAPLRADGDKPRAHLTVVRQTPTQHFKNQFPA
LHWEHELGLAFTKNRMNYTNKFLLIPESGDYFIYSQVTFRGMTSECSEIRQAGRPNKPDSITVVITKVTD
SYPEPTQLLMGTKSVCEVGSNWFQPIYLGAMFSLQEGDKLMVNVSDISLVDYTKEDKTFFGAFLLAPLRA
DGDKPRAHLTVVRQTPTQHFKNQFPALHWEHELGLAFTKNRMNYTNKFLLIPESGDYFIYSQVTFRGMTS
ECSEIRQAGRPNKPDSITVVITKVTDSYPEPTQLLMGTKSVCEVGSNWFQPIYLGAMFSLQEGDKLMVNV
SDISLVDYTKEDKTFFGAFLL

TL1W14 (Fc-scTL1A with CD4 HC sp prim_transcript) amino acid sequence (SEQ ID NO: 87)

GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSVYAPLRADGDKPRAHLTVVRQTPTQHFKNQFPALHWEHELGLAFTKNRMNYT
NKFLLIPESGDYFIYSQVTFRGMTSECSEIRQAGRPNKPDSITVVITKVTDSYPEPTQLLMGTKSVCEVG
SNWFQPIYLGAMFSLQEGDKLMVNVSDISLVDYTKEDKTFFGAFLLGGGSGGGSGGGSVYAPLRADGDKP
RAHLTVVRQTPTQHFKNQFPALHWEHELGLAFTKNRMNYTNKFLLIPESGDYFIYSQVTFRGMTSECSEI
RQAGRPNKPDSITVVITKVTDSYPEPTQLLMGTKSVCEVGSNWFQPIYLGAMFSLQEGDKLMVNVSDISL
VDYTKEDKTFFGAFLLGGGSGGGSGGGSVYAPLRADGDKPRAHLTVVRQTPTQHFKNQFPALHWEHELGL
AFTKNRMNYTNKFLLIPESGDYFIYSQVTFRGMTSECSEIRQAGRPNKPDSITVVITKVTDSYPEPTQLL
MGTKSVCEVGSNWFQPIYLGAMFSLQEGDKLMVNVSDI SLVDYTKEDKTFFGAFLL

TL1W329 (Fc-scTL1A K111A L123K M158Y Q167A E190F N207F) amino acid
sequence (SEQ ID NO: 88)

GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSVYAPLRADGDKPRAHLTVVRQTPTQHFANQFPALHWEHEKGLAFTKNRMNYT
NKFLLIPESGDYFIYSQVTFRGYTSECSEIRAAGRPNKPDSITVVITKVTDSYPFPTQLLMGTKSVCEVG
SFWFQPIYLGAMFSLQEGDKLMVNVSDISLVDYTKEDKTFFGAFLLGGGSGGGSGGGSVYAPLRADGDKP
RAHLTVVRQTPTQHFANQFPALHWEHEKGLAFTKNRMNYTNKFLLIPESGDYFIYSQVTFRGYTSECSEI
RAAGRPNKPDSITVVITKVTDSYPFPTQLLMGTKSVCEVGSFWFQPIYLGAMFSLQEGDKLMVNVSDISL
VDYTKEDKTFFGAFLLGGGSGGGSGGGSVYAPLRADGDKPRAHLTVVRQTPTQHFANQFPALHWEHEKGL
AFTKNRMNYTNKFLLIPESGDYFIYSQVTFRGYTSECSEIRAAGRPNKPDSITVVITKVTDSYPFPTQLL
MGTKSVCEVGSFWFQPIYLGAMFSLQEGDKLMVNVSDISLVDYTKEDKTFFGAFLL

TL1W327 (Fc-scTL1A K111A L123K M158Y Q167A S187L E190F) amino acid
sequence (SEQ ID NO: 89)

GSCPPCPAPELLGGPSVFLFPPKPKDTLMISRTPEVTCVVVDVSHEDPEVKENWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSVYAPLRADGDKPRAHLTVVRQTPTQHFANQFPALHWEHEKGLAFTKNRMNYT
NKFLLIPESGDYFIYSQVTFRGYTSECSEIRAAGRPNKPDSITVVITKVTDLYPFPTQLLMGTKSVCEVG
SNWFQPIYLGAMFSLQEGDKLMVNVSDISLVDYTKEDKTFFGAFLLGGGSGGGSGGGSVYAPLRADGDKP
RAHLTVVRQTPTQHFANQFPALHWEHEKGLAFTKNRMNYTNKFLLIPESGDYFIYSQVTFRGYTSECSEI
RAAGRPNKPDSITVVITKVTDLYPFPTQLLMGTKSVCEVGSNWFQPIYLGAMFSLQEGDKLMVNVSDISL
VDYTKEDKTFFGAFLLGGGSGGGSGGGSVYAPLRADGDKPRAHLTVVRQTPTQHFANQFPALHWEHEKGL
AFTKNRMNYTNKFLLIPESGDYFIYSQVTFRGYTSECSEIRAAGRPNKPDSITVVITKVTDLYPFPTQLL
MGTKSVCEVGSNWFQPIYLGAMFSLQEGDKLMVNVSDISLVDYTKEDKTFFGAFLL

TL1W328 (Fc-scTL1A K111A L123K M158Y Q167A S187L N207F) amino acid
sequence (SEQ ID NO: 90)

GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSVYAPLRADGDKPRAHLTVVRQTPTQHFANQFPALHWEHEKGLAFTKNRMNYT
NKFLLIPESGDYFIYSQVTFRGYTSECSEIRAAGRPNKPDSITVVITKVTDLYPEPTQLLMGTKSVCEVG

-continued

SFWFQPIYLGAMFSLQEGDKLMVNSDISLVDYTKEDKTFFGAFLLGGGSGGGSGGGSVYAPLRADGDKP
RAHLTVVRQTPTQHFANQFPALHWEHEKGLAFTKNRMNYTNKFLLIPESGDYFIYSQVTFRGYTSECSEI
RAAGRPNKPDSITVVITKVTDLYPEPTQLLMGTKSVCEVGSFWFQPIYLGAMFSLQEGDKLMVNVSDISL
VDYTKEDKTFFGAFLLGGGSGGGSGGGSVYAPLRADGDKPRAHLTVVROTPTQHFANQFPALHWEHEKGL
AFTKNRMNYTNKFLLIPESGDYFIYSQVTFRGYTSECSEIRAAGRPNKPDSITVVITKVTDLYPEPTQLL
MGTKSVCEVGSFWFQPIYLGAMFSLQEGDKLMVNSDISLVDYTKEDKTFFGAFLL

TL1W331 (Fc-scTL1A K111A L123K Q167A S187L E190F N207F) amino acid
sequence
(SEQ ID NO: 91)
GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSVYAPLRADGDKPRAHLTVVRQTPTQHFANQFPALHWEHEKGLAFTKNRMNYT
NKFLLIPESGDYFIYSQVTFRGMTSECSEIRAAGRPNKPDSITVVITKVTDLYPFPTQLLMGTKSVCEVG
SFWFQPIYLGAMFSLQEGDKLMVNSDISLVDYTKEDKTFFGAFLLGGGSGGGSGGGSVYAPLRADGDKP
RAHLTVVRQTPTQHFANQFPALHWEHEKGLAFTKNRMNYTNKFLLIPESGDYFIYSQVTFRGMTSECSEI
RAAGRPNKPDSITVVITKVTDLYPFPTQLLMGTKSVCEVGSFWFQPIYLGAMFSLQEGDKLMVNVSDISL
VDYTKEDKTFFGAFLLGGGSGGGSGGGSVYAPLRADGDKPRAHLTVVRQTPTQHFANQFPALHWEHEKGL
AFTKNRMNYTNKFLLIPESGDYFIYSQVTFRGMTSECSEIRAAGRPNKPDSITVVITKVTDLYPFPTOLL
MGTKSVCEVGSFWFQPIYLGAMFSLQEGDKLMVNVSDI SLVDYTKEDKTFFGAFLL TL1W61 (Fc-TL1A+His-TL1A) amino acid sequence
(SEQ ID NO: 92)
GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSLKGQEFAPSHQQVYAPLRADGDKPRAHLTVVRQTPTQHFKNQFPALHWEHEL
GLAFTKNRMNYTNKFLLIPESGDYFIYSQVTFRGMTSECSEIRQAGRPNKPDSITVVITKVTDSYPEPTQ
LLMGTKSVCEVGSNWFQPIYLGAMFSLQEGDKLMVNSDISLVDYTKEDKTFFGAFLLHHHHHHHENLYFQ
GLKGQEFAPSHQQVYAPLRADGDKPRAHLTVVRQTPTQHFKNQFPALHWEHELGLAFTKNRMNYTNKFLL
IPESGDYFIYSQVTFRGMTSECSEIRQAGRPNKPDSITVVITKVTDSYPEPTQLLMGTKSVCEVGSNWFQ
PIYLGAMFSLQEGDKLMVNSDISLVDYTKEDKTFFGAFLL TL1W3 (GD: Fc Fusion in CBIS -> homodimer Fc Fusion; GS-huIgG1 Fc -
2(G4S)-hTL1A 72-251) amino acid sequence
(SEQ ID NO: 93)
GSCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALH
NHYTQKSLSLSPGGGGGSLKGQEFAPSHQQVYAPLRADGDKPRAHLTVVRQTPTQHFKNQFPALHWEHEL
GLAFTKNRMNYTNKFLLIPESGDYFIYSQVTFRGMTSECSEIRQAGRPNKPDSITVVITKVTDSYPEPTQ
LLMGTKSVCEVGSNWFQPIYLGAMFSLQEGDKLMVNSDISLVDYTKEDKTFFGAFLL hTL1A (1-251) amino acid sequence
(SEQ ID NO: 94)
MAEDLGLSFGETASVEMLPEHGSCRPKARSSSARWALTCCLVLLLPFLAGLTTYLLVSQLRAQGEACVQFQ
ALKGQEFAPSHQQVYAPLRADGDKPRAHLTVVRQTPTQHFKNQFPALHWEHELGLAFTKNRMNYTNKFLL
IPESGDYFIYSQVTFRGMTSECSEIRQAGRPNKPDSITVVITKVTDSYPEPTQLLMGTKSVCEVGSNWFQ
PIYLGAMFSLQEGDKLMVNSDISLVDYTKEDKTFFGAFLL
TL1W81 (His-TEV-TL1A K111S) nucleotide sequence
(SEQ ID NO: 95)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAGCAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W83 (His-TEV-TL1A E120K) nucleotide sequence
(SEQ ID NO: 96)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGAAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W84 (His-TEV-TL1A E120H) nucleotide sequence
(SEQ ID NO: 97)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGCACCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA -continued CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W40 (His-TEV-TL1A L123S) nucleotide sequence (SEQ ID NO: 98)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W85 (His-TEV-TL1A) nucleotide sequence (SEQ ID NO: 99)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W86 (His-TEV-TL1A G124K) nucleotide sequence (SEQ ID NO: 100)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W89 (His-TEV-TL1A R156Y) nucleotide sequence (SEQ ID NO: 101)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCTACGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W92 (His-TEV-TL1A M158Y) nucleotide sequence (SEQ ID NO: 102)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCTACACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W97 (His-TEV-TL1A K173S) nucleotide sequence (SEQ ID NO: 103)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W98 (His-TEV-TL1A K173R) nucleotide sequence (SEQ ID NO: 104)

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC

-continued

CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATCGGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W107 (His-TEV-TL1A D186Y) nucleotide sequence
(SEQ ID NO: 105)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCTACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W113 (His-TEV-TL1A P189S) nucleotide sequence
(SEQ ID NO: 106)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACAGCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W28 (His-TEV-hTL1A 72-251 E190G) nucleotide sequence
(SEQ ID NO: 107)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGGCCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W45 (His-TEV-TL1A E190F) nucleotide sequence
(SEQ ID NO: 108)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCTTCCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W123 (His-TEV-TL1A N207S) nucleotide sequence
(SEQ ID NO: 109)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAGCTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W126 (His-TEV-TL1A F209W) nucleotide sequence
(SEQ ID NO: 110)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTGGCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W46 (His-TEV-TL1A T239W) nucleotide sequence
(SEQ ID NO: 111)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACTGGAAGGAGGATAAGACCTT
CTTCGGCGCCTTCCTGCTG TL1W137 (His-TEV-TL1A K240S) nucleotide sequence
(SEQ ID NO: 112)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAGCGAGGATAAGACCTT
CTTCGGCGCCTTCCTGCTG TL1W139 (His-TEV-TL1A E241Q) nucleotide sequence
(SEQ ID NO: 113)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGCAGGATAAGACCTT
CTTCGGCGCCTTCCTGCTG TL1W2 (His-TEV-hTL1A 72-251) nucleotide sequence
(SEQ ID NO: 114)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W47 (His-TEV-TL1A E241A) nucleotide sequence
(SEQ ID NO: 115)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGCGGATAAGACCTT
CTTCGGCGCCTTCCTGCTG TL1W136 (His-TEV-TL1A K240F) nucleotide sequence
(SEQ ID NO: 116)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCTTCGAGGATAAGACCTT
CTTCGGCGCCTTCCTGCTG TL1W138 (His-TEV-TL1A K240D) nucleotide sequence
(SEQ ID NO: 117)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC -continued AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCGACGAGGATAAGACCTT
CTTCGGCGCCTTCCTGCTG TL1W135 (His-TEV-TL1A K240A) nucleotide sequence
(SEQ ID NO: 118)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCGCCGAGGATAAGACCTT
CTTCGGCGCCTTCCTGCTG TL1W134 (His-TEV-TL1A T239K) nucleotide sequence
(SEQ ID NO: 119)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACAAGAAGGAGGATAAGACCTT
CTTCGGCGCCTTCCTGCTG TL1W133 (His-TEV-TL1A T239F) nucleotide sequence
(SEQ ID NO: 120)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACTTCAAGGAGGATAAGACCTT
CTTCGGCGCCTTCCTGCTG TL1W27 (His-TEV-hTL1A 72-251 T239E) nucleotide sequence
(SEQ ID NO: 121)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACGAAAAGGAGGATAAGACCTT
CTTCGGCGCCTTCCTGCTG TL1W132 (His-TEV-TL1A T239A) nucleotide sequence
(SEQ ID NO: 122)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACGCCAAGGAGGATAAGACCTT
CTTCGGCGCCTTCCTGCTG TL1W128 (His-TEV-TL1A Y238S) nucleotide sequence
(SEQ ID NO: 123)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATAGCACCAAGGAGGATAAGACCTT
CTTCGGCGCCTTCCTGCTG TL1W130 (His-TEV-TL1A Y238R) nucleotide sequence
(SEQ ID NO: 124)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC -continued AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATCGGACCAAGGAGGATAAGACCTT
CTTCGGCGCCTTCCTGCTG TL1W129 (His-TEV-TL1A Y238K) nucleotide sequence (SEQ ID NO: 125)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATAAGACCAAGGAGGATAAGACCTT
CTTCGGCGCCTTCCTGCTG TL1W131 (His-TEV-TL1A Y238E) nucleotide sequence (SEQ ID NO: 126)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATGAGACCAAGGAGGATAAGACCTT
CTTCGGCGCCTTCCTGCTG TL1W127 (His-TEV-TL1A Y238A) nucleotide sequence (SEQ ID NO: 127)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATGCCACCAAGGAGGATAAGACCTT
CTTCGGCGCCTTCCTGCTG TL1W24 (His-TEV-hTL1A 72-251 F209A) nucleotide sequence (SEQ ID NO: 128)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGGCCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W124 (His-TEV-TL1A N207K) nucleotide sequence (SEQ ID NO: 129)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAAGTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W122 (His-TEV-TL1A N207F) nucleotide sequence (SEQ ID NO: 130)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCTTCTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W125 (His-TEV-TL1A N207E) nucleotide sequence (SEQ ID NO: 131)

-continued
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCGAGTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W25 (His-TEV-hTL1A 72-251 N207A) nucleotide sequence
(SEQ ID NO: 132)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCGCCCTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W120 (His-TEV-TL1A S206K) nucleotide sequence
(SEQ ID NO: 133)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAAGAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W119 (His-TEV-TL1A S206F) nucleotide sequence
(SEQ ID NO: 134)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCTTCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W121 (His-TEV-TL1A S206E) nucleotide sequence
(SEQ ID NO: 135)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCGAGAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W118 (His-TEV-TL1A S206A) nucleotide sequence
(SEQ ID NO: 136)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCGCCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W116 (His-TEV-TL1A T192K) nucleotide sequence
(SEQ ID NO: 137)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCAAGCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

-continued

TL1W115 (His-TEV-TL1A T192F) nucleotide sequence
(SEQ ID NO: 138)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCTTCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W117 (His-TEV-TL1A T192E) nucleotide sequence
(SEQ ID NO: 139)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCGAGCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W114 (His-TEV-TL1A T192A) nucleotide sequence
(SEQ ID NO: 140)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCGCCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W44 (His-TEV-TL1A P189K) nucleotide sequence
(SEQ ID NO: 141)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACAAAGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W112 (His-TEV-TL1A P189F) nucleotide sequence
(SEQ ID NO: 142)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACTTCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W29 (His-TEV-hTL1A 72-251 P189A) nucleotide sequence
(SEQ ID NO: 143)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACGCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W43 (His-TEV-TL1A Y188S) nucleotide sequence
(SEQ ID NO: 144)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTCCCCCGAGCCCACCCAGCTGCTGATGGGCACC TL1W32 (His-TEV-hTL1A 72-251 Y188A) nucleotide sequence
(SEQ ID NO: 145)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCGCCCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W109 (His-TEV-TL1A S187L) nucleotide sequence
(SEQ ID NO: 146)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACCTCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W110 (His-TEV-TL1A S187K) nucleotide sequence
(SEQ ID NO: 147)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAAGTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W111 (His-TEV-TL1A S187D) nucleotide sequence
(SEQ ID NO: 148)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACGACTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W108 (His-TEV-TL1A S187A) nucleotide sequence
(SEQ ID NO: 149)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACGCCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W105 (His-TEV-TL1A T185N) nucleotide sequence
(SEQ ID NO: 150)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGAACGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W104 (His-TEV-TL1A T185L) nucleotide sequence
(SEQ ID NO: 151)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC -continued
```
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGCTCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W106 (His-TEV-TL1A T185D) nucleotide sequence (SEQ ID NO: 152)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGGACGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W103 (His-TEV-TL1A T185A) nucleotide sequence (SEQ ID NO: 153)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGGCCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W101 (His-TEV-TL1A S176N) nucleotide sequence (SEQ ID NO: 154)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CAACATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W100 (His-TEV-TL1A S176L) nucleotide sequence (SEQ ID NO: 155)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CCTCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W102 (His-TEV-TL1A S176K) nucleotide sequence (SEQ ID NO: 156)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CAAGATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W99 (His-TEV-TL1A S176A) nucleotide sequence (SEQ ID NO: 157)
```
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CGCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG
```

TL1W96 (His-TEV-TL1A R170E) nucleotide sequence (SEQ ID NO: 158)

-continued

CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAGAGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG

TL1W95 (His-TEV-TL1A Q167A) nucleotide sequence
(SEQ ID NO: 159)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACCGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W93 (His-TEV-TL1A M158K) nucleotide sequence
(SEQ ID NO: 160)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCAAGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W94 (His-TEV-TL1A M158E) nucleotide sequence
(SEQ ID NO: 161)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCGAGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W90 (His-TEV-TL1A R156K) nucleotide sequence
(SEQ ID NO: 162)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAAGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W91 (His-TEV-TL1A R156E) nucleotide sequence
(SEQ ID NO: 163)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCGAGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W88 (His-TEV-TL1A R156A) nucleotide sequence
(SEQ ID NO: 164)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCGCCGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG -continued TL1W87 (His-TEV-TL1A G124D) nucleotide sequence
(SEQ ID NO: 165)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGCTGGACCTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W38 (His-TEV-TL1A L123K) nucleotide sequence
(SEQ ID NO: 166)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGAAGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W39 (His-TEV-TL1A L123G) nucleotide sequence
(SEQ ID NO: 167)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W37 (His-TEV-TL1A L123E) nucleotide sequence
(SEQ ID NO: 168)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGAGCACGAGGAGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W41 (His-TEV-TL1A E120A) nucleotide sequence
(SEQ ID NO: 169)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGTTTCCCGCCCTCCACTGGGCGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W42 (His-TEV-TL1A F114A) nucleotide sequence
(SEQ ID NO: 170)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGAACCAGGCTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W30 (His-TEV-hTL1A 72-251 N112E) nucleotide sequence
(SEQ ID NO: 171)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCAAGGAACAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC -continued AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W82 (His-TEV-TL1A K111E) nucleotide sequence
(SEQ ID NO: 172)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCGAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W80 (His-TEV-TL1A K111A) nucleotide sequence
(SEQ ID NO: 173)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGAGGCAGAC
CCCCACCCAGCACTTCGCCAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W31 (GD: Single chain MMB in CBIS; His-TEV-hTL1A 72-251 R103Q)
nucleotide sequence
(SEQ ID NO: 174)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGCAACAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W78 (His-TEV-TL1A R103H) nucleotide sequence
(SEQ ID NO: 175)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGCACCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W79 (His-TEV-TL1A R103E) nucleotide sequence
(SEQ ID NO: 176)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGGAGCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W33 (His-TEV-hTL1A 72-251 R103A) nucleotide sequence
(SEQ ID NO: 177)
CATCATCACCACCATCACGAGAACCTGTACTTCCAAGGTCTCAAGGGCCAGGAGTTCGCTCCCTCCCATC
AGCAGGTGTACGCTCCCCTGAGAGCCGATGGCGATAAGCCCAGAGCCCACCTGACCGTCGTGGCCCAGAC
CCCCACCCAGCACTTCAAGAACCAGTTTCCCGCCCTCCACTGGGAGCACGAGCTGGGACTGGCCTTTACC
AAGAACAGAATGAATTACACCAACAAGTTTCTGCTCATCCCCGAGAGCGGAGACTACTTCATCTACTCCC
AGGTGACCTTCAGGGGCATGACAAGCGAGTGCAGCGAGATCAGACAGGCCGGAAGGCCTAATAAGCCCGA
CTCCATCACAGTGGTGATCACAAAGGTGACCGACAGCTACCCCGAGCCCACCCAGCTGCTGATGGGCACC
AAGAGCGTGTGCGAAGTGGGCAGCAACTGGTTCCAGCCCATCTACCTGGGCGCCATGTTCAGCCTGCAGG
AGGGCGACAAGCTGATGGTGAACGTGAGCGACATTTCCCTGGTCGATTACACCAAGGAGGATAAGACCTT
CTTCGGCGCCTTCCTGCTG TL1W15 (GD: Single chain protein in CBIS -> HSA C-terminal Fusion;
His-TEV-HSA(C34S)-G4S-TL1A-3(G3S)-TL1A-3(G3S)-TL1A) nucleotide
sequence
(SEQ ID NO: 178)

-continued

```
CATCATCACCACCATCACGAGAACCTGTACTTCCAAGGTGATGCTCACAAGTCCGAGGTGGCTCACAGGT
TTAAAGACCTCGGCGAGGAGAACTTCAAGGCCCTCGTCCTGATTGCTTTCGCTCAGTACCTGCAGCAGTC
CCCCTTCGAGGACCATGTCAAGCTGGTGAATGAGGTGACAGAATTCGCCAAGACCTGTGTGGCTGACGAA
TCCGCTGAGAACTGCGACAAGTCCCTGCACACCCTGTTCGGCGATAAACTGTGCACAGTGGCTACCCTCA
GAGAAACCTATGGCGAAATGGCCGACTGTTGCGCCAAGCAAGAGCCCGAGAGGAACGAATGCTTCCTCCA
GCACAAGGATGACAATCCTAACCTGCCCAGACTGGTGAGACCCGAGGTGGATGTCATGTGCACAGCCTTC
CACGATAACGAGGAGACATTCCTGAAGAAATATCTCTATGAAATCGCCAGGAGGCATCCCTACTTCTATG
CCCCCGAGCTGCTCTTCTTCGCCAAGAGGTATAAAGCCGCTTTCACCGAGTGCTGCCAGGCTGCCGACAA
GGCCGCTTGTCTGCTGCCCAAGCTGGACGAGCTGAGGGACGAGGGAAAGGCTAGCTCCGCTAAGCAGAGA
CTGAAGTGCGCCAGCCTGCAGAAATTCGGAGAAAGGGCCTTCAAGGCCTGGGCCGTGGCTAGGCTGAGCC
AGAGATTTCCTAAGGCCGAGTTTGCCGAAGTGAGCAAGCTGGTGACCGACCTGACAAAGGTCCACACAGA
ATGTTGCCACGGCGACCTGCTGGAGTGCGCCGATGATAGGGCCGATCTGGCCAAATACATCTGTGAGAAC
CAAGACTCCATCTCCTCCAAGCTGAAGGAGTGTTGCGAGAAGCCTCTGCTCGAGAAGAGCCACTGCATCG
CTGAAGTCGAGAACGACGAGATGCCTGCCGATCTCCCCTCCCTGGCCGCCGATTTCGTGGAATCCAAGGA
CGTCTGTAAGAACTACGCCGAGGCCAAGGATGTGTTCCTGGGAATGTTCCTGTACGAGTACGCTAGGAGG
CACCCTGACTATAGCGTGGTGCTCCTCCTGAGGCTGGCCAAGACATATGAGACCACCCTGGAAAAGTGCT
GCGCCGCTGCCGATCCCCATGAGTGCTATGCCAAGGTCTTCGACGAGTTTAAGCCCCTGGTGGAAGAGCC
CCAGAACCTGATCAAACAGAACTGTGAGCTGTTCGAGCAGCTCGGAGAGTACAAGTTCCAGAATGCCCTC
CTCGTGAGGTACACAAAGAAGGTCCCCCAGGTCTCCACACCTACCCTGGTGGAGGTCTCCAGAAACCTGG
GCAAGGTGGGATCCAAGTGCTGCAAGCATCCTGAGGCCAAAAGAATGCCCTGTGCTGAGGATTACCTGAG
CGTGGTCCTGAATCAGCTGTGCGTGCTGCATGAAAAACCCCCGTCTCCGATAGGGTCACAAAGTGCTGC
ACCGAGAGCCTGGTGAATAGAAGGCCCTGTTTCTCCGCCCTGGAGGTGGACGAAACCTATGTCCCCAAAG
AGTTCAACGCTGAAACATTTACCTTCCACGCTGACATTTGCACCCTGAGCGAGAAGGAGAGGCAGATCAA
GAAGCAGACAGCTCTCGTGGAGCTCGTGAAGCACAAACCTAAAGCCACAAAGGAGCAACTGAAGGCCGTC
ATGGACGACTTTGCCGCTTTCGTCGAGAAGTGCTGTAAGGCCGACGACAAGGAGACATGTTTCGCCGAGG
AGGGAAAGAAGCTGGTCGCTGCTAGCCAAGCTGCCCTGGGCCTGGGAGGAGGAGGAAGCGTGTATGCCCC
CCTGAGAGCTGACGGAGATAAGCCTAGGGCCCACCTGACCGTCGTCAGACAGACCCCTACCCAACACTTC
AAGAACCAGTTCCCCGCTCTGCACTGGGAGCACGAACTGGGCCTGGCCTTCACAAAAAACAGAATGAATT
ACACCAACAAGTTCCTCCTGATTCCCGAAAGCGGCGATTATTTTATCTACAGCCAGGTGACCTTTAGGGG
CATGACATCCGAGTGCTCCGAGATCAGACAAGCCGGAAGACCCAACAAGCCCGACTCCATCACAGTGGTC
ATCACAAAGGTGACAGATAGCTATCCTGAACCTACCCAGCTGCTGATGGGCACCAAGTCCGTCTCGTGAGG
TGGGAAGCAACTGGTTTCAACCCATCTACCTGGGCGCTATGTTCTCCCTGCAAGAGGGCGATAAGCTGAT
GGTGAATGTGTCCGACATTTCCCTGGTGGATTATACCAAAGAGGACAAGACCTTCTTTGGCGCCTTTCTC
CTGGGAGGAGGATCCGGCGGAGGATCCGGAGGCGGCTCCGTCTATGCCCCTCTGAGGGCTGACGGAGACA
AGCCCAGGGCCCATCTGACCGTGGTGAGACAAACCCCCACCCAACACTTTAAGAACCAGTTTCCTGCTCT
GCATTGGGAGCATGAGCTGGGCCTGGCCTTTACCAAAAATAGGATGAACTATACCAATAAGTTCCTGCTG
ATCCCCGAGTCCGGAGACTACTTTATCTATTCCCAGGTCACCTTCAGGGCATGACCTCCGAGTGCAGCG
AGATTAGACAGGCCGGCAGACCCAATAAACCCGACAGCATCACCGTCGTGATCACCAAAGTGACAGACTC
CTACCCCGAACCTACACAACTCCTGATGGGCACCAAAAGCGTGTGCGAAGTGGGCTCCAACTGGTTCCAG
CCCATCTACCTGGGCGCTATGTTTAGCCTGCAAGAAGGCGATAAACTGATGGTCAACGTGTCCGACATCA
GCCTGGTCGACTACACAAAAGAGGATAAGACCTTCTTCGGAGCCTTTCTGCTCGGAGGAGGATCCGGCGG
CGGCAGCGGCGGAGGCAGCGTCTACGCCCCCCTGAGAGCTGATGGCGATAAACCTAGAGCCCATCTGACA
GTGGTGAGACAGACCCCCACCCAGCATTTCAAAAACCAGTTTCCCGCCTGCATTGGGAACACGAGCTGG
GACTGGCCTTCACCAAAAACAGGATGAATTATACCAACAAATTTCTGCTGATCCCCGAATCCGGCGATTA
CTTCATCTACAGCCAAGTGACCTTCAGGGGAATGACCTCCGAATGTTCCGAAATCAGACAGGCTGGCAGG
CCCAACAAACCCGATTCCATCACCGTGGTGATCACCAAGGTGACCGACAGCTACCCCGAGCCTACCCAAC
TGCTGATGGGAACCAAGAGCGTGTGTGAGGTGGGCTCCAATTGGTTCCAGCCCATCTATCTGGGCGCCAT
GTTCAGCCTGCAGGAGGGAGACAAACTGATGGTGAACGTGTCCGATATCTCCCTCGTCGACTACACCAAG
GAGGATAAAACCTTTTTCGGCGCCTTCCTGCTC
```

TL1W9 (GD: Single chain protein in CBIS -> HSA C-terminal Fusion;
His-TEV-G-HSA (C34S)-2(G4S)-TL1A) nucleotide sequence (SEQ ID NO: 179)
```
CATCATCACCACCATCACGAGAACCTGTACTTCCAAGGTGATGCTCACAAGTCCGAGGTGGCTCACAGGT
TTAAAGACCTCGGCGAGGAGAACTTCAAGGCCCTCGTCCTGATTGCTTTCGCTCAGTACCTGCAGCAGTC
CCCCTTCGAGGACCATGTCAAGCTGGTGAATGAGGTGACAGAATTCGCCAAGACCTGTGTGGCTGACGAA
TCCGCTGAGAACTGCGACAAGTCCCTGCACACCCTGTTCGGCGATAAACTGTGCACAGTGGCTACCCTCA
GAGAAACCTATGGCGAAATGGCCGACTGTTGCGCCAAGCAAGAGCCCGAGAGGAACGAATGCTTCCTCCA
GCACAAGGATGACAATCCTAACCTGCCCAGACTGGTGAGACCCGAGGTGGATGTCATGTGCACAGCCTTC
CACGATAACGAGGAGACATTCCTGAAGAAATATCTCTATGAAATCGCCAGGAGGCATCCCTACTTCTATG
CCCCCGAGCTGCTCTTCTTCGCCAAGAGGTATAAAGCCGCTTTCACCGAGTGCTGCCAGGCTGCCGACAA
GGCCGCTTGTCTGCTGCCCAAGCTGGACGAGCTGAGGGACGAGGGAAAGGCTAGCTCCGCTAAGCAGAGA
CTGAAGTGCGCCAGCCTGCAGAAATTCGGAGAAAGGGCCTTCAAGGCCTGGGCCGTGGCTAGGCTGAGCC
AGAGATTTCCTAAGGCCGAGTTTGCCGAAGTGAGCAAGCTGGTGACCGACCTGACAAAGGTCCACACAGA
ATGTTGCCACGGCGACCTGCTGGAGTGCGCCGATGATAGGGCCGATCTGGCCAAATACATCTGTGAGAAC
CAAGACTCCATCTCCTCCAAGCTGAAGGAGTGTTGCGAGAAGCCTCTGCTCGAGAAGAGCCACTGCATCG
CTGAAGTCGAGAACGACGAGATGCCTGCCGATCTCCCCTCCCTGGCCGCCGATTTCGTGGAATCCAAGGA
CGTCTGTAAGAACTACGCCGAGGCCAAGGATGTGTTCCTGGGAATGTTCCTGTACGAGTACGCTAGGAGG
CACCCTGACTATAGCGTGGTGCTCCTCCTGAGGCTGGCCAAGACATATGAGACCACCCTGGAAAAGTGCT
GCGCCGCTGCCGATCCCCATGAGTGCTATGCCAAGGTCTTCGACGAGTTTAAGCCCCTGGTGGAAGAGCC
CCAGAACCTGATCAAACAGAACTGTGAGCTGTTCGAGCAGCTCGGAGAGTACAAGTTCCAGAATGCCCTC
CTCGTGAGGTACACAAAGAAGGTCCCCCAGGTCTCCACACCTACCCTGGTGGAGGTCTCCAGAAACCTGG
GCAAGGTGGGATCCAAGTGCTGCAAGCATCCTGAGGCCAAAAGAATGCCCTGTGCTGAGGATTACCTGAG
CGTGGTCCTGAATCAGCTGTGCGTGCTGCATGAAAAGACCCCCGTCTCCGATAGGGTCACAAAGTGCTGC
ACCGAGAGCCTGGTGAATAGAAGGCCCTGTTTCTCCGCCCTGGAGGTGGACGAAACCTATGTCCCCAAAG
AGTTCAACGCTGAAACATTTACCTTCCACGCTGACATTTGCACCCTGAGCGAGAAGGAGAGGCAGATCAA
GAAGCAGACAGCTCTCGTGGAGCTCGTGAAGCACAAACCTAAAGCCACAAAGGAGCAACTGAAGGCCGTC
ATGGACGACTTTGCCGCTTTCGTCGAGAAGTGCTGTAAGGCCGACGACAAGGAGACATGTTTCGCCGAGG
AGGGAAAGAAGCTGGTCGCTGCTAGCCAAGCTGCCCTGGGCCTGGGAGGAGGAGGAAGCGGCGGAGGAGG
ATCCCTCAAGGGCCAGGAGTTCGCTCCCTCCCATCAGCAGGTGTACGCTCCCCTGAGAGCCGATGGCGAT
AAGCCCAGAGCCCACCTGACCGTCGTGAGGCAGACCCCCACCCAGCACTTCAAGAACCAGTTTCCCGCCC
```

-continued

TCCACTGGGAGCACGAGCTGGGACTGGCCTTTACCAAGAACAGAATGAATTACACCAACAAGTTTCTGCT
CATCCCCGAGAGCGGAGACTACTTCATCTACTCCCAGGTGACCTTCAGGGGCATGACAAGCGAGTGCAGC
GAGATCAGACAGGCCGGAAGGCCTAATAAGCCCGACTCCATCACAGTGGTGATCACAAAGGTGACCGACA
GCTACCCCGAGCCCACCCAGCTGCTGATGGGCACCAAGAGCGTGTGCGAAGTGGGCAGCAACTGGTTCCA
GCCCATCTACCTGGGCGCCATGTTCAGCCTGCAGGAGGGCGACAAGCTGATGGTGAACGTGAGCGACATT
TCCCTGGTCGATTACACCAAGGAGGATAAGACCTTCTTCGGCGCCTTCCTGCTG

TL1W19 (His-TEV-TL1A-TL1A-TL1A) nucleotide sequence
(SEQ ID NO: 180)
CATCATCATCACCACCACGAGAATCTCTATTTTCAGGGCGCTCCCCTGAGAGCCGATGGCGATAAGCCTA
GAGCCCACCTGACAGTGGTGAGACAAACCCCTACACAGCACTTCAAAAATCAGTTCCCTGCCCTGCACTG
GGAACATGAGCTGGGCCTGGCCTTCACCAAGAACAGGATGAATTACACAAATAAGTTCCTGCTCATCCCT
GAGTCCGGCGACTACTTCATCTATAGCCAAGTGACCTTCAGAGGCATGACCAGCGAGTGCTCCGAGATCA
GGCAGGCTGGAAGACCTAACAAGCCCGATAGCATCACCGTGGTGATTACAAAGGTGACAGACAGCTATCC
CGAGCCCACACAGCTGCTCATGGGCACCAAAAGCGTGTGCGAAGTCGGCAGCAACTGGTTCCAGCCCATC
TACCTGGGCGCCATGTTTAGCCTGCAGGAAGGAGATAAGCTGATGGTCAATGTCTCCGATATCTCCCTGG
TGGATTACACCAAGGAGGACAAAACCTTCTTCGGCGCTTTTCTGCTGGCCCCTCTCAGGGCCGATGGAGA
TAAACCCAGGGCTCACCTGACAGTCGTCAGGCAGACCCCTACACAACACTTCAAGAATCAATTCCCCGCC
CTGCATTGGGAGCACGAACTGGGCCTGGCCTTCACAAAAAATAGGATGAACTATACCAACAAATTCCTGC
TGATCCCTGAATCCGGCGATTACTTCATCTACTCCCAGGTGACCTTCAGAGGCATGACCAGCGAATGCAG
CGAAATCAGACAAGCTGGCAGACCCAACAAACCCGACAGCATTACCGTGGTCATCACCAAGGTCACAGAT
AGCTACCCCGAACCCACACAGCTCCTGATGGGCACCAAGTCCGTCTGTGAGGTCGGCAGCAATTGGTTCC
AGCCTATCTATCTGGGCGCCATGTTTAGCCTGCAAGAGGGAGACAAACTGATGGTGAATGTGTCCGACAT
CTCCCTGGTGGATTACACCAAAGAGGATAAAACCTTTTTCGGCGCCTTCCTGCTGGCTCCTCTGAGGGCT
GACGGCGACAAGCCCAGAGCTCACCTGACCGTCGTGAGGCAAACCCCTACCCAGCACTTTAAGAACCAGT
TTCCCGCCCTGCACTGGGAGCATGAGCTGGGCCTGGCCTTTACCAAAAACAGAATGAACTACACCAACAA
GTTTCTGCTGATCCCCGAAAGCGGCGACTATTTTATCTATAGCCAGGTGACCTTTAGAGGCATGACCAGC
GAGTGTAGCGAGATTAGACAGGCTGGCAGGCCTAACAAGCCTGACAGCATCACCGTGGTGATCACCAAAG
TGACCGACTCCTACCCCGAGCCCACCCAACTGCTCATGGGCACAAAGAGCGTGTGTGAGGTGGGCTCCAA
TTGGTTTCAACCCATCTATCTGGGCGCCATGTTCAGCCTGCAAGAAGGAGACAAGCTCATGGTCAATGTG
AGCGACATCAGCCTGGTGGACTATACCAAAGAAGACAAGACCTTCTTCGGAGCCTTTCTGCTG TL1W14 (Fc-scTL1A with CD4 HC sp prim_transcript) nucleotide sequence
(SEQ ID NO: 181)
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAAGCCTGAGCCTGTCCCCTGGCGGAGGAGGAGGAAGCGTGTATGCCCCCCTGA
GAGCTGACGGAGATAAGCCTAGGGCCCACCTGACCGTCGTCAGACAGACCCCTACCCAACACTTCAAGAA
CCAGTTCCCCGCTCTGCACTGGGAGCACGAACTGGGCCTGGCCTTCACAAAAAACAGAATGAATTACACC
AACAAGTTCCTCCTGATTCCCGAAAGCGGCGATTATTTTATCTACAGCCAGGTGACCTTTAGGGGCATGA
CATCCGAGTGCTCCGAGATCAGACAAGCCGGAAGACCCAACAAGCCCGACTCCATCACAGTGGTCATCAC
AAAGGTGACAGATAGCTATCCTGAACCTACCCAGCTGCTGATGGGCACCAAGTCCGTCTGTGAGGTGGGA
AGCAACTGGTTTCAACCCATCTACCTGGGCGCTATGTTCTCCCTGCAAGAGGGCGATAAGCTGATGGTGA
ATGTGTCCGACATTTCCCTGGTGGATTATACCAAAGAGGACAAGACCTTCTTTGGCGCCTTTCTCCTGGG
AGGAGGATCCGGCGGAGGATCCGGAGGCGGCTCCGTCTATGCCCCTCTGAGGGCTGACGGAGACAAGCCC
AGGGCCCATCTGACCGTGGTGAGACAAACCCCCACCCAACACTTTAAGAACCAGTTTCCTGCTCTGCATT
GGGAGCATGAGCTGGGCCTGGCCTTTACCAAAAATAGGATGAACTATACCAATAAGTTCCTGCTGATCCC
CGAGTCCGGAGACTACTTTATCTATTCCCAGGTCACCTTCAGGGGCATGACCTCCGAGTGCAGCGAGATT
AGACAGGCCGGCAGACCCAATAAACCCGACAGCATCACCGTCGTGATCACCAAAGTGACAGACTCCTACC
CCGAACCTACACAACTCCTGATGGGCACCAAAAGCGTGTGCGAAGTGGGCTCCAACTGGTTCCAGCCCAT
CTACCTGGGCGCTATGTTTAGCCTGCAAGAAGGCGATAAACTGATGGTCAACGTGTCCGACATCAGCCTG
GTCGACTACACAAAAGAGGATAAGCCTTCTTCGGAGCCTTTCTGCTCGGAGGCGGATCCGGCGGCGGCA
GCGGCGGAGGCAGCGTCTACGCCCCCCTGAGAGCTGATGGCGATAAACCTAGAGCCCATCTGACAGTGGT
GAGACAGACCCCCACCCAGCATTTCAAAAACCAGTTTCCCGCCCTGCATTGGGAACACGAGCTGGGACTG
GCCTTCACCAAAAACAGGATGAATTATACCAACAAATTTCTGCTGATCCCCGAATCCGGCGATTACTTCA
TCTACAGCCAAGTGACCTTCAGGGGAATGACCTCCGAATGTTCCGAAATCAGACAGGCTGGCAGGCCCAA
CAAACCCGATTCCATCACCGTGGTGATCACCAAGGTGACCGACAGCTACCCCGAGCCTACCCAACTGCTG
ATGGGAACCAAGAGCGTGTGTGAGGTGGGCTCCAATTGGTTCCAGCCCATCTATCTGGGCGCCATGTTCA
GCCTGCAGGAGGGAGACAAACTGATGGTGAACGTGTCCGATATCTCCCTCGTCGACTACACCAAGGAGGA
TAAAACCTTTTTCGGCGCCTTCCTGCTC TL1W329 (Fc-scTL1A K111A L123K M158Y Q167A E190F N207F) nucleotide sequence
(SEQ ID NO: 182)
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAAGCCTGAGCCTGTCCCCTGGCGGAGGAGGAGGAAGCGTGTATGCCCCCCTGA -continued
```
GAGCTGACGGAGATAAGCCTAGGGCCCACCTGACCGTCGTCAGACAGACCCCTACCCAACACTTCGCCAA
CCAGTTCCCCGCTCTGCACTGGGAGCACGAAAAGGGCCTGGCCTTCACAAAAAACAGAATGAATTACACC
AACAAGTTCCTCCTGATTCCCGAAAGCGGCGATTATTTTATCTACAGCCAGGTGACCTTTAGGGGCTACA
CATCCGAGTGCTCCGAGATCAGAGCCGCCGGAAGACCCAACAAGCCCGACTCCATCACAGTGGTCATCAC
AAAGGTGACAGATAGCTATCCTTTCCCTACCCAGCTGCTGATGGGCACCAAGTCCGTCTGTGAGGTGGGA
AGCTTCTGGTTTCAACCCATCTACCTGGGCGCTATGTTCTCCCTGCAAGAGGGCGATAAGCTGATGGTGA
ATGTGTCCGACATTTCCCTGGTGGATTATACCAAAGAGGACAAGACCTTCTTTGGCGCCTTTCTCCTGGG
AGGAGGATCCGGCGGAGGATCCGGAGGCGGCTCCGTCTATGCCCCTCTGAGGGCTGACGGAGACAAGCCC
AGGGCCCATCTGACCGTGGTGAGACAAACCCCCACCCAACACTTTGCCAACCAGTTTCCTGCTCTGCATT
GGGAGCATGAGAAGGGCCTGGCCTTTACCAAAAATAGGATGAACTATACCAATAAGTTCCTGCTGATCCC
CGAGTCCGGAGACTACTTTATCTATTCCCAGGTCACCTTCAGGGGCTACACCTCCGAGTGCAGCGAGATT
AGAGCCGCCGGCAGACCCAATAAACCCGACAGCATCACCGTCGTGATCACCAAAGTGACAGACTCCTACC
CCTTCCCTACACAACTCCTGATGGGCACCAAAAAGCGTGTGCGAAGTGGGCTCCTTCTGGTTCCAGCCCAT
CTACCTGGGCGCTATGTTTAGCCTGCAAGAAGGCGATAAACTGATGGTCAACGTGTCCGACATCAGCCTG
GTCGACTACACAAAAGAGGATAAGACCTTCTTCGGAGCCTTTCTGCTCGGAGGAGGATCCGGCGGCGGCA
GCGGCGGAGGCAGCGTCTACGCCCCCCTGAGAGCTGATGGCGATAAACCTAGAGCCCATCTGACAGTGGT
GAGACAGACCCCCACCCAGCATTTCGCCAACCAGTTTCCCGCCCTGCATTGGGAACACGAGAAGGGACTG
GCCTTCACCAAAAACAGGATGAATTATACCAACAAATTTCTGCTGATCCCCGAATCCGGCGATTACTTCA
TCTACAGCCAAGTGACCTTCAGGGGATACACCTCCGAATGTTCCGAAATCAGAGCCGCTGGCAGGCCCAA
CAAACCCGATTCCATCACCGTGGTGATCACCAAGGTGACCGACAGCTACCCCTTCCCTACCCAACTGCTG
ATGGGAACCAAGAGCGTGTGTGAGGTGGGCTCCTTCTGGTTCCAGCCCCATCTATCTGGGCGCCATGTTCA
GCCTGCAGGAGGGAGACAAACTGATGGTGAACGTGTCCGATATCTCCCTCGTCGACTACACCAAGGAGGA
TAAAACCTTTTTCGGCGCCTTCCTGCTC
```

TL1W327 (Fc-scTL1A K111A L123K M158Y Q167A S187L E190F) nucleotide
sequence (SEQ ID NO: 183)
```
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAGCCTGAGCCTGTCCCTGGCGGAGGAGGAGGAAGCGTGTATGCCCCCCTGA
GAGCTGACGGAGATAAGCCTAGGGCCCACCTGACCGTCGTCAGACAGACCCCTACCCAACACTTCGCCAA
CCAGTTCCCCGCTCTGCACTGGGAGCACGAAAAGGGCCTGGCCTTCACAAAAAACAGAATGAATTACACC
AACAAGTTCCTCCTGATTCCCGAAAGCGGCGATTATTTTATCTACAGCCAGGTGACCTTTAGGGGCTACA
CATCCGAGTGCTCCGAGATCAGAGCCGCCGGAAGACCCAACAAGCCCGACTCCATCACAGTGGTCATCAC
AAAGGTGACAGATCTGTATCCTTTCCCTACCCAGCTGCTGATGGGCACCAAGTCCGTCTGTGAGGTGGGA
AGCAACTGGTTTCAACCCATCTACCTGGGCGCTATGTTCTCCCTGCAAGAGGGCGATAAGCTGATGGTGA
ATGTGTCCGACATTTCCCTGGTGGATTATACCAAAGAGGACAAGACCTTCTTTGGCGCCTTTCTCCTGGG
AGGAGGATCCGGCGGAGGATCCGGAGGCGGCTCCGTCTATGCCCCTCTGAGGGCTGACGGAGACAAGCCC
AGGGCCCATCTGACCGTGGTGAGACAAACCCCCACCCAACACTTTGCCAACCAGTTTCCTGCTCTGCATT
GGGAGCATGAGAAGGGCCTGGCCTTTACCAAAAATAGGATGAACTATACCAATAAGTTCCTGCTGATCCC
CGAGTCCGGAGACTACTTTATCTATTCCCAGGTCACCTTCAGGGGCTACACCTCCGAGTGCAGCGAGATT
AGAGCCGCCGGCAGACCCAATAAACCCGACAGCATCACCGTCGTGATCACCAAAGTGACAGACCTGTACC
CCTTCCCTACACAACTCCTGATGGGCACCAAAAAGCGTGTGCGAAGTGGGCTCCAACTGGTTCCAGCCCAT
CTACCTGGGCGCTATGTTTAGCCTGCAAGAAGGCGATAAACTGATGGTCAACGTGTCCGACATCAGCCTG
GTCGACTACACAAAAGAGGATAAGACCTTCTTCGGAGCCTTTCTGCTCGGAGGAGGATCCGGCGGCGGCA
GCGGCGGAGGCAGCGTCTACGCCCCCCTGAGAGCTGATGGCGATAAACCTAGAGCCCATCTGACAGTGGT
GAGACAGACCCCCACCCAGCATTTCGCCAACCAGTTTCCCGCCCTGCATTGGGAACACGAGAAGGGACTG
GCCTTCACCAAAAACAGGATGAATTATACCAACAAATTTCTGCTGATCCCCGAATCCGGCGATTACTTCA
TCTACAGCCAAGTGACCTTCAGGGGATACACCTCCGAATGTTCCGAAATCAGAGCCGCTGGCAGGCCCAA
CAAACCCGATTCCATCACCGTGGTGATCACCAAGGTGACCGACCTGTACCCCTTCCCTACCCAACTGCTG
ATGGGAACCAAGAGCGTGTGTGAGGTGGGCTCCAATTGGTTCCAGCCCCATCTATCTGGGCGCCATGTTCA
GCCTGCAGGAGGGAGACAAACTGATGGTGAACGTGTCCGATATCTCCCTCGTCGACTACACCAAGGAGGA
TAAAACCTTTTTCGGCGCCTTCCTGCTC
```

TL1W328 (Fc-scTL1A K111A L123K M158Y Q167A S187L N207F) nucleotide
sequence (SEQ ID NO: 184)
```
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAGCCTGAGCCTGTCCCTGGCGGAGGAGGAGGAAGCGTGTATGCCCCCCTGA
GAGCTGACGGAGATAAGCCTAGGGCCCACCTGACCGTCGTCAGACAGACCCCTACCCAACACTTCGCCAA
CCAGTTCCCCGCTCTGCACTGGGAGCACGAAAAGGGCCTGGCCTTCACAAAAAACAGAATGAATTACACC
AACAAGTTCCTCCTGATTCCCGAAAGCGGCGATTATTTTATCTACAGCCAGGTGACCTTTAGGGGCTACA
CATCCGAGTGCTCCGAGATCAGAGCCGCCGGAAGACCCAACAAGCCCGACTCCATCACAGTGGTCATCAC
AAAGGTGACAGATCTGTATCCTGAACCTACCCAGCTGCTGATGGGCACCAAGTCCGTCTGTGAGGTGGGA
AGCTTCTGGTTTCAACCCATCTACCTGGGCGCTATGTTCTCCCTGCAAGAGGGCGATAAGCTGATGGTGA
ATGTGTCCGACATTTCCCTGGTGGATTATACCAAAGAGGACAAGACCTTCTTTGGCGCCTTTCTCCTGGG
```

-continued

AGGAGGATCCGGCGGAGGATCCGGAGGCGGCTCCGTCTATGCCCCTCTGAGGGCTGACGGAGACAAGCCC
AGGGCCCATCTGACCGTGGTGAGACAAACCCCCACCCAACACTTTGCCAACCAGTTTCCTGCTCTGCATT
GGGAGCATGAGAAGGGCCTGGCCTTTACCAAAAATAGGATGAACTATACCAATAAGTTCCTGCTGATCCC
CGAGTCCGGAGACTACTTTATCTATTCCCAGGTCACCTTCAGGGGCTACACCTCCGAGTGCAGCGAGATT
AGAGCCGCCGGCAGACCCAATAAACCCGACAGCATCACCGTCGTGATCACCAAAGTGACAGACCTGTACC
CCGAACCTACACAACTCCTGATGGGCACCAAAAGCGTGTGCGAAGTGGGCTCCTTCTGGTTCCAGCCCAT
CTACCTGGGCGCTATGTTTAGCCTGCAAGAAGGCGATAAACTGATGGTCAACGTGTCCGACATCAGCCTG
GTCGACTACACAAAAGAGGATAAGACCTTCTTCGGAGCCTTTCTGCTCGGAGGAGGATCCGGCGGCGGCA
GCGGCGGAGGCAGCGTCTACGCCCCCCTGAGAGCTGATGGCGATAAACCTAGAGCCCATCTGACAGTGGT
GAGACAGACCCCCACCCAGCATTTCGCCAACCAGTTTCCCGCCCTGCATTGGGAACACGAGAAGGGACTG
GCCTTCACCAAAAACAGGATGAATTATACCAACAAATTTCTGCTGATCCCCGAATCCGGCGATTACTTCA
TCTACAGCCAAGTGACCTTCAGGGGATACACCTCCGAATGTTCCGAAATCAGAGCCGCTGGCAGGCCCAA
CAAACCCGATTCCATCACCGTGGTGATCACCAAGGTGACCGACCTGTACCCCGAGCCTACCCAACTGCTG
ATGGGAACCAAGAGCGTGTGTGAGGTGGGCTCCTTCTGGTTCCAGCCCATCTATCTGGGCGCCATGTTCA
GCCTGCAGGAGGGAGACAAACTGATGGTGAACGTGTCCGATATCTCCCTCGTCGACTACACCAAGGAGGA
TAAAACCTTTTTCGGCGCCTTCCTGCTC

TL1W331 (Fc-scTL1A K111A L123K Q167A S187L E190F N207F) nucleotide
sequence
(SEQ ID NO: 185)
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAAGCCTGAGCCTGTCCCCTGGCGGAGGAGGAAGCCTGTATGCCCCCCTGA
GAGCTGACGGAGATAAGCCTAGGGCCCACCTGACCGTCGTCAGACAGACCCCTACCCAACACTTCGCCAA
CCAGTTCCCCGCTCTGCACTGGGAGCACGAAAAGGGCCTGGCCTTCACAAAAAACAGAATGAATTACACC
AACAAGTTCCTCCTGATTCCCGAAAGCGGCGATTATTTTATCTACAGCCAGGTGACCTTTAGGGGCATGA
CATCCGAGTGCTCCGAGATCAGAGCCGCCGGAAGACCCAACAAGCCCGACTTCCATCACAGTGGTCATCAC
AAAGGTGACAGATCTGTATCCTTTCCCTACCCAGCTGCTGATGGGCACCAAGTCCGTCTGTGAGGTGGGA
AGCTTCTGGTTTCAACCCATCTACCTGGGCGCTATGTTCTCCCTGCAAGAGGGCGATAAGCTGATGGTGA
ATGTGTCCGACATTTCCCTGGTGGATTATACCAAAGAGGACAAGACCTTCTTTGGCGCCTTTCTCCTGGG
AGGAGGATCCGGCGGAGGATCCGGAGGCGGCTCCGTCTATGCCCCCTGAGGGCTGACGGAGACAAGCCC
AGGGCCCATCTGACCGTGGTGAGACAAACCCCCACCCAACACTTTGCCAACCAGTTTCCTGCTCTGCATT
GGGAGCATGAGAAGGGCCTGGCCTTTACCAAAAATAGGATGAACTATACCAATAAGTTCCTGCTGATCCC
CGAGTCCGGAGACTACTTTATCTATTCCCAGGTCACCTTCAGGGGCATGACCTCCGAGTGCAGCGAGATT
AGAGCCGCCGGCAGACCCAATAAACCCGACAGCATCACCGTCGTGATCACCAAAGTGACAGACCTGTACC
CCTTCCCTACACAACTCCTGATGGGCACCAAAAGCGTGTGCGAAGTGGGCTCCTTCTGGTTCCAGCCCAT
CTACCTGGGCGCTATGTTTAGCCTGCAAGAAGGCGATAAACTGATGGTCAACGTGTCCGACATCAGCCTG
GTCGACTACACAAAAGAGGATAAGACCTTCTTCGGAGCCTTTCTGCTCGGAGGAGGATCCGGCGGCGGCA
GCGGCGGAGGCAGCGTCTACGCCCCCCTGAGAGCTGATGGCGATAAACCTAGAGCCCATCTGACAGTGGT
GAGACAGACCCCCACCCAGCATTTCGCCAACCAGTTTCCCGCCCTGCATTGGGAACACGAGAAGGGACTG
GCCTTCACCAAAAACAGGATGAATTATACCAACAAATTTCTGCTGATCCCCGAATCCGGCGATTACTTCA
TCTACAGCCAAGTGACCTTCAGGGGAATGACCTCCGAATGTTCCGAAATCAGAGCCGCTGGCAGGCCCAA
CAAACCCGATTCCATCACCGTGGTGATCACCAAGGTGACCGACCTGTACCCCTTCCCTACCCAACTGCTG
ATGGGAACCAAGAGCGTGTGTGAGGTGGGCTCCTTCTGGTTCCAGCCCATCTATCTGGGCGCCATGTTCA
GCCTGCAGGAGGGAGACAAACTGATGGTGAACGTGTCCGATATCTCCCTCGTCGACTACACCAAGGAGGA
TAAAACCTTTTTCGGCGCCTTCCTGCTC TL1W61 (Fc-TL1A+His-TL1A) nucleotide sequence
(SEQ ID NO: 186)
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAAGCCTGAGCCTGTCCCCTGGCGGAGGAGGAGGAAGCCTCAAGGGCCAGGAGT
TCGCTCCCTCCCATCAGCAGGTGTACGCTCCCCTGAGAGCCGATGGCGATAAGCCCAGAGCCCACCTGAC
CGTCGTGAGGCAGACCCCCACCCAGCACTTCAAGAACCAGTTTCCCGCCCTCCACTGGGAGCACGAGCTG
GGACTGGCCTTTACCAAGAACAGAATGAATTACACCAACAAGTTTCTGCTCATCCCCGAGAGCGGAGACT
ACTTCATCTACTCCCAGGTGACCTTCAGGGGCATGACAAGCGAGTGCAGCGAGATCAGACAGGCCGGAAG
GCCTAATAAGCCCGACTCCATCACAGTGGTGATCACAAAGGTGACCGACAGCTACCCCGAGCCCACCCAG
CTGCTGATGGGCACCAAGAGCGTGTGCGAAGTGGGCAGCAACTGGTTCCAGCCCATCTACCTGGGCGCCA
TGTTCAGCCTGCAGGAGGGCGACAAGCTGATGGTGAACGTGAGCGACATTTCCCTGGTCGATTACACCAA
GGAGGATAAGACCTTCTTCGGCGCCTTCCTGCTGCATCATCACCACCATCACGAGAACCTGTACTTCCAA
GGTCTCAAGGGCCAGGAGTTCGCTCCCTCCCATCAGCAGGTGTACGCTCCCCTGAGAGCCGATGGCGATA
AGCCCAGAGCCCACCTGACCGTCGTGAGGCAGACCCCCACCCAGCACTTCAAGAACCAGTTTCCCGCCCT
CCACTGGGAGCACGAGCTGGGACTGGCCTTTACCAAGAACAGAATGAATTACACCAACAAGTTTCTGCTC
ATCCCCGAGAGCGGAGACTACTTCATCTACTCCCAGGTGACCTTCAGGGGCATGACAAGCGAGTGCAGCG
AGATCAGACAGGCCGGAAGGCCTAATAAGCCCGACTCCATCACAGTGGTGATCACAAAGGTGACCGACAG
CTACCCCGAGCCCACCCAGCTGCTGATGGGCACCAAGAGCGTGTGCGAAGTGGGCAGCAACTGGTTCCAG
CCCATCTACCTGGGCGCCATGTTCAGCCTGCAGGAGGGCGACAAGCTGATGGTGAACGTGAGCGACATTT -continued
CCCTGGTCGATTACACCAAGGAGGATAAGACCTTCTTCGGCGCCTTCCTGCTG TL1W3 (GD: Fc Fusion in CBIS -> homodimer Fc Fusion; GS-huIgG1 Fc -
2(G4S)-hTL1A 72-251) nucleotide sequence
(SEQ ID NO: 187)
GGATCCTGTCCTCCCTGCCCTGCTCCTGAACTCCTGGGCGGACCCAGCGTGTTTCTGTTCCCCCCCAAAC
CTAAAGACACACTGATGATTAGCAGAACCCCCGAGGTCACCTGCGTGGTGGTGGATGTGTCCCACGAGGA
TCCCGAGGTCAAGTTCAACTGGTACGTGGATGGCGTGGAGGTGCACAACGCCAAAACCAAGCCCAGGGAA
GAGCAGTACAACTCCACCTACAGGGTCGTGAGCGTGCTGACAGTGCTGCACCAGGACTGGCTGAACGGAA
AGGAGTACAAGTGTAAGGTCAGCAACAAGGCTCTGCCTGCCCCCATCGAGAAAACCATCAGCAAGGCCAA
GGGCCAGCCTAGGGAACCCCAGGTGTACACACTGCCCCCTTCCAGGGAGGAGATGACCAAAAACCAGGTC
AGCCTGACATGCCTGGTGAAAGGCTTCTACCCCAGCGATATCGCCGTGGAATGGGAGTCCAACGGCCAGC
CTGAGAACAACTACAAGACCACACCCCCCGTGCTGGACTCCGACGGTTCTTTTTTCCTGTACTCCAAGCT
GACCGTCGACAAGAGCAGGTGGCAACAGGGCAACGTCTTCAGCTGCAGCGTGATGCACGAAGCCCTGCAC
AACCACTACACCCAGAAAAGCCTGAGCCTGTCCCCTGGCGGAGGAGGAGGAAGCCTCAAGGGCCAGGAGT
TCGCTCCCTCCCATCAGCAGGTGTACGCTCCCCTGAGAGCCGATGGCGATAAGCCCAGAGCCCACCTGAC
CGTCGTGAGGCAGACCCCCACCCAGCACTTCAAGAACCAGTTTCCCGCCCTCCACTGGGAGCACGAGCTG
GGACTGGCCTTTACCAAGAACAGAATGAATTACACCAACAAGTTTCTGCTCATCCCCGAGAGCGGAGACT
ACTTCATCTACTCCCAGGTGACCTTCAGGGGCATGACAAGCGAGTGCAGCGAGATCAGACAGGCCGGAAG
GCCTAATAAGCCCGACTCCATCACAGTGGTGATCACAAAGGTGACCGACAGCTACCCCGAGCCCACCCAG
CTGCTGATGGGCACCAAGAGCGTGTGCGAAGTGGGCAGCAACTGGTTCCAGCCCATCTACCTGGGCGCCA
TGTTCAGCCTGCAGGAGGGCGACAAGCTGATGGTGAACGTGAGCGACATTTCCCTGGTCGATTACACCAA
GGAGGATAAGACCTTCTTCGGCGCCTTCCTGCTG It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

What is claimed is:

1. An engineered TNF-like factor 1A (TL1A) ligand, wherein the engineered TL1A ligand comprises
   a. at least one amino acid alteration of the amino acid sequence of SEQ ID NO:94 selected from the group consisting of K111, Q167, and E190 or;
   b. at least one amino acid alteration of the amino acid sequence of SEQ ID NO:94 selected from the group consisting of K111A, K111S, K111E, L123G, L123S, L123E, L123K, Q167A, S187A, S187L, S187K, S187D, E190G, E190F, N207A, N207F, N207S, N207K and N207E,
   and wherein the engineered TL1A ligand comprises a trimeric complex comprising:
   a. three TL1A monomers, wherein the three TL1A monomers form a non-covalent TL1A trimer; or
   b. three TL1A monomers, wherein the three TL1A monomers are covalently linked to form a single-chain TL1A (scTL1A) trimer.

2. The engineered TL1A ligand of claim 1, further comprising a protein stabilizing region, wherein optionally the protein stabilizing region comprises an Fc region, or a human serum albumin (HSA) region.

3. The engineered TL1A ligand of claim 1, comprising:
   a. the non-covalent TL1A trimer and one or more Fc regions;
   b. the non-covalent TL1A trimer and one or more HSA regions;

c. the scTL1A trimer and one or more Fc regions; or d. the scTL1A trimer and one or more HSA regions.

4. The engineered TL1A ligand of claim 3, comprising:

a. two non-covalent TL1A trimers and three Fc regions;

b. two scTL1A trimers and one Fc region;

c. one scTL1A trimer and one Fc region;

d. one non-covalent TL1A trimer and three HSA regions; or e. one scTL1A trimer and one HSA region.

5. The engineered TL1A ligand of claim 1, wherein the three TL1A monomers are covalently bound by a linker, wherein optionally the linker is a peptide linker, and wherein optionally the linker has an amino acid sequence of Gly-Ser or multiple repeats thereof.

6. The engineered TL1A ligand of claim 1, wherein the Fc region is a human IgG1, IgG2 or IgG4 Fc region, and wherein optionally non-covalent TL1A trimer or the scTL1A trimer is fused to the C-terminus of the Fc region.

7. The engineered TL1A ligand of claim 1, wherein:

(i) the engineered TL1A ligand comprises the amino acid sequence of any one of SEQ ID NO:1-93; or (ii) the engineered TL1A ligand comprises:

a. an amino acid sequence that is at least 80%, at least 85%, at least 90%, at least 95%, at least 98%, or 100% identical over its entire length to the amino acid sequence of SEQ ID NO:79;

b. an amino acid sequence that is at least 80%, at least 85%, at least 90%, at least 95%, at least 98%, or 100% identical over its entire length to the amino acid sequence of SEQ ID NO:72;

c. an amino acid sequence that is at least 80%, at least 85%, at least 90%, at least 95%, at least 98%, or 100% identical over its entire length to the amino acid sequence of SEQ ID NO:8;

d. an amino acid sequence that is at least 80%, at least 85%, at least 90%, at least 95%, at least 98%, or 100% identical over its entire length to the amino acid sequence of SEQ ID NO:65;

e. an amino acid sequence that is at least 80%, at least 85%, at least 90%, at least 95%, at least 98%, or 100% identical over its entire length to the amino acid sequence of SEQ ID NO:52;

f. an amino acid sequence that is at least 80%, at least 85%, at least 90%, at least 95%, at least 98%, or 100% identical over its entire length to the amino acid sequence of SEQ ID NO: 14;

g. an amino acid sequence that is at least 80%, at least 85%, at least 90%, at least 95%, at least 98%, or 100% identical over its entire length to the amino acid sequence of SEQ ID NO:36;

h. an amino acid sequence that is at least 80%, at least 85%, at least 90%, at least 95%, at least 98%, or 100% identical over its entire length to the amino acid sequence of SEQ ID NO:90;

i. an amino acid sequence that is at least 80%, at least 85%, at least 90%, at least 95%, at least 98%, or 100% identical over its entire length to the amino acid sequence of SEQ ID NO:88;

j. an amino acid sequence that is at least 80%, at least 85%, at least 90%, at least 95%, at least 98%, or 100% identical over its entire length to the amino acid sequence of SEQ ID NO:91; or k. an amino acid sequence that is at least 80%, at least 85%, at least 90%, at least 95%, at least 98%, or 100% identical over its entire length to the amino acid sequence of SEQ ID NO:89.

8. The engineered TL1A ligand of claim 1, (i) which comprises a bispecific antibody; (ii) which is fused to a heterologous polypeptide; or (iii) which is conjugated to an agent, wherein optionally the agent is a toxin.

9. The engineered TL1A ligand of claim 1 comprising: a first means capable of binding DR3 with an affinity comparable to or higher than the affinity of wildtype TL1A and a second means capable of binding DcR3 with an affinity lower than the affinity of wildtype TL1A, wherein optionally:

(i) the engineered TL1A ligand has a longer serum half-life than wildtype TL1A;

(ii) the engineered TL1A ligand has a high monodispersity and/or stability compared to wildtype TL1A;

(iii) the engineered TL1A ligand co-stimulates T cells in vitro;

(iv) the engineered TL1A ligand co-stimulates T cells in a subject; and/or (v) the engineered TL1A ligand increases production of one or more cytokines in a subject, wherein optionally the one or more cytokines comprise IFNy and TNFa, wherein optionally the subject has an autoimmune disorder or cancer optionally selected from the group consisting of ulcerative colitis, lupus, inflammatory bowel disease (IBD), chronic obstructive pulmonary disease (COPD), arthritis, multiple sclerosis, diabetes, transplant rejection, central nervous system injury, Crohn's disease, psoriasis, leukemia or lymphoma, atherosclerosis, colon cancer, breast cancer, pancreatic cancer, leukemia, lung cancer such as non-small cell lung cancer, glioblastoma, melanoma, prostate cancer, gastric cancer, pituitary adenomas, ovarian cancer, renal cancer, bladder cancer, and a sarcoma, wherein optionally the sarcoma is a rhabdomyosarcoma, and wherein optionally the subject is a subject in need thereof.

10. A nucleic acid encoding the engineered TL1A ligand of claim 1.

11. A pharmaceutical composition, comprising the engineered TL1A ligand of claim 1 or the nucleic acid encoding the engineered TL1A ligand, and a pharmaceutically acceptable excipient.

12. A method of making an engineered TL1A ligand comprising (i) a step for performing the function of introducing at least one amino acid alteration of the amino acid sequence of SEQ ID NO:94 selected from the group consisting of: K111A, L123K, M158Y, Q167A, S187L, E190F, and N207F; and (ii) a step for performing the function of producing a population of engineered TL1A ligand, wherein optionally the method further comprises the step of fusing the engineered TL1A ligand to a heterologous polypeptide, wherein optionally the heterologous polypeptide comprises a protein stabilizing region, and wherein optionally the protein stabilizing region comprises an Fc region, or a HSA region.

13. The method of claim 12, further comprising a step of generating a multimeric engineered TL1A ligand, wherein optionally:

(i) the multimeric engineered TL1A ligand comprises:

a. the non-covalent TL1A trimer and one or more Fc regions;

b. the non-covalent TL1A trimer and one or more HSA regions;

c. the scTL1A trimer and one or more Fc regions; or d. the scTL1A trimer and one or more HSA regions, or (ii) the multimeric engineered TL1A ligand comprises:

a. two non-covalent TL1A trimers and three Fc regions;

b. two scTL1A trimers and one Fc region;
c. one scTL1A trimer and one Fc region;
d. one non-covalent TL1A trimer and three HSA regions; or
e. one scTL1A trimer and one HSA region.

14. The method of claim 12, wherein the engineered TL1A ligand comprises the amino acid sequence of any one of SEQ ID NO: 1-93, or wherein the engineered TL1A ligand comprises:
   a. an amino acid sequence that is at least 80%, at least 85%, at least 90%, at least 95%, at least 98%, or 100% identical over its entire length to the amino acid sequence of SEQ ID NO:79;
   b. an amino acid sequence that is at least 80%, at least 85%, at least 90%, at least 95%, at least 98%, or 100% identical over its entire length to the amino acid sequence of SEQ ID NO:72;
   c. an amino acid sequence that is at least 80%, at least 85%, at least 90%, at least 95%, at least 98%, or 100% identical over its entire length to the amino acid sequence of SEQ ID NO:8;
   d. an amino acid sequence that is at least 80%, at least 85%, at least 90%, at least 95%, at least 98%, or 100% identical over its entire length to the amino acid sequence of SEQ ID NO:65;
   e. an amino acid sequence that is at least 80%, at least 85%, at least 90%, at least 95%, at least 98%, or 100% identical over its entire length to the amino acid sequence of SEQ ID NO:52;
   f. an amino acid sequence that is at least 80%, at least 85%, at least 90%, at least 95%, at least 98%, or 100% identical over its entire length to the amino acid sequence of SEQ ID NO: 14;
   g. an amino acid sequence that is at least 80%, at least 85%, at least 90%, at least 95%, at least 98%, or 100% identical over its entire length to the amino acid sequence of SEQ ID NO:36;
   h. an amino acid sequence that is at least 80%, at least 85%, at least 90%, at least 95%, at least 98%, or 100% identical over its entire length to the amino acid sequence of SEQ ID NO:90;
   i. an amino acid sequence that is at least 80%, at least 85%, at least 90%, at least 95%, at least 98%, or 100% identical over its entire length to the amino acid sequence of SEQ ID NO:88;
   j. an amino acid sequence that is at least 80%, at least 85%, at least 90%, at least 95%, at least 98%, or 100% identical over its entire length to the amino acid sequence of SEQ ID NO:91; or
   k. an amino acid sequence that is at least 80%, at least 85%, at least 90%, at least 95%, at least 98%, or 100% identical over its entire length to the amino acid sequence of SEQ ID NO:89.

15. The method of claim 12, wherein the engineered TL1A ligand comprises three TL1A monomers each comprising amino acids 84 to 251 of SEQ ID NO:94 with K111A, L123K, Q167A, S187L, E190F and N207F mutations.

16. The engineered TL1A ligand of claim 1, wherein the engineered TL1A ligand comprises three TL1A monomers each comprising amino acids 84 to 251 of SEQ ID NO:94 with K111A, L123K, Q167A, S187L, E190F and N207F mutations.

17. The method of claim 12 wherein the engineered TL1A ligand comprises amino acid alterations of K111A, L123K, Q167A, S187L, E190F and N207F of amino acid sequence SEQ ID NO:94.

18. The engineered TL1A ligand of claim 1, wherein the engineered TL1A ligand comprises amino acid alterations of K111A, L123K, Q167A, S187L, E190F and N207F of amino acid sequence SEQ ID NO:94.

* * * * *

SEQUENCE LISTING

```
<160> NUMBER OF SEQ ID NOS: 189

<210> SEQ ID NO 1
<211> LENGTH: 193
<212> TYPE: PRT
<213> ORGANISM: Artificial Sequence
<220> FEATURE:
<223> OTHER INFORMATION: TL1W81 (His-TEV-TL1A K111S) amino acid sequence

<400> SEQUENCE: 1

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Ser Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160
```

```
Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 2
<211> LENGTH: 193
<212> TYPE: PRT
<213> ORGANISM: Artificial Sequence
<220> FEATURE:
<223> OTHER INFORMATION: TL1W83 (His-TEV-TL1A E120K) amino acid sequence

<400> SEQUENCE: 2

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Lys His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 3
<211> LENGTH: 193
<212> TYPE: PRT
<213> ORGANISM: Artificial Sequence
<220> FEATURE:
<223> OTHER INFORMATION: TL1W84 (His-TEV-TL1A E120H) amino acid sequence

<400> SEQUENCE: 3

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp His His Glu
    50                  55                  60
```

```
Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 4
<211> LENGTH: 193
<212> TYPE: PRT
<213> ORGANISM: Artificial Sequence
<220> FEATURE:
<223> OTHER INFORMATION: TL1W40 (His-TEV-TL1A L123S) amino acid sequence

<400> SEQUENCE: 4

His His His His His His Glu Asn Leu Tyr Phe Gln Gly Leu Lys Gly
 1               5                   10                  15

Gln Glu Phe Ala Pro Ser His Gln Val Tyr Ala Pro Leu Arg Ala
                 20                  25                  30

Asp Gly Asp Lys Pro Arg Ala His Leu Thr Val Val Arg Gln Thr Pro
             35                  40                  45

Thr Gln His Phe Lys Asn Gln Phe Pro Ala Leu His Trp Glu His Glu
 50                  55                  60

Ser Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 5
<211> LENGTH: 193
<212> TYPE: PRT
<213> ORGANISM: Artificial Sequence
```

```
<220> FEATURE:
<223> OTHER INFORMATION: TL1W85 (His-TEV-TL1A G124S) amino acid sequence

<400> SEQUENCE: 5

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Ser Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 6
<211> LENGTH: 193
<212> TYPE: PRT
<213> ORGANISM: Artificial Sequence
<220> FEATURE:
<223> OTHER INFORMATION: TL1W86 (His-TEV-TL1A G124K) amino acid sequence

<400> SEQUENCE: 6

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Lys Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140
```

-continued

```
Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 7
<211> LENGTH: 193
<212> TYPE: PRT
<213> ORGANISM: Artificial Sequence
<220> FEATURE:
<223> OTHER INFORMATION: TL1W89 (His-TEV-TL1A R156Y) amino acid sequence

<400> SEQUENCE: 7

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Tyr Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 8
<211> LENGTH: 193
<212> TYPE: PRT
<213> ORGANISM: Artificial Sequence
<220> FEATURE:
<223> OTHER INFORMATION: TL1W92 (His-TEV-TL1A M158Y) amino acid sequence

<400> SEQUENCE: 8

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45
```

```
Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Tyr Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 9
<211> LENGTH: 193
<212> TYPE: PRT
<213> ORGANISM: Artificial Sequence
<220> FEATURE:
<223> OTHER INFORMATION: TL1W97 (His-TEV-TL1A K173S) amino acid sequence

<400> SEQUENCE: 9

```
His His His His His His Glu Asn Leu Tyr Phe Gln Gly Leu Lys Gly
 1               5                  10                  15

Gln Glu Phe Ala Pro Ser His Gln Gln Val Tyr Ala Pro Leu Arg Ala
                 20                  25                  30

Asp Gly Asp Lys Pro Arg Ala His Leu Thr Val Val Arg Gln Thr Pro
             35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Met Thr Ser Glu Cys Ser Glu Ile Arg Gln Ala Gly Arg
                100                 105                 110

Pro Asn Ser Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 10

```
<211> LENGTH: 193
<212> TYPE: PRT
<213> ORGANISM: Artificial Sequence
<220> FEATURE:
<223> OTHER INFORMATION: TL1W98 (His-TEV-TL1A K173R) amino acid sequence

<400> SEQUENCE: 10
```

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Arg Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

```
<210> SEQ ID NO 11
<211> LENGTH: 193
<212> TYPE: PRT
<213> ORGANISM: Artificial Sequence
<220> FEATURE:
<223> OTHER INFORMATION: TL1W107 (His-TEV-TL1A D186Y) amino acid
      sequence

<400> SEQUENCE: 11
```

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Tyr

```
                115                 120                 125
Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
        180                 185                 190

Leu

<210> SEQ ID NO 12
<211> LENGTH: 193
<212> TYPE: PRT
<213> ORGANISM: Artificial Sequence
<220> FEATURE:
<223> OTHER INFORMATION: TL1W113 (His-TEV-TL1A P189S) amino acid
      sequence

<400> SEQUENCE: 12

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Ser Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 13
<211> LENGTH: 193
<212> TYPE: PRT
<213> ORGANISM: Artificial Sequence
<220> FEATURE:
<223> OTHER INFORMATION: TL1W28 (His-TEV-hTL1A 72-251 E190G) amino acid
      sequence

<400> SEQUENCE: 13

His His His His His His Glu Asn Leu Tyr Phe Gln Gly Leu Lys Gly
1               5                   10                  15
```

```
Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Gly Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 14
<211> LENGTH: 193
<212> TYPE: PRT
<213> ORGANISM: Artificial Sequence
<220> FEATURE:
<223> OTHER INFORMATION: TL1W45 (His-TEV-TL1A E190F) amino acid sequence

<400> SEQUENCE: 14

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Phe Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
```

Leu

<210> SEQ ID NO 15
<211> LENGTH: 193
<212> TYPE: PRT
<213> ORGANISM: Artificial Sequence
<220> FEATURE:
<223> OTHER INFORMATION: TL1W123 (His-TEV-TL1A N207S) amino acid
      sequence

<400> SEQUENCE: 15

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Ser Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 16
<211> LENGTH: 193
<212> TYPE: PRT
<213> ORGANISM: Artificial Sequence
<220> FEATURE:
<223> OTHER INFORMATION: TL1W126 (His-TEV-TL1A F209W) amino acid
      sequence

<400> SEQUENCE: 16

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Trp Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 17
<211> LENGTH: 193
<212> TYPE: PRT
<213> ORGANISM: Artificial Sequence
<220> FEATURE:
<223> OTHER INFORMATION: TL1W46 (His-TEV-TL1A T239W) amino acid sequence

<400> SEQUENCE: 17

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Trp Lys Glu Asp Lys Thr Phe Phe Gly Ala Phe Leu
            180                 185                 190

Leu

<210> SEQ ID NO 18
<211> LENGTH: 193
<212> TYPE: PRT
<213> ORGANISM: Artificial Sequence
<220> FEATURE:
<223> OTHER INFORMATION: TL1W137 (His-TEV-TL1A K240S) amino acid
      sequence

<400> SEQUENCE: 18

```
His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Ser Glu Asp Lys Thr Phe Phe Gly Ala Phe Leu
                180                 185                 190

Leu
```

<210> SEQ ID NO 19
<211> LENGTH: 193
<212> TYPE: PRT
<213> ORGANISM: Artificial Sequence
<220> FEATURE:
<223> OTHER INFORMATION: TL1W139 (His-TEV-TL1A E241Q) amino acid sequence

<400> SEQUENCE: 19

```
His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140
```

```
Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Gln Asp Lys Thr Phe Phe Gly Ala Phe Leu
            180                 185                 190

Leu
```

<210> SEQ ID NO 20
<211> LENGTH: 193
<212> TYPE: PRT
<213> ORGANISM: Artificial Sequence
<220> FEATURE:
<223> OTHER INFORMATION: TL1W2 (His-TEV-hTL1A 72-251) amino acid
     sequence

<400> SEQUENCE: 20

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Gln Asp Lys Thr Phe Phe Gly Ala Phe Leu
            180                 185                 190

Leu
```

<210> SEQ ID NO 21
<211> LENGTH: 193
<212> TYPE: PRT
<213> ORGANISM: Artificial Sequence
<220> FEATURE:
<223> OTHER INFORMATION: TL1W47 (His-TEV-TL1A E241A) amino acid sequence

<400> SEQUENCE: 21

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45
```

```
Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Ala Asp Lys Thr Phe Phe Gly Ala Phe Leu
            180                 185                 190

Leu

<210> SEQ ID NO 22
<211> LENGTH: 193
<212> TYPE: PRT
<213> ORGANISM: Artificial Sequence
<220> FEATURE:
<223> OTHER INFORMATION: TL1W136 (His-TEV-TL1A K240F) amino acid
      sequence

<400> SEQUENCE: 22

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Phe Glu Asp Lys Thr Phe Phe Gly Ala Phe Leu
            180                 185                 190

Leu
```

```
<210> SEQ ID NO 23
<211> LENGTH: 193
<212> TYPE: PRT
<213> ORGANISM: Artificial Sequence
<220> FEATURE:
<223> OTHER INFORMATION: TL1W138 (His-TEV-TL1A K240D) amino acid
      sequence

<400> SEQUENCE: 23

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Asp Glu Asp Lys Thr Phe Phe Gly Ala Phe Leu
            180                 185                 190

Leu

<210> SEQ ID NO 24
<211> LENGTH: 193
<212> TYPE: PRT
<213> ORGANISM: Artificial Sequence
<220> FEATURE:
<223> OTHER INFORMATION: TL1W135 (His-TEV-TL1A K240A) amino acid
      sequence

<400> SEQUENCE: 24

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110
```

```
Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
            165                 170                 175

Leu Val Asp Tyr Thr Ala Glu Asp Lys Thr Phe Phe Gly Ala Phe Leu
        180                 185                 190

Leu

<210> SEQ ID NO 25
<211> LENGTH: 193
<212> TYPE: PRT
<213> ORGANISM: Artificial Sequence
<220> FEATURE:
<223> OTHER INFORMATION: TL1W134 (His-TEV-TL1A T239K) amino acid
      sequence

<400> SEQUENCE: 25

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
            165                 170                 175

Leu Val Asp Tyr Lys Lys Glu Asp Lys Thr Phe Phe Gly Ala Phe Leu
        180                 185                 190

Leu

<210> SEQ ID NO 26
<211> LENGTH: 193
<212> TYPE: PRT
<213> ORGANISM: Artificial Sequence
<220> FEATURE:
<223> OTHER INFORMATION: TL1W133 (His-TEV-TL1A T239F) amino acid
      sequence

<400> SEQUENCE: 26

His His His His His His Glu Asn Leu Tyr Phe Gln Gly Leu Lys Gly
```

```
1               5                   10                  15
Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Phe Lys Glu Asp Lys Thr Phe Phe Gly Ala Phe Leu
            180                 185                 190

Leu

<210> SEQ ID NO 27
<211> LENGTH: 193
<212> TYPE: PRT
<213> ORGANISM: Artificial Sequence
<220> FEATURE:
<223> OTHER INFORMATION: TL1W27 (His-TEV-hTL1A 72-251 T239E) amino acid
      sequence

<400> SEQUENCE: 27

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
```

-continued

```
                165                 170                 175
Leu Val Asp Tyr Glu Lys Glu Asp Lys Thr Phe Phe Gly Ala Phe Leu
            180                 185                 190

Leu
```

<210> SEQ ID NO 28
<211> LENGTH: 193
<212> TYPE: PRT
<213> ORGANISM: Artificial Sequence
<220> FEATURE:
<223> OTHER INFORMATION: TL1W132 (His-TEV-TL1A T239A) amino acid
      sequence

<400> SEQUENCE: 28

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Ala Lys Glu Asp Lys Thr Phe Phe Gly Ala Phe Leu
            180                 185                 190

Leu
```

<210> SEQ ID NO 29
<211> LENGTH: 193
<212> TYPE: PRT
<213> ORGANISM: Artificial Sequence
<220> FEATURE:
<223> OTHER INFORMATION: TL1W128 (His-TEV-TL1A Y238S) amino acid
      sequence

<400> SEQUENCE: 29

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60
```

```
Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Ser Thr Lys Glu Asp Lys Thr Phe Phe Gly Ala Phe Leu
            180                 185                 190

Leu
```

<210> SEQ ID NO 30
<211> LENGTH: 193
<212> TYPE: PRT
<213> ORGANISM: Artificial Sequence
<220> FEATURE:
<223> OTHER INFORMATION: TL1W130 (His-TEV-TL1A Y238R) amino acid
      sequence

<400> SEQUENCE: 30

```
His His His His His His Glu Asn Leu Tyr Phe Gln Gly Leu Lys Gly
 1               5                  10                  15

Gln Glu Phe Ala Pro Ser His Gln Gln Val Tyr Ala Pro Leu Arg Ala
                 20                  25                  30

Asp Gly Asp Lys Pro Arg Ala His Leu Thr Val Val Arg Gln Thr Pro
             35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Arg Thr Lys Glu Asp Lys Thr Phe Phe Gly Ala Phe Leu
            180                 185                 190

Leu
```

<210> SEQ ID NO 31
<211> LENGTH: 193
<212> TYPE: PRT

<213> ORGANISM: Artificial Sequence
<220> FEATURE:
<223> OTHER INFORMATION: TL1W129 (His-TEV-TL1A Y238K) amino acid sequence

<400> SEQUENCE: 31

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Lys Thr Lys Glu Asp Lys Thr Phe Phe Gly Ala Phe Leu
            180                 185                 190

Leu
```

<210> SEQ ID NO 32
<211> LENGTH: 193
<212> TYPE: PRT
<213> ORGANISM: Artificial Sequence
<220> FEATURE:
<223> OTHER INFORMATION: TL1W131 (His-TEV-TL1A Y238E) amino acid sequence

<400> SEQUENCE: 32

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125
```

```
Ser Tyr Pro Glu Pro Thr Gln Leu Leu Met Gly Thr Lys Ser Val Cys
            130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Glu Thr Lys Glu Asp Lys Thr Phe Phe Gly Ala Phe Leu
            180                 185                 190

Leu

<210> SEQ ID NO 33
<211> LENGTH: 193
<212> TYPE: PRT
<213> ORGANISM: Artificial Sequence
<220> FEATURE:
<223> OTHER INFORMATION: TL1W127 (His-TEV-TL1A Y238A) amino acid
      sequence

<400> SEQUENCE: 33

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Ala Thr Lys Glu Asp Lys Thr Phe Phe Gly Ala Phe Leu
            180                 185                 190

Leu

<210> SEQ ID NO 34
<211> LENGTH: 193
<212> TYPE: PRT
<213> ORGANISM: Artificial Sequence
<220> FEATURE:
<223> OTHER INFORMATION: TL1W24 (His-TEV-hTL1A 72-251 F209A) amino acid
      sequence

<400> SEQUENCE: 34

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
```

```
            20                  25                  30
Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Ala Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu
```

<210> SEQ ID NO 35
<211> LENGTH: 193
<212> TYPE: PRT
<213> ORGANISM: Artificial Sequence
<220> FEATURE:
<223> OTHER INFORMATION: TL1W124 (His-TEV-TL1A N207K) amino acid
      sequence

<400> SEQUENCE: 35

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Lys Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
```

180                 185                 190

Leu

<210> SEQ ID NO 36
<211> LENGTH: 193
<212> TYPE: PRT
<213> ORGANISM: Artificial Sequence
<220> FEATURE:
<223> OTHER INFORMATION: TL1W122 (His-TEV-TL1A N207F) amino acid
      sequence

<400> SEQUENCE: 36

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Phe Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 37
<211> LENGTH: 193
<212> TYPE: PRT
<213> ORGANISM: Artificial Sequence
<220> FEATURE:
<223> OTHER INFORMATION: TL1W125 (His-TEV-TL1A N207E) amino acid
      sequence

<400> SEQUENCE: 37

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

```
Leu Leu Ile Pro Glu Ser Gly Asp Tyr Phe Ile Tyr Ser Gln Val Thr
                85                  90                  95
Phe Arg Gly Met Thr Ser Glu Cys Ser Glu Ile Arg Gln Ala Gly Arg
            100                 105                 110
Pro Asn Lys Pro Asp Ser Ile Thr Val Val Ile Thr Lys Val Thr Asp
        115                 120                 125
Ser Tyr Pro Glu Pro Thr Gln Leu Leu Met Gly Thr Lys Ser Val Cys
    130                 135                 140
Glu Val Gly Ser Glu Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
            180                 185                 190
Leu
```

<210> SEQ ID NO 38
<211> LENGTH: 193
<212> TYPE: PRT
<213> ORGANISM: Artificial Sequence
<220> FEATURE:
<223> OTHER INFORMATION: TL1W25 (His-TEV-hTL1A 72-251 N207A) amino acid sequence

<400> SEQUENCE: 38

```
His His His His His His Glu Asn Leu Tyr Phe Gln Gly Leu Lys Gly
1               5                   10                  15
Gln Glu Phe Ala Pro Ser His Gln Gln Val Tyr Ala Pro Leu Arg Ala
            20                  25                  30
Asp Gly Asp Lys Pro Arg Ala His Leu Thr Val Val Arg Gln Thr Pro
        35                  40                  45
Thr Gln His Phe Lys Asn Gln Phe Pro Ala Leu His Trp Glu His Glu
    50                  55                  60
Leu Gly Leu Ala Phe Thr Lys Asn Arg Met Asn Tyr Thr Asn Lys Phe
65                  70                  75                  80
Leu Leu Ile Pro Glu Ser Gly Asp Tyr Phe Ile Tyr Ser Gln Val Thr
                85                  90                  95
Phe Arg Gly Met Thr Ser Glu Cys Ser Glu Ile Arg Gln Ala Gly Arg
            100                 105                 110
Pro Asn Lys Pro Asp Ser Ile Thr Val Val Ile Thr Lys Val Thr Asp
        115                 120                 125
Ser Tyr Pro Glu Pro Thr Gln Leu Leu Met Gly Thr Lys Ser Val Cys
    130                 135                 140
Glu Val Gly Ser Ala Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
            180                 185                 190
Leu
```

<210> SEQ ID NO 39
<211> LENGTH: 193
<212> TYPE: PRT
<213> ORGANISM: Artificial Sequence
<220> FEATURE:
<223> OTHER INFORMATION: TL1W120 (His-TEV-TL1A S206K) amino acid -continued sequence

<400> SEQUENCE: 39

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Lys Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 40
<211> LENGTH: 193
<212> TYPE: PRT
<213> ORGANISM: Artificial Sequence
<220> FEATURE:
<223> OTHER INFORMATION: TL1W119 (His-TEV-TL1A S206F) amino acid
      sequence

<400> SEQUENCE: 40

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

```
Glu Val Gly Phe Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 41
<211> LENGTH: 193
<212> TYPE: PRT
<213> ORGANISM: Artificial Sequence
<220> FEATURE:
<223> OTHER INFORMATION: TL1W121 (His-TEV-TL1A S206E) amino acid
      sequence

<400> SEQUENCE: 41

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Glu Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 42
<211> LENGTH: 193
<212> TYPE: PRT
<213> ORGANISM: Artificial Sequence
<220> FEATURE:
<223> OTHER INFORMATION: TL1W118 (His-TEV-TL1A S206A) amino acid
      sequence

<400> SEQUENCE: 42

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
```

```
            35                  40                  45
Thr Gln His Phe Lys Asn Gln Phe Pro Ala Leu His Trp Glu His Glu
 50                  55                  60
Leu Gly Leu Ala Phe Thr Lys Asn Arg Met Asn Tyr Thr Asn Lys Phe
 65                  70                  75                  80
Leu Leu Ile Pro Glu Ser Gly Asp Tyr Phe Ile Tyr Ser Gln Val Thr
                 85                  90                  95
Phe Arg Gly Met Thr Ser Glu Cys Ser Glu Ile Arg Gln Ala Gly Arg
                100                 105                 110
Pro Asn Lys Pro Asp Ser Ile Thr Val Val Ile Thr Lys Val Thr Asp
                115                 120                 125
Ser Tyr Pro Glu Pro Thr Gln Leu Leu Met Gly Thr Lys Ser Val Cys
                130                 135                 140
Glu Val Gly Ala Asn Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
                180                 185                 190

Leu
```

<210> SEQ ID NO 43
<211> LENGTH: 193
<212> TYPE: PRT
<213> ORGANISM: Artificial Sequence
<220> FEATURE:
<223> OTHER INFORMATION: TL1W116 (His-TEV-TL1A T192K) amino acid
      sequence

<400> SEQUENCE: 43

```
His His His His His His Glu Asn Leu Tyr Phe Gln Gly Leu Lys Gly
  1               5                  10                  15
Gln Glu Phe Ala Pro Ser His Gln Gln Val Tyr Ala Pro Leu Arg Ala
                 20                  25                  30
Asp Gly Asp Lys Pro Arg Ala His Leu Thr Val Val Arg Gln Thr Pro
                 35                  40                  45
Thr Gln His Phe Lys Asn Gln Phe Pro Ala Leu His Trp Glu His Glu
 50                  55                  60
Leu Gly Leu Ala Phe Thr Lys Asn Arg Met Asn Tyr Thr Asn Lys Phe
 65                  70                  75                  80
Leu Leu Ile Pro Glu Ser Gly Asp Tyr Phe Ile Tyr Ser Gln Val Thr
                 85                  90                  95
Phe Arg Gly Met Thr Ser Glu Cys Ser Glu Ile Arg Gln Ala Gly Arg
                100                 105                 110
Pro Asn Lys Pro Asp Ser Ile Thr Val Val Ile Thr Lys Val Thr Asp
                115                 120                 125
Ser Tyr Pro Glu Pro Lys Gln Leu Leu Met Gly Thr Lys Ser Val Cys
                130                 135                 140
Glu Val Gly Ser Asn Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
                180                 185                 190

Leu
```

<210> SEQ ID NO 44
<211> LENGTH: 193
<212> TYPE: PRT
<213> ORGANISM: Artificial Sequence
<220> FEATURE:
<223> OTHER INFORMATION: TL1W115 (His-TEV-TL1A T192F) amino acid
      sequence

<400> SEQUENCE: 44

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Phe Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu
```

<210> SEQ ID NO 45
<211> LENGTH: 193
<212> TYPE: PRT
<213> ORGANISM: Artificial Sequence
<220> FEATURE:
<223> OTHER INFORMATION: TL1W117 (His-TEV-TL1A T192E) amino acid
      sequence

<400> SEQUENCE: 45

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95
```

```
Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Glu Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 46
<211> LENGTH: 193
<212> TYPE: PRT
<213> ORGANISM: Artificial Sequence
<220> FEATURE:
<223> OTHER INFORMATION: TL1W114 (His-TEV-TL1A T192A) amino acid
      sequence

<400> SEQUENCE: 46

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Ala Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 47
<211> LENGTH: 193
<212> TYPE: PRT
<213> ORGANISM: Artificial Sequence
<220> FEATURE:
<223> OTHER INFORMATION: TL1W44 (His-TEV-TL1A P189K) amino acid
      sequence

<400> SEQUENCE: 47

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Lys Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 48
<211> LENGTH: 193
<212> TYPE: PRT
<213> ORGANISM: Artificial Sequence
<220> FEATURE:
<223> OTHER INFORMATION: TL1W112 (His-TEV-TL1A P189F) amino acid
      sequence

<400> SEQUENCE: 48

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Phe Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160
```

Ser Leu Gln Glu Gly Asp Lys Leu Met Val Asn Val Ser Asp Ile Ser
            165                 170                 175

Leu Val Asp Tyr Thr Lys Glu Asp Lys Thr Phe Phe Gly Ala Phe Leu
            180                 185                 190

Leu

<210> SEQ ID NO 49
<211> LENGTH: 193
<212> TYPE: PRT
<213> ORGANISM: Artificial Sequence
<220> FEATURE:
<223> OTHER INFORMATION: TL1W29 (His-TEV-hTL1A 72-251 P189A) amino acid
      sequence

<400> SEQUENCE: 49

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Ala Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 50
<211> LENGTH: 193
<212> TYPE: PRT
<213> ORGANISM: Artificial Sequence
<220> FEATURE:
<223> OTHER INFORMATION: TL1W43 (His-TEV-TL1A Y188S) amino acid sequence

<400> SEQUENCE: 50

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Ser Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 51
<211> LENGTH: 193
<212> TYPE: PRT
<213> ORGANISM: Artificial Sequence
<220> FEATURE:
<223> OTHER INFORMATION: TL1W32 (His-TEV-hTL1A 72-251 Y188A) amino acid
      sequence

<400> SEQUENCE: 51

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ser Ala Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 52
<211> LENGTH: 193

<212> TYPE: PRT
<213> ORGANISM: Artificial Sequence
<220> FEATURE:
<223> OTHER INFORMATION: TL1W109 (His-TEV-TL1A S187L) amino acid
      sequence

<400> SEQUENCE: 52

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Leu Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 53
<211> LENGTH: 193
<212> TYPE: PRT
<213> ORGANISM: Artificial Sequence
<220> FEATURE:
<223> OTHER INFORMATION: TL1W110 (His-TEV-TL1A S187K) amino acid
      sequence

<400> SEQUENCE: 53

His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp

```
            115                 120                 125
Lys Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 54
<211> LENGTH: 193
<212> TYPE: PRT
<213> ORGANISM: Artificial Sequence
<220> FEATURE:
<223> OTHER INFORMATION: TL1W111 (His-TEV-TL1A S187D) amino acid
      sequence

<400> SEQUENCE: 54

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Asp Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 55
<211> LENGTH: 193
<212> TYPE: PRT
<213> ORGANISM: Artificial Sequence
<220> FEATURE:
<223> OTHER INFORMATION: TL1W108 (His-TEV-TL1A S187A) amino acid
      sequence

<400> SEQUENCE: 55

His His His His His His Glu Asn Leu Tyr Phe Gln Gly Leu Lys Gly
1               5                   10                  15
```

```
Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
            115                 120                 125

Ala Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 56
<211> LENGTH: 193
<212> TYPE: PRT
<213> ORGANISM: Artificial Sequence
<220> FEATURE:
<223> OTHER INFORMATION: TL1W105 (His-TEV-TL1A T185N) amino acid
      sequence

<400> SEQUENCE: 56

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Asn Asp
            115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175
```

```
Leu Val Asp Tyr Thr Lys Glu Asp Lys Thr Phe Phe Gly Ala Phe Leu
            180                 185                 190

Leu

<210> SEQ ID NO 57
<211> LENGTH: 193
<212> TYPE: PRT
<213> ORGANISM: Artificial Sequence
<220> FEATURE:
<223> OTHER INFORMATION: TL1W104 (His-TEV-TL1A T185L) amino acid
      sequence

<400> SEQUENCE: 57

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Leu Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 58
<211> LENGTH: 193
<212> TYPE: PRT
<213> ORGANISM: Artificial Sequence
<220> FEATURE:
<223> OTHER INFORMATION: TL1W106 (His-TEV-TL1A T185D) amino acid
      sequence

<400> SEQUENCE: 58

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80
```

```
Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Asp Asp
        115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 59
<211> LENGTH: 193
<212> TYPE: PRT
<213> ORGANISM: Artificial Sequence
<220> FEATURE:
<223> OTHER INFORMATION: TL1W103 (His-TEV-TL1A T185A) amino acid sequence

<400> SEQUENCE: 59

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Ala Asp
        115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 60
<211> LENGTH: 193
<212> TYPE: PRT
<213> ORGANISM: Artificial Sequence
<220> FEATURE:

<223> OTHER INFORMATION: TL1W101 (His-TEV-TL1A S176N) amino acid
      sequence

<400> SEQUENCE: 60

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Asn Ile Thr Val Val Ile Thr Lys Val Thr Asp
            115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 61
<211> LENGTH: 193
<212> TYPE: PRT
<213> ORGANISM: Artificial Sequence
<220> FEATURE:
<223> OTHER INFORMATION: TL1W100 (His-TEV-TL1A S176L) amino acid
      sequence

<400> SEQUENCE: 61

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Leu Ile Thr Val Val Ile Thr Lys Val Thr Asp
            115                 120                 125

Ser Tyr Pro Glu Pro Thr Gln Leu Leu Met Gly Thr Lys Ser Val Cys

```
                130                 135                 140
Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 62
<211> LENGTH: 193
<212> TYPE: PRT
<213> ORGANISM: Artificial Sequence
<220> FEATURE:
<223> OTHER INFORMATION: TL1W102 (His-TEV-TL1A S176K) amino acid
      sequence

<400> SEQUENCE: 62

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Lys Ile Thr Val Ile Thr Lys Val Thr Asp
                115                 120                 125

Ser Tyr Pro Glu Pro Thr Gln Leu Leu Met Gly Thr Lys Ser Val Cys
130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 63
<211> LENGTH: 193
<212> TYPE: PRT
<213> ORGANISM: Artificial Sequence
<220> FEATURE:
<223> OTHER INFORMATION: TL1W99 (His-TEV-TL1A S176A) amino acid sequence

<400> SEQUENCE: 63

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
```

```
                35                  40                  45
Thr Gln His Phe Lys Asn Gln Phe Pro Ala Leu His Trp Glu His Glu
 50                  55                  60
Leu Gly Leu Ala Phe Thr Lys Asn Arg Met Asn Tyr Thr Asn Lys Phe
 65                  70                  75                  80
Leu Leu Ile Pro Glu Ser Gly Asp Tyr Phe Ile Tyr Ser Gln Val Thr
                 85                  90                  95
Phe Arg Gly Met Thr Ser Glu Cys Ser Glu Ile Arg Gln Ala Gly Arg
                100                 105                 110
Pro Asn Lys Pro Asp Ala Ile Thr Val Val Ile Thr Lys Val Thr Asp
                115                 120                 125
Ser Tyr Pro Glu Pro Thr Gln Leu Leu Met Gly Thr Lys Ser Val Cys
            130                 135                 140
Glu Val Gly Ser Asn Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
                180                 185                 190
Leu
```

<210> SEQ ID NO 64
<211> LENGTH: 193
<212> TYPE: PRT
<213> ORGANISM: Artificial Sequence
<220> FEATURE:
<223> OTHER INFORMATION: TL1W96 (His-TEV-TL1A R170E) amino acid sequence

<400> SEQUENCE: 64

```
His His His His His His Glu Asn Leu Tyr Phe Gln Gly Leu Lys Gly
 1               5                  10                  15
Gln Glu Phe Ala Pro Ser His Gln Gln Val Tyr Ala Pro Leu Arg Ala
                20                  25                  30
Asp Gly Asp Lys Pro Arg Ala His Leu Thr Val Val Arg Gln Thr Pro
            35                  40                  45
Thr Gln His Phe Lys Asn Gln Phe Pro Ala Leu His Trp Glu His Glu
 50                  55                  60
Leu Gly Leu Ala Phe Thr Lys Asn Arg Met Asn Tyr Thr Asn Lys Phe
 65                  70                  75                  80
Leu Leu Ile Pro Glu Ser Gly Asp Tyr Phe Ile Tyr Ser Gln Val Thr
                 85                  90                  95
Phe Arg Gly Met Thr Ser Glu Cys Ser Glu Ile Arg Gln Ala Gly Glu
                100                 105                 110
Pro Asn Lys Pro Asp Ser Ile Thr Val Val Ile Thr Lys Val Thr Asp
                115                 120                 125
Ser Tyr Pro Glu Pro Thr Gln Leu Leu Met Gly Thr Lys Ser Val Cys
            130                 135                 140
Glu Val Gly Ser Asn Trp Phe Gln Pro Ile Tyr Leu Gly Ala Met Phe
145                 150                 155                 160
Ser Leu Gln Glu Gly Asp Lys Leu Met Val Asn Val Ser Asp Ile Ser
                165                 170                 175
Leu Val Asp Tyr Thr Lys Glu Asp Lys Thr Phe Phe Gly Ala Phe Leu
                180                 185                 190
Leu
```

<210> SEQ ID NO 65
<211> LENGTH: 193
<212> TYPE: PRT
<213> ORGANISM: Artificial Sequence
<220> FEATURE:
<223> OTHER INFORMATION: TL1W95 (His-TEV-TL1A Q167A) amino acid sequence

<400> SEQUENCE: 65

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Ala Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu
```

<210> SEQ ID NO 66
<211> LENGTH: 193
<212> TYPE: PRT
<213> ORGANISM: Artificial Sequence
<220> FEATURE:
<223> OTHER INFORMATION: TL1W93 (His-TEV-TL1A M158K) amino acid sequence

<400> SEQUENCE: 66

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Lys Thr Ser Glu Cys Ser Glu Ile Arg Gln Ala Gly Arg
                100                 105                 110
```

```
Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 67
<211> LENGTH: 193
<212> TYPE: PRT
<213> ORGANISM: Artificial Sequence
<220> FEATURE:
<223> OTHER INFORMATION: TL1W94 (His-TEV-TL1A M158E) amino acid sequence

<400> SEQUENCE: 67

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Glu Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 68
<211> LENGTH: 193
<212> TYPE: PRT
<213> ORGANISM: Artificial Sequence
<220> FEATURE:
<223> OTHER INFORMATION: TL1W90 (His-TEV-TL1A R156K) amino acid sequence

<400> SEQUENCE: 68

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30
```

```
                 20                  25                  30
Asp Gly Asp Lys Pro Arg Ala His Leu Thr Val Val Arg Gln Thr Pro
             35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Lys Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
                115                 120                 125

Ser Tyr Pro Glu Pro Thr Gln Leu Leu Met Gly Thr Lys Ser Val Cys
                130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 69
<211> LENGTH: 193
<212> TYPE: PRT
<213> ORGANISM: Artificial Sequence
<220> FEATURE:
<223> OTHER INFORMATION: TL1W91 (His-TEV-TL1A R156E) amino acid sequence

<400> SEQUENCE: 69

His His His His His His Glu Asn Leu Tyr Phe Gln Gly Leu Lys Gly
 1               5                  10                  15

Gln Glu Phe Ala Pro Ser His Gln Gln Val Tyr Ala Pro Leu Arg Ala
                 20                  25                  30

Asp Gly Asp Lys Pro Arg Ala His Leu Thr Val Val Arg Gln Thr Pro
             35                  40                  45

Thr Gln His Phe Lys Asn Gln Phe Pro Ala Leu His Trp Glu His Glu
 50                  55                  60

Leu Gly Leu Ala Phe Thr Lys Asn Arg Met Asn Tyr Thr Asn Lys Phe
 65                  70                  75                  80

Leu Leu Ile Pro Glu Ser Gly Asp Tyr Phe Ile Tyr Ser Gln Val Thr
                 85                  90                  95

Phe Glu Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
                115                 120                 125

Ser Tyr Pro Glu Pro Thr Gln Leu Leu Met Gly Thr Lys Ser Val Cys
                130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190
```

<210> SEQ ID NO 70
<211> LENGTH: 193
<212> TYPE: PRT
<213> ORGANISM: Artificial Sequence
<220> FEATURE:
<223> OTHER INFORMATION: TL1W88 (His-TEV-TL1A R156A) amino acid sequence

<400> SEQUENCE: 70

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Ala Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 71
<211> LENGTH: 193
<212> TYPE: PRT
<213> ORGANISM: Artificial Sequence
<220> FEATURE:
<223> OTHER INFORMATION: TL1W87 (His-TEV-TL1A G124D) amino acid sequence

<400> SEQUENCE: 71

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
                20                  25                  30

Asp Gly Asp Lys Pro Arg Ala His Leu Thr Val Val Arg Gln Thr Pro
            35                  40                  45

Thr Gln His Phe Lys Asn Gln Phe Pro Ala Leu His Trp Glu His Glu
        50                  55                  60

Leu Asp Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 72
<211> LENGTH: 193
<212> TYPE: PRT
<213> ORGANISM: Artificial Sequence
<220> FEATURE:
<223> OTHER INFORMATION: TL1W38 (His-TEV-TL1A L123K) amino acid sequence

<400> SEQUENCE: 72

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Glu His Glu
    50                  55                  60

Lys Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 73
<211> LENGTH: 193
<212> TYPE: PRT
<213> ORGANISM: Artificial Sequence
<220> FEATURE:
<223> OTHER INFORMATION: TL1W39 (His-TEV-TL1A L123G) amino acid sequence

<400> SEQUENCE: 73

His His His His His His Glu Asn Leu Tyr Phe Gln Gly Leu Lys Gly

```
            1               5                  10                 15
Gln Glu Phe Ala Pro Ser His Gln Gln Val Tyr Ala Pro Leu Arg Ala
                20                  25                 30

Asp Gly Asp Lys Pro Arg Ala His Leu Thr Val Val Arg Gln Thr Pro
                35                  40                 45

Thr Gln His Phe Lys Asn Gln Phe Pro Ala Leu His Trp Glu His Glu
        50                  55                 60

Gly Gly Leu Ala Phe Thr Lys Asn Arg Met Asn Tyr Thr Asn Lys Phe
 65                 70                  75                 80

Leu Leu Ile Pro Glu Ser Gly Asp Tyr Phe Ile Tyr Ser Gln Val Thr
                85                  90                 95

Phe Arg Gly Met Thr Ser Glu Cys Ser Glu Ile Arg Gln Ala Gly Arg
                100                 105                110

Pro Asn Lys Pro Asp Ser Ile Thr Val Val Ile Thr Lys Val Thr Asp
                115                 120                125

Ser Tyr Pro Glu Pro Thr Gln Leu Leu Met Gly Thr Lys Ser Val Cys
            130                 135                140

Glu Val Gly Ser Asn Trp Phe Gln Pro Ile Tyr Leu Gly Ala Met Phe
145                 150                 155                160

Ser Leu Gln Glu Gly Asp Lys Leu Met Val Asn Val Ser Asp Ile Ser
                165                 170                175

Leu Val Asp Tyr Thr Lys Glu Asp Lys Thr Phe Phe Gly Ala Phe Leu
            180                 185                190

Leu

<210> SEQ ID NO 74
<211> LENGTH: 193
<212> TYPE: PRT
<213> ORGANISM: Artificial Sequence
<220> FEATURE:
<223> OTHER INFORMATION: TL1W37 (His-TEV-TL1A L123E) amino acid sequence

<400> SEQUENCE: 74

His His His His His His Glu Asn Leu Tyr Phe Gln Gly Leu Lys Gly
1               5                   10                 15

Gln Glu Phe Ala Pro Ser His Gln Gln Val Tyr Ala Pro Leu Arg Ala
                20                  25                 30

Asp Gly Asp Lys Pro Arg Ala His Leu Thr Val Val Arg Gln Thr Pro
                35                  40                 45

Thr Gln His Phe Lys Asn Gln Phe Pro Ala Leu His Trp Glu His Glu
        50                  55                 60

Glu Gly Leu Ala Phe Thr Lys Asn Arg Met Asn Tyr Thr Asn Lys Phe
 65                 70                  75                 80

Leu Leu Ile Pro Glu Ser Gly Asp Tyr Phe Ile Tyr Ser Gln Val Thr
                85                  90                 95

Phe Arg Gly Met Thr Ser Glu Cys Ser Glu Ile Arg Gln Ala Gly Arg
                100                 105                110

Pro Asn Lys Pro Asp Ser Ile Thr Val Val Ile Thr Lys Val Thr Asp
                115                 120                125

Ser Tyr Pro Glu Pro Thr Gln Leu Leu Met Gly Thr Lys Ser Val Cys
            130                 135                140

Glu Val Gly Ser Asn Trp Phe Gln Pro Ile Tyr Leu Gly Ala Met Phe
145                 150                 155                160

Ser Leu Gln Glu Gly Asp Lys Leu Met Val Asn Val Ser Asp Ile Ser
                165                 170                175
```

```
Leu Val Asp Tyr Thr Lys Glu Asp Lys Thr Phe Phe Gly Ala Phe Leu
            180                 185                 190

Leu

<210> SEQ ID NO 75
<211> LENGTH: 193
<212> TYPE: PRT
<213> ORGANISM: Artificial Sequence
<220> FEATURE:
<223> OTHER INFORMATION: TL1W41 (His-TEV-TL1A E120A) amino acid sequence

<400> SEQUENCE: 75

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Phe Pro Ala Leu His Trp Ala His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 76
<211> LENGTH: 193
<212> TYPE: PRT
<213> ORGANISM: Artificial Sequence
<220> FEATURE:
<223> OTHER INFORMATION: TL1W42 (His-TEV-TL1A F114A) amino acid sequence

<400> SEQUENCE: 76

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Asn Gln Ala Pro Ala Leu His Trp Glu His Glu
    50                  55                  60

Leu Gly Leu Ala Phe Thr Lys Asn Arg Met Asn Tyr Thr Asn Lys Phe
65                  70                  75                  80
```

Leu Leu Ile Pro Glu Ser Gly Asp Tyr Phe Ile Tyr Ser Gln Val Thr
            85                  90                  95

Phe Arg Gly Met Thr Ser Glu Cys Ser Glu Ile Arg Gln Ala Gly Arg
        100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 77
<211> LENGTH: 193
<212> TYPE: PRT
<213> ORGANISM: Artificial Sequence
<220> FEATURE:
<223> OTHER INFORMATION: TL1W30 (His-TEV-hTL1A 72-251 N112E) amino acid
      sequence

<400> SEQUENCE: 77

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Lys Glu Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 78
<211> LENGTH: 193
<212> TYPE: PRT
<213> ORGANISM: Artificial Sequence
<220> FEATURE:
<223> OTHER INFORMATION: TL1W82 (His-TEV-TL1A K111E) amino acid sequence

<400> SEQUENCE: 78

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Glu Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu
```

<210> SEQ ID NO 79
<211> LENGTH: 193
<212> TYPE: PRT
<213> ORGANISM: Artificial Sequence
<220> FEATURE:
<223> OTHER INFORMATION: TL1W80 (His-TEV-TL1A K111A) amino acid sequence

<400> SEQUENCE: 79

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Arg Gln Thr Pro
        35                  40                  45

Thr Gln His Phe Ala Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
                100                 105                 110

Pro Asn Lys Pro Asp Ser Ile Thr Val Val Ile Thr Lys Val Thr Asp
            115                 120                 125

Ser Tyr Pro Glu Pro Thr Gln Leu Leu Met Gly Thr Lys Ser Val Cys
        130                 135                 140

Glu Val Gly Ser Asn Trp Phe Gln Pro Ile Tyr Leu Gly Ala Met Phe
```

```
                   145                 150                 155                 160
Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 80
<211> LENGTH: 193
<212> TYPE: PRT
<213> ORGANISM: Artificial Sequence
<220> FEATURE:
<223> OTHER INFORMATION: TL1W31 (GD: Single chain MMB in CBIS; His-TEV-
      hTL1A 72-251 R103Q) amino acid sequence

<400> SEQUENCE: 80

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Gln Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu

<210> SEQ ID NO 81
<211> LENGTH: 193
<212> TYPE: PRT
<213> ORGANISM: Artificial Sequence
<220> FEATURE:
<223> OTHER INFORMATION: TL1W78 (His-TEV-TL1A R103H) amino acid sequence

<400> SEQUENCE: 81

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val His Gln Thr Pro
        35                  40                  45

Thr Gln His Phe Lys Asn Gln Phe Pro Ala Leu His Trp Glu His Glu
```

```
Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 82
<211> LENGTH: 193
<212> TYPE: PRT
<213> ORGANISM: Artificial Sequence
<220> FEATURE:
<223> OTHER INFORMATION: TL1W79 (His-TEV-TL1A R103E) amino acid sequence

<400> SEQUENCE: 82

His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Glu Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
                180                 185                 190

Leu

<210> SEQ ID NO 83
<211> LENGTH: 193
```

<212> TYPE: PRT
<213> ORGANISM: Artificial Sequence
<220> FEATURE:
<223> OTHER INFORMATION: TL1W33 (His-TEV-hTL1A 72-251 R103A) amino acid sequence

<400> SEQUENCE: 83

```
His His His His His His Glu Asn Leu Tyr Phe Gln Gly Leu Lys Gly
1               5                   10                  15

Gln Glu Phe Ala Pro Ser His Gln Gln Val Tyr Ala Pro Leu Arg Ala
            20                  25                  30

Asp Gly Asp Lys Pro Arg Ala His Leu Thr Val Val Ala Gln Thr Pro
        35                  40                  45

Thr Gln His Phe Lys Asn Gln Phe Pro Ala Leu His Trp Glu His Glu
    50                  55                  60

Leu Gly Leu Ala Phe Thr Lys Asn Arg Met Asn Tyr Thr Asn Lys Phe
65                  70                  75                  80

Leu Leu Ile Pro Glu Ser Gly Asp Tyr Phe Ile Tyr Ser Gln Val Thr
                85                  90                  95

Phe Arg Gly Met Thr Ser Glu Cys Ser Glu Ile Arg Gln Ala Gly Arg
            100                 105                 110

Pro Asn Lys Pro Asp Ser Ile Thr Val Val Ile Thr Lys Val Thr Asp
        115                 120                 125

Ser Tyr Pro Glu Pro Thr Gln Leu Leu Met Gly Thr Lys Ser Val Cys
    130                 135                 140

Glu Val Gly Ser Asn Trp Phe Gln Pro Ile Tyr Leu Gly Ala Met Phe
145                 150                 155                 160

Ser Leu Gln Glu Gly Asp Lys Leu Met Val Asn Val Ser Asp Ile Ser
                165                 170                 175

Leu Val Asp Tyr Thr Lys Glu Asp Lys Thr Phe Phe Gly Ala Phe Leu
            180                 185                 190

Leu
```

<210> SEQ ID NO 84
<211> LENGTH: 1131
<212> TYPE: PRT
<213> ORGANISM: Artificial Sequence
<220> FEATURE:
<223> OTHER INFORMATION: TL1W15 (GD: Single chain protein in CBIS -> HSA
      C-terminal Fusion; His-TEV-HSA(C34S)-G4S-TL1A-3(G3S)-TL1A-3(G3S)-
      TL1A) amino acid sequence

<400> SEQUENCE: 84

```
His His His His His His Glu Asn Leu Tyr Phe Gln Gly Asp Ala His
1               5                   10                  15

Lys Ser Glu Val Ala His Arg Phe Lys Asp Leu Gly Glu Glu Asn Phe
            20                  25                  30

Lys Ala Leu Val Leu Ile Ala Phe Ala Gln Tyr Leu Gln Gln Ser Pro
        35                  40                  45

Phe Glu Asp His Val Lys Leu Val Asn Glu Val Thr Glu Phe Ala Lys
    50                  55                  60

Thr Cys Val Ala Asp Glu Ser Ala Glu Asn Cys Asp Lys Ser Leu His
65                  70                  75                  80

Thr Leu Phe Gly Asp Lys Leu Cys Thr Val Ala Thr Leu Arg Glu Thr
                85                  90                  95

Tyr Gly Glu Met Ala Asp Cys Cys Ala Lys Gln Glu Pro Glu Arg Asn
            100                 105                 110
```

-continued

```
Glu Cys Phe Leu Gln His Lys Asp Asp Asn Pro Asn Leu Pro Arg Leu
            115                 120                 125
Val Arg Pro Glu Val Asp Val Met Cys Thr Ala Phe His Asp Asn Glu
130                 135                 140
Glu Thr Phe Leu Lys Lys Tyr Leu Tyr Glu Ile Ala Arg Arg His Pro
145                 150                 155                 160
Tyr Phe Tyr Ala Pro Glu Leu Leu Phe Phe Ala Lys Arg Tyr Lys Ala
                165                 170                 175
Ala Phe Thr Glu Cys Cys Gln Ala Ala Asp Lys Ala Ala Cys Leu Leu
            180                 185                 190
Pro Lys Leu Asp Glu Leu Arg Asp Glu Gly Lys Ala Ser Ser Ala Lys
                195                 200                 205
Gln Arg Leu Lys Cys Ala Ser Leu Gln Lys Phe Gly Glu Arg Ala Phe
            210                 215                 220
Lys Ala Trp Ala Val Ala Arg Leu Ser Gln Arg Phe Pro Lys Ala Glu
225                 230                 235                 240
Phe Ala Glu Val Ser Lys Leu Val Thr Asp Leu Thr Lys Val His Thr
                245                 250                 255
Glu Cys Cys His Gly Asp Leu Leu Glu Cys Ala Asp Asp Arg Ala Asp
            260                 265                 270
Leu Ala Lys Tyr Ile Cys Glu Asn Gln Asp Ser Ile Ser Ser Lys Leu
            275                 280                 285
Lys Glu Cys Cys Glu Lys Pro Leu Leu Glu Lys Ser His Cys Ile Ala
            290                 295                 300
Glu Val Glu Asn Asp Glu Met Pro Ala Asp Leu Pro Ser Leu Ala Ala
305                 310                 315                 320
Asp Phe Val Glu Ser Lys Asp Val Cys Lys Asn Tyr Ala Glu Ala Lys
                325                 330                 335
Asp Val Phe Leu Gly Met Phe Leu Tyr Glu Tyr Ala Arg Arg His Pro
            340                 345                 350
Asp Tyr Ser Val Val Leu Leu Leu Arg Leu Ala Lys Thr Tyr Glu Thr
            355                 360                 365
Thr Leu Glu Lys Cys Cys Ala Ala Ala Asp Pro His Glu Cys Tyr Ala
370                 375                 380
Lys Val Phe Asp Glu Phe Lys Pro Leu Val Glu Glu Pro Gln Asn Leu
385                 390                 395                 400
Ile Lys Gln Asn Cys Glu Leu Phe Glu Gln Leu Gly Glu Tyr Lys Phe
                405                 410                 415
Gln Asn Ala Leu Leu Val Arg Tyr Thr Lys Lys Val Pro Gln Val Ser
            420                 425                 430
Thr Pro Thr Leu Val Glu Val Ser Arg Asn Leu Gly Lys Val Gly Ser
            435                 440                 445
Lys Cys Cys Lys His Pro Glu Ala Lys Arg Met Pro Cys Ala Glu Asp
450                 455                 460
Tyr Leu Ser Val Val Leu Asn Gln Leu Cys Val Leu His Glu Lys Thr
465                 470                 475                 480
Pro Val Ser Asp Arg Val Thr Lys Cys Cys Thr Glu Ser Leu Val Asn
                485                 490                 495
Arg Arg Pro Cys Phe Ser Ala Leu Glu Val Asp Glu Thr Tyr Val Pro
            500                 505                 510
Lys Glu Phe Asn Ala Glu Thr Phe Thr Phe His Ala Asp Ile Cys Thr
            515                 520                 525
Leu Ser Glu Lys Glu Arg Gln Ile Lys Lys Gln Thr Ala Leu Val Glu
```

```
            530                 535                 540
Leu Val Lys His Lys Pro Lys Ala Thr Lys Glu Gln Leu Lys Ala Val
545                 550                 555                 560

Met Asp Asp Phe Ala Ala Phe Val Glu Lys Cys Cys Lys Ala Asp Asp
                    565                 570                 575

Lys Glu Thr Cys Phe Ala Glu Glu Gly Lys Lys Leu Val Ala Ala Ser
                580                 585                 590

Gln Ala Ala Leu Gly Leu Gly Gly Gly Ser Val Tyr Ala Pro Leu
                595                 600                 605

Arg Ala Asp Gly Asp Lys Pro Arg Ala His Leu Thr Val Val Arg Gln
                610                 615                 620

Thr Pro Thr Gln His Phe Lys Asn Gln Phe Pro Ala Leu His Trp Glu
625                 630                 635                 640

His Glu Leu Gly Leu Ala Phe Thr Lys Asn Arg Met Asn Tyr Thr Asn
                    645                 650                 655

Lys Phe Leu Leu Ile Pro Glu Ser Gly Asp Tyr Phe Ile Tyr Ser Gln
                660                 665                 670

Val Thr Phe Arg Gly Met Thr Ser Glu Cys Ser Glu Ile Arg Gln Ala
                    675                 680                 685

Gly Arg Pro Asn Lys Pro Asp Ser Ile Thr Val Val Ile Thr Lys Val
690                 695                 700

Thr Asp Ser Tyr Pro Glu Pro Thr Gln Leu Leu Met Gly Thr Lys Ser
705                 710                 715                 720

Val Cys Glu Val Gly Ser Asn Trp Phe Gln Pro Ile Tyr Leu Gly Ala
                    725                 730                 735

Met Phe Ser Leu Gln Glu Gly Asp Lys Leu Met Val Asn Val Ser Asp
                740                 745                 750

Ile Ser Leu Val Asp Tyr Thr Lys Glu Asp Lys Thr Phe Phe Gly Ala
                755                 760                 765

Phe Leu Leu Gly Gly Gly Ser Gly Gly Gly Ser Gly Gly Gly Ser Val
770                 775                 780

Tyr Ala Pro Leu Arg Ala Asp Gly Asp Lys Pro Arg Ala His Leu Thr
785                 790                 795                 800

Val Val Arg Gln Thr Pro Thr Gln His Phe Lys Asn Gln Phe Pro Ala
                    805                 810                 815

Leu His Trp Glu His Glu Leu Gly Leu Ala Phe Thr Lys Asn Arg Met
                    820                 825                 830

Asn Tyr Thr Asn Lys Phe Leu Leu Ile Pro Glu Ser Gly Asp Tyr Phe
                835                 840                 845

Ile Tyr Ser Gln Val Thr Phe Arg Gly Met Thr Ser Glu Cys Ser Glu
850                 855                 860

Ile Arg Gln Ala Gly Arg Pro Asn Lys Pro Asp Ser Ile Thr Val Val
865                 870                 875                 880

Ile Thr Lys Val Thr Asp Ser Tyr Pro Glu Pro Thr Gln Leu Leu Met
                    885                 890                 895

Gly Thr Lys Ser Val Cys Glu Val Gly Ser Asn Trp Phe Gln Pro Ile
                900                 905                 910

Tyr Leu Gly Ala Met Phe Ser Leu Gln Glu Gly Asp Lys Leu Met Val
                915                 920                 925

Asn Val Ser Asp Ile Ser Leu Val Asp Tyr Thr Lys Glu Asp Lys Thr
                930                 935                 940

Phe Phe Gly Ala Phe Leu Leu Gly Gly Gly Ser Gly Gly Gly Ser Gly
945                 950                 955                 960
```

-continued

```
Gly Gly Ser Val Tyr Ala Pro Leu Arg Ala Asp Gly Asp Lys Pro Arg
            965                 970                 975

Ala His Leu Thr Val Val Arg Gln Thr Pro Thr Gln His Phe Lys Asn
            980                 985                 990

Gln Phe Pro Ala Leu His Trp Glu His Glu Leu Gly Leu Ala Phe Thr
            995                 1000                1005

Lys Asn Arg Met Asn Tyr Thr Asn Lys Phe Leu Leu Ile Pro Glu
        1010                1015                1020

Ser Gly Asp Tyr Phe Ile Tyr Ser Gln Val Thr Phe Arg Gly Met
        1025                1030                1035

Thr Ser Glu Cys Ser Glu Ile Arg Gln Ala Gly Arg Pro Asn Lys
        1040                1045                1050

Pro Asp Ser Ile Thr Val Val Ile Thr Lys Val Thr Asp Ser Tyr
        1055                1060                1065

Pro Glu Pro Thr Gln Leu Leu Met Gly Thr Lys Ser Val Cys Glu
        1070                1075                1080

Val Gly Ser Asn Trp Phe Gln Pro Ile Tyr Leu Gly Ala Met Phe
        1085                1090                1095

Ser Leu Gln Glu Gly Asp Lys Leu Met Val Asn Val Ser Asp Ile
        1100                1105                1110

Ser Leu Val Asp Tyr Thr Lys Glu Asp Lys Thr Phe Phe Gly Ala
        1115                1120                1125

Phe Leu Leu
        1130

<210> SEQ ID NO 85
<211> LENGTH: 788
<212> TYPE: PRT
<213> ORGANISM: Artificial Sequence
<220> FEATURE:
<223> OTHER INFORMATION: TL1W9 (GD: Single chain protein in CBIS -> HSA
      C-terminal Fusion; His-TEV-G-HSA (C34S)-2(G4S)-TL1A) amino acid
      sequence

<400> SEQUENCE: 85

His His His His His His Glu Asn Leu Tyr Phe Gln Gly Asp Ala His
1               5                   10                  15

Lys Ser Glu Val Ala His Arg Phe Lys Asp Leu Gly Glu Glu Asn Phe
            20                  25                  30

Lys Ala Leu Val Leu Ile Ala Phe Ala Gln Tyr Leu Gln Gln Ser Pro
        35                  40                  45

Phe Glu Asp His Val Lys Leu Val Asn Glu Val Thr Glu Phe Ala Lys
    50                  55                  60

Thr Cys Val Ala Asp Glu Ser Ala Glu Asn Cys Asp Lys Ser Leu His
65                  70                  75                  80

Thr Leu Phe Gly Asp Lys Leu Cys Thr Val Ala Thr Leu Arg Glu Thr
                85                  90                  95

Tyr Gly Glu Met Ala Asp Cys Cys Ala Lys Gln Glu Pro Glu Arg Asn
            100                 105                 110

Glu Cys Phe Leu Gln His Lys Asp Asp Asn Pro Asn Leu Pro Arg Leu
        115                 120                 125

Val Arg Pro Glu Val Asp Val Met Cys Thr Ala Phe His Asp Asn Glu
    130                 135                 140

Glu Thr Phe Leu Lys Lys Tyr Leu Tyr Glu Ile Ala Arg Arg His Pro
145                 150                 155                 160
```

Tyr Phe Tyr Ala Pro Glu Leu Leu Phe Phe Ala Lys Arg Tyr Lys Ala
            165                 170                 175

Ala Phe Thr Glu Cys Cys Gln Ala Ala Asp Lys Ala Ala Cys Leu Leu
            180                 185                 190

Pro Lys Leu Asp Glu Leu Arg Asp Glu Gly Lys Ala Ser Ser Ala Lys
            195                 200                 205

Gln Arg Leu Lys Cys Ala Ser Leu Gln Lys Phe Gly Glu Arg Ala Phe
            210                 215                 220

Lys Ala Trp Ala Val Ala Arg Leu Ser Gln Arg Phe Pro Lys Ala Glu
225                 230                 235                 240

Phe Ala Glu Val Ser Lys Leu Val Thr Asp Leu Thr Lys Val His Thr
            245                 250                 255

Glu Cys Cys His Gly Asp Leu Leu Glu Cys Ala Asp Asp Arg Ala Asp
            260                 265                 270

Leu Ala Lys Tyr Ile Cys Glu Asn Gln Asp Ser Ile Ser Ser Lys Leu
            275                 280                 285

Lys Glu Cys Cys Glu Lys Pro Leu Leu Glu Lys Ser His Cys Ile Ala
            290                 295                 300

Glu Val Glu Asn Asp Glu Met Pro Ala Asp Leu Pro Ser Leu Ala Ala
305                 310                 315                 320

Asp Phe Val Glu Ser Lys Asp Val Cys Lys Asn Tyr Ala Glu Ala Lys
            325                 330                 335

Asp Val Phe Leu Gly Met Phe Leu Tyr Glu Tyr Ala Arg Arg His Pro
            340                 345                 350

Asp Tyr Ser Val Val Leu Leu Leu Arg Leu Ala Lys Thr Tyr Glu Thr
            355                 360                 365

Thr Leu Glu Lys Cys Cys Ala Ala Ala Asp Pro His Glu Cys Tyr Ala
            370                 375                 380

Lys Val Phe Asp Glu Phe Lys Pro Leu Val Glu Glu Pro Gln Asn Leu
385                 390                 395                 400

Ile Lys Gln Asn Cys Glu Leu Phe Glu Gln Leu Gly Glu Tyr Lys Phe
            405                 410                 415

Gln Asn Ala Leu Leu Val Arg Tyr Thr Lys Lys Val Pro Gln Val Ser
            420                 425                 430

Thr Pro Thr Leu Val Glu Val Ser Arg Asn Leu Gly Lys Val Gly Ser
            435                 440                 445

Lys Cys Cys Lys His Pro Glu Ala Lys Arg Met Pro Cys Ala Glu Asp
            450                 455                 460

Tyr Leu Ser Val Val Leu Asn Gln Leu Cys Val Leu His Glu Lys Thr
465                 470                 475                 480

Pro Val Ser Asp Arg Val Thr Lys Cys Cys Thr Glu Ser Leu Val Asn
            485                 490                 495

Arg Arg Pro Cys Phe Ser Ala Leu Glu Val Asp Glu Thr Tyr Val Pro
            500                 505                 510

Lys Glu Phe Asn Ala Glu Thr Phe Thr Phe His Ala Asp Ile Cys Thr
            515                 520                 525

Leu Ser Glu Lys Glu Arg Gln Ile Lys Lys Gln Thr Ala Leu Val Glu
            530                 535                 540

Leu Val Lys His Lys Pro Lys Ala Thr Lys Glu Gln Leu Lys Ala Val
545                 550                 555                 560

Met Asp Asp Phe Ala Ala Phe Val Glu Lys Cys Cys Lys Ala Asp Asp
            565                 570                 575

Lys Glu Thr Cys Phe Ala Glu Glu Gly Lys Lys Leu Val Ala Ala Ser

```
                580             585             590
Gln Ala Ala Leu Gly Leu Gly Gly Gly Ser Gly Gly Gly Gly Ser
            595             600             605
Leu Lys Gly Gln Glu Phe Ala Pro Ser His Gln Gln Val Tyr Ala Pro
610             615                 620
Leu Arg Ala Asp Gly Asp Lys Pro Arg Ala His Leu Thr Val Val Arg
625                 630              635                 640
Gln Thr Pro Thr Gln His Phe Lys Asn Gln Phe Pro Ala Leu His Trp
                645             650                 655
Glu His Glu Leu Gly Leu Ala Phe Thr Lys Asn Arg Met Asn Tyr Thr
            660             665             670
Asn Lys Phe Leu Leu Ile Pro Glu Ser Gly Asp Tyr Phe Ile Tyr Ser
            675             680             685
Gln Val Thr Phe Arg Gly Met Thr Ser Glu Cys Ser Glu Ile Arg Gln
            690             695             700
Ala Gly Arg Pro Asn Lys Pro Asp Ser Ile Thr Val Ile Thr Lys
705             710             715             720
Val Thr Asp Ser Tyr Pro Glu Pro Thr Gln Leu Leu Met Gly Thr Lys
                725             730             735
Ser Val Cys Glu Val Gly Ser Asn Trp Phe Gln Pro Ile Tyr Leu Gly
            740             745             750
Ala Met Phe Ser Leu Gln Glu Gly Asp Lys Leu Met Val Asn Val Ser
            755             760             765
Asp Ile Ser Leu Val Asp Tyr Thr Lys Glu Asp Lys Thr Phe Phe Gly
770             775             780
Ala Phe Leu Leu
785

<210> SEQ ID NO 86
<211> LENGTH: 511
<212> TYPE: PRT
<213> ORGANISM: Artificial Sequence
<220> FEATURE:
<223> OTHER INFORMATION: TL1W19 (His-TEV-TL1A-TL1A-TL1A) amino acid
      sequence

<400> SEQUENCE: 86

His His His His His His Glu Asn Leu Tyr Phe Gln Gly Ala Pro Leu
1               5                   10                  15
Arg Ala Asp Gly Asp Lys Pro Arg Ala His Leu Thr Val Val Arg Gln
            20                  25                  30
Thr Pro Thr Gln His Phe Lys Asn Gln Phe Pro Ala Leu His Trp Glu
        35                  40                  45
His Glu Leu Gly Leu Ala Phe Thr Lys Asn Arg Met Asn Tyr Thr Asn
    50                  55                  60
Lys Phe Leu Leu Ile Pro Glu Ser Gly Asp Tyr Phe Ile Tyr Ser Gln
65                  70                  75                  80
Val Thr Phe Arg Gly Met Thr Ser Glu Cys Ser Glu Ile Arg Gln Ala
                85                  90                  95
Gly Arg Pro Asn Lys Pro Asp Ser Ile Thr Val Val Ile Thr Lys Val
            100                 105                 110
Thr Asp Ser Tyr Pro Glu Pro Thr Gln Leu Leu Met Gly Thr Lys Ser
        115                 120                 125
Val Cys Glu Val Gly Ser Asn Trp Phe Gln Pro Ile Tyr Leu Gly Ala
    130                 135                 140
```

```
Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
            165                 170                 175

Phe Leu Leu Ala Pro Leu Arg Ala Asp Gly Asp Lys Pro Arg Ala His
            180                 185                 190

Leu Thr Val Val Arg Gln Thr Pro Thr Gln His Phe Lys Asn Gln Phe
            195                 200                 205

Pro Ala Leu His Trp Glu His Glu Leu Gly Leu Ala Phe Thr Lys Asn
            210                 215                 220

Arg Met Asn Tyr Thr Asn Lys Phe Leu Leu Ile Pro Glu Ser Gly Asp
225                 230                 235                 240

Tyr Phe Ile Tyr Ser Gln Val Thr Phe Arg Gly Met Thr Ser Glu Cys
            245                 250                 255

Ser Glu Ile Arg Gln Ala Gly Arg Pro Asn Lys Pro Asp Ser Ile Thr
            260                 265                 270

Val Val Ile Thr Lys Val Thr Asp Ser Tyr Pro Glu Pro Thr Gln Leu
            275                 280                 285

Leu Met Gly Thr Lys Ser Val Cys Glu Val Gly Ser Asn Trp Phe Gln
            290                 295                 300

Pro Ile Tyr Leu Gly Ala Met Phe Ser Leu Gln Glu Gly Asp Lys Leu
305                 310                 315                 320

Met Val Asn Val Ser Asp Ile Ser Leu Val Asp Tyr Thr Lys Glu Asp
            325                 330                 335

Lys Thr Phe Phe Gly Ala Phe Leu Leu Ala Pro Leu Arg Ala Asp Gly
            340                 345                 350

Asp Lys Pro Arg Ala His Leu Thr Val Val Arg Gln Thr Pro Thr Gln
            355                 360                 365

His Phe Lys Asn Gln Phe Pro Ala Leu His Trp Glu His Glu Leu Gly
            370                 375                 380

Leu Ala Phe Thr Lys Asn Arg Met Asn Tyr Thr Asn Lys Phe Leu Leu
385                 390                 395                 400

Ile Pro Glu Ser Gly Asp Tyr Phe Ile Tyr Ser Gln Val Thr Phe Arg
            405                 410                 415

Gly Met Thr Ser Glu Cys Ser Glu Ile Arg Gln Ala Gly Arg Pro Asn
            420                 425                 430

Lys Pro Asp Ser Ile Thr Val Val Ile Thr Lys Val Thr Asp Ser Tyr
            435                 440                 445

Pro Glu Pro Thr Gln Leu Leu Met Gly Thr Lys Ser Val Cys Glu Val
450                 455                 460

Gly Ser Asn Trp Phe Gln Pro Ile Tyr Leu Gly Ala Met Phe Ser Leu
465                 470                 475                 480

Gln Glu Gly Asp Lys Leu Met Val Asn Val Ser Asp Ile Ser Leu Val
            485                 490                 495

Asp Tyr Thr Lys Glu Asp Lys Thr Phe Phe Gly Ala Phe Leu Leu
            500                 505                 510
```

<210> SEQ ID NO 87
<211> LENGTH: 756
<212> TYPE: PRT
<213> ORGANISM: Artificial Sequence
<220> FEATURE:
<223> OTHER INFORMATION: TL1W14 (Fc-scTL1A with CD4 HC sp
      prim_transcript) amino acid sequence

<400> SEQUENCE: 87

-continued

```
Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Val Tyr Ala Pro Leu Arg Ala Asp Gly Asp Lys Pro
225                 230                 235                 240

Arg Ala His Leu Thr Val Val Arg Gln Thr Pro Thr Gln His Phe Lys
                245                 250                 255

Asn Gln Phe Pro Ala Leu His Trp Glu His Glu Leu Gly Leu Ala Phe
            260                 265                 270

Thr Lys Asn Arg Met Asn Tyr Thr Asn Lys Phe Leu Leu Ile Pro Glu
        275                 280                 285

Ser Gly Asp Tyr Phe Ile Tyr Ser Gln Val Thr Phe Arg Gly Met Thr
    290                 295                 300

Ser Glu Cys Ser Glu Ile Arg Gln Ala Gly Arg Pro Asn Lys Pro Asp
305                 310                 315                 320

Ser Ile Thr Val Val Ile Thr Lys Val Thr Asp Ser Tyr Pro Glu Pro
                325                 330                 335

Thr Gln Leu Leu Met Gly Thr Lys Ser Val Cys Glu Val Gly Ser Asn
            340                 345                 350

Trp Phe Gln Pro Ile Tyr Leu Gly Ala Met Phe Ser Leu Gln Glu Gly
        355                 360                 365

Asp Lys Leu Met Val Asn Val Ser Asp Ile Ser Leu Val Asp Tyr Thr
    370                 375                 380

Lys Glu Asp Lys Thr Phe Phe Gly Ala Phe Leu Leu Gly Gly Gly Ser
385                 390                 395                 400

Gly Gly Gly Ser Gly Gly Gly Ser Val Tyr Ala Pro Leu Arg Ala Asp
                405                 410                 415
```

Gly Asp Lys Pro Arg Ala His Leu Thr Val Val Arg Gln Thr Pro Thr
            420                 425                 430

Gln His Phe Lys Asn Gln Phe Pro Ala Leu His Trp Glu His Glu Leu
        435                 440                 445

Gly Leu Ala Phe Thr Lys Asn Arg Met Asn Tyr Thr Asn Lys Phe Leu
450                 455                 460

Leu Ile Pro Glu Ser Gly Asp Tyr Phe Ile Tyr Ser Gln Val Thr Phe
465                 470                 475                 480

Arg Gly Met Thr Ser Glu Cys Ser Glu Ile Arg Gln Ala Gly Arg Pro
                485                 490                 495

Asn Lys Pro Asp Ser Ile Thr Val Val Ile Thr Lys Val Thr Asp Ser
            500                 505                 510

Tyr Pro Glu Pro Thr Gln Leu Leu Met Gly Thr Lys Ser Val Cys Glu
        515                 520                 525

Val Gly Ser Asn Trp Phe Gln Pro Ile Tyr Leu Gly Ala Met Phe Ser
530                 535                 540

Leu Gln Glu Gly Asp Lys Leu Met Val Asn Val Ser Asp Ile Ser Leu
545                 550                 555                 560

Val Asp Tyr Thr Lys Glu Asp Lys Thr Phe Phe Gly Ala Phe Leu Leu
                565                 570                 575

Gly Gly Gly Ser Gly Gly Gly Ser Gly Gly Gly Ser Val Tyr Ala Pro
            580                 585                 590

Leu Arg Ala Asp Gly Asp Lys Pro Arg Ala His Leu Thr Val Val Arg
        595                 600                 605

Gln Thr Pro Thr Gln His Phe Lys Asn Gln Phe Pro Ala Leu His Trp
610                 615                 620

Glu His Glu Leu Gly Leu Ala Phe Thr Lys Asn Arg Met Asn Tyr Thr
625                 630                 635                 640

Asn Lys Phe Leu Leu Ile Pro Glu Ser Gly Asp Tyr Phe Ile Tyr Ser
                645                 650                 655

Gln Val Thr Phe Arg Gly Met Thr Ser Glu Cys Ser Glu Ile Arg Gln
            660                 665                 670

Ala Gly Arg Pro Asn Lys Pro Asp Ser Ile Thr Val Val Ile Thr Lys
        675                 680                 685

Val Thr Asp Ser Tyr Pro Glu Pro Thr Gln Leu Leu Met Gly Thr Lys
690                 695                 700

Ser Val Cys Glu Val Gly Ser Asn Trp Phe Gln Pro Ile Tyr Leu Gly
705                 710                 715                 720

Ala Met Phe Ser Leu Gln Glu Gly Asp Lys Leu Met Val Asn Val Ser
                725                 730                 735

Asp Ile Ser Leu Val Asp Tyr Thr Lys Glu Asp Lys Thr Phe Phe Gly
            740                 745                 750

Ala Phe Leu Leu
        755

<210> SEQ ID NO 88
<211> LENGTH: 756
<212> TYPE: PRT
<213> ORGANISM: Artificial Sequence
<220> FEATURE:
<223> OTHER INFORMATION: TL1W329 (Fc-scTL1A K111A L123K M158Y Q167A
    E190F N207F) amino acid sequence

<400> SEQUENCE: 88

Gly Ser Cys Pro Pro Cys Pro Ala Pro Glu Leu Leu Gly Gly Pro Ser
1               5                   10                  15

```
Val Phe Leu Phe Pro Pro Lys Pro Lys Asp Thr Leu Met Ile Ser Arg
             20                  25                  30

Thr Pro Glu Val Thr Cys Val Val Asp Val Ser His Glu Asp Pro
         35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
             100                 105                 110

Ile Ser Lys Ala Lys Gly Gln Pro Arg Glu Pro Gln Val Tyr Thr Leu
         115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                 165                 170                 175

Ser Asp Gly Ser Phe Phe Leu Tyr Ser Lys Leu Thr Val Asp Lys Ser
             180                 185                 190

Arg Trp Gln Gln Gly Asn Val Phe Ser Cys Ser Val Met His Glu Ala
         195                 200                 205

Leu His Asn His Tyr Thr Gln Lys Ser Leu Ser Leu Ser Pro Gly Gly
     210                 215                 220

Gly Gly Gly Ser Val Tyr Ala Pro Leu Arg Ala Asp Gly Asp Lys Pro
225                 230                 235                 240

Arg Ala His Leu Thr Val Val Arg Gln Thr Pro Thr Gln His Phe Ala
                 245                 250                 255

Asn Gln Phe Pro Ala Leu His Trp Glu His Glu Lys Gly Leu Ala Phe
             260                 265                 270

Thr Lys Asn Arg Met Asn Tyr Thr Asn Lys Phe Leu Leu Ile Pro Glu
         275                 280                 285

Ser Gly Asp Tyr Phe Ile Tyr Ser Gln Val Thr Phe Arg Gly Tyr Thr
290                 295                 300

Ser Glu Cys Ser Glu Ile Arg Ala Ala Gly Arg Pro Asn Lys Pro Asp
305                 310                 315                 320

Ser Ile Thr Val Val Ile Thr Lys Val Thr Asp Ser Tyr Pro Phe Pro
                 325                 330                 335

Thr Gln Leu Leu Met Gly Thr Lys Ser Val Cys Glu Val Gly Ser Phe
             340                 345                 350

Trp Phe Gln Pro Ile Tyr Leu Gly Ala Met Phe Ser Leu Gln Glu Gly
         355                 360                 365

Asp Lys Leu Met Val Asn Val Ser Asp Ile Ser Leu Val Asp Tyr Thr
             370                 375                 380

Lys Glu Asp Lys Thr Phe Phe Gly Ala Phe Leu Leu Gly Gly Gly Ser
385                 390                 395                 400

Gly Gly Gly Ser Gly Gly Gly Ser Val Tyr Ala Pro Leu Arg Ala Asp
                 405                 410                 415

Gly Asp Lys Pro Arg Ala His Leu Thr Val Val Arg Gln Thr Pro Thr
             420                 425                 430
```

Gln His Phe Ala Asn Gln Phe Pro Ala Leu His Trp Glu His Glu Lys
435                 440                 445

Gly Leu Ala Phe Thr Lys Asn Arg Met Asn Tyr Thr Asn Lys Phe Leu
450                 455                 460

Leu Ile Pro Glu Ser Gly Asp Tyr Phe Ile Tyr Ser Gln Val Thr Phe
465                 470                 475                 480

Arg Gly Tyr Thr Ser Glu Cys Ser Glu Ile Arg Ala Ala Gly Arg Pro
                485                 490                 495

Asn Lys Pro Asp Ser Ile Thr Val Ile Thr Lys Val Thr Asp Ser
            500                 505                 510

Tyr Pro Phe Pro Thr Gln Leu Leu Met Gly Thr Lys Ser Val Cys Glu
        515                 520                 525

Val Gly Ser Phe Trp Phe Gln Pro Ile Tyr Leu Gly Ala Met Phe Ser
    530                 535                 540

Leu Gln Glu Gly Asp Lys Leu Met Val Asn Val Ser Asp Ile Ser Leu
545                 550                 555                 560

Val Asp Tyr Thr Lys Glu Asp Lys Thr Phe Phe Gly Ala Phe Leu Leu
                565                 570                 575

Gly Gly Gly Ser Gly Gly Gly Ser Gly Gly Gly Ser Val Tyr Ala Pro
            580                 585                 590

Leu Arg Ala Asp Gly Asp Lys Pro Arg Ala His Leu Thr Val Val Arg
        595                 600                 605

Gln Thr Pro Thr Gln His Phe Ala Asn Gln Phe Pro Ala Leu His Trp
    610                 615                 620

Glu His Glu Lys Gly Leu Ala Phe Thr Lys Asn Arg Met Asn Tyr Thr
625                 630                 635                 640

Asn Lys Phe Leu Leu Ile Pro Glu Ser Gly Asp Tyr Phe Ile Tyr Ser
                645                 650                 655

Gln Val Thr Phe Arg Gly Tyr Thr Ser Glu Cys Ser Glu Ile Arg Ala
            660                 665                 670

Ala Gly Arg Pro Asn Lys Pro Asp Ser Ile Thr Val Val Ile Thr Lys
        675                 680                 685

Val Thr Asp Ser Tyr Pro Phe Pro Thr Gln Leu Leu Met Gly Thr Lys
    690                 695                 700

Ser Val Cys Glu Val Gly Ser Phe Trp Phe Gln Pro Ile Tyr Leu Gly
705                 710                 715                 720

Ala Met Phe Ser Leu Gln Glu Gly Asp Lys Leu Met Val Asn Val Ser
                725                 730                 735

Asp Ile Ser Leu Val Asp Tyr Thr Lys Glu Asp Lys Thr Phe Phe Gly
            740                 745                 750

Ala Phe Leu Leu
    755

<210> SEQ ID NO 89
<211> LENGTH: 756
<212> TYPE: PRT
<213> ORGANISM: Artificial Sequence
<220> FEATURE:
<223> OTHER INFORMATION: TL1W327 (Fc-scTL1A K111A L123K M158Y Q167A
      S187L E190F) amino acid sequence

<400> SEQUENCE: 89

Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

-continued

```
Thr Pro Glu Val Thr Cys Val Val Asp Val Ser His Glu Asp Pro
         35                  40                  45
Glu Val Lys Phe Asn Trp Tyr Val Asp Gly Val Glu Val His Asn Ala
 50                  55                  60
Lys Thr Lys Pro Arg Glu Gln Tyr Asn Ser Thr Tyr Arg Val Val
 65                  70                  75                  80
Ser Val Leu Thr Val Leu His Gln Asp Trp Leu Asn Gly Lys Glu Tyr
             85                  90                  95
Lys Cys Lys Val Ser Asn Lys Ala Leu Pro Ala Pro Ile Glu Lys Thr
                100                 105                 110
Ile Ser Lys Ala Lys Gly Gln Pro Arg Glu Pro Gln Val Tyr Thr Leu
            115                 120                 125
Pro Pro Ser Arg Glu Glu Met Thr Lys Asn Gln Val Ser Leu Thr Cys
        130                 135                 140
Leu Val Lys Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Tyr Ser Lys Leu Thr Val Asp Lys Ser
            180                 185                 190
Arg Trp Gln Gln Gly Asn Val Phe Ser Cys Ser Val Met His Glu Ala
        195                 200                 205
Leu His Asn His Tyr Thr Gln Lys Ser Leu Ser Leu Ser Pro Gly Gly
    210                 215                 220
Gly Gly Gly Ser Val Tyr Ala Pro Leu Arg Ala Asp Gly Asp Lys Pro
225                 230                 235                 240
Arg Ala His Leu Thr Val Val Arg Gln Thr Pro Thr Gln His Phe Ala
                245                 250                 255
Asn Gln Phe Pro Ala Leu His Trp Glu His Glu Lys Gly Leu Ala Phe
            260                 265                 270
Thr Lys Asn Arg Met Asn Tyr Thr Asn Lys Phe Leu Leu Ile Pro Glu
        275                 280                 285
Ser Gly Asp Tyr Phe Ile Tyr Ser Gln Val Thr Phe Arg Gly Tyr Thr
    290                 295                 300
Ser Glu Cys Ser Glu Ile Arg Ala Ala Gly Arg Pro Asn Lys Pro Asp
305                 310                 315                 320
Ser Ile Thr Val Val Ile Thr Lys Val Thr Asp Leu Tyr Pro Phe Pro
                325                 330                 335
Thr Gln Leu Leu Met Gly Thr Lys Ser Val Cys Glu Val Gly Ser Asn
            340                 345                 350
Trp Phe Gln Pro Ile Tyr Leu Gly Ala Met Phe Ser Leu Gln Glu Gly
        355                 360                 365
Asp Lys Leu Met Val Asn Val Ser Asp Ile Ser Leu Val Asp Tyr Thr
    370                 375                 380
Lys Glu Asp Lys Thr Phe Phe Gly Ala Phe Leu Gly Gly Gly Ser
385                 390                 395                 400
Gly Gly Gly Ser Gly Gly Gly Ser Val Tyr Ala Pro Leu Arg Ala Asp
                405                 410                 415
Gly Asp Lys Pro Arg Ala His Leu Thr Val Val Arg Gln Thr Pro Thr
            420                 425                 430
Gln His Phe Ala Asn Gln Phe Pro Ala Leu His Trp Glu His Glu Lys
        435                 440                 445
```

Gly Leu Ala Phe Thr Lys Asn Arg Met Asn Tyr Thr Asn Lys Phe Leu
450                 455                 460

Leu Ile Pro Glu Ser Gly Asp Tyr Phe Ile Tyr Ser Gln Val Thr Phe
465                 470                 475                 480

Arg Gly Tyr Thr Ser Glu Cys Ser Glu Ile Arg Ala Ala Gly Arg Pro
                485                 490                 495

Asn Lys Pro Asp Ser Ile Thr Val Val Ile Thr Lys Val Thr Asp Leu
            500                 505                 510

Tyr Pro Phe Pro Thr Gln Leu Leu Met Gly Thr Lys Ser Val Cys Glu
        515                 520                 525

Val Gly Ser Asn Trp Phe Gln Pro Ile Tyr Leu Gly Ala Met Phe Ser
530                 535                 540

Leu Gln Glu Gly Asp Lys Leu Met Val Asn Val Ser Asp Ile Ser Leu
545                 550                 555                 560

Val Asp Tyr Thr Lys Glu Asp Lys Thr Phe Phe Gly Ala Phe Leu Leu
                565                 570                 575

Gly Gly Gly Ser Gly Gly Gly Ser Gly Gly Gly Ser Val Tyr Ala Pro
            580                 585                 590

Leu Arg Ala Asp Gly Asp Lys Pro Arg Ala His Leu Thr Val Val Arg
        595                 600                 605

Gln Thr Pro Thr Gln His Phe Ala Asn Gln Phe Pro Ala Leu His Trp
610                 615                 620

Glu His Glu Lys Gly Leu Ala Phe Thr Lys Asn Arg Met Asn Tyr Thr
625                 630                 635                 640

Asn Lys Phe Leu Leu Ile Pro Glu Ser Gly Asp Tyr Phe Ile Tyr Ser
                645                 650                 655

Gln Val Thr Phe Arg Gly Tyr Thr Ser Glu Cys Ser Glu Ile Arg Ala
            660                 665                 670

Ala Gly Arg Pro Asn Lys Pro Asp Ser Ile Thr Val Val Ile Thr Lys
        675                 680                 685

Val Thr Asp Leu Tyr Pro Phe Pro Thr Gln Leu Leu Met Gly Thr Lys
690                 695                 700

Ser Val Cys Glu Val Gly Ser Asn Trp Phe Gln Pro Ile Tyr Leu Gly
705                 710                 715                 720

Ala Met Phe Ser Leu Gln Glu Gly Asp Lys Leu Met Val Asn Val Ser
                725                 730                 735

Asp Ile Ser Leu Val Asp Tyr Thr Lys Glu Asp Lys Thr Phe Phe Gly
            740                 745                 750

Ala Phe Leu Leu
        755

<210> SEQ ID NO 90
<211> LENGTH: 756
<212> TYPE: PRT
<213> ORGANISM: Artificial Sequence
<220> FEATURE:
<223> OTHER INFORMATION: TL1W328 (Fc-scTL1A K111A L123K M158Y Q167A
    S187L N207F) amino acid sequence

<400> SEQUENCE: 90

Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Val Tyr Ala Pro Leu Arg Ala Asp Gly Asp Lys Pro
225                 230                 235                 240

Arg Ala His Leu Thr Val Val Arg Gln Thr Pro Thr Gln His Phe Ala
                245                 250                 255

Asn Gln Phe Pro Ala Leu His Trp Glu His Glu Lys Gly Leu Ala Phe
            260                 265                 270

Thr Lys Asn Arg Met Asn Tyr Thr Asn Lys Phe Leu Leu Ile Pro Glu
        275                 280                 285

Ser Gly Asp Tyr Phe Ile Tyr Ser Gln Val Thr Phe Arg Gly Tyr Thr
    290                 295                 300

Ser Glu Cys Ser Glu Ile Arg Ala Ala Gly Arg Pro Asn Lys Pro Asp
305                 310                 315                 320

Ser Ile Thr Val Val Ile Thr Lys Val Thr Asp Leu Tyr Pro Glu Pro
                325                 330                 335

Thr Gln Leu Leu Met Gly Thr Lys Ser Val Cys Glu Val Gly Ser Phe
            340                 345                 350

Trp Phe Gln Pro Ile Tyr Leu Gly Ala Met Phe Ser Leu Gln Glu Gly
        355                 360                 365

Asp Lys Leu Met Val Asn Val Ser Asp Ile Ser Leu Val Asp Tyr Thr
    370                 375                 380

Lys Glu Asp Lys Thr Phe Phe Gly Ala Phe Leu Leu Gly Gly Gly Ser
385                 390                 395                 400

Gly Gly Gly Ser Gly Gly Ser Val Tyr Ala Pro Leu Arg Ala Asp
                405                 410                 415

Gly Asp Lys Pro Arg Ala His Leu Thr Val Val Arg Gln Thr Pro Thr
            420                 425                 430

Gln His Phe Ala Asn Gln Phe Pro Ala Leu His Trp Glu His Glu Lys
        435                 440                 445

Gly Leu Ala Phe Thr Lys Asn Arg Met Asn Tyr Thr Asn Lys Phe Leu
    450                 455                 460

```
Leu Ile Pro Glu Ser Gly Asp Tyr Phe Ile Tyr Ser Gln Val Thr Phe
465                 470                 475                 480

Arg Gly Tyr Thr Ser Glu Cys Ser Glu Ile Arg Ala Ala Gly Arg Pro
            485                 490                 495

Asn Lys Pro Asp Ser Ile Thr Val Val Ile Thr Lys Val Thr Asp Leu
        500                 505                 510

Tyr Pro Glu Pro Thr Gln Leu Leu Met Gly Thr Lys Ser Val Cys Glu
    515                 520                 525

Val Gly Ser Phe Trp Phe Gln Pro Ile Tyr Leu Gly Ala Met Phe Ser
530                 535                 540

Leu Gln Glu Gly Asp Lys Leu Met Val Asn Val Ser Asp Ile Ser Leu
545                 550                 555                 560

Val Asp Tyr Thr Lys Glu Asp Lys Thr Phe Phe Gly Ala Phe Leu Leu
            565                 570                 575

Gly Gly Gly Ser Gly Gly Gly Ser Gly Gly Ser Val Tyr Ala Pro
        580                 585                 590

Leu Arg Ala Asp Gly Asp Lys Pro Arg Ala His Leu Thr Val Val Arg
    595                 600                 605

Gln Thr Pro Thr Gln His Phe Ala Asn Gln Phe Pro Ala Leu His Trp
610                 615                 620

Glu His Glu Lys Gly Leu Ala Phe Thr Lys Asn Arg Met Asn Tyr Thr
625                 630                 635                 640

Asn Lys Phe Leu Leu Ile Pro Glu Ser Gly Asp Tyr Phe Ile Tyr Ser
            645                 650                 655

Gln Val Thr Phe Arg Gly Tyr Thr Ser Glu Cys Ser Glu Ile Arg Ala
        660                 665                 670

Ala Gly Arg Pro Asn Lys Pro Asp Ser Ile Thr Val Val Ile Thr Lys
    675                 680                 685

Val Thr Asp Leu Tyr Pro Glu Pro Thr Gln Leu Leu Met Gly Thr Lys
690                 695                 700

Ser Val Cys Glu Val Gly Ser Phe Trp Phe Gln Pro Ile Tyr Leu Gly
705                 710                 715                 720

Ala Met Phe Ser Leu Gln Glu Gly Asp Lys Leu Met Val Asn Val Ser
            725                 730                 735

Asp Ile Ser Leu Val Asp Tyr Thr Lys Glu Asp Lys Thr Phe Phe Gly
        740                 745                 750

Ala Phe Leu Leu
    755
```

<210> SEQ ID NO 91
<211> LENGTH: 756
<212> TYPE: PRT
<213> ORGANISM: Artificial Sequence
<220> FEATURE:
<223> OTHER INFORMATION: TL1W331 (Fc-scTL1A K111A L123K Q167A S187L
      E190F N207F) amino acid sequence

<400> SEQUENCE: 91

```
Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60
```

```
Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
210                 215                 220

Gly Gly Gly Ser Val Tyr Ala Pro Leu Arg Ala Asp Gly Asp Lys Pro
225                 230                 235                 240

Arg Ala His Leu Thr Val Val Arg Gln Thr Pro Thr Gln His Phe Ala
                245                 250                 255

Asn Gln Phe Pro Ala Leu His Trp Glu His Glu Lys Gly Leu Ala Phe
            260                 265                 270

Thr Lys Asn Arg Met Asn Tyr Thr Asn Lys Phe Leu Leu Ile Pro Glu
        275                 280                 285

Ser Gly Asp Tyr Phe Ile Tyr Ser Gln Val Thr Phe Arg Gly Met Thr
290                 295                 300

Ser Glu Cys Ser Glu Ile Arg Ala Ala Gly Arg Pro Asn Lys Pro Asp
305                 310                 315                 320

Ser Ile Thr Val Val Ile Thr Lys Val Thr Asp Leu Tyr Pro Phe Pro
                325                 330                 335

Thr Gln Leu Leu Met Gly Thr Lys Ser Val Cys Glu Val Gly Ser Phe
            340                 345                 350

Trp Phe Gln Pro Ile Tyr Leu Gly Ala Met Phe Ser Leu Gln Glu Gly
        355                 360                 365

Asp Lys Leu Met Val Asn Val Ser Asp Ile Ser Leu Val Asp Tyr Thr
370                 375                 380

Lys Glu Asp Lys Thr Phe Phe Gly Ala Phe Leu Leu Gly Gly Gly Ser
385                 390                 395                 400

Gly Gly Gly Ser Gly Gly Gly Ser Val Tyr Ala Pro Leu Arg Ala Asp
                405                 410                 415

Gly Asp Lys Pro Arg Ala His Leu Thr Val Val Arg Gln Thr Pro Thr
            420                 425                 430

Gln His Phe Ala Asn Gln Phe Pro Ala Leu His Trp Glu His Glu Lys
        435                 440                 445

Gly Leu Ala Phe Thr Lys Asn Arg Met Asn Tyr Thr Asn Lys Phe Leu
450                 455                 460

Leu Ile Pro Glu Ser Gly Asp Tyr Phe Ile Tyr Ser Gln Val Thr Phe
465                 470                 475                 480
```

```
Arg Gly Met Thr Ser Glu Cys Ser Glu Ile Arg Ala Ala Gly Arg Pro
                    485                 490                 495

Asn Lys Pro Asp Ser Ile Thr Val Val Ile Thr Lys Val Thr Asp Leu
            500                 505                 510

Tyr Pro Phe Pro Thr Gln Leu Leu Met Gly Thr Lys Ser Val Cys Glu
        515                 520                 525

Val Gly Ser Phe Trp Phe Gln Pro Ile Tyr Leu Gly Ala Met Phe Ser
    530                 535                 540

Leu Gln Glu Gly Asp Lys Leu Met Val Asn Val Ser Asp Ile Ser Leu
545                 550                 555                 560

Val Asp Tyr Thr Lys Glu Asp Lys Thr Phe Phe Gly Ala Phe Leu Leu
                565                 570                 575

Gly Gly Gly Ser Gly Gly Gly Ser Gly Gly Gly Ser Val Tyr Ala Pro
                580                 585                 590

Leu Arg Ala Asp Gly Asp Lys Pro Arg Ala His Leu Thr Val Val Arg
                595                 600                 605

Gln Thr Pro Thr Gln His Phe Ala Asn Gln Phe Pro Ala Leu His Trp
        610                 615                 620

Glu His Glu Lys Gly Leu Ala Phe Thr Lys Asn Arg Met Asn Tyr Thr
625                 630                 635                 640

Asn Lys Phe Leu Leu Ile Pro Glu Ser Gly Asp Tyr Phe Ile Tyr Ser
                645                 650                 655

Gln Val Thr Phe Arg Gly Met Thr Ser Glu Cys Ser Glu Ile Arg Ala
            660                 665                 670

Ala Gly Arg Pro Asn Lys Pro Asp Ser Ile Thr Val Val Ile Thr Lys
        675                 680                 685

Val Thr Asp Leu Tyr Pro Phe Pro Thr Gln Leu Leu Met Gly Thr Lys
    690                 695                 700

Ser Val Cys Glu Val Gly Ser Phe Trp Phe Gln Pro Ile Tyr Leu Gly
705                 710                 715                 720

Ala Met Phe Ser Leu Gln Glu Gly Asp Lys Leu Met Val Asn Val Ser
                725                 730                 735

Asp Ile Ser Leu Val Asp Tyr Thr Lys Glu Asp Lys Thr Phe Phe Gly
            740                 745                 750

Ala Phe Leu Leu
            755

<210> SEQ ID NO 92
<211> LENGTH: 601
<212> TYPE: PRT
<213> ORGANISM: Artificial Sequence
<220> FEATURE:
<223> OTHER INFORMATION: TL1W61 (Fc-TL1A+His-TL1A) amino acid sequence

<400> SEQUENCE: 92

Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80
```

-continued

Ser Val Leu Thr Val Leu His Gln Asp Trp Leu Asn Gly Lys Glu Tyr
            85                  90                  95
Lys Cys Lys Val Ser Asn Lys Ala Leu Pro Ala Pro Ile Glu Lys Thr
        100                 105                 110
Ile Ser Lys Ala Lys Gly Gln Pro Arg Glu Pro Gln Val Tyr Thr Leu
        115                 120                 125
Pro Pro Ser Arg Glu Glu Met Thr Lys Asn Gln Val Ser Leu Thr Cys
130                 135                 140
Leu Val Lys Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Tyr Ser Lys Leu Thr Val Asp Lys Ser
            180                 185                 190
Arg Trp Gln Gln Gly Asn Val Phe Ser Cys Ser Val Met His Glu Ala
        195                 200                 205
Leu His Asn His Tyr Thr Gln Lys Ser Leu Ser Leu Ser Pro Gly Gly
        210                 215                 220
Gly Gly Gly Ser Leu Lys Gly Gln Glu Phe Ala Pro Ser His Gln Gln
225                 230                 235                 240
Val Tyr Ala Pro Leu Arg Ala Asp Gly Asp Lys Pro Arg Ala His Leu
                245                 250                 255
Thr Val Val Arg Gln Thr Pro Thr Gln His Phe Lys Asn Gln Phe Pro
            260                 265                 270
Ala Leu His Trp Glu His Glu Leu Gly Leu Ala Phe Thr Lys Asn Arg
        275                 280                 285
Met Asn Tyr Thr Asn Lys Phe Leu Leu Ile Pro Glu Ser Gly Asp Tyr
        290                 295                 300
Phe Ile Tyr Ser Gln Val Thr Phe Arg Gly Met Thr Ser Glu Cys Ser
305                 310                 315                 320
Glu Ile Arg Gln Ala Gly Arg Pro Asn Lys Pro Asp Ser Ile Thr Val
                325                 330                 335
Val Ile Thr Lys Val Thr Asp Ser Tyr Pro Glu Pro Thr Gln Leu Leu
            340                 345                 350
Met Gly Thr Lys Ser Val Cys Glu Val Gly Ser Asn Trp Phe Gln Pro
        355                 360                 365
Ile Tyr Leu Gly Ala Met Phe Ser Leu Gln Glu Gly Asp Lys Leu Met
        370                 375                 380
Val Asn Val Ser Asp Ile Ser Leu Val Asp Tyr Thr Lys Glu Asp Lys
385                 390                 395                 400
Thr Phe Phe Gly Ala Phe Leu Leu His His His His His His Glu Asn
                405                 410                 415
Leu Tyr Phe Gln Gly Leu Lys Gly Gln Glu Phe Ala Pro Ser His Gln
            420                 425                 430
Gln Val Tyr Ala Pro Leu Arg Ala Asp Gly Asp Lys Pro Arg Ala His
        435                 440                 445
Leu Thr Val Val Arg Gln Thr Pro Thr Gln His Phe Lys Asn Gln Phe
        450                 455                 460
Pro Ala Leu His Trp Glu His Glu Leu Gly Leu Ala Phe Thr Lys Asn
465                 470                 475                 480
Arg Met Asn Tyr Thr Asn Lys Phe Leu Leu Ile Pro Glu Ser Gly Asp
                485                 490                 495
Tyr Phe Ile Tyr Ser Gln Val Thr Phe Arg Gly Met Thr Ser Glu Cys

```
            500                 505                 510
Ser Glu Ile Arg Gln Ala Gly Arg Pro Asn Lys Pro Asp Ser Ile Thr
            515                 520                 525

Val Val Ile Thr Lys Val Thr Asp Ser Tyr Pro Glu Pro Thr Gln Leu
        530                 535                 540

Leu Met Gly Thr Lys Ser Val Cys Glu Val Gly Ser Asn Trp Phe Gln
545                 550                 555                 560

Pro Ile Tyr Leu Gly Ala Met Phe Ser Leu Gln Glu Gly Asp Lys Leu
                565                 570                 575

Met Val Asn Val Ser Asp Ile Ser Leu Val Asp Tyr Thr Lys Glu Asp
            580                 585                 590

Lys Thr Phe Phe Gly Ala Phe Leu Leu
        595                 600

<210> SEQ ID NO 93
<211> LENGTH: 408
<212> TYPE: PRT
<213> ORGANISM: Artificial Sequence
<220> FEATURE:
<223> OTHER INFORMATION: TL1W3 (GD: Fc Fusion in CBIS -> homodimer Fc
      Fusion; GS-huIgG1 Fc - 2(G4S)-hTL1A 72-251) amino acid sequence

<400> SEQUENCE: 93

Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Leu Lys Gly Gln Glu Phe Ala Pro Ser His Gln Gln
225                 230                 235                 240

Val Tyr Ala Pro Leu Arg Ala Asp Gly Asp Lys Pro Arg Ala His Leu
                245                 250                 255
```

Thr Val Val Arg Gln Thr Pro Thr Gln His Phe Lys Asn Gln Phe Pro
            260                 265                 270

Ala Leu His Trp Glu His Glu Leu Gly Leu Ala Phe Thr Lys Asn Arg
        275                 280                 285

Met Asn Tyr Thr Asn Lys Phe Leu Leu Ile Pro Glu Ser Gly Asp Tyr
    290                 295                 300

Phe Ile Tyr Ser Gln Val Thr Phe Arg Gly Met Thr Ser Glu Cys Ser
305                 310                 315                 320

Glu Ile Arg Gln Ala Gly Arg Pro Asn Lys Pro Asp Ser Ile Thr Val
                325                 330                 335

Val Ile Thr Lys Val Thr Asp Ser Tyr Pro Glu Pro Thr Gln Leu Leu
            340                 345                 350

Met Gly Thr Lys Ser Val Cys Glu Val Gly Ser Asn Trp Phe Gln Pro
        355                 360                 365

Ile Tyr Leu Gly Ala Met Phe Ser Leu Gln Glu Gly Asp Lys Leu Met
    370                 375                 380

Val Asn Val Ser Asp Ile Ser Leu Val Asp Tyr Thr Lys Glu Asp Lys
385                 390                 395                 400

Thr Phe Phe Gly Ala Phe Leu Leu
                405

<210> SEQ ID NO 94
<211> LENGTH: 251
<212> TYPE: PRT
<213> ORGANISM: Artificial Sequence
<220> FEATURE:
<223> OTHER INFORMATION: hTL1A (1-251) amino acid sequence

<400> SEQUENCE: 94

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 95
<211> LENGTH: 579
<212> TYPE: DNA
<213> ORGANISM: Artificial Sequence
<220> FEATURE:
<223> OTHER INFORMATION: TL1W81 (His-TEV-TL1A K111S) nucleotide sequence

<400> SEQUENCE: 95

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcagca accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 96
<211> LENGTH: 579
<212> TYPE: DNA
<213> ORGANISM: Artificial Sequence
<220> FEATURE:
<223> OTHER INFORMATION: TL1W83 (His-TEV-TL1A E120K) nucleotide sequence

<400> SEQUENCE: 96

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tggaagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 97
<211> LENGTH: 579
<212> TYPE: DNA
<213> ORGANISM: Artificial Sequence
<220> FEATURE:
<223> OTHER INFORMATION: TL1W84 (His-TEV-TL1A E120H) nucleotide sequence

<400> SEQUENCE: 97

| | |
|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tggcaccacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 98
<211> LENGTH: 579
<212> TYPE: DNA
<213> ORGANISM: Artificial Sequence
<220> FEATURE:
<223> OTHER INFORMATION: TL1W40 (His-TEV-TL1A L123S) nucleotide sequence

<400> SEQUENCE: 98

| | |
|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agtcgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 99
<211> LENGTH: 579
<212> TYPE: DNA
<213> ORGANISM: Artificial Sequence
<220> FEATURE:
<223> OTHER INFORMATION: TL1W85 (His-TEV-TL1A) nucleotide sequence

<400> SEQUENCE: 99

| | |
|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgagcct ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 100
<211> LENGTH: 579
<212> TYPE: DNA
<213> ORGANISM: Artificial Sequence
<220> FEATURE:
<223> OTHER INFORMATION: TL1W86 (His-TEV-TL1A G124K) nucleotide sequence

<400> SEQUENCE: 100

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgaagct ggcctttacc aagaacagaa tgaattacac caacaagttt     240
ctgctcatcc ccgagagcgg agactacttc atctactccc aggtgacctt cagggggcatg    300
acaagcgagt gcagcgagat cagacaggcc ggaaggccta ataagcccga ctccatcaca     360
gtggtgatca aaaggtgac cgacagctac cccgagccca cccagctgct gatgggcacc      420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 101
<211> LENGTH: 579
<212> TYPE: DNA
<213> ORGANISM: Artificial Sequence
<220> FEATURE:
<223> OTHER INFORMATION: TL1W89 (His-TEV-TL1A R156Y) nucleotide sequence

<400> SEQUENCE: 101

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt ctacggcatg     300
acaagcgagt gcagcgagat cagacaggcc ggaaggccta ataagcccga ctccatcaca     360
gtggtgatca aaaggtgac cgacagctac cccgagccca cccagctgct gatgggcacc      420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 102
<211> LENGTH: 579
<212> TYPE: DNA
<213> ORGANISM: Artificial Sequence
<220> FEATURE:
<223> OTHER INFORMATION: TL1W92 (His-TEV-TL1A M158Y) nucleotide sequence

<400> SEQUENCE: 102

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
```

```
ctgctcatcc ccgagagcgg agactacttc atctactccc aggtgacctt caggggctac      300
acaagcgagt gcagcgagat cagacaggcc ggaaggccta ataagcccga ctccatcaca      360
gtggtgatca caaaggtgac cgacagctac cccgagccca cccagctgct gatgggcacc      420
aagagcgtgt gcgaagtggg cagcaactgg ttccagccca tctacctggg cgccatgttc      480
agcctgcagg agggcgacaa gctgatggtg aacgtgagcg acatttccct ggtcgattac      540
accaaggagg ataagacctt cttcggcgcc ttcctgctg                             579
```

<210> SEQ ID NO 103
<211> LENGTH: 579
<212> TYPE: DNA
<213> ORGANISM: Artificial Sequence
<220> FEATURE:
<223> OTHER INFORMATION: TL1W97 (His-TEV-TL1A K173S) nucleotide sequence

<400> SEQUENCE: 103

```
catcatcacc accatcacga gaacctgtac ttccaaggtc tcaagggcca ggagttcgct      60
ccctcccatc agcaggtgta cgctcccctg agagccgatg gcgataagcc cagagcccac      120
ctgaccgtcg tgaggcagac ccccacccag cacttcaaga accagtttcc cgccctccac      180
tgggagcacg agctgggact ggcctttacc aagaacagaa tgaattacac caacaagttt      240
ctgctcatcc ccgagagcgg agactacttc atctactccc aggtgacctt caggggcatg      300
acaagcgagt gcagcgagat cagacaggcc ggaaggccta atagcccga ctccatcaca      360 gtggtgatca caaaggtgac cgacagctac cccgagccca cccagctgct gatgggcacc      420
aagagcgtgt gcgaagtggg cagcaactgg ttccagccca tctacctggg cgccatgttc      480
agcctgcagg agggcgacaa gctgatggtg aacgtgagcg acatttccct ggtcgattac      540
accaaggagg ataagacctt cttcggcgcc ttcctgctg                             579
```

<210> SEQ ID NO 104
<211> LENGTH: 579
<212> TYPE: DNA
<213> ORGANISM: Artificial Sequence
<220> FEATURE:
<223> OTHER INFORMATION: TL1W98 (His-TEV-TL1A K173R) nucleotide sequence

<400> SEQUENCE: 104

```
catcatcacc accatcacga gaacctgtac ttccaaggtc tcaagggcca ggagttcgct      60
ccctcccatc agcaggtgta cgctcccctg agagccgatg gcgataagcc cagagcccac      120
ctgaccgtcg tgaggcagac ccccacccag cacttcaaga accagtttcc cgccctccac      180
tgggagcacg agctgggact ggcctttacc aagaacagaa tgaattacac caacaagttt      240
ctgctcatcc ccgagagcgg agactacttc atctactccc aggtgacctt caggggcatg      300
acaagcgagt gcagcgagat cagacaggcc ggaaggccta atcggcccga ctccatcaca      360
gtggtgatca caaaggtgac cgacagctac cccgagccca cccagctgct gatgggcacc      420
aagagcgtgt gcgaagtggg cagcaactgg ttccagccca tctacctggg cgccatgttc      480
agcctgcagg agggcgacaa gctgatggtg aacgtgagcg acatttccct ggtcgattac      540
accaaggagg ataagacctt cttcggcgcc ttcctgctg                             579
```

<210> SEQ ID NO 105
<211> LENGTH: 579
<212> TYPE: DNA
<213> ORGANISM: Artificial Sequence
<220> FEATURE:
<223> OTHER INFORMATION: TL1W107 (His-TEV-TL1A D186Y) nucleotide -continued sequence

<400> SEQUENCE: 105

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac ctacagctac cccgagccca ccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 106
<211> LENGTH: 579
<212> TYPE: DNA
<213> ORGANISM: Artificial Sequence
<220> FEATURE:
<223> OTHER INFORMATION: TL1W113 (His-TEV-TL1A P189S) nucleotide
      sequence

<400> SEQUENCE: 106

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac agcgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 107
<211> LENGTH: 579
<212> TYPE: DNA
<213> ORGANISM: Artificial Sequence
<220> FEATURE:
<223> OTHER INFORMATION: TL1W28 (His-TEV-hTL1A 72-251 E190G) nucleotide
      sequence

<400> SEQUENCE: 107

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccggcccca cccagctgct gatgggcacc | 420 |

```
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 108
<211> LENGTH: 579
<212> TYPE: DNA
<213> ORGANISM: Artificial Sequence
<220> FEATURE:
<223> OTHER INFORMATION: TL1W45 (His-TEV-TL1A E190F) nucleotide sequence

<400> SEQUENCE: 108

```
catcatcacc accatcacga gaacctgtac ttccaaggtc tcaagggcca ggagttcgct     60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac ccctttccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 109
<211> LENGTH: 579
<212> TYPE: DNA
<213> ORGANISM: Artificial Sequence
<220> FEATURE:
<223> OTHER INFORMATION: TL1W123 (His-TEV-TL1A N207S) nucleotide
      sequence

<400> SEQUENCE: 109

```
catcatcacc accatcacga gaacctgtac ttccaaggtc tcaagggcca ggagttcgct     60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcagctgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 110
<211> LENGTH: 579
<212> TYPE: DNA
<213> ORGANISM: Artificial Sequence
<220> FEATURE:
<223> OTHER INFORMATION: TL1W126 (His-TEV-TL1A F209W) nucleotide
      sequence

<400> SEQUENCE: 110

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaaggtgac cgacagctac cccgagccca cccagctgct gatgggcacc     420
aagagcgtgt gcgaagtggg cagcaactgg tggcagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 111
<211> LENGTH: 579
<212> TYPE: DNA
<213> ORGANISM: Artificial Sequence
<220> FEATURE:
<223> OTHER INFORMATION: TL1W46 (His-TEV-TL1A T239W) nucleotide sequence

<400> SEQUENCE: 111

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
tggaaggagg ataagacctt cttcggcgcc ttcctgctg                            579
```

<210> SEQ ID NO 112
<211> LENGTH: 579
<212> TYPE: DNA
<213> ORGANISM: Artificial Sequence
<220> FEATURE:
<223> OTHER INFORMATION: TL1W137 (His-TEV-TL1A K240S) nucleotide
      sequence

<400> SEQUENCE: 112

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
```
accagcgagg ataagacctt cttcggcgcc ttcctgctg         579

<210> SEQ ID NO 113
<211> LENGTH: 579
<212> TYPE: DNA
<213> ORGANISM: Artificial Sequence
<220> FEATURE:
<223> OTHER INFORMATION: TL1W139 (His-TEV-TL1A E241Q) nucleotide
      sequence

<400> SEQUENCE: 113
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg catttccct ggtcgattac    540
accaagcagg ataagacctt cttcggcgcc ttcctgctg                          579

<210> SEQ ID NO 114
<211> LENGTH: 579
<212> TYPE: DNA
<213> ORGANISM: Artificial Sequence
<220> FEATURE:
<223> OTHER INFORMATION: TL1W2 (His-TEV-hTL1A 72-251) nucleotide
      sequence

<400> SEQUENCE: 114
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg catttccct ggtcgattac    540
accaaggagg ataagacctt cttcggcgcc ttcctgctg                          579

<210> SEQ ID NO 115
<211> LENGTH: 579
<212> TYPE: DNA
<213> ORGANISM: Artificial Sequence
<220> FEATURE:
<223> OTHER INFORMATION: TL1W47 (His-TEV-TL1A E241A) nucleotide sequence

<400> SEQUENCE: 115
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180

```
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaggtgac cgacagctac cccgagccca cccagctgct gatgggcacc     420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggcgg ataagacctt cttcggcgcc ttcctgctg                           579
```

```
<210> SEQ ID NO 116
<211> LENGTH: 579
<212> TYPE: DNA
<213> ORGANISM: Artificial Sequence
<220> FEATURE:
<223> OTHER INFORMATION: TL1W136 (His-TEV-TL1A K240F) nucleotide
      sequence

<400> SEQUENCE: 116
```

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc    420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accttcgagg ataagacctt cttcggcgcc ttcctgctg                          579
```

```
<210> SEQ ID NO 117
<211> LENGTH: 579
<212> TYPE: DNA
<213> ORGANISM: Artificial Sequence
<220> FEATURE:
<223> OTHER INFORMATION: TL1W138 (His-TEV-TL1A K240D) nucleotide
      sequence

<400> SEQUENCE: 117
```

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc    420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accgacgagg ataagacctt cttcggcgcc ttcctgctg                          579
```

```
<210> SEQ ID NO 118
```

<211> LENGTH: 579
<212> TYPE: DNA
<213> ORGANISM: Artificial Sequence
<220> FEATURE:
<223> OTHER INFORMATION: TL1W135 (His-TEV-TL1A K240A) nucleotide
      sequence

<400> SEQUENCE: 118

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accgccgagg ataagacctt cttcggcgcc ttcctgctg | 579 |

<210> SEQ ID NO 119
<211> LENGTH: 579
<212> TYPE: DNA
<213> ORGANISM: Artificial Sequence
<220> FEATURE:
<223> OTHER INFORMATION: TL1W134 (His-TEV-TL1A T239K) nucleotide
      sequence

<400> SEQUENCE: 119

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| aagaaggagg ataagacctt cttcggcgcc ttcctgctg | 579 |

<210> SEQ ID NO 120
<211> LENGTH: 579
<212> TYPE: DNA
<213> ORGANISM: Artificial Sequence
<220> FEATURE:
<223> OTHER INFORMATION: TL1W133 (His-TEV-TL1A T239F) nucleotide
      sequence

<400> SEQUENCE: 120

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |

| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| ttcaaggagg ataagacctt cttcggcgcc ttcctgctg | 579 |

<210> SEQ ID NO 121
<211> LENGTH: 579
<212> TYPE: DNA
<213> ORGANISM: Artificial Sequence
<220> FEATURE:
<223> OTHER INFORMATION: TL1W27 (His-TEV-hTL1A 72-251 T239E) nucleotide sequence

<400> SEQUENCE: 121

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| gaaaaggagg ataagacctt cttcggcgcc ttcctgctg | 579 |

<210> SEQ ID NO 122
<211> LENGTH: 579
<212> TYPE: DNA
<213> ORGANISM: Artificial Sequence
<220> FEATURE:
<223> OTHER INFORMATION: TL1W132 (His-TEV-TL1A T239A) nucleotide sequence

<400> SEQUENCE: 122

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| gccaaggagg ataagacctt cttcggcgcc ttcctgctg | 579 |

<210> SEQ ID NO 123
<211> LENGTH: 579
<212> TYPE: DNA
<213> ORGANISM: Artificial Sequence
<220> FEATURE:
<223> OTHER INFORMATION: TL1W128 (His-TEV-TL1A Y238S) nucleotide
      sequence

<400> SEQUENCE: 123

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgatagc   540
accaaggagg ataagacctt cttcggcgcc ttcctgctg                          579
```

<210> SEQ ID NO 124
<211> LENGTH: 579
<212> TYPE: DNA
<213> ORGANISM: Artificial Sequence
<220> FEATURE:
<223> OTHER INFORMATION: TL1W130 (His-TEV-TL1A Y238R) nucleotide
      sequence

<400> SEQUENCE: 124

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgatcgg   540
accaaggagg ataagacctt cttcggcgcc ttcctgctg                          579
```

<210> SEQ ID NO 125
<211> LENGTH: 579
<212> TYPE: DNA
<213> ORGANISM: Artificial Sequence
<220> FEATURE:
<223> OTHER INFORMATION: TL1W129 (His-TEV-TL1A Y238K) nucleotide
      sequence

<400> SEQUENCE: 125

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
```

```
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgataag    540
accaaggagg ataagacctt cttcggcgcc ttcctgctg                           579
```

<210> SEQ ID NO 126
<211> LENGTH: 579
<212> TYPE: DNA
<213> ORGANISM: Artificial Sequence
<220> FEATURE:
<223> OTHER INFORMATION: TL1W131 (His-TEV-TL1A Y238E) nucleotide
      sequence

<400> SEQUENCE: 126

```
catcatcacc accatcacga gaacctgtac ttccaaggtc tcaagggcca ggagttcgct     60
ccctcccatc agcaggtgta cgctccccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgatgag   540
accaaggagg ataagacctt cttcggcgcc ttcctgctg                           579
```

<210> SEQ ID NO 127
<211> LENGTH: 579
<212> TYPE: DNA
<213> ORGANISM: Artificial Sequence
<220> FEATURE:
<223> OTHER INFORMATION: TL1W127 (His-TEV-TL1A Y238A) nucleotide
      sequence

<400> SEQUENCE: 127

```
catcatcacc accatcacga gaacctgtac ttccaaggtc tcaagggcca ggagttcgct     60
ccctcccatc agcaggtgta cgctccccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgatgcc   540
accaaggagg ataagacctt cttcggcgcc ttcctgctg                           579
```

<210> SEQ ID NO 128
<211> LENGTH: 579
<212> TYPE: DNA
<213> ORGANISM: Artificial Sequence
<220> FEATURE:
<223> OTHER INFORMATION: TL1W24 (His-TEV-hTL1A 72-251 F209A) nucleotide
      sequence

<400> SEQUENCE: 128

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc   420
aagagcgtgt gcgaagtggg cagcaactgg gcccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 129
<211> LENGTH: 579
<212> TYPE: DNA
<213> ORGANISM: Artificial Sequence
<220> FEATURE:
<223> OTHER INFORMATION: TL1W124 (His-TEV-TL1A N207K) nucleotide
    sequence

<400> SEQUENCE: 129

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc   420
aagagcgtgt gcgaagtggg cagcaagtgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 130
<211> LENGTH: 579
<212> TYPE: DNA
<213> ORGANISM: Artificial Sequence
<220> FEATURE:
<223> OTHER INFORMATION: TL1W122 (His-TEV-TL1A N207F) nucleotide
    sequence

<400> SEQUENCE: 130

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc   420
```

```
aagagcgtgt gcgaagtggg cagcttctgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 131
<211> LENGTH: 579
<212> TYPE: DNA
<213> ORGANISM: Artificial Sequence
<220> FEATURE:
<223> OTHER INFORMATION: TL1W125 (His-TEV-TL1A N207E) nucleotide
      sequence

<400> SEQUENCE: 131

```
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcgagtgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 132
<211> LENGTH: 579
<212> TYPE: DNA
<213> ORGANISM: Artificial Sequence
<220> FEATURE:
<223> OTHER INFORMATION: TL1W25 (His-TEV-hTL1A 72-251 N207A) nucleotide
      sequence

<400> SEQUENCE: 132

```
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcgcctgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 133
<211> LENGTH: 579
<212> TYPE: DNA
<213> ORGANISM: Artificial Sequence
<220> FEATURE:
<223> OTHER INFORMATION: TL1W120 (His-TEV-TL1A S206K) nucleotide
      sequence

<400> SEQUENCE: 133

```
catcatcacc accatcacga aacctgtac ttccaaggtc tcaagggcca ggagttcgct      60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg caagaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 134
<211> LENGTH: 579
<212> TYPE: DNA
<213> ORGANISM: Artificial Sequence
<220> FEATURE:
<223> OTHER INFORMATION: TL1W119 (His-TEV-TL1A S206F) nucleotide sequence

<400> SEQUENCE: 134

```
catcatcacc accatcacga aacctgtac ttccaaggtc tcaagggcca ggagttcgct      60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cttcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 135
<211> LENGTH: 579
<212> TYPE: DNA
<213> ORGANISM: Artificial Sequence
<220> FEATURE:
<223> OTHER INFORMATION: TL1W121 (His-TEV-TL1A S206E) nucleotide sequence

<400> SEQUENCE: 135

```
catcatcacc accatcacga aacctgtac ttccaaggtc tcaagggcca ggagttcgct      60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cgagaactgg ttccagccca tctacctggg cgccatgttc    480
agcctgcagg agggcgacaa gctgatggtg aacgtgagcg acatttccct ggtcgattac    540
```

<210> SEQ ID NO 136
<211> LENGTH: 579
<212> TYPE: DNA
<213> ORGANISM: Artificial Sequence
<220> FEATURE:
<223> OTHER INFORMATION: TL1W118 (His-TEV-TL1A S206A) nucleotide sequence

<400> SEQUENCE: 136

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cgccaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 137
<211> LENGTH: 579
<212> TYPE: DNA
<213> ORGANISM: Artificial Sequence
<220> FEATURE:
<223> OTHER INFORMATION: TL1W116 (His-TEV-TL1A T192K) nucleotide sequence

<400> SEQUENCE: 137

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca agcagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                            579
```

<210> SEQ ID NO 138
<211> LENGTH: 579
<212> TYPE: DNA
<213> ORGANISM: Artificial Sequence
<220> FEATURE:
<223> OTHER INFORMATION: TL1W115 (His-TEV-TL1A T192F) nucleotide sequence

<400> SEQUENCE: 138

```
catcatcacc accatcacga gaacctgtac ttccaaggtc tcaagggcca ggagttcgct      60
ccctcccatc agcaggtgta cgctcccctg agagccgatg gcgataagcc cagagcccac     120
```

```
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccct ccagctgct gatgggcacc     420 aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 139
<211> LENGTH: 579
<212> TYPE: DNA
<213> ORGANISM: Artificial Sequence
<220> FEATURE:
<223> OTHER INFORMATION: TL1W117 (His-TEV-TL1A T192E) nucleotide
      sequence

<400> SEQUENCE: 139

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagcccg agcagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                            579
```

<210> SEQ ID NO 140
<211> LENGTH: 579
<212> TYPE: DNA
<213> ORGANISM: Artificial Sequence
<220> FEATURE:
<223> OTHER INFORMATION: TL1W114 (His-TEV-TL1A T192A) nucleotide
      sequence

<400> SEQUENCE: 140

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagcccg cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                            579
```

<210> SEQ ID NO 141
<211> LENGTH: 579
<212> TYPE: DNA
<213> ORGANISM: Artificial Sequence
<220> FEATURE:
<223> OTHER INFORMATION: TL1W44 (His-TEV-TL1A P189K) nucleotide sequence

<400> SEQUENCE: 141

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |
| ctgctcatcc | ccgagagcgg | agactacttc | atctactccc | aggtgacctt | caggggcatg | 300 |
| acaagcgagt | gcagcgagat | cagacaggcc | ggaaggccta | ataagcccga | ctccatcaca | 360 |
| gtggtgatca | aaaggtgac | cgacagctac | aaagagccca | cccagctgct | gatgggcacc | 420 |
| aagagcgtgt | gcgaagtggg | cagcaactgg | ttccagccca | tctacctggg | cgccatgttc | 480 |
| agcctgcagg | agggcgacaa | gctgatggtg | aacgtgagcg | acatttccct | ggtcgattac | 540 |
| accaaggagg | ataagacctt | cttcggcgcc | ttcctgctg | | | 579 |

<210> SEQ ID NO 142
<211> LENGTH: 579
<212> TYPE: DNA
<213> ORGANISM: Artificial Sequence
<220> FEATURE:
<223> OTHER INFORMATION: TL1W112 (His-TEV-TL1A P189F) nucleotide sequence

<400> SEQUENCE: 142

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |
| ctgctcatcc | ccgagagcgg | agactacttc | atctactccc | aggtgacctt | caggggcatg | 300 |
| acaagcgagt | gcagcgagat | cagacaggcc | ggaaggccta | ataagcccga | ctccatcaca | 360 |
| gtggtgatca | aaaggtgac | cgacagctac | ttcgagccca | cccagctgct | gatgggcacc | 420 |
| aagagcgtgt | gcgaagtggg | cagcaactgg | ttccagccca | tctacctggg | cgccatgttc | 480 |
| agcctgcagg | agggcgacaa | gctgatggtg | aacgtgagcg | acatttccct | ggtcgattac | 540 |
| accaaggagg | ataagacctt | cttcggcgcc | ttcctgctg | | | 579 |

<210> SEQ ID NO 143
<211> LENGTH: 579
<212> TYPE: DNA
<213> ORGANISM: Artificial Sequence
<220> FEATURE:
<223> OTHER INFORMATION: TL1W29 (His-TEV-hTL1A 72-251 P189A) nucleotide sequence

<400> SEQUENCE: 143

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |

```
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac gccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 144
<211> LENGTH: 579
<212> TYPE: DNA
<213> ORGANISM: Artificial Sequence
<220> FEATURE:
<223> OTHER INFORMATION: TL1W43 (His-TEV-TL1A Y188S) nucleotide sequence

<400> SEQUENCE: 144

```
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctcc ccgagcccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 145
<211> LENGTH: 579
<212> TYPE: DNA
<213> ORGANISM: Artificial Sequence
<220> FEATURE:
<223> OTHER INFORMATION: TL1W32 (His-TEV-hTL1A 72-251 Y188A) nucleotide
      sequence

<400> SEQUENCE: 145

```
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagcgcc ccgagcccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 146
<211> LENGTH: 579
<212> TYPE: DNA
<213> ORGANISM: Artificial Sequence
<220> FEATURE:
<223> OTHER INFORMATION: TL1W109 (His-TEV-TL1A S187L) nucleotide
      sequence

<400> SEQUENCE: 146

| | | |
|---|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacctctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 147
<211> LENGTH: 579
<212> TYPE: DNA
<213> ORGANISM: Artificial Sequence
<220> FEATURE:
<223> OTHER INFORMATION: TL1W110 (His-TEV-TL1A S187K) nucleotide
      sequence

<400> SEQUENCE: 147

| | | |
|---|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacaagtac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 148
<211> LENGTH: 579
<212> TYPE: DNA
<213> ORGANISM: Artificial Sequence
<220> FEATURE:
<223> OTHER INFORMATION: TL1W111 (His-TEV-TL1A S187D) nucleotide
      sequence

<400> SEQUENCE: 148

| | | |
|---|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |

| gtggtgatca caaaggtgac cgacgactac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 149
<211> LENGTH: 579
<212> TYPE: DNA
<213> ORGANISM: Artificial Sequence
<220> FEATURE:
<223> OTHER INFORMATION: TL1W108 (His-TEV-TL1A S187A) nucleotide
      sequence

<400> SEQUENCE: 149

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgac cgacgcctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 150
<211> LENGTH: 579
<212> TYPE: DNA
<213> ORGANISM: Artificial Sequence
<220> FEATURE:
<223> OTHER INFORMATION: TL1W105 (His-TEV-TL1A T185N) nucleotide
      sequence

<400> SEQUENCE: 150

| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga ctccatcaca | 360 |
| gtggtgatca caaaggtgaa cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 151
<211> LENGTH: 579
<212> TYPE: DNA
<213> ORGANISM: Artificial Sequence
<220> FEATURE:
<223> OTHER INFORMATION: TL1W104 (His-TEV-TL1A T185L) nucleotide
      sequence

<400> SEQUENCE: 151

```
catcatcacc accatcacga gaacctgtac ttccaaggtc tcaagggcca ggagttcgct     60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgct cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 152
<211> LENGTH: 579
<212> TYPE: DNA
<213> ORGANISM: Artificial Sequence
<220> FEATURE:
<223> OTHER INFORMATION: TL1W106 (His-TEV-TL1A T185D) nucleotide
      sequence

<400> SEQUENCE: 152

```
catcatcacc accatcacga gaacctgtac ttccaaggtc tcaagggcca ggagttcgct     60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgga cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 153
<211> LENGTH: 579
<212> TYPE: DNA
<213> ORGANISM: Artificial Sequence
<220> FEATURE:
<223> OTHER INFORMATION: TL1W103 (His-TEV-TL1A T185A) nucleotide
      sequence

<400> SEQUENCE: 153

```
catcatcacc accatcacga gaacctgtac ttccaaggtc tcaagggcca ggagttcgct     60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtggc cgacagctac cccgagccca cccagctgct gatgggcacc    420
```

| | |
|---|---|
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 154
<211> LENGTH: 579
<212> TYPE: DNA
<213> ORGANISM: Artificial Sequence
<220> FEATURE:
<223> OTHER INFORMATION: TL1W101 (His-TEV-TL1A S176N) nucleotide sequence

<400> SEQUENCE: 154

| | |
|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga caacatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 155
<211> LENGTH: 579
<212> TYPE: DNA
<213> ORGANISM: Artificial Sequence
<220> FEATURE:
<223> OTHER INFORMATION: TL1W100 (His-TEV-TL1A S176L) nucleotide sequence

<400> SEQUENCE: 155

| | |
|---|---|
| catcatcacc accatcacga gaacctgtac ttccaaggtc tcaagggcca ggagttcgct | 60 |
| ccctcccatc agcaggtgta cgctcccctg agagccgatg gcgataagcc cagagcccac | 120 |
| ctgaccgtcg tgaggcagac ccccacccag cacttcaaga accagtttcc cgccctccac | 180 |
| tgggagcacg agctgggact ggcctttacc aagaacagaa tgaattacac caacaagttt | 240 |
| ctgctcatcc ccgagagcgg agactacttc atctactccc aggtgacctt caggggcatg | 300 |
| acaagcgagt gcagcgagat cagacaggcc ggaaggccta ataagcccga cctcatcaca | 360 |
| gtggtgatca caaaggtgac cgacagctac cccgagccca cccagctgct gatgggcacc | 420 |
| aagagcgtgt gcgaagtggg cagcaactgg ttccagccca tctacctggg cgccatgttc | 480 |
| agcctgcagg agggcgacaa gctgatggtg aacgtgagcg acatttccct ggtcgattac | 540 |
| accaaggagg ataagacctt cttcggcgcc ttcctgctg | 579 |

<210> SEQ ID NO 156
<211> LENGTH: 579
<212> TYPE: DNA
<213> ORGANISM: Artificial Sequence
<220> FEATURE:
<223> OTHER INFORMATION: TL1W102 (His-TEV-TL1A S176K) nucleotide sequence

<400> SEQUENCE: 156

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga caagatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 157
<211> LENGTH: 579
<212> TYPE: DNA
<213> ORGANISM: Artificial Sequence
<220> FEATURE:
<223> OTHER INFORMATION: TL1W99 (His-TEV-TL1A S176A) nucleotide sequence

<400> SEQUENCE: 157

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga cgccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 158
<211> LENGTH: 579
<212> TYPE: DNA
<213> ORGANISM: Artificial Sequence
<220> FEATURE:
<223> OTHER INFORMATION: TL1W96 (His-TEV-TL1A R170E) nucleotide sequence

<400> SEQUENCE: 158

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggagagccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 159
<211> LENGTH: 579
<212> TYPE: DNA
<213> ORGANISM: Artificial Sequence
<220> FEATURE:
<223> OTHER INFORMATION: TL1W95 (His-TEV-TL1A Q167A) nucleotide sequence

<400> SEQUENCE: 159

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |
| ctgctcatcc | ccgagagcgg | agactacttc | atctactccc | aggtgacctt | caggggcatg | 300 |
| acaagcgagt | gcagcgagat | cagagccgcc | ggaaggccta | ataagcccga | ctccatcaca | 360 |
| gtggtgatca | caaaggtgac | cgacagctac | cccgagccca | cccagctgct | gatgggcacc | 420 |
| aagagcgtgt | gcgaagtggg | cagcaactgg | ttccagccca | tctacctggg | cgccatgttc | 480 |
| agcctgcagg | agggcgacaa | gctgatggtg | aacgtgagcg | acatttccct | ggtcgattac | 540 |
| accaaggagg | ataagacctt | cttcggcgcc | ttcctgctg | | | 579 |

<210> SEQ ID NO 160
<211> LENGTH: 579
<212> TYPE: DNA
<213> ORGANISM: Artificial Sequence
<220> FEATURE:
<223> OTHER INFORMATION: TL1W93 (His-TEV-TL1A M158K) nucleotide sequence

<400> SEQUENCE: 160

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |
| ctgctcatcc | ccgagagcgg | agactacttc | atctactccc | aggtgacctt | caggggcaag | 300 |
| acaagcgagt | gcagcgagat | cagacaggcc | ggaaggccta | ataagcccga | ctccatcaca | 360 |
| gtggtgatca | caaaggtgac | cgacagctac | cccgagccca | cccagctgct | gatgggcacc | 420 |
| aagagcgtgt | gcgaagtggg | cagcaactgg | ttccagccca | tctacctggg | cgccatgttc | 480 |
| agcctgcagg | agggcgacaa | gctgatggtg | aacgtgagcg | acatttccct | ggtcgattac | 540 |
| accaaggagg | ataagacctt | cttcggcgcc | ttcctgctg | | | 579 |

<210> SEQ ID NO 161
<211> LENGTH: 579
<212> TYPE: DNA
<213> ORGANISM: Artificial Sequence
<220> FEATURE:
<223> OTHER INFORMATION: TL1W94 (His-TEV-TL1A M158E) nucleotide sequence

<400> SEQUENCE: 161

| | | | | | |
|---|---|---|---|---|---|
| catcatcacc | accatcacga | gaacctgtac | ttccaaggtc | tcaagggcca | ggagttcgct | 60 |
| ccctcccatc | agcaggtgta | cgctcccctg | agagccgatg | gcgataagcc | cagagcccac | 120 |
| ctgaccgtcg | tgaggcagac | ccccacccag | cacttcaaga | accagtttcc | cgccctccac | 180 |
| tgggagcacg | agctgggact | ggcctttacc | aagaacagaa | tgaattacac | caacaagttt | 240 |

```
ctgctcatcc ccgagagcgg agactacttc atctactccc aggtgacctt caggggcgag    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579

<210> SEQ ID NO 162
<211> LENGTH: 579
<212> TYPE: DNA
<213> ORGANISM: Artificial Sequence
<220> FEATURE:
<223> OTHER INFORMATION: TL1W90 (His-TEV-TL1A R156K) nucleotide sequence

<400> SEQUENCE: 162
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt caagggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579

<210> SEQ ID NO 163
<211> LENGTH: 579
<212> TYPE: DNA
<213> ORGANISM: Artificial Sequence
<220> FEATURE:
<223> OTHER INFORMATION: TL1W91 (His-TEV-TL1A R156E) nucleotide sequence

<400> SEQUENCE: 163
catcatcacc accatcacga gaacctgtac ttccaaggtc tcaagggcca ggagttcgct    60
ccctcccatc agcaggtgta cgctcccctg agagccgatg gcgataagcc cagagcccac    120
ctgaccgtcg tgaggcagac ccccacccag cacttcaaga accagtttcc cgccctccac    180
tgggagcacg agctgggact ggcctttacc aagaacagaa tgaattacac caacaagttt    240
ctgctcatcc ccgagagcgg agactacttc atctactccc aggtgacctt cgagggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579

<210> SEQ ID NO 164
<211> LENGTH: 579
<212> TYPE: DNA
<213> ORGANISM: Artificial Sequence
<220> FEATURE:
<223> OTHER INFORMATION: TL1W88 (His-TEV-TL1A R156A) nucleotide sequence
```

<400> SEQUENCE: 164

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctgggact ggcctttacc aagaacagaa tgaattacac caacaagttt     240
ctgctcatcc ccgagagcgg agactacttc atctactccc aggtgacctt cgccggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                             579
```

<210> SEQ ID NO 165
<211> LENGTH: 579
<212> TYPE: DNA
<213> ORGANISM: Artificial Sequence
<220> FEATURE:
<223> OTHER INFORMATION: TL1W87 (His-TEV-TL1A G124D) nucleotide sequence

<400> SEQUENCE: 165

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agctggacct ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cagcaactgg ttccagccca tctacctggg cgccatgttc     480
agcctgcagg agggcgacaa gctgatggtg aacgtgagcg acatttccct ggtcgattac     540
accaaggagg ataagacctt cttcggcgcc ttcctgctg                             579
```

<210> SEQ ID NO 166
<211> LENGTH: 579
<212> TYPE: DNA
<213> ORGANISM: Artificial Sequence
<220> FEATURE:
<223> OTHER INFORMATION: TL1W38 (His-TEV-TL1A L123K) nucleotide sequence

<400> SEQUENCE: 166

```
catcatcacc accatcacga gaacctgtac ttccaaggtc tcaagggcca ggagttcgct      60
ccctcccatc agcaggtgta cgctcccctg agagccgatg gcgataagcc cagagcccac     120
ctgaccgtcg tgaggcagac ccccacccag cacttcaaga accagtttcc cgccctccac     180
tgggagcacg agaagggact ggcctttacc aagaacagaa tgaattacac caacaagttt     240
ctgctcatcc ccgagagcgg agactacttc atctactccc aggtgacctt caggggcatg     300
acaagcgagt gcagcgagat cagacaggcc ggaaggccta ataagcccga ctccatcaca     360
gtggtgatca caaggtgac cgacagctac cccgagccca cccagctgct gatgggcacc     420
aagagcgtgt gcgaagtggg cagcaactgg ttccagccca tctacctggg cgccatgttc     480
```
agcctgcagg agggcgacaa gctgatggtg aacgtgagcg acatttccct ggtcgattac   540
accaaggagg ataagacctt cttcggcgcc ttcctgctg                          579

<210> SEQ ID NO 167
<211> LENGTH: 579
<212> TYPE: DNA
<213> ORGANISM: Artificial Sequence
<220> FEATURE:
<223> OTHER INFORMATION: TL1W39 (His-TEV-TL1A L123G) nucleotide sequence

<400> SEQUENCE: 167
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg agggggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579

<210> SEQ ID NO 168
<211> LENGTH: 579
<212> TYPE: DNA
<213> ORGANISM: Artificial Sequence
<220> FEATURE:
<223> OTHER INFORMATION: TL1W37 (His-TEV-TL1A L123E) nucleotide sequence

<400> SEQUENCE: 168
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180
tgggagcacg aggagggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579

<210> SEQ ID NO 169
<211> LENGTH: 579
<212> TYPE: DNA
<213> ORGANISM: Artificial Sequence
<220> FEATURE:
<223> OTHER INFORMATION: TL1W41 (His-TEV-TL1A E120A) nucleotide sequence

<400> SEQUENCE: 169
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcaaga accagtttcc cgccctccac   180

```
tgggcgcacg agctgggact ggcctttacc aagaacagaa tgaattacac caacaagttt    240
ctgctcatcc ccgagagcgg agactacttc atctactccc aggtgacctt caggggcatg    300
acaagcgagt gcagcgagat cagacaggcc ggaaggccta ataagcccga ctccatcaca    360
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 170
<211> LENGTH: 579
<212> TYPE: DNA
<213> ORGANISM: Artificial Sequence
<220> FEATURE:
<223> OTHER INFORMATION: TL1W42 (His-TEV-TL1A F114A) nucleotide sequence

<400> SEQUENCE: 170

```
catcatcacc accatcacga gaacctgtac ttccaaggtc tcaagggcca ggagttcgct    60
ccctcccatc agcaggtgta cgctccccctg agagccgatg gcgataagcc cagagcccac   120
ctgaccgtcg tgaggcagac ccccacccag cacttcaaga accaggctcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 171
<211> LENGTH: 579
<212> TYPE: DNA
<213> ORGANISM: Artificial Sequence
<220> FEATURE:
<223> OTHER INFORMATION: TL1W30 (His-TEV-hTL1A 72-251 N112E) nucleotide
      sequence

<400> SEQUENCE: 171

```
catcatcacc accatcacga gaacctgtac ttccaaggtc tcaagggcca ggagttcgct    60
ccctcccatc agcaggtgta cgctccccctg agagccgatg gcgataagcc cagagcccac   120
ctgaccgtcg tgaggcagac ccccacccag cacttcaagg aacagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 172
<211> LENGTH: 579

<212> TYPE: DNA
<213> ORGANISM: Artificial Sequence
<220> FEATURE:
<223> OTHER INFORMATION: TL1W82 (His-TEV-TL1A K111E) nucleotide sequence

<400> SEQUENCE: 172

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcgaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 173
<211> LENGTH: 579
<212> TYPE: DNA
<213> ORGANISM: Artificial Sequence
<220> FEATURE:
<223> OTHER INFORMATION: TL1W80 (His-TEV-TL1A K111A) nucleotide sequence

<400> SEQUENCE: 173

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgaggcagac ccccacccag cacttcgcca accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579
```

<210> SEQ ID NO 174
<211> LENGTH: 579
<212> TYPE: DNA
<213> ORGANISM: Artificial Sequence
<220> FEATURE:
<223> OTHER INFORMATION: TL1W31 (GD: Single chain MMB in CBIS; His-TEV-hTL1A 72-251 R103Q) nucleotide sequence

<400> SEQUENCE: 174

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgcaacagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
```

```
gtggtgatca caaaggtgac cgacagctac cccgagccca cccagctgct gatgggcacc    420
aagagcgtgt gcgaagtggg cagcaactgg ttccagccca tctacctggg cgccatgttc    480
agcctgcagg agggcgacaa gctgatggtg aacgtgagcg acatttccct ggtcgattac    540
accaaggagg ataagacctt cttcggcgcc ttcctgctg                           579
```

<210> SEQ ID NO 175
<211> LENGTH: 579
<212> TYPE: DNA
<213> ORGANISM: Artificial Sequence
<220> FEATURE:
<223> OTHER INFORMATION: TL1W78 (His-TEV-TL1A R103H) nucleotide sequence

<400> SEQUENCE: 175

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tgcaccagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                           579
```

<210> SEQ ID NO 176
<211> LENGTH: 579
<212> TYPE: DNA
<213> ORGANISM: Artificial Sequence
<220> FEATURE:
<223> OTHER INFORMATION: TL1W79 (His-TEV-TL1A R103E) nucleotide sequence

<400> SEQUENCE: 176

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tggagcagac ccccacccag cacttcaaga accagtttcc cgccctccac   180
tgggagcacg agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaaggtgac cgacagctac cccgagccca cccagctgct gatgggcacc   420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                           579
```

<210> SEQ ID NO 177
<211> LENGTH: 579
<212> TYPE: DNA
<213> ORGANISM: Artificial Sequence
<220> FEATURE:
<223> OTHER INFORMATION: TL1W33 (His-TEV-hTL1A 72-251 R103A) nucleotide
       sequence

<400> SEQUENCE: 177

```
catcatcacc accatcacga gaacctgtac ttccaaggtc tcaagggcca ggagttcgct    60
ccctcccatc agcaggtgta cgctcccctg agagccgatg gcgataagcc cagagcccac   120
ctgaccgtcg tggcccagac ccccacccag cacttcaaga accagtttcc cgccctccac   180
tgggagcaca agctgggact ggcctttacc aagaacagaa tgaattacac caacaagttt   240
ctgctcatcc ccgagagcgg agactacttc atctactccc aggtgacctt caggggcatg   300
acaagcgagt gcagcgagat cagacaggcc ggaaggccta ataagcccga ctccatcaca   360
gtggtgatca caaggtgac cgacagctac cccgagccca cccagctgct gatgggcacc    420
aagagcgtgt gcgaagtggg cagcaactgg ttccagccca tctacctggg cgccatgttc   480
agcctgcagg agggcgacaa gctgatggtg aacgtgagcg acatttccct ggtcgattac   540
accaaggagg ataagacctt cttcggcgcc ttcctgctg                          579

<210> SEQ ID NO 178
<211> LENGTH: 3393
<212> TYPE: DNA
<213> ORGANISM: Artificial Sequence
<220> FEATURE:
<223> OTHER INFORMATION: TL1W15 (GD: Single chain protein in CBIS -> HSA
      C-terminal Fusion; His-TEV-HSA(C34S)-G4S-TL1A-3(G3S)-TL1A-3(G3S)-
      TL1A) nucleotide sequence

<400> SEQUENCE: 178
catcatcacc accatcacga gaacctgtac ttccaaggtg atgctcacaa gtccgaggtg    60
gctcacaggt ttaaagacct cggcgaggag aacttcaagg ccctcgtcct gattgctttc   120
gctcagtacc tgcagcagtc cccctttcgag gaccatgtca agctggtgaa tgaggtgaca   180
gaattcgcca agacctgtgt ggctgacgaa tccgctgaga actgcgacaa gtccctgcac   240
accctgttcg gcgataaact gtgcacagtg gctaccctca gagaaaccta tggcgaaatg   300
gccgactgtt gcgccaagca agagcccgag aggaacgaat gcttcctcca gcacaaggat   360
gacaatccta acctgcccag actggtgaga cccgaggtgg atgtcatgtg cacagccttc   420
cacgataacg aggagacatt cctgaagaaa tatctctatg aaatcgccag gaggcatccc   480
tacttctatg cccccgagct gctcttcttc gccaagaggt ataaagccgc tttcaccgag   540
tgctgccagg ctgccgacaa ggccgcttgt ctgctgccca agctggacga gctgagggac   600
gagggaaagg ctagctccgc taagcagaga ctgaagtgcg ccagcctgca gaaattcgga   660
gaaagggcct tcaaggcctg gccgtggct aggctgagcc agagatttcc taaggccgag   720
tttgccgaag tgagcaagct ggtgaccgac ctaacaaagg tccacacaga tgttgccac    780 ggcgacctgc tggagtgcgc cgatgatagg gccgatctgg ccaaatacat ctgtgagaac   840
caagactcca tctcctccaa gctgaaggag tgttgcgaga gcctctgct cgagaagagc    900 cactgcatcg ctgaagtcga gaacgacgag atgcctgccg atctccctc cctggccgcc   960 gatttcgtgg aatccaagga cgtctgtaag aactacgccg aggccaagga tgtgttcctg  1020
ggaatgttcc tgtacgagta cgctaggagg caccctgact atagcgtggt gctcctcctg  1080
aggctggcca agacatatga gaccaccctg gaaaagtgct gcgccgctgc cgatccccat  1140
gagtgctatg ccaaggtctt cgacgagttt aagcccctgg tggaagagcc ccagaacctg  1200
atcaaacaga actgtgagct gttcgagcag ctcggagagt acaagttcca gaatgccctc  1260
ctcgtgaggt acacaaagaa ggtcccccag gtctccacac ctaccctggt ggaggtctcc  1320
agaaacctgg gcaaggtggg gatccaagtgc tgcaagcatc ctgaggccaa aagaatgccc  1380
```

```
tgtgctgagg attacctgag cgtggtcctg aatcagctgt gcgtgctgca tgaaaaaacc      1440
cccgtctccg atagggtcac aaagtgctgc accgagagcc tggtgaatag aaggccctgt      1500
ttctccgccc tggaggtgga cgaaacctat gtccccaaag agttcaacgc tgaaacattt      1560
accttccacg ctgacatttg caccctgagc gagaaggaga ggcagatcaa gaagcagaca      1620
gctctcgtgg agctcgtgaa gcacaaacct aaagccacaa aggagcaact gaaggccgtc      1680
atggacgact tgccgctttt cgtcgagaag tgctgtaagg ccgacgacaa ggagacatgt      1740
ttcgccgagg agggaaagaa gctggtcgct gctagccaag ctgccctggg cctgggagga      1800
ggaggaagcg tgtatgcccc cctgagagct gacggagata agcctagggc ccacctgacc      1860
gtcgtcagac agacccctac ccaacacttc aagaaccagt tccccgctct gcactgggag      1920
cacgaactgg gcctggcctt cacaaaaaac agaatgaatt acaccaacaa gttcctcctg      1980
attcccgaaa gcggcgatta ttttatctac agccaggtga cctttagggg catgacatcc      2040
gagtgctccg agatcagaca agccggaaga cccaacaagc ccgactccat cacagtggtc      2100
atcacaaagg tgacagatag ctatcctgaa cctacccagc tgctgatggg caccaagtcc      2160
gtctgtgagg tgggaagcaa ctggtttcaa cccatctacc tgggcgctat gttctccctg      2220
caagagggcg ataagctgat ggtgaatgtg tccgacattt ccctggtgga ttataccaaa      2280
gaggacaaga ccttctttgg cgcctttctc ctgggaggag atccggcgg aggatccgga      2340
ggcggctccg tctatgcccc tctgagggct gacggagaca gcccagggc ccatctgacc      2400
gtggtgagac aaaccccac ccaacacttt aagaaccagt ttcctgctct gcattgggag      2460
catgagctgg gcctggcctt taccaaaaat aggatgaact ataccaataa gttcctgctg      2520
atccccgagt ccggagacta ctttatctat tcccaggtca ccttcagggg catgacctcc      2580
gagtgcagcg agattagaca ggccggcaga cccaataaac ccgacagcat caccgtcgtg      2640
atcaccaaag tgacagactc ctaccccgaa cctacacaac tcctgatggg caccaaaagc      2700
gtgtgcgaag tgggctccaa ctggttccag cccatctacc tgggcgctat gtttagcctg      2760
caagaaggcg ataaactgat ggtcaacgtg tccgacatca gcctggtcga ctacacaaaa      2820
gaggataaga ccttcttcgg agcctttctg ctcggaggag atccggcgg cggcagcggc      2880
ggagcagcg tctacgcccc cctgagagct gatggcgata aacctagagc ccatctgaca      2940
gtggtgagac agaccccac ccagcatttc aaaaaccagt ttccgccct gcattgggaa      3000
cacgagctgg gactggcctt caccaaaaac aggatgaatt ataccaacaa atttctgctg      3060
atccccgaat ccggcgatta cttcatctac agccaagtga ccttcagggg aatgaccttcc      3120
gaatgttccg aaatcagaca ggctggcagg cccaacaaac ccgattccat caccgtggtg      3180
atcaccaagg tgaccgacag ctaccccgag cctacccaac tgctgatggg aaccaagagc      3240
gtgtgtgagg tgggctccaa ttggttccag cccatctatc tgggcgccat gttcagcctg      3300
caggagggag acaaactgat ggtgaacgtg tccgatatct ccctcgtcga ctacaccaag      3360
gaggataaaa ccttttttcgg cgccttcctg ctc                                 3393
```

<210> SEQ ID NO 179
<211> LENGTH: 2364
<212> TYPE: DNA
<213> ORGANISM: Artificial Sequence
<220> FEATURE:
<223> OTHER INFORMATION: TL1W9 (GD: Single chain protein in CBIS -> HSA
      C-terminal Fusion; His-TEV-G-HSA (C34S)-2(G4S)-TL1A) nucleotide
      sequence

<400> SEQUENCE: 179

-continued

```
catcatcacc accatcacga gaacctgtac ttccaaggtg atgctcacaa gtccgaggtg      60
gctcacaggt ttaaagacct cggcgaggag aacttcaagg ccctcgtcct gattgctttc     120
gctcagtacc tgcagcagtc ccccttcgag gaccatgtca agctggtgaa tgaggtgaca     180
gaattcgcca agacctgtgt ggctgacgaa tccgctgaga ctgcgacaa gtccctgcac      240
accctgttcg gcgataaact gtgcacagtg ctaccctca gagaaaccta tggcgaaatg      300
gccgactgtt gcgccaagca agagcccgag aggaacgaat gcttcctcca gcacaaggat     360
gacaatccta acctgcccag actggtgaga cccgaggtgg atgtcatgtg cacagccttc     420
cacgataacg aggagacatt cctgaagaaa tatctctatg aaatcgccag gaggcatccc     480
tacttctatg cccccgagct gctcttcttc gccaagaggt ataaagccgc tttcaccgag     540
tgctgccagc tgccgacaa ggccgcttgt ctgctgccca gctggacga gctgagggac      600
gagggaaagg ctagctccgc taagcagaga ctgaagtgcg ccagcctgca gaaattcgga     660
gaaagggcct tcaaggcctg ggccgtggct aggctgagcc agagatttcc taaggccgag     720
tttgccgaag tgagcaagct ggtgaccgac ctgacaaagg tccacacaga atgttgccac     780
ggcgacctgc tggagtgcgc cgatgatagg gccgatctgg ccaaatacat ctgtgagaac     840
caagactcca tctcctccaa gctgaaggag tgttgcgaga gcctctgct cgagaagagc     900
cactgcatcg ctgaagtcga gaacgacgag atgcctgccg atctccctc cctgccgcc     960
gatttcgtgg aatccaagga cgtctgtaag aactacgccg aggccaagga tgtgttcctg    1020
ggaatgttcc tgtacgagta cgctaggagg caccctgact atagcgtggt gctcctcctg    1080
aggctggcca agacatatga gaccaccctg gaaaagtgct gcgccgctgc cgatccccat    1140
gagtgctatg ccaaggtctt cgacgagttt aagcccctgg tggaagagcc ccagaacctg    1200
atcaaacaga actgtgagct gttcgagcag ctcggagagt acaagttcca gaatgccctc    1260
ctcgtgaggt acacaaagaa ggtcccccag gtctccacac ctaccctggt ggaggtctcc    1320
agaaacctgg gcaaggtggg atccaagtgc tgcaagcatc ctgaggccaa agaatgccc     1380
tgtgctgagg attacctgag cgtggtcctg aatcagctgt gcgtgctgca tgaaaagacc    1440
cccgtctccg ataggggtcac aaagtgctgc accgagagcc tggtgaatag aaggccctgt    1500
ttctccgccc tggaggtgga cgaaacctat gtccccaaag agttcaacgc tgaaacattt    1560
accttccacg ctgacatttg cacccctgagc gagaaggaga ggcagatcaa gaagcagaca    1620
gctctcgtgg agctcgtgaa gcacaaacct aaagccacaa aggagcaact gaaggccgtc    1680
atggacgact ttgccgcttt cgtcgagaag tgctgtaagg ccgacgacaa ggagacatgt    1740
ttcgccgagg agggaaagaa gctggtcgct gctagccaag ctgccctggg cctgggagga    1800
ggaggaagcg gcgaggagg atccctcaag gccaggagt tcgctccctc ccatcagcag     1860
gtgtacgctc ccctgagagc cgatggcgat aagcccagag cccacctgac cgtcgtgagg    1920
cagacccca cccagcactt caagaaccag tttcccgccc tccactggga gcacgagctg    1980
ggactggcct ttaccaagaa cagaatgaat tacaccaaca gtttctgct catccccgag     2040
agcggagact acttcatcta ctcccaggtg accttcagggg gcatgacaag cgagtgcagc    2100
gagatcagac aggccggaag gcctaataag cccgactcca tcacagtggt gatcacaaag    2160
gtgaccgaca gctaccccga gcccacccag ctgctgatgg gcaccaagag cgtgtgcgaa    2220
gtgggcagca actggttcca gcccatctac ctgggcgcca tgttcagcct gcaggagggc    2280
gacaagctga tggtgaacgt gagcgacatt tccctggtcg attacaccaa ggaggataag    2340
```

```
accttcttcg gcgccttcct gctg                                          2364
```

<210> SEQ ID NO 180
<211> LENGTH: 1533
<212> TYPE: DNA
<213> ORGANISM: Artificial Sequence
<220> FEATURE:
<223> OTHER INFORMATION: TL1W19 (His-TEV-TL1A-TL1A-TL1A) nucleotide
      sequence

<400> SEQUENCE: 180

```
catcatcatc accaccacga gaatctctat tttcagggcg ctcccctgag agccgatggc    60
gataagccta gagcccacct gacagtggtg agacaaaccc ctacacagca cttcaaaaat   120
cagttccctg ccctgcactg ggaacatgag ctgggcctgg ccttcaccaa gaacaggatg   180
aattacacaa ataagttcct gctcatccct gagtccggcg actacttcat ctatagccaa   240
gtgaccttca gaggcatgac cagcgagtgc tccgagatca ggcaggctgg aagacctaac   300
aagcccgata gcatcaccgt ggtgattaca aaggtgacag acagctatcc cgagcccaca   360
cagctgctca tgggcaccaa aagcgtgtgc gaagtcggca gcaactggtt ccagcccatc   420
tacctgggcg ccatgtttag cctgcaggaa ggagataagc tgatggtcaa tgtctccgat   480
atctccctgg tggattacac caaggaggac aaaaccttct tcggcgcttt tctgctggcc   540
cctctcaggg ccgatggaga taaacccagg gctcacctga cagtcgtcag gcagacccct   600
acacaacact tcaagaatca attccccgcc ctgcattggg agcacgaact gggcctggcc   660
ttcacaaaaa ataggatgaa ctataccaac aaattcctgc tgatccctga atccggcgat   720
tacttcatct actcccaggt gaccttcaga ggcatgacca gcgaatgcag cgaaatcaga   780
caagctggca gacccaacaa acccgacagc attaccgtgg tcatcaccaa ggtcacagat   840
agctaccccg aacccacaca gctcctgatg ggcaccaagt ccgtctgtga ggtcggcagc   900
aattggttcc agcctatcta tctgggcgcc atgtttagcc tgcaagaggg agacaaactg   960
atggtgaatg tgtccgacat ctccctggtg gattacacca agaggataaa acctttttc   1020
ggcgccttcc tgctggctcc tctgagggct gacggcgaca gcccagagc tcacctgacc  1080
gtcgtgaggc aaaccctac ccagcacttt aagaaccagt ttcccgccct gcactgggag   1140
catgagctgg gcctgccctt taccaaaaac agaatgaact acaccaacaa gtttctgctg   1200
atccccgaaa gcggcgacta ttttatctat agccaggtga cctttagagg catgaccagc   1260
gagtgtagcg agattagaca ggctggcagg cctaacaagc tgacagcat caccgtggtg   1320
atcaccaaag tgaccgactc ctaccccgag cccacccaac tgctcatggg cacaaagagc   1380
gtgtgtgagg tgggctccaa ttggtttcaa cccatctatc tgggcgccat gttcagcctg   1440
caagaaggag acaagctcat ggtcaatgtg agcgacatca gcctggtgga ctataccaaa   1500
gaagacaaga ccttcttcgg agcctttctg ctg                               1533
```

<210> SEQ ID NO 181
<211> LENGTH: 2268
<212> TYPE: DNA
<213> ORGANISM: Artificial Sequence
<220> FEATURE:
<223> OTHER INFORMATION: TL1W14 (Fc-scTL1A with CD4 HC sp
      prim_transcript) nucleotide sequence

<400> SEQUENCE: 181

```
ggatcctgtc ctccctgccc tgctcctgaa ctcctgggcg acccagcgt gtttctgttc    60
ccccccaaac ctaaagacac actgatgatt agcagaaccc ccgaggtcac ctgcgtggtg   120
```

```
gtggatgtgt cccacgagga tcccgaggtc aagttcaact ggtacgtgga tggcgtggag    180
gtgcacaacg ccaaaaccaa gcccagggaa gagcagtaca actccaccta cagggtcgtg    240
agcgtgctga cagtgctgca ccaggactgg ctgaacggaa aggagtacaa gtgtaaggtc    300
agcaacaagg ctctgcctgc ccccatcgag aaaaccatca gcaaggccaa gggccagcct    360
agggaacccc aggtgtacac actgccccct ccagggagg agatgaccaa aaaccaggtc    420
agcctgacat gcctggtgaa aggcttctac cccagcgata tcgccgtgga atgggagtcc    480
aacggccagc ctgagaacaa ctacaagacc acaccccccg tgctggactc cgacggttct    540
tttttcctgt actccaagct gaccgtcgac aagagcaggt ggcaacaggg caacgtcttc    600
agctgcagcg tgatgcacga agccctgcac aaccactaca cccagaaaag cctgagcctg    660
tcccctggcg gaggaggagg aagcgtgtat gcccccctga gctgacgg agataagcct    720 agggcccacc tgaccgtcgt cagacagacc cctacccaac acttcaagaa ccagttcccc    780
gctctgcact gggagcacga actgggcctg gccttcacaa aaaacagaat gaattacacc    840
aacaagttcc tcctgattcc cgaaagcggc gattatttta tctacagcca ggtgacctttt   900 aggggcatga catccgagtg ctccgagatc agacaagccg gaagacccaa caagcccgac    960
tccatcacag tggtcatcac aaaggtgaca gatagctatc ctgaacctac ccagctgctg   1020
atgggcacca gtccgtctg tgaggtggga agcaactggt tcaacccat ctacctgggc    1080 gctatgttct ccctgcaaga gggcgataag ctgatggtga atgtgtccga catttccctg   1140
gtggattata ccaaagagga caagaccttc tttggcgcct ttctcctggg aggaggatcc   1200
ggcggaggat ccggaggcgg ctccgtctat gcccctctga gggctgacgg agacaagccc   1260
agggcccatc tgaccgtggt gagacaaacc cccacccaac actttaagaa ccagtttcct   1320
gctctgcatt gggagcatga gctgggcctg gcctttacca aaaataggat gaactatacc   1380
aataagttcc tgctgatccc cgagtccgga gactacttta tctattccca ggtcaccttc   1440
aggggcatga cctccgagtg cagcgagatt agacaggccg gcagacccaa taaacccgac   1500
agcatcaccg tcgtgatcac caaagtgaca gactcctacc ccgaacctac acaactcctg   1560
atgggcacca aaagcgtgtg cgaagtgggc tccaactggt tccagcccat ctacctgggc   1620
gctatgttta gcctgcaaga aggcgataaa ctgatggtca acgtgtccga catcagcctg   1680
gtcgactaca caaaagagga taagaccttc ttcggagcct ttctgctcgg aggaggatcc   1740
ggcggcggca gcggcggagg cagcgtctac gcccccctga gctgatggc gataaacct    1800 agagcccatc tgcacagtggt gagacagacc cccacccagc atttcaaaaa ccagtttccc   1860
gccctgcatt gggaacacga gctgggactg gccttcacca aaaacaggat gaattatacc   1920
aacaaatttc tgctgatccc cgaatccggc gattacttca tctacagcca agtgaccttc   1980
aggggaatga cctccgaatg ttccgaaatc agacaggctg gcaggcccaa caaacccgat   2040
tccatcaccg tggtgatcac caaggtgacc gacagctacc ccgagcctac caactgctg    2100 atgggaacca agagcgtgtg tgaggtgggc tccaattggt tccagcccat ctatctgggc   2160
gccatgttca gcctgcagga gggagacaaa ctgatggtga acgtgtccga tatctccctc   2220
gtcgactaca ccaaggagga taaaaccttt ttcggcgcct cctgctc                 2268

<210> SEQ ID NO 182
<211> LENGTH: 2268
<212> TYPE: DNA
<213> ORGANISM: Artificial Sequence
<220> FEATURE:
```

<223> OTHER INFORMATION: TL1W329 (Fc-scTL1A K111A L123K M158Y Q167A E190F N207F) nucleotide sequence

<400> SEQUENCE: 182

```
ggatcctgtc ctccctgccc tgctcctgaa ctcctgggcg acccagcgt gtttctgttc      60
ccccccaaac ctaaagacac actgatgatt agcagaaccc ccgaggtcac ctgcgtggtg    120
gtggatgtgt cccacgagga tcccgaggtc aagttcaact ggtacgtgga tggcgtggag    180
gtgcacaacg ccaaaaccaa gcccagggaa gagcagtaca ctccaccta  cagggtcgtg    240
agcgtgctga cagtgctgca ccaggactgg ctgaacggaa aggagtacaa gtgtaaggtc    300
agcaacaagg ctctgcctgc ccccatcgag aaaaccatca gcaaggccaa gggccagcct    360
agggaacccc aggtgtacac actgcccct  tccagggagg agatgaccaa aaaccaggtc    420
agcctgacat gcctggtgaa aggcttctac cccagcgata tcgccgtgga atgggagtcc    480
aacggccagc ctgagaacaa ctacaagacc acccccccg  tgctggactc cgacggttct    540
ttttcctgt  actccaagct gaccgtcgac aagagcaggt ggcaacaggg caacgtcttc    600
agctgcagcg tgatgcacga agccctgcac aaccactaca cccagaaaag cctgagcctg    660
tccccctggcg gaggaggagg aagcgtgtat gcccccctga gctgacgg  agataagcct    720
agggcccacc tgaccgtcgt cagacagacc cctacccaac acttcgccaa ccagttcccc    780
gctctgcact gggagcacga aaagggcctg gccttcacaa aaacagaat  gaattacacc    840
aacaagttcc tcctgattcc cgaaagcggc gattatttta tctacagcca ggtgacctttt   900
aggggctaca catccgagtg ctccgagatc agagccgccg aagacccaa  caagcccgac    960
tccatcacag tggtcatcac aaaggtgaca gatagctatc ctttccctac ccagctgctg   1020
atgggcacca gtccgtctg  tgaggtggga agcttctggt ttcaacccat ctacctgggc   1080
gctatgttct ccctgcaaga gggcgataag ctgatggtga atgtgtccga catttccctg   1140
gtggattata ccaaagagga caagaccttc tttggcgcct ttctcctggg aggaggatcc   1200
ggcggaggat ccggaggcgg ctccgtctat gcccctctga gggctgacgg agacaagccc   1260
agggcccatc tgaccgtggt gagacaaacc cccacccaac actttgccaa ccagtttcct   1320
gctctgcatt gggagcatga aaagggcctg gcctttacca aaaataggat gaactatacc   1380
aataagttcc tgctgatccc cgagtccgga gactactta  tctattccca ggtcaccttc   1440
aggggctaca cctccgagtg cagcgagatt agagccgccg gcagacccaa taaacccgac   1500
agcatcaccg tcgtgatcac caaagtgaca gactcctacc ccttccctac acaactcctg   1560
atgggcacca aaagcgtgtg cgaagtgggc tccttctggt tccagcccat ctacctgggc   1620
gctatgttta gcctgcaaga aggcgataaa ctgatggtca acgtgtccga catcagcctg   1680
gtcgactaca aaagagga  taagaccttc ttcggagcct ttctgctcgg aggaggatcc   1740
ggcggcggca gcggcggagg cagcgtctac gccccctga  gctgatgg  cgataaacct   1800
agagcccatc tgacagtggt gagacagacc cccacccagc atttcgccaa ccagtttccc   1860
gccctgcatt gggaacacga aagggactg  gccttcacca aaacaggat  gaattatacc   1920
aacaaatttc tgctgatccc cgaatccggc gattacttca tctacagcca agtgaccttc   1980
aggggataca cctccgaatg ttccgaaatc agagccgctg caggcccaa  caaacccgat   2040
tccatcaccg tggtgatcac caaggtgacc gacagctacc ccttccctac ccaactgctg   2100
atgggaacca gagcgtgtg  tgaggtgggc tccttctggt tccagcccat ctatctgggc   2160
gccatgttca gcctgcagga gggagacaaa ctgatggtga acgtgtccga tatctcccto   2220
```
gtcgactaca ccaaggagga taaaaccttt ttcggcgcct tcctgctc          2268

<210> SEQ ID NO 183
<211> LENGTH: 2268
<212> TYPE: DNA
<213> ORGANISM: Artificial Sequence
<220> FEATURE:
<223> OTHER INFORMATION: TL1W327 (Fc-scTL1A K111A L123K M158Y Q167A
      S187L E190F) nucleotide sequence

<400> SEQUENCE: 183

```
ggatcctgtc ctccctgccc tgctcctgaa ctcctgggcg acccagcgt gtttctgttc    60
ccccccaaac ctaaagacac actgatgatt agcagaaccc ccgaggtcac ctgcgtggtg   120
gtggatgtgt cccacgagga tcccgaggtc aagttcaact ggtacgtgga tggcgtggag   180
gtgcacaacg ccaaaaccaa gcccagggaa gagcagtaca ctccaccta cagggtcgtg   240
agcgtgctga cagtgctgca ccaggactgg ctgaacggaa aggagtacaa gtgtaaggtc   300
agcaacaagg ctctgcctgc ccccatcgag aaaaccatca gcaaggccaa gggccagcct   360
agggaacccc aggtgtacac actgccccct tccagggagg agatgaccaa aaaccaggtc   420
agcctgacat gcctggtgaa aggcttctac cccagcgata tcgccgtgga atgggagtcc   480
aacggccagc ctgagaacaa ctacaagacc acacccccg tgctggactc cgacggttct   540
ttttccctgt actccaagct gaccgtcgac aagagcaggt ggcaacaggg caacgtcttc   600
agctgcagcg tgatgcacga agccctgcac aaccactaca cccagaaaag cctgagcctg   660
tcccctggcg gaggaggagg aagcgtgtat gcccccctga gctgacgg agataagcct   720
agggcccacc tgaccgtcgt cagacagacc cctacccaac acttcgccaa ccagttcccc   780
gctctgcact gggagcacga aaagggcctg gccttcacaa aaacagaat gaattacacc   840
aacaagttcc tcctgattcc cgaaagcggc gattattta tctacagcca ggtgaccttt   900
aggggctaca catccgagtg ctccgagatc agagccgccg aagacccaa caagcccgac   960
tccatcacag tggtcatcac aaaggtgaca gatctgtatc ctttccctac ccagctgctg  1020
atgggcacca gtccgtctg tgaggtggga agcaactggt tcaaacccat ctacctgggc  1080
gctatgttct ccctgcaaga gggcgataag ctgatggtga atgtgtccga catttccctg  1140
gtggattata ccaaagagga caagaccttc tttggcgcct ttctcctggg aggaggatcc  1200
ggcggaggat ccggaggcgg ctccgtctat gcccctctga gggctgacgg agacaagccc  1260
agggcccatc tgaccgtggt gagacaaacc cccacccaac actttgccaa ccagtttcct  1320
gctctgcatt gggagcatga aagggcctg gcctttacca aaaataggat gaactatacc  1380
aataagttcc tgctgatccc cgagtccgga gactacttta tctattccca ggtcaccttc  1440
aggggctaca cctccgagtg cagcgagatt agagccgccg gcagacccaa taaacccgac  1500
agcatcaccg tcgtgatcac caaagtgaca gacctgtacc ccttccctac acaactcctg  1560
atgggcacca aaagcgtgtg cgaagtgggc tccaactggt tccagcccat ctacctgggc  1620
gctatgttta gcctgcaaga aggcgataaa ctgatggtca acgtgtccga catcagcctg  1680
gtcgactaca caaagagga taagaccttc ttcggagcct ttctgctcgg aggaggatcc  1740
ggcggcggca gcggcggagg cagcgtctac gcccccctga gctgatgg cgataaacct  1800
agagcccatc tgacagtggt gagacagacc cccacccagc atttcgccaa ccagtttccc  1860
gccctgcatt gggaacacga aagggactg gccttcacca aaaacaggat gaattatacc  1920
aacaaatttc tgctgatccc cgaatccggc gattacttca tctacagcca agtgaccttc  1980
```

```
agggggataca cctccgaatg ttccgaaatc agagccgctg gcaggcccaa caaacccgat   2040
tccatcaccg tggtgatcac caaggtgacc gacctgtacc ccttccctac ccaactgctg   2100
atgggaacca agagcgtgtg tgaggtgggc tccaattggt tccagcccat ctatctgggc   2160
gccatgttca gcctgcagga gggagacaaa ctgatggtga acgtgtccga tatctccctc   2220
gtcgactaca ccaaggagga taaaaccttt ttcggcgcct tcctgctc              2268
```

<210> SEQ ID NO 184
<211> LENGTH: 2268
<212> TYPE: DNA
<213> ORGANISM: Artificial Sequence
<220> FEATURE:
<223> OTHER INFORMATION: TL1W328 (Fc-scTL1A K111A L123K M158Y Q167A
      S187L N207F) nucleotide sequence

<400> SEQUENCE: 184

```
ggatcctgtc ctccctgccc tgctcctgaa ctcctgggcg acccagcgt gtttctgttc    60 ccccccaaac ctaaagacac actgatgatt agcagaaccc ccgaggtcac ctgcgtggtg   120
gtggatgtgt cccacgagga tcccgaggtc aagttcaact ggtacgtgga tggcgtggag   180
gtgcacaacg ccaaaaccaa gccccaggaa gagcagtaca actccaccta cagggtcgtg   240
agcgtgctga cagtgctgca ccaggactgg ctgaacggaa aggagtacaa gtgtaaggtc   300
agcaacaagg ctctgcctgc ccccatcgag aaaaccatca gcaaggccaa gggccagcct   360
agggaacccc aggtgtacac actgcccct tccagggagg agatgaccaa aaaccaggtc   420
agcctgacat gcctggtgaa aggcttctac cccagcgata tcgccgtgga atgggagtcc   480
aacggccagc ctgagaacaa ctacaagacc acaccccccg tgctggactc cgacggttct   540
tttttcctgt actccaagct gaccgtcgac aagagcaggt ggcaacaggg caacgtcttc   600
agctgcagcg tgatgcacga agccctgcac aaccactaca cccagaaaag cctgagcctg   660
tcccctggcg gaggaggagg aagcgtgtat gcccccctga gctgacggg agataagcct   720 agggcccacc tgaccgtcgt cagacagacc cctacccaac acttcgccaa ccagttcccc   780
gctctgcact gggagcacga aaagggcctg gccttcacaa aaaacagaat gaattacacc   840
aacaagttcc tcctgattcc cgaaagcggc gattatttta tctacagcca ggtgacctt    900 agggggctaca catccgagtg ctccgagatc agagccgccg aagacccaa caagcccgac   960 tccatcacag tggtcatcac aaaggtgaca gatctgtatc ctgaacctac ccagctgctg   1020
atgggcacca gtccgtctg tgaggtggga agcttctggt ttcaacccat ctacctgggc   1080
gctatgttct ccctgcaaga gggcgataag ctgatggtga atgtgtccga catttccctg   1140
gtggattata ccaaagagga caagaccttc tttggcgcct ttctcctggg aggaggatcc   1200
ggcggaggat ccggaggcgg ctccgtctat gcccctctga gggctgacgg agacaagccc   1260
agggcccatc tgaccgtggt gagacaaacc cccacccaac actttgccaa ccagtttcct   1320
gctctgcatt gggagcatga aagggcctg gcctttacca aaaataggat gaactatacc   1380
aataagttcc tgctgatccc cgagtccgga gactacttta tctattccca ggtcaccttc   1440
aggggctaca cctccgagtg cagcgagatt agagccgccg gcagacccaa taaacccgac   1500
agcatcaccg tcgtgatcac caagtgaca gacctgtacc ccgaacctac acaactcctg   1560
atgggcacca aaagcgtgtg cgaagtgggc tccttctggt tccagcccat ctacctgggc   1620
gctatgttta gcctgcaaga aggcgataaa ctgatggtca acgtgtccga catcagcctg   1680
gtcgactaca caaaagagga taagaccttc ttcggagcct ttctgctcgg aggaggatcc   1740
```

```
ggcggcggca gcggcggagg cagcgtctac gccccctga gagctgatgg cgataaacct    1800
agagcccatc tgacagtggt gagacagacc cccacccagc atttcgccaa ccagtttccc    1860
gccctgcatt gggaacacga aagggactg gccttcacca aaaacaggat gaattatacc    1920
aacaaatttc tgctgatccc cgaatccggc gattacttca tctacagcca agtgaccttc    1980
aggggataca cctccgaatg ttccgaaatc agagccgctg gcaggcccaa caaacccgat    2040
tccatcaccg tggtgatcac caaggtgacc gacctgtacc ccgagcctac ccaactgctg    2100
atgggaacca gagcgtgtg tgaggtgggc tccttctggt tccagcccat ctatctgggc    2160
gccatgttca gcctgcagga gggagacaaa ctgatggtga acgtgtccga tatctccctc    2220
gtcgactaca ccaaggagga taaaaccttt ttcggcgcct tcctgctc               2268
```

<210> SEQ ID NO 185
<211> LENGTH: 2268
<212> TYPE: DNA
<213> ORGANISM: Artificial Sequence
<220> FEATURE:
<223> OTHER INFORMATION: TL1W331 (Fc-scTL1A K111A L123K Q167A S187L E190F N207F) nucleotide sequence

<400> SEQUENCE: 185

```
ggatcctgtc ctccctgccc tgctcctgaa ctcctgggcg acccagcgt gtttctgttc      60 ccccccaaac ctaaagacac actgatgatt agcagaaccc ccgaggtcac ctgcgtggtg    120
gtggatgtgt cccacgagga tcccgaggtc aagttcaact ggtacgtgga tggcgtggag    180
gtgcacaacg ccaaaaccaa gcccaggaa gagcagtaca actccaccta cagggtcgtg    240
agcgtgctga cagtgctgca ccaggactgg ctgaacggaa aggagtacaa gtgtaaggtc    300
agcaacaagg ctctgcctgc cccatcgag aaaaccatca gcaaggccaa gggccagcct    360
agggaacccc aggtgtacac actgcccct tccagggagg agatgaccaa aaaccaggtc    420
agcctgacat gcctggtgaa aggcttctac cccagcgata tcgccgtgga atgggagtcc    480
aacggccagc ctgagaacaa ctacaagacc acaccccccg tgctggactc cgacggttct    540
tttttcctgt actccaagct gaccgtcgac aagagcaggt ggcaacaggg caacgtcttc    600
agctgcagcg tgatgcacga agccctgcac aaccactaca cccagaaaag cctgagcctg    660 tccctggcg aggaggagg aagcgtgtat gccccctga gagctgacgg agataagcct    720
agggcccacc tgaccgtcgt cagacagacc cctacccaac acttcgccaa ccagttcccc    780
gctctgcact gggagcacga aagggcctg gccttcacaa aaacagaat gaattacacc    840 aacaagttcc tcctgattcc cgaaagcggc gattattta tctacagcca ggtgaccttt    900 agggcatga catccgagtg ctccgagatc agagccgccg gaagacccaa caagcccgac    960
tccatcacag tggtcatcac aaaggtgaca gatctgtatc cttccctac ccagctgctg   1020 atgggcacca gtccgtctg tgaggtggga agcttctggt tcaaccccat ctacctgggc   1080
gctatgttct ccctgcaaga gggcgataag ctgatggtga atgtgtccga catttccctg   1140
gtggattata ccaaagagga caagaccttc tttggcgcct ttctcctggg aggaggatcc   1200
ggcggaggat ccgaggcgg ctccgtctat gccctctga ggctgacgg agacaagccc   1260 agggcccatc tgaccgtggt gagacaaacc cccacccaac actttgccaa ccagtttcct   1320
gctctgcatt gggagcatga aagggcctg gcctttacca aaataggat gaactatacc   1380 aataagttcc tgctgatccc cgagtccgga gactacttta tctattccca ggtcaccttc   1440 agggcatga cctccgagtg cagcgagatt agagccgccg gcagacccaa taaacccgac   1500
```

| | | |
|---|---|---|
| agcatcaccg tcgtgatcac caaagtgaca gacctgtacc ccttccctac acaactcctg | 1560 | |
| atgggcacca aaagcgtgtg cgaagtgggc tccttctggt tccagcccat ctacctgggc | 1620 | |
| gctatgttta gcctgcaaga aggcgataaa ctgatggtca acgtgtccga catcagcctg | 1680 | |
| gtcgactaca caaaagagga taagaccttc ttcggagcct ttctgctcgg aggaggatcc | 1740 | |
| ggcggcggca gcggcggagg cagcgtctac gcccccctga gagctgatgg cgataaacct | 1800 | |
| agagcccatc tgacagtggt gagacagacc cccacccagc atttcgccaa ccagtttccc | 1860 | |
| gccctgcatt gggaacacga agggactg gccttcacca aaaacaggat gaattatacc | 1920 | |
| aacaaatttc tgctgatccc cgaatccggc gattacttca tctacagcca agtgaccttc | 1980 | |
| aggggaatga cctccgaatg ttccgaaatc agagccgctg gcaggcccaa caaacccgat | 2040 | |
| tccatcaccg tggtgatcac caaggtgacc gacctgtacc ccttccctac ccaactgctg | 2100 | |
| atgggaacca agagcgtgtg tgaggtgggc tccttctggt tccagcccat ctatctgggc | 2160 | |
| gccatgttca gcctgcagga gggagacaaa ctgatggtga acgtgtccga tatctccctc | 2220 | |
| gtcgactaca ccaaggagga taaaaccttt ttcggcgcct tcctgctc | 2268 | |

<210> SEQ ID NO 186
<211> LENGTH: 1803
<212> TYPE: DNA
<213> ORGANISM: Artificial Sequence
<220> FEATURE:
<223> OTHER INFORMATION: TL1W61 (Fc-TL1A+His-TL1A) nucleotide sequence

<400> SEQUENCE: 186

| | | |
|---|---|---|
| ggatcctgtc ctccctgccc tgctcctgaa ctcctgggcg gacccagcgt gtttctgttc | 60 | |
| cccccaaac ctaaagacac actgatgatt agcagaaccc ccgaggtcac ctgcgtggtg | 120 | |
| gtggatgtgt cccacgagga tcccgaggtc aagttcaact ggtacgtgga tggcgtggag | 180 | |
| gtgcacaacg ccaaaaccaa gccccaggga gagcagtaca actccaccta cagggtcgtg | 240 | |
| agcgtgctga cagtgctgca ccaggactgg ctgaacggaa aggagtacaa gtgtaaggtc | 300 | |
| agcaacaagg ctctgcctgc ccccatcgag aaaaccatca gcaaggccaa gggccagcct | 360 | |
| agggaacccc aggtgtacac actgcccct tccaggagg agatgaccaa aaaccaggtc | 420 | |
| agcctgacat gcctggtgaa aggcttctac cccagcgata tcgccgtgga atgggagtcc | 480 | |
| aacggccagc ctgagaacaa ctacaagacc acaccccccg tgctggactc cgacggttct | 540 | |
| tttttcctgt actccaagct gaccgtcgac aagagcaggt ggcaacaggg caacgtcttc | 600 | |
| agctgcagcg tgatgcacga agccctgcac aaccactaca cccagaaaag cctgagcctg | 660 | |
| tcccctggcg gaggaggagg aagcctcaag gccaggagt cgctcccctc ccatcagcag | 720 | |
| gtgtacgctc ccctgagagc cgatggcgat aagcccagag cccacctgac cgtcgtgagg | 780 | |
| cagacccca cccagcactt caagaaccag tttcccgccc tccactggga gcacgagctg | 840 | |
| ggactggcct ttaccaagaa cagaatgaat tacaccaaca gtttctgct catccccgag | 900 | |
| agcggagact acttcatcta ctcccaggtg accttcaggg gcatgacaag cgagtgcagc | 960 | |
| gagatcagac aggccggaag gcctaataag cccgactcca tcacagtggt gatcacaaag | 1020 | |
| gtgaccgaca gctaccccga gcccacccag ctgctgatgg caccaagag cgtgtgcgaa | 1080 | |
| gtgggcagca actggttcca gcccatctac ctgggcgcca tgttcagcct gcaggagggc | 1140 | |
| gacaagctga tggtgaacgt gagcgacatt tccctggtcg attacaccaa ggaggataag | 1200 | |
| accttcttcg gcgccttcct gctgcatcat caccaccatc acgagaacct gtacttccaa | 1260 | |
| ggtctcaagg ccaggagtt cgctcccctcc catcagcagg tgtacgctcc cctgagagcc | 1320 | |

```
gatggcgata agcccagagc ccacctgacc gtcgtgaggc agaccccccac ccagcacttc    1380 aagaaccagt ttcccgccct ccactgggag cacgagctgg gactggcctt taccaagaac    1440
agaatgaatt acaccaacaa gtttctgctc atccccgaga gcggagacta cttcatctac    1500
tcccaggtga ccttcagggg catgacaagc gagtgcagcg agatcagaca ggccggaagg    1560
cctaataagc ccgactccat cacagtggtg atcacaaagg tgaccgacag ctaccccgag    1620
cccacccagc tgctgatggg caccaagagc gtgtgcgaag tgggcagcaa ctggttccag    1680
cccatctacc tgggcgccat gttcagcctg caggagggcg acaagctgat ggtgaacgtg    1740
agcgacattt ccctggtcga ttacaccaag gaggataaga ccttcttcgg cgccttcctg    1800
ctg                                                                  1803
```

<210> SEQ ID NO 187
<211> LENGTH: 1224
<212> TYPE: DNA
<213> ORGANISM: Artificial Sequence
<220> FEATURE:
<223> OTHER INFORMATION: TL1W3 (GD: Fc Fusion in CBIS -> homodimer Fc
      Fusion; GS-huIgG1 Fc - 2(G4S)-hTL1A 72-251) nucleotide sequence

<400> SEQUENCE: 187

```
ggatcctgtc ctccctgccc tgctcctgaa ctcctgggcg gacccagcgt gtttctgttc     60 cccccaaac ctaagacac actgatgatt agcagaaccc ccgaggtcac ctgcgtggtg     120
gtggatgtgt cccacgagga tcccgaggtc aagttcaact ggtacgtgga tggcgtggag    180
gtgcacaacg ccaaaaccaa gcccagggaa gagcagtaca ctccaccta cagggtcgtg     240 agcgtgctga cagtgctgca ccaggactgg ctgaacggaa aggagtacaa gtgtaaggtc    300
agcaacaagg ctctgcctgc ccccatcgag aaaaccatca gcaaggccaa gggccagcct    360 agggaaccc aggtgtacac actgcccct tccagggagg agatgaccaa aaaccaggtc    420
agcctgacat gcctggtgaa aggcttctac cccagcgata tcgccgtgga atgggagtcc    480
aacggccagc ctgagaacaa ctacaagacc acaccccccg tgctggactc cgacggttct    540
tttttcctgt actccaagct gaccgtcgac aagagcaggt ggcaacaggg caacgtcttc    600
agctgcagcg tgatgcacga agccctgcac aaccactaca cccagaaaag cctgagcctg    660
tcccctggcg gaggaggagg aagcctcaag ggccaggagt cgctccctc ccatcagcag    720 gtgtacgctc ccctgagagc cgatggcgat aagcccagag cccacctgac cgtcgtgagg    780
cagaccccca cccagcactt caagaaccag tttcccgccc tccactggga gcacgagctg    840
ggactggcct ttaccaagaa cagaatgaat tacaccaaca gtttctgct catccccgag    900 agcggagact acttcatcta ctcccaggtg accttcaggg gcatgacaag cgagtgcagc    960
gagatcagac aggccggaag gcctaataag cccgactcca tcacagtggt gatcacaaag    1020
gtgaccgaca gctaccccga gcccacccag ctgctgatgg gcaccaagag cgtgtgcgaa    1080
gtgggcagca actggttcca gcccatctac ctgggcgcca tgttcagcct gcaggagggc    1140
gacaagctga tggtgaacgt gagcgacatt tccctggtcg attacaccaa ggaggataag    1200
accttcttcg gcgccttcct gctg                                          1224
```

<210> SEQ ID NO 188
<211> LENGTH: 222
<212> TYPE: PRT
<213> ORGANISM: Artificial Sequence
<220> FEATURE:
<223> OTHER INFORMATION: Exemplary Fc region sequence

<400> SEQUENCE: 188

```
Gly Ser Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Glu Glu Met Thr Lys Asn Gln Val Ser Leu Thr Cys
            130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro
    210                 215                 220
```

<210> SEQ ID NO 189
<211> LENGTH: 7
<212> TYPE: PRT
<213> ORGANISM: Artificial Sequence
<220> FEATURE:
<223> OTHER INFORMATION: Synthetic peptides
<220> FEATURE:
<221> NAME/KEY: MOD_RES
<222> LOCATION: (7)..(7)
<223> OTHER INFORMATION: X is G or S

<400> SEQUENCE: 189

```
Glu Asn Leu Tyr Phe Gln Xaa
1               5
```